US009454640B2

(12) United States Patent
Famili et al.

(10) Patent No.: US 9,454,640 B2
(45) Date of Patent: Sep. 27, 2016

(54) MAMMALIAN CELL LINE MODELS AND RELATED METHODS

(75) Inventors: Imandokht Famili, San Diego, CA (US); Christophe H. Schilling, San Diego, CA (US)

(73) Assignee: Intrexon CEU, Inc., Blacksburg, VA (US)

( * ) Notice: Subject to any disclaimer, the term of this patent is extended or adjusted under 35 U.S.C. 154(b) by 1108 days.

(21) Appl. No.: 13/203,470

(22) PCT Filed: Feb. 26, 2010

(86) PCT No.: PCT/US2010/000576
§ 371 (c)(1),
(2), (4) Date: Apr. 5, 2012

(87) PCT Pub. No.: WO2010/098865
PCT Pub. Date: Sep. 2, 2010

(65) Prior Publication Data
US 2012/0185226 A1 Jul. 19, 2012

Related U.S. Application Data

(60) Provisional application No. 61/155,660, filed on Feb. 26, 2009, provisional application No. 61/244,809, filed on Sep. 22, 2009.

(51) Int. Cl.
*G06F 19/00* (2011.01)
*G06F 19/10* (2011.01)
*G06F 19/12* (2011.01)

(52) U.S. Cl.
CPC ..................... *G06F 19/12* (2013.01)

(58) Field of Classification Search
None
See application file for complete search history.

(56) References Cited

U.S. PATENT DOCUMENTS

| | | | |
|---|---|---|---|
| 2003/0059792 A1* | 3/2003 | Palsson et al. | 435/6 |
| 2003/0154003 A1 | 8/2003 | Eker et al. | |
| 2003/0228567 A1 | 12/2003 | Famili et al. | |
| 2003/0233218 A1 | 12/2003 | Schilling | |
| 2004/0029149 A1 | 2/2004 | Palsson et al. | |
| 2004/0072723 A1 | 4/2004 | Palsson et al. | |
| 2005/0202426 A1 | 9/2005 | Short et al. | |
| 2005/0272128 A1 | 12/2005 | Umana et al. | |
| 2006/0147899 A1 | 7/2006 | Famili et al. | |
| 2007/0016390 A1 | 1/2007 | Bernardo et al. | |
| 2008/0133196 A1* | 6/2008 | Palsson et al. | 703/11 |
| 2009/0061445 A1* | 3/2009 | Oltvai et al. | 435/6 |
| 2009/0275096 A1* | 11/2009 | Burgard et al. | 435/141 |
| 2010/0280803 A1* | 11/2010 | Famili et al. | 703/2 |
| 2011/0010150 A1* | 1/2011 | Palsson et al. | 703/2 |
| 2011/0213603 A1* | 9/2011 | Palsson et al. | 703/11 |
| 2013/0090859 A1* | 4/2013 | Palsson et al. | 702/19 |

FOREIGN PATENT DOCUMENTS

| | | |
|---|---|---|
| WO | WO 00/46405 | 8/2000 |
| WO | WO 03/106998 | 12/2003 |
| WO | 2004035009 | 4/2004 |

OTHER PUBLICATIONS

Andersen et al., "Recombinant protein expression for therapeutic applications," Current Opinion in Biotechnology, 13(2):117-123 (2002).
Hossler et al., "GlycoVis: Visualizing Glycan Distribution in the Protein N-Glycosylation Pathway in Mammalian Cells," Biotechnology and Bioengineering, 95(5):946-960 (2006).
Umana et al., "A Mathematical Model of N-Linked Glycoform Biosynthesis," Biotechnology and Bioengineering, 55 (6):890-908 (1997).
International Search report for PCT/US10/00576 dated Jul. 20, 2010 (4 pages).
Written Opinion of the International Search Report for PCT/US10/00576 dated Jul. 20, 2010 (6 pages).
Gambhir et al., "Analysis of cellular metabolism of hybridoma cells at distinct physiological states," Journal of Bioscience and Bioengineering, 95(4):317-327 (2003).
Bonarius et al., "Metabolic flux analysis of hybridoma cells in different culture media using mass balances," Biotechnology and Bioengineering, 50(3):299-318 (1996).
Trawick et al., "Use of constraint-based modeling for the prediction and validation of antimicrobial targets," Biochemical Pharmacology, 71(7): 1026-1035 (2006).
Supplemental European Search Report for EP 10746553.6, dated Feb. 5, 2015 (9 pages).
Supplementary European Search Report for EP 10 74 6553 dated May 21, 2015 (12 pages).
Allison et al., "Deciphering the Mechanisms of Therapeutic Protein Production," CEP Magazine, 103:48-52 (2007).
Altamirano et al., "Analysis of CHO Cells Metabolic Redistribution in a Glutamate-Based Defined Medium in Continuous Culture," Biotechnol. Prog., 17:1032-1041 (2001).
Altamirano et al., "Considerations on the lactate consumption by CHO cells in the presence of galactose," Journal of Biotechnology, 125:547-556 (2006).
Aoki-Kinoshita et al., "Gene Annotation and Pathway Mapping in KEGG," Methods Mol. Biol., 396:71-92 (2007).
Ayusawa et al., "Selection of Mammalian Thymidine Auxotrophic Cell Mutants Defective in Thymidylate Synthase by Their Reduced Sensitivity to Methotrexate," Somatic Cell Genetics, 7(5):523-534 (1981).
Baik et al., "Initial Transcriptome and Proteome Analyses of Low Culture Temerature-Induced Expression in CHO Cells Producing Erythropoietin," Biotechnol. Bioeng., 93:361-371 (2006).
Barnes et al., "Advances in animal cell recombinant protein production: GS-NS0 expression system," Cytotechnology, 32:109-123 (2000).

(Continued)

*Primary Examiner* — Lori A Clow
(74) *Attorney, Agent, or Firm* — Jones Day

(57) ABSTRACT

The invention provides models and methods useful for optimizing cell lines. The invention provides methods and computer readable medium or media containing such methods. Such a computer readable medium or media can comprise commands for carrying out a method of the invention. The methods of the invention can be utilized to model improved characteristics of a cell line, for example, improved product production, improved growth, improved culture characteristics, and the like.

25 Claims, 36 Drawing Sheets

(56) References Cited

OTHER PUBLICATIONS

Barnes et al., "Stability of Protein Production From Recombinant Mammalian Cells," Biotechnol. Bioeng., 81:631-639 (2003).
Barthelmes et al., "Brenda, Amenda and Frenda: the enzyme information system in 2007," Nucleic Acids Research, 35:D511-D514 (2007).
Bertrand et al., "Comparison of antisense oligonucleotides and siRNAs in cell culture and in vivo," Bichem. Biophys. Res. Commun., 296(4):1000-1004 (2002).
Birch, John, "Mammalian Cell Culture: Current Status, Future Prospects," Cell Culture and Upstream Processing, Berlin, Sep. 2004 (38 pages total).
Bonarius et al., "Metabolic Flux Anaylsis of Hybridoma Cells in Different Culture Media Using Mass Balances," Biotechnol. Bioeng. 50, 299-318 (1996).
Bonarius et al., Metabolite-Balancing Techinques Vs. 13c Tracer Experiments to Determine Metabolic Fluxes in Hybridoma Cells. Biotechnol. Bioeng. 58, 258-262 (1998).
Boutet et al., "The Manually Annotated Section of the UniProt Knowledge Base," Methods Mol. Biol., 406:89-112 (2007).
Boyer, Paul D., "What makes ATP synthase spin?" Nature, 402 (6759):247, 249 (1999).
Brorson et al., "Impact of Cell Culture Process Changes of Endogenous Retrovirus Expression," Biotechnol. Bioeng., 80:257-267 (2002).
Browne et al., "Selection methods for high-producing mammalian cell lines," Trends in Biotechnology, 25(9):425-432 (2007).
Carbone et al., "Expression and characterization of a human pyruvate carboxylase variant by retroviral gene transfer," Biochem. J., 370:275-282 (2003).
Chen et al., "Engineering of a Mammalian Cell Line for Reduction of Lactate Formation and High Monoclonal Antibody Production," Biotechnical Bioeng., 72:55-61 (2001).
Choi et al., "Beneficial Effect of Silkworm Hemolymph on CHO Cell System: Inhibition of Apoptosis and Increase of EPO Production," Biotechnol. Bioeng., 91:793-800 (2005).
Cockett et al., "High Level Expression of Tissue Inhibitor of Metalloproteinases in Chinese Hamster Ovary Cells Using Glutamine Synthetase Gene Amplification," Biotechnology, 8:662-667 (1990).
Cotter et al., "Cell death (apoptosis) in cell culture systems," Trends Biotechnol., 13:150-155 (1995).
Covert et al., "Integrating high-throughput and computational data elucidates bacterial networks," Nature, 429:92-96 (2004).
Covert et al., "Metabolic Modeling of Microbial Strains in Silico," Trends in Biochemical Sciences 25, 179-186 (2001).
Covert et al., "Regulation of Gene Expression in Flux Balance Models of Metabolism," J. Theor. Biol. 213, 73-88 (2001).
Covert et al., "Transcriptional Regulations in Constraints-based Metabolic Models of *Escherichia coli*," J. Biol. Chem. 277, 28058-28064 (2002).
DeLeon et al., "Comparative Transcriptional Analysis of Mouse Hybridoma and Recombinant Chinese Hamster Ovary Cells Undergoing Butyrate Treatment," Journal of Bioscience and Bioengineering, 103(1):82-91 (2007).
DeLuna et al., "NADP-Glutamate Dehydrogenase Isoenzymes of Saccharomyces cerevisiae," J. Biol. Chem., 276(47):43775-43783 (2001).
Duarte et al., "Global reconstruction of the human metabolic network based on genomic and bibliomic data," Proc. Natl. Acad. Sci. U.S.A., 104:1777-1782 (2007).
Edwards et al., "Characterizing the Metabolic Phenotype: A Phenotype Phase Plane Analysis," Biotech. Bioeng.77, 27-36 (2002).
Edwards et al., "Metabolic flux balance analysis and the in silico analysis of *Es-cherichia coli* K-12 gene deletions," BMC Bioinformatics 1:1 (2000).
Edwards et al., "Metabolic modelling of microbes: the flux-balanace approach.," Environ. Microbiol. 4(3) 133-140 (2002).
Edwards et al., "System Properties of the Haemophilus influenzae Rd Metabolic Genotype," J. Biol. Chem. 274 17410-17416 (1999).
Edwards et al., "The *Escherichia coli* MG1655 in silico metabolic genotype: Its definition, characteristics, and capabilities," Proc. Natl. Acad. Sci. U.S.A.97 5528-5533 (2000).
Ernst et al., "Evaluation of a genomics platform for cross-species transcriptome analysis of recombinant CHO cells," Biotechnol. J., 1:639-650 (2006).
Famili et al., "Saccharomyces cerevisiae phenotypes can be predicted by using constraint-based analysis of a genome-scale reconstructed metabolic network," Proc. Natl. Acad. Sci. U.S.A.100, 13134-13139 (2003).
Fire et al., "Potent and specific genetic interference by double-stranded RNA in Caenorhabditis elegans," Nature, 391:806-811 (1998).
Forster et al., "Genome-Scale Reconstruction of the Saccharomyces cerevisiae Metabolic Network," Genome Research13, 244-253 (2003).
Forster et al., "Large-Scale Evaluation of In Silico Gene Deletions in Saccharomyces cerevisiae," OMICS A Journal of Integrative Biology 7, 193-202 (2003).
Furukawa et al., "Effect of culture temperature on a recombinant CHO cell line producing a C-terminal α-amidating enzyme," Cytotechnology, 26:153-164 (1998).
Garnick, R.L., "Experience with Viral Contamination in Cell Culture," Cytotechnology, 88:49-56 (1993).
Hamosh et al., "Online Mendelian Inheritance in Man (OMIM), a knowledgebase of human genes and genetic disorders," Nucleic Acids Res., 33:D514-D517 (2005).
Hannah et al., "In Vitro Regulatio of Low-Density Lipoprotein Receptor Interaction by Fatty Acids," Metabolism, 44:1428-1434 (1995).
Harrison et al., "Cell culture media," General Techniques of Cell Culture, Chapter 3: 31-59 (1997).
Hayduk et al., "A two-dimensional electrophoresis map of Chinese hamster ovary cell proteins based on fluorescence staining," Electrophoresis, 25:2545-2556 (2004).
Hayduk et al., "Cytochalasin D Can Improve Heterologous Protein Productivity in Adherent Chinese Hamster Ovary Cells," Biotechonol. Bioeng., 90:354-364 (2005).
Hayter et al., "Chinese hamster ovary cell growth and interferon production kinetics in stirred batch culture," Appl. Microbiol. Biotechnol., 34:559-564 (1991).
Hayter et al., "The Effect of the Dilution Rate on CHO Cell Physiology and Recombinant Interferon-γ Production in Glucose-Limited Chemostat Culture," Biotechnol. Bioeng., 42:1077-1085 (1993).
Hossler et al., "Glyco Vis: Visualizing Glycan Distribution in the Protein N-Glycosylation Pathway in Mammalian Cells," Biotechnol. Bioeng. 95, 946-960 (2006).
Ideker et al., Integrated Genomic and Proteomic Analyses of a Systematically Perturbed Metabolic Network, Science 292 929-934 (2001).
Ill et al., "Risk reduction in biotherapeutic products," Curr. Opin. Drug Discov. Develop., 12:296-304 (2009).
International Conference on Harmonisation of Technical Requirements for Registration of Pharmaceuticals for Human Use, "Derivation and Characterization of Cell Substrates Used for Production of Biotechnological/Biological Products Q5D," pp. 1-13, (Jul. 16, 1997).
International Conference on Harmonisation of Technical Requirements for Registration of Pharmaceuticals for Human Use, "Viral Safety Evaluation of Biotechnology Products Derived from Cell Lines of Human or Animal Origin Q5A (R1)," pp. 1-27, (Sep. 23, 1999).
Irani et al., "Expression of recombinant cytoplasmic yeast pyruvate carboxylase for the improvement of the production of human erythropoietin by recombinant BHK-21 cells," Journal of Biotechnology, 93:269-282 (2002).
Irani et al., "Improvement of the Primary Metabolism of Cell Cultures by Introducing a New Cytoplasmic Pyruvate Carboxylase Reaction," Biotechnol. Bioeng., 66:238-246 (1999).

(56) References Cited

OTHER PUBLICATIONS

Jayapal et al., "Recombinant Protein Therapeutics from CHO Cells—20 Years and Counting," Chem. Eng. Progress, 103:40-47 (2007).

Jeong et al., "Blocking of Acidosis-Mediated Apoptosis by a Redcution of Lactate Dehydrogenase Activity through Antisense mRNA Expression," Biochem. Biophys. Res. Commun., 289(5):1141-1149 (2001).

Jeong et al., "Effects of lactate dehydrogenase suppression and glycerol-3-phosphate dehydrogenase overexpression on cellulare metabolism," Mol. Cell. Biochem., 284:1-8 (2006).

Jitrapakdee et al., "Structure, function and regulation of pyruvate carboxylase," Biochem. J., 340:1-16 (1999).

Kaiser, Jocelyn, "Stimulus Funding Elicits a Tidal Wave of 'Challenge Grants'," Biomedical Research, 324:867 (2009).

Kamath, Lakshmi, "Keeping Up with Protein Demand," Drug Discovery & Development, 8(12):34 (Dec. 2005).

Kaufmann et al., "Influence of Low Temperature on Productivity, Proteome and Protein Phosphorylation of CHO cells," Biotechnol. Bioeng., 63:572-582 (1999).

Kim et al., "Down-regulation of lactate dehydrogenase-A by siRNAs for reduced lactic acid formation of Chinese hamster ovary cells producing thrombopoietin," Appl. Microbiol. Biotechnol., 74:152-159 (2007).

Kim et al., "Functional expression of human pyruvate carboxylase for reduced lactic acid formation of Chinese hamster ovary cells (DG44)," Appl. Microbiol. Biotechnol., 76:659-665 (2007).

Kovas, E., "Cell Metabolism and Virus," Experientia, 17:153-160 (1961).

Krambeck et al., "A Mathematical Model of N-Linked Glycosylation," Biotechnol. Bioeng., 92:711-728 (2005).

Kumar et al., "Proteomic Profiling of Secreted Proteins from CHO Cells Using Surface-Enhanced Laser Desorption Ionization Time-of-Flight Mass Spectrometry," Biotechnol. Prog., 24:273-278 (2008).

Landini, M.P., "Early Enhanced Glucose Uptake in Human Cytomegalovirus-infected Cells," J. Gen. Virol., 65:1229-1232 (1984).

Lao et al., "Effects of Ammonium and Lactate on Growth and Metabolism of a Recombinant Chinese Hamster Ovary Cell Culture," Biotechnol. Prog., 13:688-691 (1997).

Lee et al., "A rationale for cystine supplementation in severe homocystinuria," j. Inherit. Metab. Dis., 30:35-38 (2007).

Lee et al., "Purification and Properties of a NADPH-Dependent Erythrose Reductase from the Newly Isolated Torula coralline," Biotechnol. Prog 19, 495-500 (2003).

Lemotte et al., "Na-butyrate increases the production and $\alpha 2,6$-sialylation of recombinant interferon-$\gamma$ expressed by $\alpha 2,6$-sialyltransferase engineered CHO cells," Cytotechnology, 29:55-64 (1999).

Lincoln et al., "Cell Culture Contamination: Sources, Consequences, Prevention, and Elimination," Methods Cell Biol., 57:49-65 (1998).

Liu et al., "Pentanoic Acid, a Novel Protein Synthesis Stimulant for Chinese Hamster Ovary (CHO) Cells," Journal of Bioscience and Bioengineering, 91(1): 71-75 (2001).

Lu et al., "Insight into metabolism of CHO cells at low glucose concentration on the basis of the determination of intracellular metabolites," Process Biochemistry, 40:1917-1921 (2005).

Mahadevan et al., "The effects of alternate optimal solutions in constraint-based genome-scale metabolic models," Metab. Eng. 5, 264-276 (2003).

Maranga et al., "Characterization of Changes in PER.C6 Cellular Metabolism During Growth and Propogation of a Replication-Deficient Adenovirus Vector," Biotechnol. Bioeng., 90:645-655 (2005).

Merten, O.W., "Virus contaminations of cell cultures—A biotechnological view," Cytotechnology, 39:91-116 (2002).

Moehle et al., "Targeted gene addition into a specified location in the human genome using designed zinc finger nucleases," Proc. Natl. Acad. Sci. U.S.A., 104(9):3055-3060 (2007).

Mols et al., "Recombinant Interferon-$\gamma$ Secreted by Chinese Hamster Ovary-320 Cells Cultivated in Suspension in Protein-Free Media is Protected Against Extracellular Proteolysis by the Expression of Natural Protease Inhibitors and by the Addition of Plant Protein Hydrolysates to the Culture Medium," In Vitro Cell Del. Biol. Anim., 41:83-91 (2005).

Moore et al., "Experience in Cell Line Testing," Dev. Biol. Stand., 76:51-56 (1992).

Mulligan et al., "Expression of a Bacterial Gene in Mammalian Cells," Science, 209:1422-1427 (1980).

Munger et al., "Dynamics of the Cellular Metabolome during Human Cytomegalovirus Infection," PLoS Pathog., 2:e132 (2006).

Munger et al., "Systems-level metabolic flux profiling identities fatty acid sythesis as a target for antiviral therapy," Nature Biotechnology, 26:1179-1186 (2008).

Namjoshi et al., "Unveiling Steady-State Multiplicity in Hybridoma Cultures: The Cybernetic Approach," Biotechnical Bioeng., 81:80-91 (2003).

Narkewicz et al., "Evidence for intracellular partitioning of serine and glycine metabolism in Chinese hamster ovary cells," Biochem. J., 313(Pt.3):991-996 (1996).

Nielsen et al., "Cell Cycle Model to Describe Animal Cell Size Variation and Lag between Cell Number and Biomass Dynamics," Biotechnol. Bioeng., 56:372-379 (1997).

Nissom et al., "Transcriptome and Proteome Profiling to Understanding the Biology of High Productivity CHO Cells," Mol. Biotechnol., 34:125-140 (2006).

Nyberg et al., "Metabolic Effects on Recombinant Interferon-$\gamma$ Glycosylation in Continuous Culture of Chinese Hamster Ovary Cells," Biotechnol. Bioeng., 62:336-347 (1999).

Nyberg et al., "Metabolism of Peptide Amino Acids by Chinese Hamster Ovary Cells Grown in a Complex Medium," Biotechnol. Bioeng., 62:324-335 (1999).

Oh et al., "Effect of N-Acetylcystein on Butyrate-Treated Chinese Hamster Ovary Cells to Improve the Production of Recombinant Human Interferon-$\beta$-1 a," Biotechnol. Prog., 21:1154-1164 (2005).

Ozturk et al., "Growth, Metabolic, and Antibody Production Kinetics of Hybridoma Cell Culture: 2. Effects of Serum Concentration, Dissolved Oxygen Concentration, and Medium pH in a Batch Reactor," Biotechnol. Prog., 7:481-494 (1991).

Page et al., "High Level Expression of the Humanized Monoclonal Antibody Campath-1H in Chinese Hamster Ovary Cells," Biotechnology, 9:64-68 (1991).

Palsson, B., "The challenges of in silico biology," Nat. Biotechnol. 18, 1147-1150 (2000).

Pissarra, Pedro de Noronha, "Changes in the business of culture," Nat. Biotechnol., 22:1355-1356 (2004).

Podglajen-Wecxsteen et al., "Tyrosinose Oculo-Cutanee de Type II," Ann. Dermatol. Vereol., 120:139-142 (1993).

Polastro et al., "Redefining the biotech sector," Scrip Magazine, 114:29-31 (2002).

Price et al., "Genome-Scale Models of Microbial Cells: Evalulating the Consequences of Constraints," Nat. Rev. Microbiol. 2, 886-897 (2004).

Provost et al., "Dynamic metabolic modelling under the balanced growth condition," Journal of Process Control, 14:717-728 (2004).

Provost et al., "Metabolic design of macroscopic bioreaction models: application to Chinese hamster ovary cells," Bioprocess Biosyst Eng., 29:349-366 (2006).

Pruitt et al., "NCBI reference sequences (RefSeq): a curated non-redundant sequence database of genomes, transcripts and proteins," Nucleic Acids Research, 35:D61-D65 (2007).

Robertson, J.S., "Strategy for Adventitious Agent Assays," Dev. Biol. Stand., 88:37-40 (1996).

Rodriguez et al., "Enhanced Production of Monomeric Interferon-$\beta$ by CHO Cells through the Control of Culture Conditions," Biotechnol. Prog., 21:22-30 (2005).

Rognstad et al., "The Metabolism of L-[3-3H]Lactate by Isolated Hamster Liver Cells," Biochimica et Biophysica Acta, 437:16-21 (1976).

(56) References Cited

OTHER PUBLICATIONS

Rose et al., "Mammalian Cell Culture," Handbook of Industrial Cell Culture, pp. 69-103 (2003).
Santiago et al., "Targeted gene knockout in mammalian cells by using engineered zinc-finger nucleases," Proc. Natl. Acad. Sci. U.S.A., 105(15):5809-5814 (2008).
Savinell et al., "Network Analysis of Intermediary Metabolism using Linear Optimization. I. Development of Mathmatical Formalism," J. theor. Biol. 152: 421-454 (1992).
Savinell et al., "Network Analysis of Intermediary Metabolism using Linear Optimization. II. Interpretation of Hybridoma Cell Metabolism," J. theor. Biol. 152: 455-437 (1992).
Schiff, "Review: production, characterization, and testing of banked mammalian cell substrates used to produce biological products," In Vitro Cell Dev. Biol. Anim. 41(3-4):65-70 (2005).
Schilling et al., "Assessment of the metabolic capabilities of Haemophilus influenzae Rd through a genome-scale pathway analysis," J. Theor. Biol. 203(3):249-283 (2000).
Schilling et al., "Genome-Scale Metabolic Model of Helicobacter pylori 26695," J. Bateriol. 184, 4582-4593 (2002).
Schilling et al."Toward Metabolic Phenomics: Analysis of Genomic Data Using Flux Balances," Biotechnol. Prog. 15, 288-295 (1999).
Schlaeger, "The protein hydrolysate, Primatone RL, is a cost-effective multiple growth promoter of mammalian cell culture in serum-containing and serum-free media and displays anti-apoptosis properties," J. Immunol. Methods 194(2):191-199 (1996).
Schuster et al., "Exploring the pathway structure of metabolism: decomposition into subnetworks and application to Mycoplasma pneumoniae," Bioinformatics 18, 351-361 (2002).
Seagle et al., "High-throughput nuclear magnetic resonance metabolomic footprinting for tissue engineering," Tissue Eng. Part C Methods 14(2):107-118 (2008).
Seewoster et al., "Influence of targeted asparagine starvation on extra- and intracellular amino acid pools of cultivated Chinese hamster ovary cells," Appl. Microbiol. Biotechnol. 44(3-4):344-350 (1995).
Segre et al., "Analysis of optimality in natural and perturbed metabolic networks," Proc. Natl. Acad. Sci. U.S.A. 99, 15112-15117 (2002).
Seth et al., "In pursuit of a super producer-alternative paths to high producing recombinant mammalian cells," Curr. Opin. Biotechnol. 18(6):557-564 (2007) (Epub Dec. 21, 2007).
Sheikh et al., "Modeling hybridoma cell metabolism using a generic genome-scale metabolic model of Mus musculus," Biotechnol. Prog. 21(1):112-121 (2005).
Simpson et al., "Bcl-2 over-expression reduces growth rate and prolongs G1 phase in continuous chemostat cultures of hybridoma cells," Biotechnol. Bioeng. 64(2):174-186 (1999).
Sleight et al., "Regulation of phosphatidylcholine biosynthesis in mammalian cells. III. Effects of alterations in the phospholipid compositions of Chinese hamster ovary and LM cells on the activity and distribution of CTP:phosphocholine cytidylyltransferase," J. Biol. Chem. 258(2):836-839 (1983).
Sorlie et al., "Gene expression patterns of breast carcinomas distinguish tumor subclasses with clinical implications," Proc. Natl. Acad. Sci. U.S.A. 98, 10869-10874 (2001).
Sung et al., "Influence of co-down-regulation of caspase-3 and caspase-7 by siRNAs on sodium butyrate-induced apoptotic cell death of Chinese hamster ovary cells producing thrombopoietin," Metab. Eng. 9(5-6):452-464 (2007) (Epub Aug. 25, 2007).
Sung et al., "Influence of down-regulation of caspase-3 by siRNAs on sodium-butyrate-induced apoptotic cell death of Chinese hamster ovary cells producing thrombopoietin," Metab. Eng. 7(5-6):457-466 (2005) (Epub Sep. 19, 2005).
TechNote: Antibiotic-Free Systems for Production. Genetic Engineering & Biotechnology News, vol. 26, No. 14, pp. 1-3 (2006).
U.S. Department of Health and Human Services Food and Drug Administration Center for Biologics Evaluation Research, "Points to Consider in the Manufacture and Testing of Monoclonal Antibody Products for Human Use," pp. 1-50, (Feb. 28, 1997).
Urlaub et al., "Isolation of Chinese hamster cell mutants deficient in dihydrofolate reductase activity," Proc. Natl. Acad. Sci. U.S.A. 77(7):4216-4220 (1980).
Urnov et al., "Highly efficient endogenous human gene correction using designed zinc-finger nucleases," Nature 435(7042):646-651 (2005) (Epub Apr. 3, 2005).
Van Dyk et al., "Identification of cellular changes associated with increased production of human growth hormone in a recombinant Chinese hamster ovary cell line," Proteomics 3(2):147-156 (2003).
Varma et al., "Metabolic Flux Balancing: Basic Concepts, Scientific and Practical Use," Bio/Technology 12, 994-998 (1994).
Varma et al., "Stoichiometric Flux Balance Models Quantitatively Predict Growth and Metabolic By-Product Secretion in Wild-Type *Escherichia coli* W3110," Appl. Environ. Microbiol. 60, 3724-3731 (1994).
Varma et al., "Stoichiometric Interpretation of *Escherichia coli* Glucose Catabolism under Various Oxygenation Rates," Appl. Environ. Microbiol. 59, 2465-2473 (1993).
Vo et al., "Reconstruction and functional characterization of the human mitochondrial metabolic network based on proteomic and biochemical data," J. Biol. Chem. 279(38):39532-39540 (2004) (Epub Jun. 17, 2004).
Walsh, "Biopharmaceutical benchmarks—2003," Nat. Biotechnol. 21(8):865-870 (2003).
Waterston et al., "Initial sequencing and comparative analysis of the mouse genome," Nature 420(6915):520-562 (2002).
Wlaschin et al., "A scaffold for the Chinese hamster genome," Biotechnol. Bioeng. 98(2):429-439 (2007).
Wlaschin et al., "EST sequencing for gene discovery in Chinese hamster ovary cells," Biotechnol. Bioeng. 91(5):592-606 (2005).
Woolley et al., "The application of SELDI-TOF mass spectrometry to mammalian cell culture," Biotechnol. Adv. 27(2):177-184 (2009) (Epub Nov. 13, 2008).
Woolley et al., "The isolation and identification of a secreted biomarker associated with cell stress in serum-free CHO cell culture," Biotechnol. Bioeng. 104(3):590-600 (2009).
Wurm, "Production of recombinant protein therapeutics in cultivated mammalian cells," Nat. Biotechnol. 22(11):1393-1398 (2004).
Xie et al., "Fed-batch cultivation of animal cells using different medium design concepts and feeding strategies," Biotechnol. Bioeng. 95(2):270-284 (2006).
Xie et al., "Applications of improved stoichiometric model in medium design and fed-batch cultivation of animal cells in bioreactor," Cytotechnology 15, 17-29 (1994).
Xie et al., "Energy Metabolism and ATP Balance in Animal Cell Cultivation Using a Stoichiometrically Based Reaction Network," Biotechnol. Bioeng. 52, 591-601 (1996).
Xie et al., "Integrated approaches to the design of media and feeding strategies for fed-batch cultures of animal cells," Trends Biotechnol. 15, 109-113 (1997).
Xie et al., "Material Balance Studies on Animal Cell Metabolism Using a Stoichiometrically Based Reaction Network," Biotechnol. Bioeng. 52, 579-590 (1996).
Xie et al., "Stoichiometric Analysis of Animal Cell Growth and Its Application in Medium Design," Biotechnol. Bioeng. 43, 1164-1174 (1994).
Zhang et al., "Metabolic characteristics of recombinant Chinese hamster ovary cells expressing glutamine synthetase in presence and absence of glutamine," Cytotechnology 51(1):21-28 (2006) (Epub Aug. 5, 2006).
Communication from European Patent Office for 10 746 553.6 dated Feb. 8, 2016 (4 pages).

\* cited by examiner

| Abbreviation | Equation | Flux 1 | Flux 2 | Diff. |
|---|---|---|---|---|
| EX_ergst(e) | [e] : ergst <==> | 0 | -0.000071 | 0.000071 |
| EX_etoh(e) | [e] : etoh <==> | 0 | 9.624164 | 9.624164 |
| EX_for(e) | [e] : for <==> | 0 | 0.005434 | 0.005434 |
| EX_glyc(e) | [e] : glyc <==> | 0 | 0.693104 | 0.693104 |
| EX_hdcea(e) | [e] : hdcea <==> | 0 | -0.000962 | 0.000962 |
| EX_ocdca(e) | [e] : ocdca <==> | 0 | -0.000283 | 0.000283 |
| EX_ocdcea(e) | [e] : ocdcea <==> | 0 | -0.001357 | 0.001357 |
| EX_ocdcya(e) | [e] : ocdcya <==> | 0 | -0.000509 | 0.000509 |
| EX_succ(e) | [e] : succ <==> | 0 | 0.011171 | 0.011171 |
| EX_zymst(e) | [e] : zymst <==> | 0 | -0.000152 | 0.000151 |
| EX_co2(e) | [e] : co2 <==> | 3.030205 | 10.010325 | 6.98012 |
| EX_glc(e) | [e] : glc-D <==> | 1.103788 | -5.826064 | 4.722276 |
| EX_h(e) | [e] : h <==> | 0.50425 | 0.533957 | 0.029707 |
| EX_nh4(e) | [e] : nh4 <==> | -0.55925 | -0.564842 | 0.005592 |
| EX_pi(e) | [e] : pi <==> | -0.01977 | -0.019968 | 0.000198 |
| EX_so4(e) | [e] : so4 <==> | -0.00773 | -0.007807 | 0.000077 |
| EX_h2o(e) | [e] : h2o <==> | 4.222129 | 0.903552 | -3.318577 |
| EX_o2(e) | [e] : o2 <==> | 2.958422 | 0 | -2.958422 |
| EX_13BDglcn(e) | [e] : 13BDglcn <==> | 0 | 0 | 0 |
| EX_1acgpcho_SC(e) | [e] : 1acgpcho_SC <.. | 0 | 0 | 0 |
| EX_4abut(e) | [e] : 4abut <==> | 0 | 0 | 0 |
| EX_5aop(e) | [e] : 5aop <==> | 0 | 0 | 0 |
| EX_8aonn(e) | [e] : 8aonn <==> | 0 | 0 | 0 |
| EX_abt(e) | [e] : abt-L <==> | 0 | 0 | 0 |
| EX_ac(e) | [e] : ac <==> | 0 | 0 | 0 |

MAMMALIAN CELL LINE MODELS AND RELATED METHODS

This application claims the benefit of priority to U.S. Provisional Application Ser. No. 61/155,660, filed Feb. 26, 2009, and U.S. Provisional Application Ser. No. 61/244,809, filed Sep. 22, 2009, each of which the entire contents is incorporated by reference.

This invention was made with government support under grant number 1 R43 GM078885-01 and 1R43GM084535-01 awarded by the National Institute of General Medical Sciences, and 9R44CA139977-02, awarded by the National Cancer Institute. The government has certain rights in the invention.

BACKGROUND OF THE INVENTION

The present invention relates generally to improving and optimizing cell culture for bioproduction and, more specifically, to computational methods for simulating and predicting improved and/or optimized cell culture conditions for bioproduction.

Protein-based therapeutic products have contributed immensely to healthcare and constitute a large and growing percentage of the total pharmaceutical market. Therapeutic proteins first entered the market less than 20 years ago and have already grown to encompass 10-30% of the total US market for pharmaceuticals. The trend towards therapeutic proteins is accelerating. In recent years, more than half of the new molecular entities to receive FDA approval were biologics produced mostly in mammalian cell systems, and an estimated 700 or more protein-based therapeutics are at various stages of clinical development, with 150 to 200 in late-stage trials.

Over the past two decades, substantial progress has been made to overcome some of the key barriers to large-scale mammalian cell culture, including improvements in vector design, host cell engineering, medium development, screening methods and process engineering, resulting in yield improvements of up to 100-fold over titers seen in the mid 1980's. Despite these improvements, developing new biopharmaceutical products remains an expensive and lengthy process, typically taking six years from pre-clinical process development to product launch, where 20-30% of the total cost is associated with process development and clinical manufacturing. Production costs by mammalian cell culture remain high, and new methods to provide a more effective approach to optimize overall process development are of highest interest to the industry, particularly as regulatory constraints on development timelines remain interest to the industry, particularly as regulatory constraints on development timelines remain stringent and production demands for new therapeutics are rapidly rising, especially for the quantities required for treatment of chronic diseases. Production costs are a major concern for management planning, especially with intense product competition, patent expirations, introduction of second-generation therapeutics and accompanying price pressure, and pricing constraints imposed by regulators and reimbursement agencies. Reducing the cost of therapeutic protein development and manufacturing would do much to ensure that the next generation of medicines can be created in amounts large enough to meet patients' needs, and at a price low enough that patients can afford.

Thus, there exists a need to improve and optimize cell cultures for bioproduction of desired products such as biologics. The present invention satisfies this need and provides related advantages as well.

SUMMARY OF INVENTION

The invention provides models and methods useful for optimizing cell lines. The invention provides methods and computer readable medium or media containing such methods. Such a computer readable medium or media can comprise commands for carrying out a method of the invention. The methods of the invention can be utilized to model improved characteristics of a cell line, for example, improved product production, improved growth, improved culture characteristics, and the like. The invention provides models and methods useful for optimizing cell lines. The invention provides computer readable medium or media. Such a computer readable medium or media can comprise a data structure relating a plurality of reactants to a plurality of reactions from a cell, each of the reactions comprising a reactant identified as a substrate of the reaction, a reactant identified as a product of the reaction and a stoichiometric coefficient relating the substrate and the product; a constraint set for said plurality of reactions for said data structures, and commands for determining at least one flux distribution that minimizes or maximizes an objective function when the constraint set is applied to the data structure, wherein the at least one flux distribution is predictive of a physiological function of the cell. The invention additionally provides methods for predicting a physiological function of a cell.

BRIEF DESCRIPTION OF THE DRAWINGS

FIG. 9A shows that, when product formation is limited by ATP requirements, decrease in ATPm improves the maximum product formation rate. FIG. 9B shows that, in the NS0 model, monoclonal antibody (MAb) production is largely unaffected by $ATP_{lumped}$. MAb synthesis is instead limited by the availability of amino acids. At very high $ATP_{lumped}$ values, MAb production becomes limited by the imposed network energy demands.

FIG. 10 shows metabolic efficiency for nutrient utilization in microbes and mammalian cell lines. Inefficiency in nutrient utilization in mammalian cell lines is represented in the metabolic model as the maximization of the total nutrient uptake rates, including glucose and amino acids. μ, growth rate; glc, glucose; aa, amino acids; s.t., subject to.

DETAILED DESCRIPTION OF THE INVENTION

Figure 1:
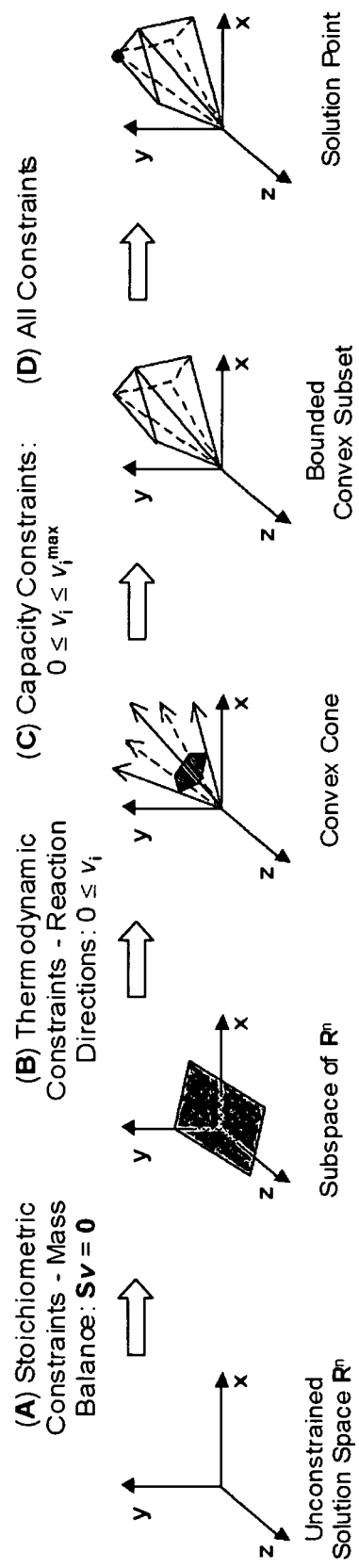
FIG. 1 illustrates an example of the successive imposition of governing constraints used to determine the feasible set. Each constraint including the (A) stoichiometric, (B) thermodynamics, and (C) enzyme capacity constraints reduces the size of the feasible set (shown in blue) and is represented through the incorporation of a set of mathematical statements. In the limiting case where all constraints on the metabolic network are known (D), for example, with known enzyme kinetics and gene regulation, the feasible set may be reduced to a single point. The single point must lie within the feasible set.

The invention provides in silico models that describe the interconnections between genes in a cell genome and their associated reactions and reactants. As disclosed herein, protein-based therapeutic products have contributed immensely to healthcare and constitute a large and growing percentage of the total pharmaceutical drugs. The majority of these FDA approved products are manufactured using mammalian cell culture systems. Over the past 10-20 years substantial progress has been made to overcome some of the key barriers to large-scale mammalian cell culture. Despite these improvements, the development of new biopharmaceutical products remains an expensive and lengthy process, where 20-30% of the total cost is associated with process development and clinical manufacturing. Production of therapeutic protein in mammalian cell lines is hampered by a number of standing issues. For example, selection of high-producing mammalian cell lines represents a bottleneck in process development for the production of biopharmaceuticals. Production of therapeutic proteins in mammalian cell lines has been dominated by the use of selection markers that have metabolic origin. However, the current selection methods are hampered by a number of disadvantages, including extensive development timelines and cost. In addition, most process optimization strategies are currently performed using a trial and error approach where cells are treated as a 'black box' and process outputs are improved over several months by laborious experimentation. These empirical optimization techniques are widely used because in most cases little is known about the underlying physiological interactions that impact growth and protein production in the host cell lines. A fundamental understanding of cell line physiology and metabolism, enabled by computational modeling and simulation technologies, can greatly improve and accelerate media and process development in mammalian cell line systems.

In one embodiment, the present invention provides cell line metabolic models. Using a computational platform, a number of metabolic network reconstructions have been generated for production mammalian cell lines, including hybridoma, NS0, and CHO. The integrated computational and experimental modeling platform allows for the development of metabolic models of mammalian cells, media and process optimization and development, understanding metabolism under different genetic and environmental conditions, engineering cell lines, and developing novel selection systems. Thus, the invention provides methods and in silico models to simulate cell line metabolism (Example III), improve and optimize cell culture media and cell culture processes (Example V), improve and increase protein production (Example V), identify new selection systems (Example VII), identify biomarkers for cell culture contamination, for example, with viruses or bacteria (Example VIII), and improving metabolic characteristics of a cell line (Example IX).

In another embodiment, the invention provides media and/or process optimization and development. A computational modeling platform and expertise was used in metabolic modeling and mammalian cell culture to reduce byproduct formation in a GS-NS0 murine myeloma cell line. To implement the model-driven media optimization approach, a metabolic model for NS0 cell containing 456 metabolites and 470 metabolic reactions was reconstructed. As disclosed herein, the model was used to develop nutritional modifications to the basal media to reduce byproduct formation and improve growth and productivity. Experimental evaluation of the model-based media formulations in NS0 cell culture showed significant improvements over traditional methods for media analysis and resulted in approximately 12% lower lactate and up to 67% higher final product titers. This media and process optimization platform can significantly improve the existing timelines associated with therapeutic protein production in mammalian cell lines. The media and process optimization platform can be used by: (1) reconstructing, refining, and expanding metabolic models of mammalian cell lines including hybridoma, NS0, and CHO cell lines, (2) integrating a transient flux balance approach for quantitative implementation of media designs, and (3) validating the final framework using case studies for antibody production in production cell lines. This platform can be used to reduce the timelines to develop an optimized media that results in lower byproduct formation and higher productivity in cell culture through rational selection of nutrient supplementation and process optimization strategies.

In another embodiment, the invention models allow understanding of metabolism in mammalian cell lines and cell line engineering. Using an integrated computational and experimental approach, the invention also allows characterization of metabolism in production cell lines. For example, the effect of sodium butyrate supplementation, commonly used to enhance protein expression, on CHO cell metabolism was studied using its metabolic network reconstruction and predicted alternative strategies that result in similar metabolic characteristics without the addition of sodium butyrate. The reconstructed networks can be used to develop a rational approach for recombinant protein production in CHO cell lines to: (a) generate fundamental understanding for cell line response to environmental and genetic changes, and (b) develop novel metabolic interventions for improved protein production.

In yet another embodiment, the invention provides cell line engineering and novel selection system design. In addition, the methods and models of the invention can utilize the knowledge of a whole cell metabolism and is capable to provide rational designs for identifying new selection systems. An integrated computational and experimental approach can be used to identify novel selection systems in CHO cell line and experimentally implement the most promising and advantageous candidate to validate the approach. This approach can be implemented in three stages: (1) identify essential metabolic reactions that are candidate targets for designing novel and superior selection systems using a reconstructed metabolic model of a cell line such as hybridoma, NS0, or CHO, rank-order and prioritize the candidate targets based on a number of criteria including the predicted stringent specificity of the new selection system and improved cell physiology, (2) experimentally implement the top candidate selection system in a cell line using experimental techniques such as by first creating an auxotrophic clone, transiently transfecting cells with a selection vector that includes an antibody-expressing gene, and selecting protein producing cell lines based on their auxotrophy, and (3) evaluate the development and implementation of a model-based selection system in CHO cells by comparing experimentally generated cell culture data with those calculated by the reconstructed model. This integrated computational and experimental platform allows for design of new and superior metabolic selection systems in mammalian based protein production by computationally identifying and experimentally developing novel selection systems.

As disclosed herein, in one embodiment, a computational modeling approach is used for the design of mammalian cell culture media to reduce byproduct formation and increase protein production. Although this approach was implemented using a reconstructed metabolic model for NS0 cell line and NS0 cell culture experiments (see Examples and Table 22), the computational modeling and experimental implementation are applicable to any cell lines such as mammalian cell line, including but not limited to the human- or animal-derived cell lines, for example, Chinese Hamster Ovary (CHO), BHK, NS0, SP2/0, 3T3, Hybridoma, C127, HEK293, PER.C6, HepG2, HeLa, MRC5, WI38, MDCK, Vero, COS, including modified versions of such cell lines, such as GS-NS0 or CHO DHFR. It is understood that such cell lines are merely exemplary and that the methods are applicable to any cell line for which sufficient information on metabolic reactions is known or can be deduced from other cells or related organisms, as disclosed herein. The methods of the invention can additionally be applied to other cell lines such as plant or insect cells and to design or modify media, process and cell lines. Such cell lines are useful for production of biologics, including but not limited to growth factors, monoclonal antibodies, hormones, cytokines, fusion proteins, recombinant enzymes, recombinant vaccines, viruses, anticoagulants, and nucleic acids. In one embodiment, the cell lines are derived from a multicellular organism such as an animal, for example, a human, a plant or an insect.

As exemplified herein, a model was used to study the fate of nutrients and source of byproduct formation in a parental and an IgG producing cell culture, and to develop nutritional modifications to the basal media that resulted in byproduct reduction as well as growth and productivity improvements.

The model-driven media formulations were experimentally implemented in a GS-NS0 murine myeloma cell line. Experimental results showed significant improvements over traditional methods for media optimization and resulted in approximately 12% lower lactate and up to 67% higher final product titers (see Examples). In addition to media optimization and development, such a computational modeling approach can be used to design cell culture processes, that is, process design, and to engineer cell lines, that is, cell line engineering, to improve a desired characteristic including, but not limited to, biomass production, viable cell density, product yields, and/or product titers to improve the overall productivity of the cell culture.

As disclosed herein, the methods of the invention are useful in applying computational metabolic models for a cell line, in particular a mammalian cell line, such as human or animal-derived cell line, including but not limited to Chinese Hamster Ovary (CHO), BHK, NS0, SP2/0, 3T3, Hybridoma, C127, HEK293, PER.C6, HepG2, HeLa, MRC5, WI38, MDCK, Vero, COS, and any variation of those, for example, GS-NS0 or CHO DHFR cell lines, that are used for production of biologics such as protein products. Exemplary biologics include, but are not limited to, growth factors, monoclonal antibodies, hormones, cytokines, fusion proteins, recombinant enzymes, recombinant vaccines, viruses, anticoagulants, and nucleic acids. In addition, the methods of the invention can be used to develop a computational metabolic model for engineering and optimizing cell culture media, that is, media optimization, designing cell culture process, that is, process design, and engineering the cell, that is, cell line engineering, to improve biomass production, product yield, and/or product titers, that is, to improve the overall cell culture productivity, reduce byproduct formation, or improve any desired metabolic characteristic in a cell culture. In an embodiment, maximization of the nutrient uptake rates or energy maintenance can be used as the objective function for simulating mammalian cell line physiology and cell culture.

The models of the invention are based on a data structure relating a plurality of reactants to a plurality of reactions, wherein each of the reactions includes a reactant identified as a substrate of the reaction, a reactant identified as a product of the reaction and a stoichiometric coefficient relating the substrate and the product. The reactions included in the data structure can be those that are common to all or most cells or to a particular type or species of cell, for example a particular cell line, such as core metabolic reactions, or reactions specific for one or more given cell type.

As used herein, the term "reaction" is intended to mean a conversion that consumes a substrate or forms a product that occurs in or by a cell. The term can include a conversion that occurs due to the activity of one or more enzymes that are genetically encoded by a genome of the cell. The term can also include a conversion that occurs spontaneously in a cell. Conversions included in the term include, for example, changes in chemical composition such as those due to nucleophilic or electrophilic addition, nucleophilic or electrophilic substitution, elimination, isomerization, deamination, phosphorylation, methylation, reduction, oxidation or changes in location such as those that occur due to a transport reaction that moves a reactant from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term "reactant" is intended to mean a chemical that is a substrate or a product of a reaction that occurs in or by a cell. The term can include substrates or products of reactions performed by one or more enzymes encoded by a genome, reactions occurring in cells or organisms that are performed by one or more non-genetically encoded macromolecule, protein or enzyme, or reactions that occur spontaneously in a cell. Metabolites are understood to be reactants within the meaning of the term. It will be understood that when used in reference to an in silico model or data structure, a reactant is intended to be a representation of a chemical that is a substrate or a product of a reaction that occurs in or by a cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more reactants and the number of one or more products in a chemical reaction. Typically, the numbers are integers as they denote the number of molecules of each reactant in an elementally balanced chemical equation that describes the corresponding conversion. However, in some cases the numbers can take on non-integer values, for example, when used in a lumped reaction or to reflect empirical data.

As used herein, the term "plurality," when used in reference to reactions or reactants is intended to mean at least 2 reactions or reactants. The term can include any number of reactions or reactants in the range from 2 to the number of naturally occurring reactants or reactions for a particular of cell or cells. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular cell or cells including a *Homo sapiens* cell or cells, such as at least 20%, 30%, 50%, 60%, 75%, 90%, 95% or 98% of the total number of naturally occurring reactions that occur in a particular *Homo sapiens* cell.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, or a stoichiometric coefficient.

As used herein, the term "constraint" is intended to mean an upper or lower boundary for a reaction. A boundary can specify a minimum or maximum flow of mass, electrons or energy through a reaction. A boundary can further specify directionality of a reaction. A boundary can be a constant value such as zero, infinity, or a numerical value such as an integer. Alternatively, a boundary can be a variable boundary value as set forth below.

As used herein, the term "variable," when used in reference to a constraint is intended to mean capable of assuming any of a set of values in response to being acted upon by a constraint function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "activity," when used in reference to a cell, is intended to mean the magnitude or rate of a change from an initial state to a final state. The term can include, for example, the amount of a chemical consumed or produced by a cell, the rate at which a chemical is consumed or produced by a cell, the amount or rate of growth of a cell or the amount of or rate at which energy, mass or electrons flow through a particular subset of reactions.

Depending on the application, the plurality of reactions for a cell model or method of the invention, can include reactions selected from core metabolic reactions or peripheral metabolic reactions. As used herein, the term "core," when used in reference to a metabolic pathway, is intended to mean a metabolic pathway selected from glycolysis/gluconeogenesis, the pentose phosphate pathway (PPP), the tricarboxylic acid (TCA) cycle, glycogen storage, electron transfer system (ETS), the malate/aspartate shuttle, the glycerol phosphate shuttle, and plasma and mitochondrial membrane transporters. As used herein, the term "peripheral," when used in reference to a metabolic pathway, is intended to mean a metabolic pathway that includes one or more reactions that are not a part of a core metabolic pathway.

A plurality of reactants can be related to a plurality of reactions in any data structure that represents, for each reactant, the reactions by which it is consumed or produced. Thus, the data structure, which is referred to herein as a "reaction network data structure," serves as a representation of a biological reaction network or system. An example of a reaction network that can be represented in a reaction network data structure of the invention is the collection of reactions that constitute the metabolic reactions of cell lines, as described in the Examples. The choice of reactions to include in a particular reaction network data structure, from among all the possible reactions that can occur in a cell being modeled depends on the cell type and the physiological condition being modeled, and can be determined experimentally or from the literature, as described further below. Thus, the choice of reactions to include in a particular reaction network data structure can be selected depending on whether media optimization, cell line optimization, process development, or other methods and desired results disclosed herein are selected.

The reactions to be included in a particular network data structure can be determined experimentally using, for example, gene or protein expression profiles, where the molecular characteristics of the cell can be correlated to the expression levels. The expression or lack of expression of genes or proteins in a cell type can be used in determining whether a reaction is included in the model by association to the expressed gene(s) and or protein(s). Thus, it is possible to use experimental technologies to determine which genes and/or proteins are expressed in a specific cell type, and to further use this information to determine which reactions are present in the cell type of interest. In this way a subset of reactions from all of those reactions that can occur in cells in generally, for example, mammalian cells, are selected to comprise the set of reactions that represent a specific cell type. cDNA expression profiles have been demonstrated to be useful, for example, for classification of breast cancer cells (Sorlie et al., *Proc. Natl. Acad. Sci. U.S.A.* 98(19): 10869-10874 (2001)). Media composition plays an important role in mammalian cell line protein production. The composition of the feed medium can affect cell growth, protein production, protein quality, and downstream protein purification (Rose et al., *Handbook of Industrial Cell Culture* (Humana Press, Totowa), pp. 69-103 (2003)). Inadequate medium formulation can lead to cell death and reduced productivity or posttranslational processing. On the other hand, a medium with too high a concentration of nutrients can shift metabolism, causing toxic accumulation of byproducts such as lactate and ammonia (Rose et al., supra, 2003). Most large-scale processes are operated using animal serum free media. Excluding serum from the cell culture media minimizes the risk of viral contamination and adventitious agents transmission. Added benefits in using serum free media include increased consistency in growth and productivity, a more simplified downstream purification process, and reduced medium formulation costs (Rose et al., supra, 2003).

Low biomass concentration in standard mammalian cell culture reduces productivity and product titers in mammalian cell cultures compared to microbial systems (Sheikh et al., *Biotechnol Prog.* 21:112-121 (2005)). Byproduct formation of lactate, alanine, and ammonia in mammalian cell culture can reduce biomass yield and protein production, cause toxic accumulation, and inhibit cell growth (Rose et al., supra, 2003; Namjoshi et al., *Biotechnol Bioeng* 81:80-

91 (2003)). Although byproduct formation in mammalian cell lines is similar to what is observed in *E. coli* and yeast, its underlying mechanism remains unclear (Sheikh et al., supra, 2005). In microbial systems, this metabolic overflow is reduced by maintaining glucose at low levels. In mammalian cell culture however, low substrate concentrations induce apoptosis and cell death, which limits the use of this strategy in large-scale protein production processes (Cotter and al Rubeai, *Trends Biotechnol* 13:150-155 (1995)). Cell line engineering strategies to knockout lactate dehyogenase in hybridoma and express yeast pyruvate carboxylase in baby hamster kidney (BHK) cell lines have also shown moderate improvements in biomass and product titer (Chen et al., *Biotechnol Bioeng* 72:55-61 (2001); Irani et al., *J Biotechnol* 93:269-282 (2002)). In addition, generating a stable engineered cell line can be time consuming and laborious. Alternative strategies are needed to reduce byproduct formation with minimum or no cell line engineering approaches.

Currently, most process optimization strategies are performed using a trial and error approach, where process outputs are improved laboriously by experimentation. In general, nutrient components in the cell culture media are determined using one or a combination of the following strategies (Rose et al., supra, 2003): borrowing—adopting a medium composition from the published literature; component swapping—swapping one media component for another at the same usage level; depletion analysis—continuously supplying the media with the depleting nutrients; one-at-a-time—adjusting one component at a time and maintaining the others the same; statistical approaches, including but not limited to full factorial design, partial factorial design, and Plackett-Burman design; optimization techniques, including but not limited to response surface methodology, simplex search and multiple linear regression; computational methods, including but not limited to evolutionary algorithm, genetic algorithm, particle swarm optimization, neural networks and fuzzy logic.

Computational strategies listed above require large sets of experimental data for algorithmic training and in general do not provide a complete solution for media development and optimization in mammalian cell culture. An optimized medium using a laboratory scale cell culture is often not robust to scale-up changes at the manufacturing stage, and requires re-optimization. The lot-to-lot variability in serum-based media components generates inconsistency in growth and protein productivity in mammalian cell cultures. Repeated runs on a media formula can show different nutrient depletion patterns that are in general unexplainable by the existing media design strategies. Overall, media optimization is often performed with little knowledge about how, why, or where the nutrients are used and whether the depleted components are catabolized by the cell or simply degraded without any metabolic benefits to the cell culture. In essence, the cell is treated as a black box. Opening this black box and understanding the fundamental physiological interaction of the cell can lead to more informed and rational approaches for media optimization and cell line engineering and can greatly improve the protein production in mammalian cell lines.

Recent efforts in stoichiometric modeling of mammalian cell lines has been made. Unlike the trial and error strategies that are commonly used in therapeutic protein production, metabolic modeling provides a clear definition for metabolism in the host cell lines and offers a rational approach for designing and optimizing protein production. Computational metabolic modeling can serve as a design and diagnostic tool to: identify what pathways are being used under specified genetic and environmental conditions; determine the fate of nutrients in the cell; identify the source of waste products; examine the effect of eliminating existing reactions or adding new pathways to the host cell line, analyze the effect of adding nutrients to the media, interpret process changes, for example, scale-up, at the metabolic level, and generate rational design strategies for media optimization, process development, and cell engineering. Computational models have been developed to study protein production in mammalian cell lines using a variety of modeling approaches including metabolic flux analysis (MFA) or flux balance analysis (FBA) (Sheikh et al., supra, 2005; Xie and Wang, *Biotechnol Bioeng* 52:579-590 (1996); Xie and Wang, *Biotechnol Bioeng* 52:591-601 (1996); Savinell and Palsson, *J. Theor. Biol* 154:421-454 (1992a); Savinell and Palsson, *J. Theor. Biol* 154:455-473 (1992b)). MFA-based models have been used to develop strategies for media design in batch and fed-batch hybridoma cell culture using a lumped "black box" model containing simplified stoichiometric equations (Xie and Wang, *Cytotechnology* 15:17-29 (1994); Xie and Wang, *Biotechnol Bioeng* 95:270-284 (2006); Xie and Wang, *Biotechnol Bioeng* 43:1164-1174 (1994)). FBA-based models have also been used to study hybridoma cell culture (Sheikh et al., supra, 2005; Savinell and Paulsson, supra, 1992a; Savinell and Palsson, supra, 1992b). As described previously, four objective functions were used to study metabolism in a hybridoma: (1) minimizing ATP production, (2) minimizing moles of nutrient uptake, (3) minimizing mass nutrient uptake, and (4) minimizing NADH production (Savinell and Palsson, supra, 1992a). Although no single objective was found to govern cell behavior, minimizing redox production gave results that were most similar to hybridoma cell behavior. Also described previously, three alternative objective functions were examined, including maximizing growth, minimizing substrate uptake rate, and production of monoclonal antibody (Sheikh et al., supra, 2005). The model correctly predicted growth, lactate, and ammonia production when glucose, oxygen, and glutamine uptake was constrained to experimentally measured values. However, the model did not predict the production of alanine and did not provide any explanation for why animal cells oxidize glutamine partially. Neither of the FBA-based models described previously (Savinell and Palsson, supra, 1992a; Sheikh et al., supra, 2005) were utilized to design or optimize cell culture media.

Metabolic models can be used for rational bioprocess design. Any attempt to improve protein production by overcoming fundamental metabolic limitations requires a platform for the comprehensive analysis of cellular metabolic systems. Genome-scale models of metabolism offer the most effective way to achieve a high-level characterization and representation of metabolism. These models reconcile all of the existing genetic, biochemical, and physiological data into a metabolic reconstruction encompassing all of the metabolic capabilities and fitness of an organism. These in silico models serve as the most concise representation of collective biological knowledge on the metabolism of a microorganism. As such they become the focal point for the integrative analysis of vast amounts of experimental data and a central resource to design experiments, interpret experimental data, and drive research programs. It is recognized that the construction of genome-scale in silico models is important to integrate large amounts of diverse high-throughput datasets and to prospectively design experiments to systematically fill in gaps in the knowledge base of particular organisms (Ideker et al., *Science* 292:929-934 (2001)).

Constructing and demonstrating the use of genome-scale models of metabolism has been described. Previously published in silico representations of metabolism include those for *Escherichia coli* MG1655 (Edwards and Palsson, *Proc. Natl. Acad. Sci. USA* 97:5528-5533 (2000)), *H. influenzae* Rd (Edwards and Palsson, *J. Biol. Chem.* 274:17410-17416 (1999); Schilling and Palsson, *J. Theor. Biol.* 203:249-283 (2000)), *H. pylori* (Schilling et al., *J. Bacteriol.* 184:4582-4593 (2002)), and *S. cerevisiae* (Forster et al., *Genome Res* 13:244-253 (2003)). The general process has been previously published along with various applications of the in silico models (Schilling et al., *Biotechnol. Prog.* 15:288-295 (1999)); Covert et al., *Trends Biochem. Sci.* 26:179-186 (2001)).

In combination with appropriate simulation methods, these models can also be used to generate hypotheses to guide experimental design efforts and to improve the efficiency of bioprocess design and optimization. When properly integrated with experimental technologies, an extremely powerful combined platform for metabolic engineering can be implemented for a wide range of applications within industrial pharmaceutical and biotechnology for production and development of healthcare products, therapeutic proteins, and biologics.

In one embodiment, the invention provides a computer readable medium or media, comprising a data structure relating a plurality of reactants to a plurality of reactions from a cell, each of the reactions comprising a reactant identified as a substrate of the reaction, a reactant identified as a product of the reaction and a stoichiometric coefficient relating the substrate and the product; a constraint set for said plurality of reactions for said data structures, and commands for determining at least one flux distribution that minimizes or maximizes an objective function when the constraint set is applied to the data structure, wherein the at least one flux distribution is predictive of a physiological function of the cell. For example, the data structure can comprise a reaction network. In addition, the data structure can comprise a plurality of reaction networks.

In a particular embodiment, the computer readable medium or media can comprise at least one reaction that is annotated to indicate an associated gene or protein. In addition, the computer readable medium or media can further comprise a gene database having information characterizing the associated gene. At least one of the reactions in the data structure can be a regulated reaction. In addition, the constraint set can include a variable constraint for the regulated reaction.

In another embodiment, the cell can be optimized to increase product yield, to minimize scale up variability, to minimize batch to batch variability or optimized to minimize clonal variability. Additionally, the cell can be optimized to improve cell productivity in stationary phase.

In another embodiment, the cell is derived from an animal, plant or insect. As used herein, a "derived from an animal, plant or insect" refers to a cell that is of animal, plant or insect origin that has been obtained from an animal, plant or insect. Such a cell can be an established cell line or a primary culture. Cell lines are commercially available and can be obtained, for example, from sources such as the American Type American Type Culture Collection (ATCC) (Manassas Va.) or other commercial sources. In a particular embodiment, the cell can be a mammalian cell, such as a mammalian cell line including, but not limited to, Chinese Hamster Ovary (CHO), BHK, NS0, SP2/0, 3T3, Hybridoma, C127, HEK293, PER.C6, HepG2, HeLa, MRC5, WI38, MDCK, Vero, and COS. It is understood that cell variants, such as CHO DHFR-cells or GS-NS0 cells, and the like, which can be used with non-selection systems, as disclosed herein. Generally the cells of the invention are obtained from a multicellular organism, in particular a eukaryotic cell from a multicellular organism, in contrast to a cell that exists as a single celled organism such as yeast. Thus, a eukaryotic cell from a multicellular organism as used herein specifically excludes yeast cells.

The invention provides a method for predicting a culture condition for a eukaryotic cell from a multicellular organism. The method can include the steps of providing a data structure relating a plurality of reactants to a plurality of reactions from a cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a constraint set for the plurality of reactions for the data structure; providing an objective function, wherein the objective function is uptake rate of two or more nutrients, wherein the two or more nutrients are carbon sources; and determining at least one flux distribution that minimizes or maximizes the objective function when the constraint set is applied to the data structure, wherein the at least one flux distribution is predictive of a culture condition for the eukaryotic cell. In such a method, the objective function can further comprise product formation, energy synthesis, biomass production, or a combination thereof. Alternatively, the objective function can further comprise decreasing byproduct formation.

Additionally in such a method of the invention, the culture condition can be optimized culture medium for the cell, optimized cell culture process, optimized cell productivity, and metabolic engineering of the cell. The optimized cell productivity can be, for example, increased biomass production or increased product yield. The culture condition can be reduced scale up variability, reduced batch to batch variability, reduced clonal variability, improved cell growth, viable cell density or cell productivity in exponential growth phase or stationary phase or other desired culture conditions.

It is understood that the methods of the invention disclosed herein are generally performed on a computer. Thus, the methods of the invention can be performed, for example, with appropriate computer executable commands stored on a computer readable medium or media that carry out the steps of any of the methods disclosed herein. For example, if desired, a data structure can be stored on a computer readable medium or media and accessed to provide the data structure for use with a method of the invention. Additionally, if desired, any and up to all commands for performing the steps of a method of the invention can be stored on a computer readable medium or media and utilized to perform the steps of a method of the invention. Thus, the invention provides a computer readable medium or media having stored thereon computer executable commands for performing the steps of any method of the invention.

In one embodiment, the invention provides a computer readable medium or media having stored thereon commands for performing the computer executable steps of providing a data structure relating a plurality of reactants to a plurality of reactions from a cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a constraint set for the plurality of reactions for the data structure; providing an objective function, wherein the objective function is uptake rate of two or more nutrients, wherein the two or more nutrients are carbon sources; and determining at least one flux distribution that minimizes or maximizes the objective function when the constraint set is applied to the data structure, wherein the at least one flux distribution is predictive of a culture condition for the eukaryotic cell. The computer readable medium or media can include additional steps of such a method of the invention, as disclosed herein.

As used herein, a "culture condition" when used in reference to a cell refers to the state of a cell under a given set of conditions in a cell culture. Such a culture condition can be a condition of a cell culture or an in silico model of a cell in culture. A cell culture or tissue culture is understood by those skilled in the art to include an in vitro culture of a cell, in particular a cell culture of a eukaryotic cell from a multicellular organism. Such an in vitro culture refers to the well known meaning of occurring outside an organism, although it is understood that such cells in culture are living cells. A culture condition can refer to the base state or steady state of a cell under a set of conditions or the state of a cell when such conditions are altered, either in an actual cell culture or in an in silico model of a cell culture. For example, a culture condition can refer to the state of a cell, in culture, as calculated based on the cell modeling methods, as disclosed herein. In addition, a culture condition can refer to the state of a cell under an altered set of conditions, for example, the state of a cell as calculated under the conditions of an optimized cell culture medium, optimized cell culture process, optimized cell productivity or after metabolic engineering, including any or all of these conditions as calculated using the in silico models as disclosed herein. Additional exemplary culture conditions include, but are not limited to, reduced scale up variability, reduced batch to batch variability, reduced clonal variability, improved cell growth, viable cell density or cell productivity in exponential growth phase or stationary phase. Such altered conditions can be included in a model of the invention or methods of producing such a model by applying an appropriate constraint set and objective function to achieve the desired result, as disclosed herein and as understood by those skilled in the art.

The methods of the invention as disclosed herein can be used to produce an in silico model of a cell culture. Such an in silico model is generally produced to obtain a culture condition that is the base state of a cell. Once a base model is established, the model can be further refined or altered by selecting a different constraint set or objective function than used in the base state model to achieve a desired outcome. The selection of appropriate constraint sets and/or objective functions to achieve a desired outcome are well known to those skilled in the art.

In embodiments of the invention, an objective function can be the uptake rate of two or more nutrients. In a cell culture, it is understood that a nutrient is provided from the extracellular environment, generally in the culture media, although a nutrient can also be provided from a second cell in a co-culture if such a cell secretes a product that functions as a nutrient for the other cell in the co-culture. The components of a culture medium for providing nutrients to a cell in culture, either to maintain cell viability or cell growth, are well known to those skilled in the art. Such nutrients include, but are not limited to, carbon source, inorganic salts, metals, vitamins, amino acids, fatty acids, and the like (see, for example, Harrison and Rae, *General Techniques of Cell Culture*, chapter 3, pp. 31-59, Cambridge University Press, Cambridge United Kingdom (1997)). Such nutrients can be provided as a defined medium or supplemented with nutrient sources such as serum, as is well known to those skilled in the art. The culture medium generally includes carbohydrate as a source of carbon. Exemplary carbohydrates that can be used as a carbon source include, but are not limited to, sugars such as glucose, galactose, fructose, sucrose, and the like. It is understood that any nutrient that contains carbon and can be utilized by the cell in culture as a carbon source can be considered a nutrient that is a carbon source. Nutrients in the extracellular environment available to a cell include those substrates or products of an extracellular exchange reaction, including transport or transformation reactions. Thus, any reaction that allows transport or transformation of a nutrient in the extracellular environment, including but not limited to those shown in Tables 21-23 as exemplary reactions, for utilization inside the cell where the nutrient contains carbon is considered to be a nutrient that is a carbon source. Numerous commercial sources are available for various culture media. In particular embodiments of the invention, the methods of the invention utilize an objective function that includes the uptake rate of two or more nutrients that are carbon sources, although it is understood that the uptake of other nutrients can additionally or alternatively be used in the methods of the invention as a parameter of an objective function. As disclosed herein, cells from a multicellular organism have evolved to be bathed in nutrients. A cell from a multicellular organism therefore generally has an inefficient uptake of nutrients. Previously, it was considered that a cell in culture would generally uptake one carbon source. The present invention is based, in part, on the observation and unexpected results obtained by modeling the uptake of two or more nutrients, in particular two or more carbon sources.

As disclosed herein, the invention can be used to generate models of a cultured cell that allow various culture conditions to be tested and, if desired, optimized, by selecting appropriate constraint sets and/or objective functions that achieve a desired culture condition. Exemplary culture conditions are disclosed herein and include, but are not limited to, product formation, energy synthesis, biomass production, byproduct formation, optimizing cell culture medium for a cell, optimizing a cell culture process, optimizing cell productivity, metabolically engineering a cell, reducing scale up variability, reducing batch to batch variability, reducing clonal variability, and the like. In some cases, a desired culture condition includes increasing or improving on a condition, for example, increasing product yield, biomass, cell growth, viable cell density, cell productivity, and the like. In other cases, a desired culture condition includes decreasing, reducing or minimizing an effect, for example, decreasing byproduct formation, reducing scale up variability, reducing batch to batch variability, reducing clonal variability, and the like. It is further understood that any number of desirable culture conditions can be combined, either simultaneously or sequentially, for calculation by a method of the invention to achieve a desired outcome. For example, it can be desirable to increase cell productivity by increasing biomass and/or increasing the yield or titer of a product. Therefore, increased biomass and increased product yield can be included, for example, as an objective function or as a component of an objective function combined with another component, for example, uptake rate of a nutrient. Additionally, it can be desirable to both increase product yield and decrease byproduct formation, so these could similarly be combined, for example, as an objective function. Exemplary combinations are described, for example, in Table 7. It is understood that any combination of desired culture conditions can be utilized to achieve an improved or optimized culture condition. One skilled in the art, based on the methods disclosed herein and those well known to those skilled in the art, can select an appropriate constraint set and/or objective function to achieve a desired outcome of a culture condition. As used herein, when used in the context of a culture condition, an optimized culture condition such as optimized growth medium, optimized cell culture process, or optimized cell productivity is intended to mean an improvement relative to another condition. The use of the term optimized or improved culture condition is distinct from an optimization problem as known to those skilled in the mathematical arts.

The methods of the invention can be used to optimize or improve a culture medium to increase growth or viability of a cell in culture, for example, growth rate, cell density in suspension culture, product production in exponential growth or stationary phase, and the like. Additionally, the methods of the invention can be used to optimize or increase a cell culture process, also referred to herein as process design. Process design as used herein generally refers to the design and engineering of scale up from small to large scale processes, in particular as they are used in an industrial and commercial scale for culture of cells. Process design is well known to those skilled in the art and can include, for example, the size and type of culture vessels, oxygenation, replenishment of media and nutrients, removal of media containing growth inhibitory byproducts, harvesting of a desired product, and the like. The methods disclosed herein can be used to model culture conditions relating to process design to improve or optimize a cell culture process. The methods of the invention can further be used to optimize or improve cell productivity, for example, increasing biomass production or increasing product yield or titer, or a combination thereof. The methods of the invention can also be used to identify the distinct and significant difference between, for example, (a) laboratory and large scale cell cultures (to reduce scale-up variability), (b) different bioreactor and/or shake flask culture conditions performed with the same cells, media, and cell culture parameters (to reduce batch-to-batch variability), and (c) different clones (to reduce clonal variability).

To optimize a culture condition, the model generated by a method of the invention is used to simulate flux distribution for each condition using the maximization of uptake of nutrients, alone or in combination with maximization or minimization of energy production, byproduct formation, growth, and/or product formation. As disclosed herein, Flux Variability Analysis (FVA) or other suitable analytical methods can be performed for each cultivation conditions. For example, in the case of reducing scale up variability, that is laboratory scale versus large scale conditions, FVA can be performed for each condition to identify a range of flux values for each reaction in the metabolic model. Next, significantly reduced or significantly elevated fluxes in the different cultivation conditions are compared for each reaction. From this comparison, significant metabolic changes can be identified that are indicative of the observed differences. The knowledge obtained by analyzing the data in the context of the reconstructed model is used to identify design parameters that should be monitored or controlled in cell culture to prevent variability in cell culture condition that would result in scale up variability or batch to batch variability. In addition, by determining the variability under different culture conditions and optimizing or improving the conditions of a cell culture, for example by determining limiting nutrient(s) and providing increased amounts of such nutrients in the media, clonal variability can be reduced by reducing selective pressures that could result in the selection of clones with a phenotype that differs from a desired parental cell line. One skilled in the art will readily know appropriate selection of a constraint set or objective function to achieve a desired outcome of a culture condition using the methods and models of the invention.

The models and methods of the invention are particularly useful to optimize cells, culture medium or production of a desired product, as disclosed herein. Exemplary desired products include, but are not limited to, growth factors, monoclonal antibodies, hormones, cytokines, fusion proteins, enzymes, vaccines, viruses, anticoagulants, and nucleic acids. It is understood that, with respect to a cell producing a desired product, the product is produced at an increased level relative to a native parental cell and therefore is considered to be an exogenous product. The models and methods of the invention are based on selecting a desired objective function and generating a model based on the methods disclosed herein. For example, the methods and models can be used to optimize uptake rate of one or more nutrients, energy synthesis, biomass production, or a combination thereof. In addition, the methods and models of the invention can be used to optimize a culture medium for the cell, optimize a cell culture process, optimize cell productivity, or metabolic engineering of said cell. For example, optimized cell productivity can include increased biomass production, increased product yield, or increased product titers.

"Exogenous" as it is used herein is intended to mean that the referenced molecule or the referenced activity is introduced into the host organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the host organism. When used in reference to a biosynthetic activity, the term refers to an activity that is introduced into the host reference organism. The source can be, for example, a homologous or heterologous encoding nucleic acid that expresses the referenced activity following introduction into the host organism. Therefore, the term "endogenous" refers to a referenced molecule or activity that is present in the host. Similarly, the term when used in reference to expression of an encoding nucleic acid refers to expression of an encoding nucleic acid contained within the organism. The term "heterologous" refers to a molecule or activity derived from a source other than the referenced species whereas "homologous" refers to a molecule or activity derived from the host organism. Accordingly, exogenous expression of an encoding nucleic acid of the invention can utilize either or both a heterologous or homologous encoding nucleic acid. Thus, it is understood that a desired product produced by a cell of the invention is an exogenous product, that is, a product introduced that is not normally expressed by the cell or having an increased level of expression relative to a native parental cell. Therefore, such a cell line has been engineered, either recombinantly or by selection, to have increased expression of a desired product, including but not limited to growth factors, monoclonal antibodies, hormones, cytokines, fusion proteins, enzymes, vaccines, viruses, anticoagulants, and nucleic acids. Such an increased expression can occur by recombinantly expressing a nucleic acid that is a desired product or a nucleic acid encoding a desired product. Alternatively, increased expression can occur by genetically modifying the cell to increase expression of a promoter and/or enhancer, either constitutively or by introducing an inducible promoter and/or enhancer.

As disclosed herein, the data structure can comprise a set of linear algebraic equations. In addition, the commands can comprise an optimization problem. In another embodiment, at least one reactant in the plurality of reactants or at least one reaction in the plurality of reactions can be annotated with an assignment to a subsystem or compartment. For example, a first substrate or product in the plurality of reactions can be assigned to a first compartment and a second substrate or product in the plurality of reactions can be assigned to a second compartment. Furthermore, at least a first substrate or product, or more substrates or products, in the plurality of reactions can be assigned to a first compartment and at least a second substrate or product, or more substrates or products, in the plurality of reactions can be assigned to a second compartment. In addition, a plurality of reactions can be annotated to indicate a plurality of associated genes and the gene database can comprise information characterizing the plurality of associated genes.

In another embodiment, the invention provides a method for predicting a physiological function of a cell. The method can include the steps of providing a data structure relating a plurality of reactants to a plurality of reactions from a cell, each of the reactions comprising a reactant identified as a substrate of the reaction, a reactant identified as a product of the reaction and a stoichiometric coefficient relating the substrate and the product; providing a constraint set for said plurality of reactions for said data structures; providing an objective function, and determining at least one flux distribution that minimizes or maximizes an objective function when the constraint set is applied to the data structure, wherein the at least one flux distribution is predictive of a physiological function of the cell. In methods of the invention, the data structure can comprise a reaction network. In addition, the data structure can comprise a plurality of reaction networks.

If desired, at least one of the reactions can be annotated to indicate an associated gene. In addition, the method can further comprise a gene database having information characterizing the associated gene. In another embodiment, at least one of the reactions can be a regulated reaction. In yet another embodiment, the constraint set can include a variable constraint for the regulated reaction.

As disclosed herein, the methods and models of the invention provide computational metabolic models for cells, such as a mammalian cell line, that can be used for production of a desired product or biologic, including but not limited to growth factors, monoclonal antibodies, hormones, cytokines, fusion proteins, recombinant enzymes, recombinant vaccines, viruses, anticoagulants, and nucleic acids. The use of a computational metabolic model can be used for engineering and optimizing cell culture media (media optimization), designing cell culture process (process design), and engineering the cell (cell line engineering) to improve biomass production, product yield, and/or product titers, that is, to improve the overall cell culture productivity. For example, maximization of the nutrient uptake rates can be used as the objective function in methods of the invention for simulating a cell's physiology and or growth and/or productivity in cell culture.

As disclosed herein, the methods and models of the invention can be used for media optimization, process optimization and/or development, cell line engineering, selection system design, cell line models, including models as disclosed herein such as Hybridoma, NS0, CHO. The invention additional provides models of cell lines based on reactions as found, for example, in Tables 19-23, including deletion designs and metabolic models. The methods and models can be used, for example, to improve yield of desired products; to address and optimize scale-up variability, for example, using the model to understand scale-up variability; to address and optimize batch-to-batch variability, for example, using the models to better understand batch to batch variability; to address and optimize clonal differences, for example, using the models to study the metabolic differences in clones following transfection; to improved productivity in stationary phase, for example, using the models to better understand the impact of changes to media when cells are growing in the stationary phase; and to develop novel selection systems, for example, to identify novel selection systems using the model and develop experimentally additional selection systems for engineering a host organism.

The methods and models of the invention can additionally be used, for example, to identify biofluid-based biomarkers for human inborn errors of metabolism; to identify biomarkers for the progression, development, and onset of diseases such as cancer; to identify biomarkers for assessing toxicology and clinical safety of therapeutic compounds; and to identify biomarkers for use in drug discovery to determine the effect(s) of a therapeutic agent through an analysis and comparison to an untreated individual. Such methods and models are based on selecting a suitable system and applying the methods disclosed herein to achieve a desired outcome, for example, selecting a suitable individual or group of individuals having inborn errors of metabolism, having a disease diagnosis such as cancer diagnosis or a predisposition to develop a disease, exposure to toxic chemicals, treatment with a therapeutic agent, and the like. The identified biomarkers can be used in various applications, including, but not limited to, diagnostics, therapy selection, and monitoring of therapeutic effectiveness.

The invention additionally provides computer readable medium or media, comprising a data structure relating a plurality of reactants to a plurality of reactions from a cell, each of the reactions comprising a reactant identified as a substrate of the reaction, a reactant identified as a product of the reaction and a stoichiometric coefficient relating the substrate and the product; a constraint set for the plurality of reactions for the data structures, and commands for determining at least one flux distribution that minimizes or maximizes an objective function when the constraint set is applied to the data structure, wherein the objective function identifies a target selectable marker reaction or reactant and wherein the at least one flux distribution is predictive of a physiological function of the cell. Thus, as disclosed herein, the invention provides a method to identify novel target pathways, reactions or reactants that can be used as new selectable markers for engineering a recombinant cell line.

The invention additionally provides a method for identifying a target selectable marker for a cell. The method can include the steps of providing a first data structure relating a plurality of reactants to a plurality of reactions from a cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a constraint set for the plurality of reactions for the first data structure; providing an objective function, wherein the objective function is uptake rate of two or more nutrients, wherein the two or more nutrients are carbon sources; determining at least one flux distribution that minimizes or maximizes the objective function when the constraint set is applied to the data structure; deleting a reaction from the data structure to generate a second data structure and repeating steps of providing a constraint set, providing an objective function and determining at least one flux distribution as discussed above; optionally repeating the deleting step by deleting a different reaction, wherein the at least one flux distribution determined with the second data structure is predictive of a reaction required for cell growth or cell viability, thereby identifying a target selectable marker reaction or reactant. Such a method can further comprise providing the second data structure; providing one or more extracellular substrates or products corresponding to one or more reactions of the one or more extracellular exchange reactions to the second data structure to generate a third data structure; providing a constraint set for the plurality of reactions for the third data structure; providing an objective function, wherein the objective function is cell viability or growth; and determining at least one flux distribution that minimizes or maximizes the objective function when the constraint set is applied to the third data structure, wherein the at least one flux distribution determined with the third data structure is predictive of an extracellular substrate or product that complements the target selectable marker reaction or reactant, thereby identifying a selectable marker reaction or reactant. In such a method, the objective function can further comprise uptake rate of the one or more extracellular substrates or products.

The invention additionally provides a computer readable medium or media having stored thereon computer executable commands for performing the steps of providing a first data structure relating a plurality of reactants to a plurality of reactions from a cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a constraint set for the plurality of reactions for the first data structure; providing an objective function, wherein the objective function is uptake rate of two or more nutrients, wherein the two or more nutrients are carbon sources; determining at least one flux distribution that minimizes or maximizes the objective function when the constraint set is applied to the data structure; deleting a reaction from the data structure to generate a second data structure and repeating steps of providing a constraint set, providing an objective function and determining at least one flux distribution as discussed above; optionally repeating the deleting step by deleting a different reaction, wherein the at least one flux distribution determined with the second data structure is predictive of a reaction required for cell growth or cell viability, thereby identifying a target selectable marker reaction or reactant. A computer readable medium or media can further comprise commands for performing the steps of providing the second data structure; providing one or more extracellular substrates or products corresponding to one or more reactions of the one or more extracellular exchange reactions to the second data structure to generate a third data structure; providing a constraint set for the plurality of reactions for the third data structure; providing an objective function, wherein the objective function is cell viability or growth; and determining at least one flux distribution that minimizes or maximizes the objective function when the constraint set is applied to the third data structure, wherein the at least one flux distribution determined with the third data structure is predictive of an extracellular substrate or product that complements the target selectable marker reaction or reactant, thereby identifying a selectable marker reaction or reactant.

As used herein, a "selectable marker" is well known to those skilled in molecular biology and refers to a gene whose expression allows the identification of cells that have been transformed or transfected with a vector containing the marker gene, that is, the presence or absence of the gene (selectable marker) can be selected for, generally based on an altered growth or cell viability characteristic of the cell. Well known exemplary selectable markers used routinely in cell culture include, for example, the dihydrofolate reductase (DHFR) and glutamine synthetase (GS) selection systems. The methods of the invention allow the identification of target selectable markers by using in silico models of a cell to identify a reaction that is required for cell viability or cell growth, that is, an essential reaction. Generally, selectable markers are utilized such that a cell will either die in the absence of a product produced by the selectable marker or will not grow, either case of which will prevent a cell lacking a complementary product from growing. The methods of the invention are based on deleting a reaction from a data structure containing a plurality of reactions and determining whether the deletion has an effect on cell viability or growth. If the deletion results in no cell growth or in cell death, then the deleted reaction is a target selectable marker. The method can be used to determine any of a number of target selectable markers by optionally repeating deleting different reactions. In a method of the invention, a single reaction is deleted to test for the effect on cell growth or viability, although multiple reactions can be deleted, if desired. In general, if a reaction is deleted from a data structure and the deletion has no effect on cell growth or viability, then a different reaction is deleted from the data structure and tested for its effect on cell growth or viability. Accordingly, in such a method, the data structure generally has only one reaction deleted at a time to test for the effect on cell growth or viability. As used herein, inhibiting cell growth generally includes preventing cell division or slowing the rate of cell division so that the doubling time of the cell is substantially reduced, for example, at least 2-fold, 3-fold, 4-fold, 5-fold, 10-fold, or even further reduction in doubling time, so long as the difference in growth rate from a cell containing the selectable marker is sufficient to differentiate the presence or absence of the selectable marker.

After identifying a target selectable marker reaction or reactant, the deleted data structure that identifies a reaction or reactant required for cell growth or viability can be tested for the ability to support cell growth or viability by the addition of an extracellular reaction to the data structure that complements the deleted reaction. For example, if a reaction is deleted and the deletion results in cell death or no cell growth, the product of that reaction can be used to complement the missing reaction and cause the cell to resume cell growth or viability. To be particularly useful as a selectable marker and selection system, it is desirable to be able to complement the missing reaction by addition of a component to the cell culture medium. Therefore, for a deleted reaction to be useful as a selectable marker, the deleted product must either be provided in the culture medium and transported into the cell or a precursor of the product transported into the cell and either transformed or converted to the missing product. To test for this possibility, one or more extracellular exchange reactions, which could potentially result in transport of the deleted product or a precursor of the product, is added to the data structure with the deleted reaction, and the cell is tested for whether cell growth or viability is recovered or resumed. If cell growth and viability is recovered with the addition of the extracellular substrate or product that can be transported, transformed or converted into the product intracellularly, then the deleted reaction and the complementary extracellular product or substrate can function as a selectable marker system. As used herein, a substrate or product that "complements" a target selectable marker refers to a substrate or product that, when added to a cell culture (in vitro or in silico), allows a cell having a deleted reaction (target selectable marker) required for cell growth or cell viability to restore cell growth or viability to the cell. Thus, the methods of the invention can be used to identify target selectable marker reactions or reactants and a selectable marker reaction or reactant with a complementary substrate or product that restores cell growth or viability.

The invention also provides a method for predicting a physiological function of a cell, comprising providing a data structure relating a plurality of reactants to a plurality of reactions from a cell, each of the reactions comprising a reactant identified as a substrate of the reaction, a reactant identified as a product of the reaction and a stoichiometric coefficient relating the substrate and the product; providing a constraint set for the plurality of reactions for the data structures; providing an objective function, and determining at least one flux distribution that minimizes or maximizes an objective function when the constraint set is applied to the data structure, wherein the objective function identifies a target selectable marker reaction or reactant and wherein the at least one flux distribution is predictive of a physiological function of the cell.

The invention additionally provides a method for predicting a biomarker for a contaminant of a cell culture of a eukaryotic cell from a multicellular organism. The method can include the steps of providing a first data structure relating a plurality of reactants to a plurality of reactions from a non-contaminated cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a second data structure relating a plurality of reactants to a plurality of reactions from a contaminated cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a constraint set for the plurality of reactions for the first and second data structures; providing an objective function, wherein the objective function is uptake rate of one or more nutrients, wherein the two or more nutrients are carbon sources; determining at least one flux distribution that minimizes or maximizes the objective function when the constraint set is applied to the first data structure; determining at least one flux distribution that minimizes or maximizes the objective function when the constraint set is applied to the second data structure; comparing the at least one flux distribution determined for the first data structure with the at least one flux distribution determined for the second data structure, wherein a difference in the at least one flux distribution for the first and second data structures is predictive of a biomarker for a contaminant of the cell culture. In such a method, the objective function can further comprise secretion rate of one or more products.

The invention additionally provides a computer readable medium or media having stored thereon computer executable commands for performing the steps of providing a first data structure relating a plurality of reactants to a plurality of reactions from a non-contaminated cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a second data structure relating a plurality of reactants to a plurality of reactions from a contaminated cell, each of the reactions comprising a reactant identified as a substrate of the reaction, a reactant identified as a product of the reaction and a stoichiometric coefficient relating the substrate and the product, wherein the plurality of reactions comprises one or more extracellular exchange reactions; providing a constraint set for the plurality of reactions for the first and second data structures; providing an objective function, wherein the objective function is uptake rate of one or more nutrients, wherein the two or more nutrients are carbon sources; determining at least one flux distribution that minimizes or maximizes the objective function when the constraint set is applied to the first data structure; determining at least one flux distribution that minimizes or maximizes the objective function when the constraint set is applied to the second data structure; comparing the at least one flux distribution determined for the first data structure with the at least one flux distribution determined for the second data structure, wherein a difference in the at least one flux distribution for the first and second data structures is predictive of a biomarker for a contaminant of the cell culture.

As disclosed herein, a biomarker for a cell culture contaminant such as a viral or bacterial contaminant can be identified using methods of the invention. The differences between a contaminated versus non-contaminated cell culture allow the identification of biomarker, that is, a marker produced by the cell that differentiates between a contaminated versus non-contaminated cell culture, useful for monitoring for potential contamination of a cell culture (see Example VIII).

As disclosed herein, the methods of the invention can be used to generate models of an organism in culture. For example, exemplary models have been generated using methods of the invention (see Examples and Tables 21-23). In particular, exemplary models have been generated for a hybridoma cell line (Table 21), an NS0 cell line (Table 22) and a CHO cell line (Table 23). The invention additionally provides a model comprising a selection of reactions of any of those shown in Tables 21-23, including up to all of the reactions in Tables 21-23 for the respective models.

The invention also provides a computer readable medium or media having stored thereon computer executable commands for performing methods utilizing any of the models of Tables 21-23. In one embodiment, the invention provides a computer readable medium or media containing commands to perform the steps of providing a data structure relating a plurality of reactants to a plurality of reactions, wherein the plurality of reactants and plurality of reactions are a selection of reactants and reactions as shown in Table 23 for a Chinese hamster ovary (CHO) cell; providing a constraint set for the plurality of reactions for the data structure; and determining at least one flux distribution that minimizes or maximizes an objective function when the constraint set is applied to the data structure, wherein the at least one flux distribution is predictive of a physiological function of the CHO cell.

In another embodiment, the invention provides a computer readable medium or media containing commands to perform the steps of providing a data structure relating a plurality of reactants to a plurality of reactions, wherein the plurality of reactants and plurality of reactions are a selection of reactants and reactions as shown in Table 21 for a hybridoma cell; providing a constraint set for the plurality of reactions for the data structure, and determining at least one flux distribution that minimizes or maximizes an objective function when the constraint set is applied to the data structure, wherein the at least one flux distribution is predictive of a physiological function of the hybridoma cell.

In another embodiment, the invention provides a computer readable medium or media containing commands to perform the steps of providing a data structure relating a plurality of reactants to a plurality of reactions, wherein the plurality of reactants and plurality of reactions are a selection of reactants and reactions as shown in Table 22 for an NS0 cell; providing a constraint set for the plurality of reactions for the data structure, and determining at least one flux distribution that minimizes or maximizes an objective function when the constraint set is applied to the data structure, wherein the at least one flux distribution is predictive of a physiological function of the NS0 cell.

As used herein, a "selection of reactants and reactions" when used with reference to a model of the invention means that a suitable number of the reactions and reactants, including up to all the reactions and reactants, can be selected from a list of reactions for use of the model. For example, any and up to all the reactions as shown in Tables 21-23 can be a selection of reactants and reactions, so long as the selected reactions are sufficient to provide an in silico model suitable for a desired purpose, such as those disclosed herein. It is understood that, if desired, a selection of reactions can include a net reaction between more than one of the individual reactions shown in Tables 21-23. For example, if reaction 1 converts substrate A to product B, and reaction 2 converts substrate B to product C, a net reaction of the conversion of substrate A to product C can be used in the selection of reactions and reactants for use of a model of the invention. One skilled in the art will recognize that such a net reaction conserves stoichiometry between the conversion of A to B to C or A to C and will therefore satisfy the requirements for utilizing the model. In a particular embodiment, the invention provides a model of a CHO cell with all the reactions of Table 23, a hybridoma cell with all the reactions of Table 21, and an NS0 cell with all the reactions of Table 22, either individually as shown in Tables 21-23 or with one or more net reactions, as discussed above.

The reactants to be used in a reaction network data structure of the invention can be obtained from or stored in a compound database. As used herein, the term "compound database" is intended to mean a computer readable medium or media containing a plurality of molecules that includes substrates and products of biological reactions. The plurality of molecules can include molecules found in multiple organisms or cell types, thereby constituting a universal compound database. Alternatively, the plurality of molecules can be limited to those that occur in a particular organism or cell type, thereby constituting an organism-specific or cell type-specific compound database. Each reactant in a compound database can be identified according to the chemical species and the cellular compartment in which it is present. Thus, for example, a distinction can be made between glucose in the extracellular compartment versus glucose in the cytosol. Additionally each of the reactants can be specified as a metabolite of a primary or secondary metabolic pathway. Although identification of a reactant as a metabolite of a primary or secondary metabolic pathway does not indicate any chemical distinction between the reactants in a reaction, such a designation can assist in visual representations of large networks of reactions.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the interior space of an organelle such as a mitochondrium, endoplasmic reticulum, Golgi apparatus, vacuole or nucleus; or any subcellular space that is separated from another by a membrane or other physical barrier. For example, a mitochondrial compartment is a subdivided region of the intracellular space of a cell, which in turn, is a subdivided region of a cell or tissue. A subdivided region also can include, for example, different regions or systems of a tissue, organ or physiological system of an organism. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of metabolic reactions of a cell line that exhibit biochemical or physiological interactions. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced inter-conversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus a reaction that simply transports a metabolite from the extracellular environment to the cytosol, without changing its chemical composition is solely classified as a translocation, while a reaction that takes an extracellular substrate and converts it into a cytosolic product is both a translocation and a transformation. Further, intra-system reactions can include reactions representing one or more biochemical or physiological functions of an independent cell, tissue, organ or physiological system. An "extracellular exchange reaction" as used herein refers in particular to those reactions that traverse the cell membrane and exchange substrates and products between the extracellular environment and intracellular environment of a cell. Such extracellular exchange reactions include, for example, translocation and transformation reactions between the extracellular environment and intracellular environment of a cell.

Exchange reactions are those which constitute sources and sinks, allowing the passage of metabolites into and out of a compartment or across a hypothetical system boundary. These reactions are included in a model for simulation purposes and represent the metabolic demands placed a cell. While they may be chemically balanced in certain cases, they are typically not balanced and can often have only a single substrate or product. As a matter of convention the exchange reactions are further classified into demand exchange and input/output exchange reactions.

The metabolic demands placed on a cell metabolic reaction network can be readily determined from the dry weight composition of the cell, which is available in the published literature or which can be determined experimentally. The uptake rates and maintenance requirements for a cell line can also be obtained from the published literature or determined experimentally.

Input/output exchange reactions are used to allow extracellular reactants to enter or exit the reaction network represented by a model of the invention. For each of the extracellular metabolites a corresponding input/output exchange reaction can be created. These reactions are always reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reactions can be introduced for any metabolite in a model of the invention. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion or muscle contraction; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

Constraint-based modeling can be used to model and predict cellular behavior in reconstructed networks. In order to analyze, interpret, and predict cellular behavior using approaches other than the constraint-based modeling approach, each individual step in a biochemical network is described, normally with a rate equation that requires a number of kinetic constants. However, it is currently not possible to formulate this level of description of cellular processes on a genome scale. The kinetic parameters cannot be estimated from the genome sequence, and these parameters are not available in the literature in the abundance required for accurate modeling. In the absence of kinetic information, it is still possible to assess the capabilities and performance of integrated cellular processes and incorporate data that can be used to constrain these capabilities.

To accomplish suitable modeling, a constraint-based approach for modeling can be implemented. Rather than attempting to calculate and predict exactly what a metabolic network does, the range of possible phenotypes that a metabolic system can display is narrowed based on the successive imposition of governing physico-chemical constraints (Palsson, *Nat. Biotechnol.* 18:1147-1150 (2000)). Thus, instead of calculating an exact phenotypic solution, that is, exactly how the cell behaves under given genetic and environmental conditions, the feasible set of phenotypic solutions in which the cell can operate is determined (FIG. 1).

Such a constraint-based approach provides a basis for understanding the structure and function of biochemical networks through an incremental process. This incremental refinement presently occurs in the following four steps, each of which involves consideration of fundamentally different constraints: (1) the imposition of stoichiometric constraints that represent flux balances; (2) the utilization of limited thermodynamic constraints to restrict the directional flow through enzymatic reactions; (3) the addition of capacity constraints to account for the maximum flux through individual reactions; and (4) the imposition of regulatory constraints, where available.

Each step provides increasing amounts of information that can be used to further reduce the range of feasible flux distributions and phenotypes that a metabolic network can display. Each of these constraints can be described mathematically, offering a concise geometric interpretation of the effects that each successive constraint places on metabolic function (FIG. 1). In combination with linear programming, constraint-based modeling has been used to represent probable physiological functions such as biomass and ATP production. Constraint-based modeling approaches have been reviewed in detail (Schilling et al., *Biotechnol. Prog.* 15:288-295 (1999); Varma and Palsson, *Bio/Technology* 12:994-998 (1994); Edwards et al., *Environ. Microbiol.* 4:133-140 (2002); Price et al., *Nat. Rev. Microbiol.* 2:886-897 (2004)).

Figure 2:
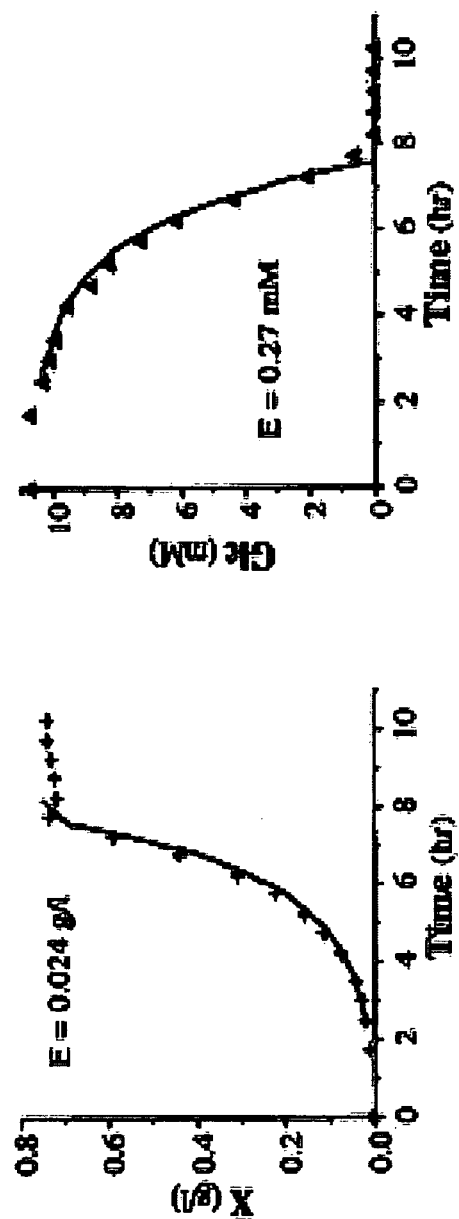
FIG. 2 shows analysis of an *E. coli* batch culture showing time profiles of total cell and glucose concentrations. The solid lines are the flux balance model predictions of the time profiles for the bioreactor, and points are experimental measurements (adopted from Varma and Palsson, *Appl. Environ. Microbiol.* 60:3724-3731 (1994)).

Transient flux balance analysis can also be used. A number of computational modeling methods have been developed based on the basic premise of the constraint-based approach, including the transient flux balance analysis (Varma and Palsson, *Appl. Environ. Microbiol.* 60:3724-3731 (1994); Price et al., *Nat. Rev. Microbiol.* 2:886-897 (2004)). Transient flux balance analysis is a well-established approach for computing the time profile of consumed and secreted metabolites in a bioreactor, predicted based on the computed values from a steady state constraint-based metabolic model (Covert et al., *J. Theor. Biol.* 213:73-88 (2001)); Varma and Palsson, *Appl. Environ. Microbiol.* 60:3724-3731 (1994); Covert and Palsson, *J. Biol. Chem.* 277:28058-28064 (2002)). This approach has been successfully used to predict growth and metabolic byproduct secretion in wild-type *E. coli* in aerobic and anaerobic batch and fed-batch bioreactors (FIG. 2), and to improve the predictability of the metabolic models using transcriptional regulatory constraints (Varma and Palsson, supra, 2004; Covert and Palsson, supra, 2002).

Figure 3:
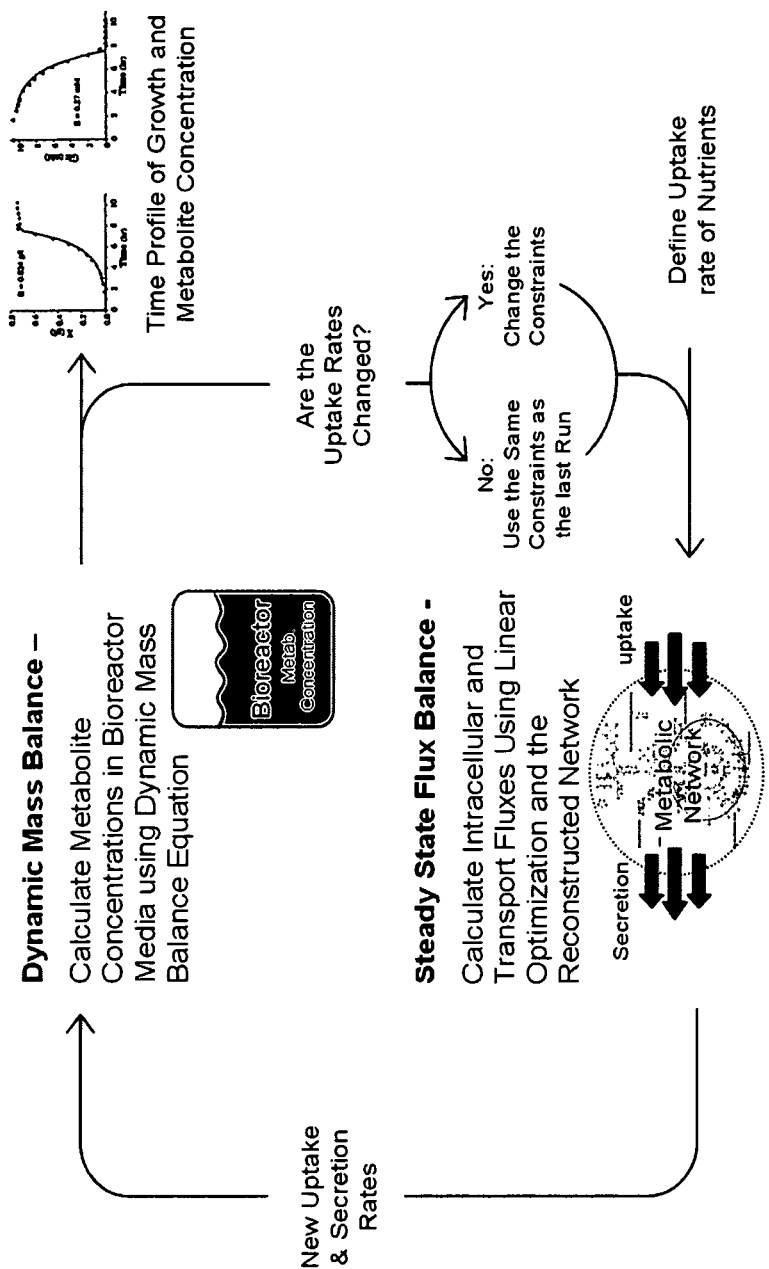
FIG. 3 shows a flow diagram of transient flux balance calculation. Since time constants associated with metabolism are fast (on the order of milliseconds to tens of seconds) as compared to the time constants associated with cell growth (on the order of hours to days), metabolism can be considered to be in a quasi steady state (Covert et al., *J. Theor. Biol.* 213:73-88 (2001)). As a result, metabolic flux rates in the cell can be computed using a steady state flux balance analysis using a metabolic model, and metabolite concentrations in the cell culture can be computed using the standard dynamic mass balance equation. Transient flux balance analysis thus links the calculated steady state rates from metabolic flux analysis to dynamic changes in metabolite concentrations in cell culture, and vice versa.

Briefly, a time profile of metabolite concentrations is calculated by the transient flux balance analysis in an iterative two-step process, where: (1) uptake and secretion rate of metabolites are determined using a metabolic network and linear optimization, and (2) the metabolite concentrations in the bioreactor are calculated using the dynamic mass balance equation (FIG. 3). A set of uptake rates of nutrients can be used to constrain the flux balance calculation in the metabolic network. Using linear optimization, an intracellular flux distribution is calculated and metabolite secretion rates are determined in the metabolic network. The calculated secretion rates are then used to determine the concentration of metabolites in the bioreactor media using the standard dynamic mass balance equations, $$S - S_o = q_s \int X_v dt \quad \text{Equation (1),}$$

where S is a consumed nutrient or produced metabolite concentration, $S_o$ is the initial or previous time point metabolite concentration, and $X_v$ is the viable cell concentration. Cell specific growth rate is computed using standard growth equation, $$X_v = X_{v,o} e^{\mu t} \quad \text{Equation (2),}$$

where $X_{v,o}$ is the initial cell concentration and $\mu$ is cell specific growth rate. This procedure is repeated in small arbitrary time intervals for the duration of bioreactor or cell culture experiment from which a time profile of metabolite and cell concentration can be graphically displayed (see, for example, FIG. 2). Transient analysis can thus estimate the time profile of the metabolite concentrations and determine the duration of the cell culture, that is, when the cells run out of nutrients and growth of the cell culture ceases.

Figure 4:
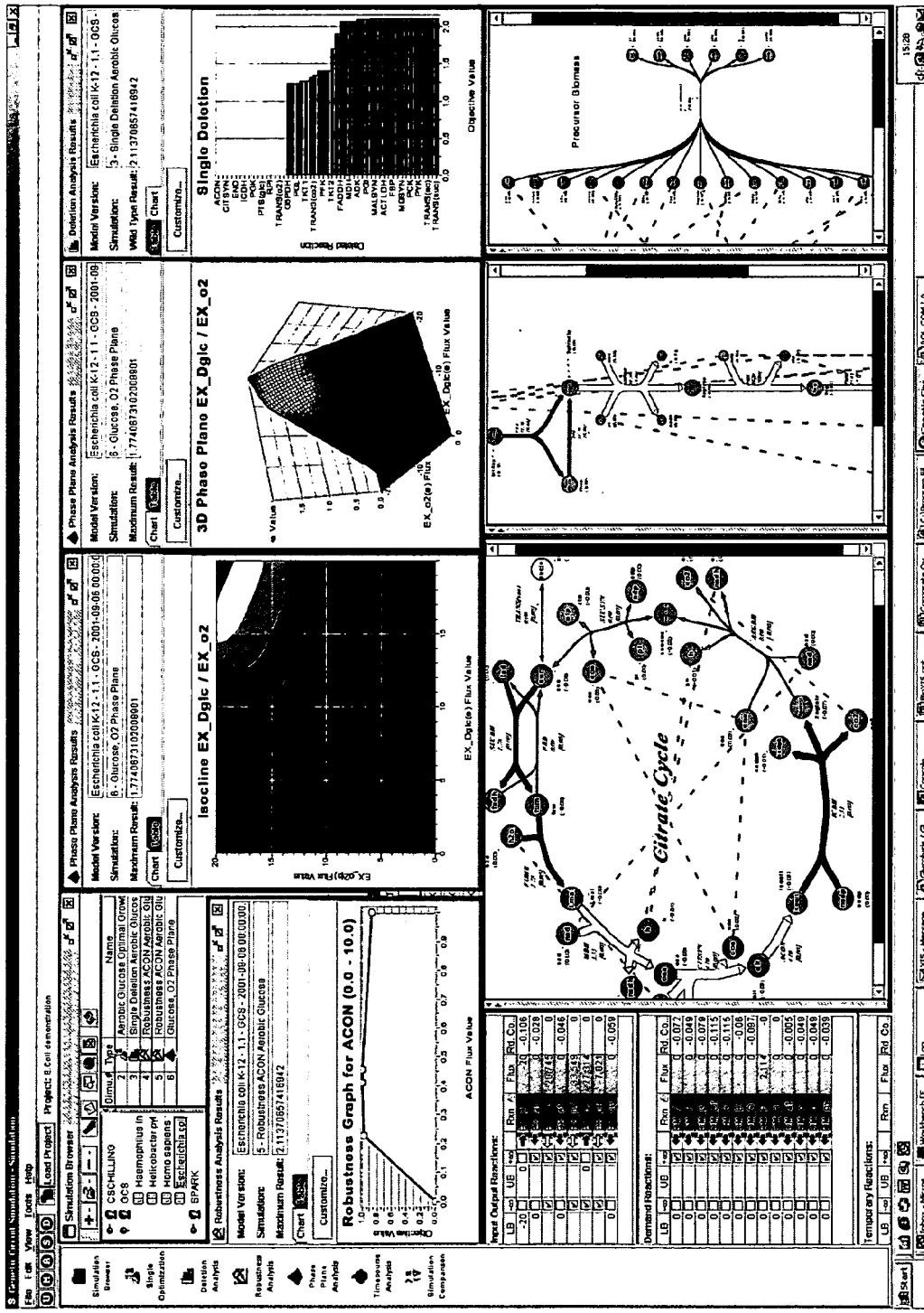
FIG. 4 shows screenshots from the Simulation Module of SimPheny™ V3.0.

The SimPheny™ method or similar modeling method can also be used (see U.S. publication 20030233218). Exemplary modeling methods are also described in U.S. publications 2004/0029149 and 2006/0147899. Improving the efficiency of biological discovery and delivering on the potential of model-driven systems biology requires the development of a computational infrastructure to support collaborative model development, simulation, and data integration/management. In addition, such a high performance-computing platform should embrace the iterative nature of modeling and simulation to allow the value of a model to increase in time as more information is incorporated. One such modeling method is called SimPheny™, short for Simulating Phenotypes, which allows the integration of simulation based systems biology for solving complex biological problems (FIG. 4). SimPheny™ was developed to support multi-user research in concentrated or distributed environments to allow effective collaboration. It serves as the basis for a model-centric approach to biological discovery. The SimPheny™ method has been described previously (see U.S. publication 2003/0233218; WO03106998).

The SimPheny™ method allows the modeling of biochemical reaction networks and metabolism in organism-specific models. The platform supports the development of metabolic models, all of the necessary simulation activities, and the capability to integrate various experimental data. The system is divided into a number of discrete modules to support various activities associated with modeling and simulation. The modules include: (1) universal data, (2) model development, (3) atlas design, (4) simulation, (5) content mining, (6) experimental data analysis, and (7) pathway predictor.

Figure 5:
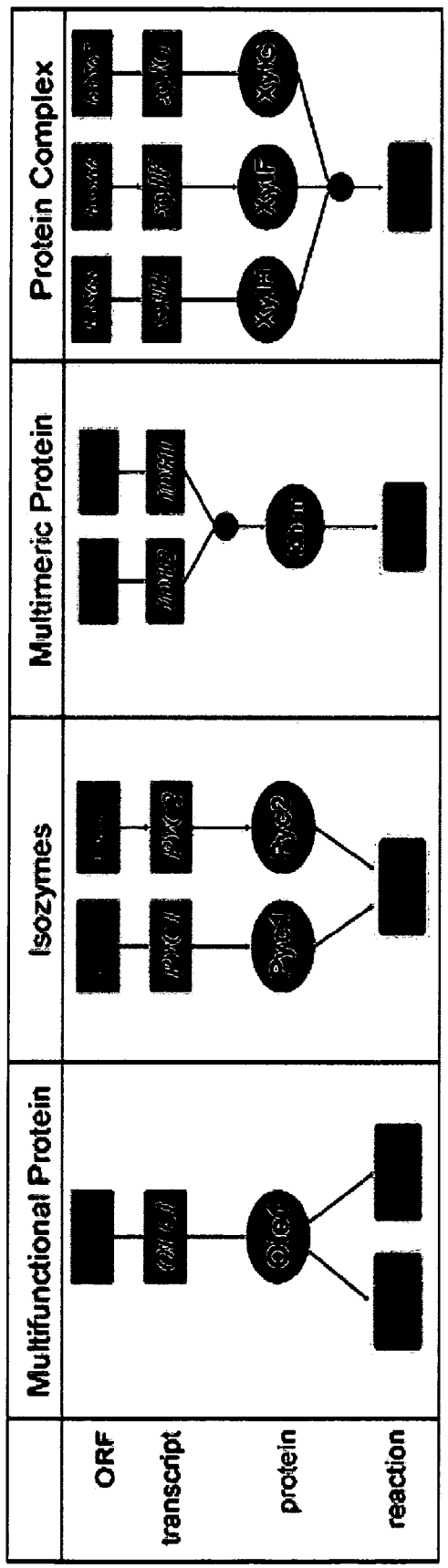
FIG. 5 shows an example of a gene-protein-reaction (GPR) association schema in SimPheny™. Multi-functional proteins, isozymes, multimeric proteins, and protein complexes can be represented by linking the open reading frame (ORF) in a genome sequence to a corresponding transcript, a functional protein, and biochemical reaction(s).

Each of these modules encapsulates activities that are crucial to supporting the iterative model development process. They are all fully integrated with each other so that information created in one module can be utilized where appropriate in other modules. Within the universal data module, all of the data concerning chemical compounds, reactions, and organisms is maintained, providing the underlying information required for constructing cellular models. The model-development module is used to create a model and assign all the appropriate reactions to a model along with specifying any related information such as the genetic associations (FIG. 5) and reference information related to the reaction in the model and the model in general. The atlas design module is used to design metabolic maps and organize them into collections or maps (an atlas). Models are used to simulate the phenotypic behavior of an organism under changing genetic circumstances and environmental conditions. These simulations are performed within the simulation module that enables the use of optimization strategies to calculate cellular behavior. In addition to calculated simulation results, this module allows for the viewing of results in a wide variety of contexts. In order to browse and mine the biological content of all the models and associated genomics for the model organisms, a separate module for data mining can be used. Thus, SimPheny™ represents an exemplary tool that provides the power of modeling and simulation within a systems biology research strategy.

The representation of a reaction network with a set of linear algebraic equations presented as a stoichiometric matrix has been described (U.S. publication 2006/0147899). A reaction network can be represented as a set of linear algebraic equations which can be presented as a stoichiometric matrix S, with S being an m×n matrix where m corresponds to the number of reactants or metabolites and n corresponds to the number of reactions taking place in the network. Each column in the matrix corresponds to a particular reaction n, each row corresponds to a particular reactant m, and each $S_{mn}$ element corresponds to the stoichiometric coefficient of the reactant m in the reaction denoted n. The stoichiometric matrix can include intra-system reactions which are related to reactants that participate in the respective reactions according to a stoichiometric coefficient having a sign indicative of whether the reactant is a substrate or product of the reaction and a value correlated with the number of equivalents of the reactant consumed or produced by the reaction. Exchange reactions are similarly correlated with a stoichiometric coefficient. The same compound can be treated separately as an internal reactant and an external reactant such that an exchange reaction exporting the compound is correlated by stoichiometric coefficients of −1 and 1, respectively. However, because the compound is treated as a separate reactant by virtue of its compartmental location, a reaction which produces the internal reactant but does not act on the external reactant is correlated by stoichiometric coefficients of 1 and 0, respectively. Demand reactions such as growth can also be included in the stoichiometric matrix being correlated with substrates by an appropriate stoichiometric coefficient.

As disclosed herein, a stoichiometric matrix provides a convenient format for representing and analyzing a reaction network because it can be readily manipulated and used to compute network properties, for example, by using linear programming or general convex analysis. A reaction network data structure can take on a variety of formats so long as it is capable of relating reactants and reactions in the manner exemplified herein for a stoichiometric matrix and in a manner that can be manipulated to determine an activity of one or more reactions using methods such as those exemplified herein. Other examples of reaction network data structures that are useful in the invention include a connected graph, list of chemical reactions or a table of reaction equations.

A reaction network data structure can be constructed to include all reactions that are involved in metabolism occurring in a cell line or any portion thereof. A portion of an cell's metabolic reactions that can be included in a reaction network data structure of the invention includes, for example, a central metabolic pathway such as glycolysis, the TCA cycle, the PPP or ETS; or a peripheral metabolic pathway such as amino acid biosynthesis, amino acid degradation, purine biosynthesis, pyrimidine biosynthesis, lipid biosynthesis, fatty acid metabolism, vitamin or cofactor biosynthesis, transport processes and alternative carbon source catabolism. Examples of individual pathways are described in the Examples. Other examples of portions of metabolic reactions that can be included in a reaction network data structure of the invention include, for example, TAG biosynthesis, muscle contraction requirements, bicarbonate buffer system and/or ammonia buffer system. Specific examples of these and other reactions are described further below and in the Examples. Depending upon a particular application, a reaction network data structure can include a plurality of reactions including any or all of the reactions known in a cell or organism.

For some applications, it can be advantageous to use a reaction network data structure that includes a minimal number of reactions to achieve a particular activity under a particular set of environmental conditions. A reaction network data structure having a minimal number of reactions can be identified by performing the simulation methods described below in an iterative fashion where different reactions or sets of reactions are systematically removed and the effects observed. Accordingly, the invention provides a computer readable medium, containing a data structure relating a plurality of reactants to a plurality of reactions.

Depending upon the particular cell type, the physiological conditions being tested, and the desired activity of a model or method of the invention, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in a cell or organism or that are desired to simulate the activity of the full set of reactions occurring in a cell or organism. A reaction network data structure that is substantially complete with respect to the metabolic reactions of a cell or organism provides an advantage of being relevant to a wide range of conditions to be simulated, whereas those with smaller numbers of metabolic reactions are specific to a particular subset of conditions to be simulated.

A reaction network data structure can include one or more reactions that occur in or by a cell or organism and that do not occur, either naturally or following manipulation, in or by another organism, such as *Saccharomyces cerevisiae*. It is understood that a reaction network data structure of a particular cell type can also include one or more reactions that occur in another cell type. Addition of such heterologous reactions to a reaction network data structure of the invention can be used in methods to predict the consequences of heterologous gene transfer and protein expression.

The reactions included in a reaction network data structure of the invention can be metabolic reactions. A reaction network data structure can also be constructed to include other types of reactions such as regulatory reactions, signal transduction reactions, cell cycle reactions, reactions involved in apoptosis, reactions involved in responses to hypoxia, reactions involved in responses to cell-cell or cell-substrate interactions, reactions involved in protein synthesis and regulation thereof, reactions involved in gene transcription and translation, and regulation thereof, and reactions involved in assembly of a cell and its subcellular components.

A reaction network data structure or index of reactions used in the data structure such as that available in a metabolic reaction database, as described above, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction, a subset of reactions to which the reaction belongs, citations to references from which information was obtained, or a level of confidence with which a reaction is believed to occur in a cell or organism. A computer readable medium or media of the invention can include a gene database containing annotated reactions. Such information can be obtained during the course of building a metabolic reaction database or model of the invention as described below.

As used herein, the term "gene database" is intended to mean a computer readable medium or media that contains at least one reaction that is annotated to assign a reaction to one or more macromolecules that perform the reaction or to assign one or more nucleic acid that encodes the one or more macromolecules that perform the reaction. A gene database can contain a plurality of reactions, some or all of which are annotated. An annotation can include, for example, a name for a macromolecule; assignment of a function to a macromolecule; assignment of an organism that contains the macromolecule or produces the macromolecule; assignment of a subcellular location for the macromolecule; assignment of conditions under which a macromolecule is regulated with respect to performing a reaction, being expressed or being degraded; assignment of a cellular component that regulates a macromolecule; an amino acid or nucleotide sequence for the macromolecule; an mRNA isoform, enzyme isoform, or any other desirable annotation or annotation found for a macromolecule in a genome database such as those that can be found in Genbank, a site maintained by the NCBI (ncbi.nlm.gov), the Kyoto Encyclopedia of Genes and Genomes (KEGG) (www.genome.ad.jp/kegg/), the protein database SWISS-PROT (ca.expasy.org/sprot/), the LocusLink database maintained by the NCBI (www.ncbi.nlm.nih.gov/LocusLink/), the Enzyme Nomenclature database maintained by G. P. Moss of Queen Mary and Westfield College in the United Kingdom (www.chem.qmw.ac.uk/iubmb/enzyme/).

A gene database of the invention can include a substantially complete collection of genes or open reading frames in a cell or organism, substantially complete collection of the macromolecules encoded by the cell's or organism's genome. Alternatively, a gene database can include a portion of genes or open reading frames in an organism or a portion of the macromolecules encoded by the organism's genome, such as the portion that includes substantially all metabolic genes or macromolecules. The portion can be at least 10%, 15%, 20%, 25%, 50%, 75%, 90% or 95% of the genes or open reading frames encoded by the organism's genome, or the macromolecules encoded therein. A gene database can also include macromolecules encoded by at least a portion of the nucleotide sequence for the organism's genome such as at least 10%, 15%, 20%, 25%, 50%, 75%, 90% or 95% of the organism's genome. Accordingly, a computer readable medium or media of the invention can include at least one reaction for each macromolecule encoded by a portion of a cell or organism's genome.

An in silico model of cell of the invention can be built by an iterative process which includes gathering information regarding particular reactions to be added to a model, representing the reactions in a reaction network data structure, and performing preliminary simulations wherein a set of constraints is placed on the reaction network and the output evaluated to identify errors in the network. Errors in the network such as gaps that lead to non-natural accumulation or consumption of a particular metabolite can be identified as described below and simulations repeated until a desired performance of the model is attained. Combination of the central metabolism and the cell specific reaction networks into a single model produces, for example, a cell specific reaction network.

Information to be included in a data structure of the invention can be gathered from a variety of sources including, for example, annotated genome sequence information and biochemical literature. Sources of annotated human genome sequence information include, for example, KEGG, SWISS-PROT, LocusLink, the Enzyme Nomenclature database, the International Human Genome Sequencing Consortium and commercial databases. KEGG contains a broad range of information, including a substantial amount of metabolic reconstruction. The genomes of 304 organisms can be accessed here, with gene products grouped by coordinated functions, often represented by a map (e.g., the enzymes involved in glycolysis would be grouped together). The maps are biochemical pathway templates which show enzymes connecting metabolites for various parts of metabolism. These general pathway templates are customized for a given organism by highlighting enzymes on a given template which have been identified in the genome of the organism. Enzymes and metabolites are active and yield useful information about stoichiometry, structure, alternative names and the like, when accessed.

SWISS-PROT contains detailed information about protein function. Accessible information includes alternate gene and gene product names, function, structure and sequence information, relevant literature references, and the like. LocusLink contains general information about the locus where the gene is located and, of relevance, tissue specificity, cellular location, and implication of the gene product in various disease states.

The Enzyme Nomenclature database can be used to compare the gene products of two organisms. Often the gene names for genes with similar functions in two or more organisms are unrelated. When this is the case, the E.C. (Enzyme Commission) numbers can be used as unambiguous indicators of gene product function. The information in the Enzyme Nomenclature database is also published in Enzyme Nomenclature (Academic Press, San Diego, Calif., 1992) with 5 supplements to date, all found in the European Journal of Biochemistry (Blackwell Science, Malden, Mass.).

Sources of biochemical information include, for example, general resources relating to metabolism, resources relating specifically to a particular cell's or organism's metabolism, and resources relating to the biochemistry, physiology and pathology of specific cell types.

Sources of general information relating to metabolism, which can be used to generate human reaction databases and models, include J. G. Salway, *Metabolism at a Glance*, $2^{nd}$ ed., Blackwell Science, Malden, Mass. (1999) and T. M. Devlin, ed., *Textbook of Biochemistry with Clinical Correlations*, $4^{th}$ ed., John Wiley and Sons, New York, N.Y. (1997). Human metabolism-specific resources include J. R. Bronk, *Human Metabolism: Functional Diversity and Integration*, Addison Wesley Longman, Essex, England (1999).

In the course of developing an in silico model of metabolism, the types of data that can be considered include, for example, biochemical information which is information related to the experimental characterization of a chemical reaction, often directly indicating a protein(s) associated with a reaction and the stoichiometry of the reaction or indirectly demonstrating the existence of a reaction occurring within a cellular extract; genetic information, which is information related to the experimental identification and genetic characterization of a gene(s) shown to code for a particular protein(s) implicated in carrying out a biochemical event; genomic information, which is information related to the identification of an open reading frame and functional assignment, through computational sequence analysis, that is then linked to a protein performing a biochemical event; physiological information, which is information related to overall cellular physiology, fitness characteristics, substrate utilization, and phenotyping results, which provide evidence of the assimilation or dissimilation of a compound used to infer the presence of specific biochemical event (in particular translocations); and modeling information, which is information generated through the course of simulating activity of cells, tissues or physiological systems using methods such as those described herein which lead to predictions regarding the status of a reaction such as whether or not the reaction is required to fulfill certain demands placed on a metabolic network. Additional information that can be considered includes, for example, cell type-specific or condition-specific gene expression information, which can be determined experimentally, such as by gene array analysis or from expressed sequence tag (EST) analysis, or obtained from the biochemical and physiological literature.

The majority of the reactions occurring in a cell's or organism's reaction networks are catalyzed by enzymes/proteins, which are created through the transcription and translation of the genes found within the chromosome in the cell. The remaining reactions occur either spontaneously or through non-enzymatic processes. Furthermore, a reaction network data structure can contain reactions that add or delete steps to or from a particular reaction pathway. For example, reactions can be added to optimize or improve performance of a model for multicellular interactions in view of empirically observed activity. Alternatively, reactions can be deleted to remove intermediate steps in a pathway when the intermediate steps are not necessary to model flux through the pathway. For example, if a pathway contains 3 nonbranched steps, the reactions can be combined or added together to give a net reaction, thereby reducing memory required to store the reaction network data structure and the computational resources required for manipulation of the data structure.

The reactions that occur due to the activity of gene-encoded enzymes can be obtained from a genome database which lists genes identified from genome sequencing and subsequent genome annotation. Genome annotation consists of the locations of open reading frames and assignment of function from homology to other known genes or empirically determined activity. Such a genome database can be acquired through public or private databases containing annotated nucleic acid or protein sequences, including *Homo sapiens* sequences. If desired, a model developer can perform a network reconstruction and establish the model content associations between the genes, proteins, and reactions as described, for example, in Covert et al. *Trends in Biochemical Sciences* 26:179-186 (2001) and Palsson, WO 00/46405.

As reactions are added to a reaction network data structure or metabolic reaction database, those having known or putative associations to the proteins/enzymes which allow/catalyze the reaction and the associated genes that code for these proteins can be identified by annotation. Accordingly, the appropriate associations for all of the reactions to their related proteins or genes or both can be assigned. These associations can be used to capture the non-linear relationship between the genes and proteins as well as between proteins and reactions. In some cases one gene codes for one protein which then perform one reaction. However, often there are multiple genes which are required to create an active enzyme complex and often there are multiple reactions that can be carried out by one protein or multiple proteins that can carry out the same reaction. These associations capture the logic (i.e. AND or OR relationships) within the associations. Annotating a metabolic reaction database with these associations can allow the methods to be used to determine the effects of adding or eliminating a particular reaction not only at the reaction level, but at the genetic or protein level in the context of running a simulation or predicting an activity.

A reaction network data structure of the invention can be used to determine the activity of one or more reactions in a plurality of reactions occurring in a cell independent of any knowledge or annotation of the identity of the protein that performs the reaction or the gene encoding the protein. A model that is annotated with gene or protein identities can include reactions for which a protein or encoding gene is not assigned. While a large portion of the reactions in a cellular metabolic network are associated with genes in the organism's genome, there are also a substantial number of reactions included in a model for which there are no known genetic associations. Such reactions can be added to a reaction database based upon other information that is not necessarily related to genetics such as biochemical or cell based measurements or theoretical considerations based on observed biochemical or cellular activity. For example, there are many reactions that can either occur spontaneously or are not protein-enabled reactions. Furthermore, the occurrence of a particular reaction in a cell for which no associated proteins or genetics have been currently identified can be indicated during the course of model building by the iterative model building methods of the invention.

The reactions in a reaction network data structure or reaction database can be assigned to subsystems by annotation, if desired. The reactions can be subdivided according to biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., *J. Theor. Biol.* 203:249-283 (2000), and in Schuster et al., *Bioinformatics* 18:351-361 (2002). The use of subsystems can be advantageous for a number of analysis methods, such as extreme pathway analysis, and can make the management of model content easier. Although assigning reactions to subsystems can be achieved without affecting the use of the entire model for simulation, assigning reactions to subsystems can allow a user to search for reactions in a particular subsystem which may be useful in performing various types of analyses. Therefore, a reaction network data structure can include any number of desired subsystems including, for example, 2 or more subsystems, 5 or more subsystems, 10 or more subsystems, 25 or more subsystems or 50 or more subsystems.

The reactions in a reaction network data structure or metabolic reaction database can be annotated with a value indicating the confidence with which the reaction is believed to occur in a cell or organism. The level of confidence can be, for example, a function of the amount and form of supporting data that is available. This data can come in various forms including published literature, documented experimental results, or results of computational analyses. Furthermore, the data can provide direct or indirect evidence for the existence of a chemical reaction in a cell based on genetic, biochemical, and/or physiological data.

Constraints can be placed on the value of any of the fluxes in the metabolic network using a constraint set. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure. Based on the in vivo environment where multiple cells interact, such as in a human organism, the metabolic resources available to the cell for biosynthesis of essential molecules can be determined.

As described previously (see U.S. publication 2006/014789), for a reaction network, constraints can be placed on each reaction, with the constraints provided in a format that can be used to constrain the reactions of a stoichiometric matrix. The format for the constraints used for a matrix or in linear programming can be conveniently represented as a linear inequality such as $$b_j \leq v_j \leq a_j; j=1 \ldots n \qquad (Eq.\ 3)$$

where $v_j$ is the metabolic flux vector, $b_j$ is the minimum flux value and $a_j$ is the maximum flux value. Thus, $a_j$ can take on a finite value representing a maximum allowable flux through a given reaction or $b_j$ can take on a finite value representing minimum allowable flux through a given reaction. Additionally, if one chooses to leave certain reversible reactions or transport fluxes to operate in a forward and reverse manner the flux may remain unconstrained by setting $b_j$ to negative infinity and $a_j$ to positive infinity. If reactions proceed only in the forward reaction, $b_j$ is set to zero while $a_j$ is set to positive infinity. As an example, to simulate the event of a genetic deletion or non-expression of a particular protein, the flux through all of the corresponding metabolic reactions related to the gene or protein in question are reduced to zero by setting $a_j$ and $b_j$ to be zero. Furthermore, if one wishes to simulate the absence of a particular growth substrate one can simply constrain the corresponding transport fluxes that allow the metabolite to enter the cell to be zero by setting $a_j$ and $b_j$ to be zero. On the other hand, if a substrate is only allowed to enter or exit the cell via transport mechanisms, the corresponding fluxes can be properly constrained to reflect this scenario.

The ability of a reaction to be actively occurring is dependent on a large number of additional factors beyond just the availability of substrates. These factors, which can be represented as variable constraints in the models and methods of the invention include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism. Regulation can be represented in an in silico model by providing a variable constraint as set forth below.

As used herein, the term "regulated," when used in reference to a reaction in a data structure, is intended to mean a reaction that experiences an altered flux due to a change in the value of a constraint or a reaction that has a variable constraint.

As used herein, the term "regulatory reaction" is intended to mean a chemical conversion or interaction that alters the activity of a protein, macromolecule or enzyme. A chemical conversion or interaction can directly alter the activity of a protein, macromolecule or enzyme such as occurs when the protein, macromolecule or enzyme is post-translationally modified or can indirectly alter the activity of a protein, macromolecule or enzyme such as occurs when a chemical conversion or binding event leads to altered expression of the protein, macromolecule or enzyme. Thus, transcriptional or translational regulatory pathways can indirectly alter a protein, macromolecule or enzyme or an associated reaction. Similarly, indirect regulatory reactions can include reactions that occur due to downstream components or participants in a regulatory reaction network. When used in reference to a data structure or in silico model, for example, the term is intended to mean a first reaction that is related to a second reaction by a function that alters the flux through the second reaction by changing the value of a constraint on the second reaction.

As used herein, the term "regulatory data structure" is intended to mean a representation of an event, reaction or network of reactions that activate or inhibit a reaction, the representation being in a format that can be manipulated or analyzed. An event that activates a reaction can be an event that initiates the reaction or an event that increases the rate or level of activity for the reaction. An event that inhibits a reaction can be an event that stops the reaction or an event that decreases the rate or level of activity for the reaction. Reactions that can be represented in a regulatory data structure include, for example, reactions that control expression of a macromolecule that in turn, performs a reaction such as transcription and translation reactions, reactions that lead to post translational modification of a protein or enzyme such as phosphorylation, dephosphorylation, prenylation, methylation, oxidation or covalent modification, reactions that process a protein or enzyme such as removal of a pre- or pro-sequence, reactions that degrade a protein or enzyme or reactions that lead to assembly of a protein or enzyme.

As used herein, the term "regulatory event" is intended to mean a modifier of the flux through a reaction that is independent of the amount of reactants available to the reaction. A modification included in the term can be a change in the presence, absence, or amount of an enzyme that performs a reaction. A modifier included in the term can be a regulatory reaction such as a signal transduction reaction or an environmental condition such as a change in pH, temperature, redox potential or time. It will be understood that when used in reference to a model or data structure of the invention, a regulatory event is intended to be a representation of a modifier of the flux through reaction that is independent of the amount of reactants available to the reaction.

The effects of regulation on one or more reactions that occur in a cell can be predicted using an in silico cell model of the invention. Regulation can be taken into consideration in the context of a particular condition being examined by providing a variable constraint for the reaction in an in silico model. Such constraints constitute condition-dependent constraints. A data structure can represent regulatory reactions as Boolean logic statements (Reg-reaction). The variable takes on a value of 1 when the reaction is available for use in the reaction network and will take on a value of 0 if the reaction is restrained due to some regulatory feature. A series of Boolean statements can then be introduced to mathematically represent the regulatory network as described for example in Covert et al. *J. Theor. Biol.* 213:73-88 (2001). For example, in the case of a transport reaction (A_in) that imports metabolite A, where metabolite A inhibits reaction R2, a Boolean rule can state that:

$$Reg\text{-}R2 = IF\ NOT(A\_in). \qquad (Eq.\ 4)$$

This statement indicates that reaction R2 can occur if reaction A_in is not occurring (i.e. if metabolite A is not present). Similarly, it is possible to assign the regulation to a variable A which would indicate an amount of A above or below a threshold that leads to the inhibition of reaction R2. Any function that provides values for variables corresponding to each of the reactions in the biochemical reaction network can be used to represent a regulatory reaction or set of regulatory reactions in a regulatory data structure. Such functions can include, for example, fuzzy logic, heuristic rule-based descriptions, differential equations or kinetic equations detailing system dynamics.

A reaction constraint placed on a reaction can be incorporated into an in silico model using the following general equation:

$$(\text{Reg-Reaction})^* b_j \leq v_j \leq a_j^* (\text{Reg-Reaction}),$$
$$\forall j=1 \ldots n \quad (\text{Eq. 5})$$

For the example of reaction R2 this equation is written as follows:

$$(0)^* \text{Reg-}R2 \leq R2 \leq (\infty)^* \text{Reg-}R2. \quad (\text{Eq. 6})$$

Thus, during the course of a simulation, depending upon the presence or absence of metabolite A in the interior of the cell where reaction R2 occurs, the value for the upper boundary of flux for reaction R2 will change from 0 to infinity, respectively. With the effects of a regulatory event or network taken into consideration by a constraint function and the condition-dependent constraints set to an initial relevant value, the behavior of the reaction network can be simulated for the conditions considered as set forth below.

Although regulation has been exemplified above for the case where a variable constraint is dependent upon the outcome of a reaction in the data structure, a plurality of variable constraints can be included in an in silico model to represent regulation of a plurality of reactions. Furthermore, in the exemplary case set forth above, the regulatory structure includes a general control stating that a reaction is inhibited by a particular environmental condition. Using a general control of this type, it is possible to incorporate molecular mechanisms and additional detail into the regulatory structure that is responsible for determining the active nature of a particular chemical reaction within an organism.

Regulation can also be simulated by a model of the invention and used to predict a physiological function of a cell without knowledge of the precise molecular mechanisms involved in the reaction network being modeled. Thus, the model can be used to predict, in silico, overall regulatory events or causal relationships that are not apparent from in vivo observation of any one reaction in a network or whose in vivo effects on a particular reaction are not known. Such overall regulatory effects can include those that result from overall environmental conditions such as changes in pH, temperature, redox potential, or the passage of time.

Those of skill in the art will recognize that instructions for the software implementing a method and model of the present disclosure can be written in any known computer language, such as Java, C, C++, Visual Basic, FORTRAN or COBOL, and compiled using any compatible compiler; and that the software can run from instructions stored in a memory or computer-readable medium on a computing system.

A computing system can be a single computer executing the instructions or a plurality of computers in a distributed computing network executing parts of the instructions sequentially or in parallel. The single computer or one of the plurality of computers can comprise a single processor (for example, a microprocessor or digital signal processor) executing assigned instructions or a plurality of processors executing different parts of the assigned instructions sequentially or in parallel. The single computer or one of the plurality of the computers can further comprise one or more of a system unit housing, a video display device, a memory, computational entities such as operating systems, drivers, graphical user interfaces, applications programs, and one or more interaction devices, such as a touch pad or screen. Such interaction devices or graphical user interfaces, and the like, can be used to output a result to a user, including a visual output or data output, as desired.

A memory or computer-readable medium for storing the software implementing a method and model of the present disclosure can be any medium that participates in providing instructions to a processor for execution. Such a medium may take many forms, including, but not limited to, non-volatile media, volatile media, and transmission media. Non-volatile media include, for example, optical or magnetic disks. Volatile media include dynamic memory. Transmission media include coaxial cables, copper wire, and fiber optics. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. A carrier wave can also be used but is distinct from a computer readable medium or media. Thus, a computer readable medium or media as used herein specifically excludes a carrier wave.

The memory or computer-readable medium can be contained within a single computer or distributed in a network. A network can be any of a number of network systems known in the art such as a Local Area Network (LAN), or a Wide Area Network (WAN). The LAN or WAN can be a wired network (e.g., Ethernet) or a wireless network (e.g., WLAN). Client-server environments, database servers and networks that can be used to implement certain aspects of the present disclosure are well known in the art. For example, database servers can run on an operating system such as UNIX, running a relational database management system, a World Wide Web application and a World Wide Web server. Other types of memories and computer readable media area also contemplated to function within the scope of the present disclosure.

A database or data structure embodying certain aspects or components of the present disclosure can be represented in a markup language format including, for example, Standard Generalized Markup Language (SGML), Hypertext Markup Language (HTML) or Extensible Markup Language (XML). Markup languages can be used to tag the information stored in a database or data structure of the invention, thereby providing convenient annotation and transfer of data between databases and data structures. In particular, an XML format can be useful for structuring the data representation of reactions, reactants, and their annotations; for exchanging database contents, for example, over a network or the Internet; for updating individual elements using the document object model; or for providing different access to multiple users for different information content of a database or data structure embodying certain aspects of the present disclosure. XML programming methods and editors for writing XML codes are known in the art as described, for example, in Ray, "Learning XML" O'Reilly and Associates, Sebastopol, Calif. (2001).

Those of skill in the art would appreciate that the various illustrative blocks, modules, elements, components, methods, and algorithms described herein may be implemented as electronic hardware, computer software, or combinations of both. Furthermore, these may be partitioned differently than what is described. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans can implement the described functionality in varying ways for each particular application.

A set of constraints can be applied to a reaction network data structure to simulate the flux of mass through the reaction network under a particular set of environmental conditions specified by a constraints set. Because the time constants characterizing metabolic transients and/or metabolic reactions are typically very rapid, on the order of milli-seconds to seconds, compared to the time constants of cell growth on the order of hours to days, the transient mass balances can be simplified to only consider the steady state behavior. Referring now to an example where the reaction network data structure is a stoichiometric matrix, the steady state mass balances can be applied using the following system of linear equations $$S \cdot v = 0 \quad \text{(Eq. 7)}$$

where S is the stoichiometric matrix as defined above and v is the flux vector. This equation defines the mass, energy, and redox potential constraints placed on the metabolic network as a result of stoichiometry. Together Equations 1 and 5 representing the reaction constraints and mass balances, respectively, effectively define the capabilities and constraints of the metabolic genotype and the organism's metabolic potential. All vectors, v, that satisfy Equation 5 are said to occur in the mathematical nullspace of S. Thus, the null space defines steady-state metabolic flux distributions that do not violate the mass, energy, or redox balance constraints. Typically, the number of fluxes is greater than the number of mass balance constraints, thus a plurality of flux distributions satisfy the mass balance constraints and occupy the null space. The null space, which defines the feasible set of metabolic flux distributions, is further reduced in size by applying the reaction constraints set forth in Equation 1 leading to a defined solution space. A point in this space represents a flux distribution and hence a metabolic phenotype for the network. An optimal solution within the set of all solutions can be determined using mathematical optimization methods when provided with a stated objective and a constraint set. The calculation of any solution constitutes a simulation of the model.

Objectives for activity of a cell can be chosen. While the overall objective of a multi-cellular organism may be growth or reproduction, individual human cell types generally have much more complex objectives, even to the seemingly extreme objective of apoptosis (programmed cell death), which may benefit the organism but certainly not the individual cell. For example, certain cell types may have the objective of maximizing energy production, while others have the objective of maximizing the production of a particular hormone, extracellular matrix component, or a mechanical property such as contractile force. In cases where cell reproduction is slow, such as human skeletal muscle, growth and its effects need not be taken into account. In other cases, biomass composition and growth rate could be incorporated into a "maintenance" type of flux, where rather than optimizing for growth, production of precursors is set at a level consistent with experimental knowledge and a different objective is optimized.

Certain cell types, including cancer cells, can be viewed as having an objective of maximizing cell growth. Growth can be defined in terms of biosynthetic requirements based on literature values of biomass composition or experimentally determined values such as those obtained as described above. Thus, biomass generation can be defined as an exchange reaction that removes intermediate metabolites in the appropriate ratios and represented as an objective function. In addition to draining intermediate metabolites this reaction flux can be formed to utilize energy molecules such as ATP, NADH and NADPH so as to incorporate any maintenance requirement that must be met. This new reaction flux then becomes another constraint/balance equation that the system must satisfy as the objective function. Using a stoichiometric matrix as an example, adding such a constraint is analogous to adding an additional column $V_{growth}$ to the stoichiometric matrix to represent fluxes to describe the production demands placed on the metabolic system. Setting this new flux as the objective function and asking the system to maximize the value of this flux for a given set of constraints on all the other fluxes is then a method to simulate the growth of the organism.

Continuing with the example of the stoichiometric matrix applying a constraint set to a reaction network data structure can be illustrated as follows. The solution to equation 5 can be formulated as an optimization problem, in which the flux distribution that minimizes a particular objective is found. Mathematically, this optimization problem can be stated as:

$$\text{Minimize } Z \quad \text{(Eq. 8)}$$

$$\text{where } z = \Sigma c_i \cdot v_i \quad \text{(Eq. 9)}$$

where Z is the objective which is represented as a linear combination of metabolic fluxes $v_i$ using the weights $c_i$ in this linear combination. The optimization problem can also be stated as the equivalent maximization problem; i.e. by changing the sign on Z. Any commands for solving the optimization problem can be used including, for example, linear programming commands.

A computer system of the invention can further include a user interface capable of receiving a representation of one or more reactions. A user interface of the invention can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to a cell's physiology. Also, the user interface can display a graphical representation of a reaction network or the results of a simulation using a model of the invention.

Once an initial reaction network data structure and set of constraints has been created, this model can be tested by preliminary simulation. During preliminary simulation, gaps in the network or "dead-ends" in which a metabolite can be produced but not consumed or where a metabolite can be consumed but not produced can be identified. Based on the results of preliminary simulations, areas of the metabolic reconstruction that require an additional reaction can be identified. The determination of these gaps can be readily calculated through appropriate queries of the reaction network data structure and need not require the use of simulation strategies, however, simulation would be an alternative approach to locating such gaps.

In the preliminary simulation testing and model content refinement stage the existing model is subjected to a series of functional tests to determine if it can perform basic requirements such as the ability to produce the required biomass constituents and generate predictions concerning the basic physiological characteristics of the particular cell type being modeled. The more preliminary testing that is conducted, the higher the quality of the model that will be generated. Typically, the majority of the simulations used in this stage of development will be single optimizations. A single optimization can be used to calculate a single flux distribution demonstrating how metabolic resources are routed determined from the solution to one optimization problem. An optimization problem can be solved using linear programming as disclosed herein. The result can be viewed as a display of a flux distribution on a reaction map. Temporary reactions can be added to the network to determine if they should be included into the model based on modeling/simulation requirements.

Once a model of the invention is sufficiently complete with respect to the content of the reaction network data structure according to the criteria set forth above, the model can be used to simulate activity of one or more reactions in a reaction network. The results of a simulation can be displayed in a variety of formats including, for example, a table, graph, reaction network, flux distribution map or a phenotypic phase plane graph.

As used herein, the term "physiological function," when used in reference to a cell, is intended to mean an activity of the cell as a whole. An activity included in the term can be the magnitude or rate of a change from an initial state of a cell to a final state of the cell. An activity included in the term can be, for example, growth, energy production, redox equivalent production, biomass production, development, or consumption of carbon nitrogen, sulfur, phosphate, hydrogen or oxygen. An activity can also be an output of a particular reaction that is determined or predicted in the context of substantially all of the reactions that affect the particular reaction in a cell or that occur in a cell. Examples of a particular reaction included in the term are production of biomass precursors, production of a protein, production of an amino acid, production of a purine, production of a pyrimidine, production of a lipid, production of a fatty acid, production of a cofactor or transport of a metabolite, and the like. A physiological function can include an emergent property which emerges from the whole but not from the sum of parts where the parts are observed in isolation (see for example, Palsson, *Nat. Biotech* 18:1147-1150 (2000)).

A physiological function of reactions can be determined using phase plane analysis of flux distributions. Phase planes are representations of the feasible set which can be presented in two or three dimensions. As an example, two parameters that describe the growth conditions such as substrate and oxygen uptake rates can be defined as two axes of a two-dimensional space. The optimal flux distribution can be calculated from a reaction network data structure and a set of constraints as set forth above for all points in this plane by repeatedly solving the linear programming problem while adjusting the exchange fluxes defining the two-dimensional space. A finite number of qualitatively different metabolic pathway utilization patterns can be identified in such a plane, and lines can be drawn to demarcate these regions. The demarcations defining the regions can be determined using shadow prices of linear optimization as described, for example in Chvatal, *Linear Programming* New York, W.H. Freeman and Co. (1983). The regions are referred to as regions of constant shadow price structure. The shadow prices define the intrinsic value of each reactant toward the objective function as a number that is either negative, zero, or positive and are graphed according to the uptake rates represented by the x and y axes. When the shadow prices become zero as the value of the uptake rates are changed there is a qualitative shift in the optimal reaction network.

One demarcation line in the phenotype phase plane is defined as the line of optimality (LO). This line represents the optimal relation between respective metabolic fluxes. The LO can be identified by varying the x-axis flux and calculating the optimal y-axis flux with the objective function defined as the growth flux. From the phenotype phase plane analysis the conditions under which a desired activity is optimal can be determined. The maximal uptake rates lead to the definition of a finite area of the plot that is the predicted outcome of a reaction network within the environmental conditions represented by the constraint set. Similar analyses can be performed in multiple dimensions where each dimension on the plot corresponds to a different uptake rate. These and other methods for using phase plane analysis, such as those described in Edwards et al., *Biotech Bioeng.* 77:27-36 (2002), can be used to analyze the results of a simulation using an in silico model of the invention.

A physiological function of a cell can also be determined using a reaction map to display a flux distribution. A reaction map of a cell can be used to view reaction networks at a variety of levels. In the case of a cellular metabolic reaction network, a reaction map can contain the entire reaction complement representing a global perspective. Alternatively, a reaction map can focus on a particular region of metabolism such as a region corresponding to a reaction subsystem described above or even on an individual pathway or reaction.

The methods of the invention can be used to determine the activity of a plurality of cell reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, transport of a metabolite, metabolism of an alternative carbon source, or other reactions as disclosed herein.

The methods of the invention can be used to determine a phenotype of a cell mutant. The activity of one or more reactions can be determined using the methods described herein, wherein the reaction network data structure lacks one or more gene-associated reactions that occur in a cell or organism. Alternatively, the methods can be used to determine the activity of one or more reactions when a reaction that does not naturally occur in the model of a cell or organism, for example, is added to the reaction network data structure. Deletion of a gene can also be represented in a model of the invention by constraining the flux through the reaction to zero, thereby allowing the reaction to remain within the data structure. Thus, simulations can be made to predict the effects of adding or removing genes to or from a cell. The methods can be particularly useful for determining the effects of adding or deleting a gene that encodes for a gene product that performs a reaction in a peripheral metabolic pathway.

A target for an agent that affects a function of a cell can be predicted using the methods of the invention, for example a target pathway for determining a selectable marker for a cell line, as disclosed herein. Such predictions can be made by removing a reaction to simulate total inhibition or prevention by a drug or agent. Alternatively, partial inhibition or reduction in the activity a particular reaction can be predicted by performing the methods with altered constraints. For example, reduced activity can be introduced into a model of the invention by altering the $a_j$ or $b_j$ values for the metabolic flux vector of a target reaction to reflect a finite maximum or minimum flux value corresponding to the level of inhibition. Similarly, the effects of activating a reaction, by initiating or increasing the activity of the reaction, can be predicted by performing the methods with a reaction network data structure lacking a particular reaction or by altering the $a_j$ or $b_j$ values for the metabolic flux vector of a target reaction to reflect a maximum or minimum flux value corresponding to the level of activation. The methods can be particularly useful for identifying a target in a peripheral metabolic pathway.

The methods of the invention can be used to determine the effects of one or more environmental components or conditions on an activity of, for example, a physiological function of a cell such as a media component or nutrient, as disclosed herein. As set forth above, an exchange reaction can be added to a reaction network data structure corresponding to uptake of an environmental component, release of a component to the environment, or other environmental demand. The effect of the environmental component or condition can be further investigated by running simulations with adjusted $a_j$ or $b_j$ values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a cell such as the medium in which the cell is grown can be taken up and metabolized. The environmental component can also be a combination of components present for example in a minimal medium composition. Thus, the methods can be used to determine an optimal or minimal medium composition that is capable of supporting a particular activity of a cell.

It is understood that modifications which do not substantially affect the activity of the various embodiments of this invention are also provided within the definition of the invention provided herein. Accordingly, the following examples are intended to illustrate but not limit the present invention.

Example I

Metabolic Model for NS0 Cell Line and Optimization of Media Formula

This example describes metabolic network reconstruction of the NS0 cell line.

A metabolic model for NS0 cell line was reconstructed and used to optimize media formulation in a GS-NS0 murine myeloma cell line, which expresses a human anti-rabies IgG monoclonal antibody. Although the model-based media optimization approach has been exemplified using an NS0 metabolic model and NS0 cell culture experiments, this approach is equally applicable to other cell lines, including but not limited to human- or animal-derived cell lines, for example, Chinese Hamster Ovary (CHO), BHK, NS0, SP2/0, 3T3, Hybridoma, C127, HEK293, PER.C6, HepG2, HeLa, MRC5, WI38, MDCK, Vero, COS, or modified cell lines such as GS-NS0 or CHO DHFR⁻. Such cell lines can be used, for example, for production of biologics, including but not limited to growth factors, monoclonal antibodies, hormones, cytokines, fusion proteins, recombinant enzymes, recombinant vaccines, viruses, anticoagulants, and nucleic acids.

NS0 is a mouse myeloma cell used in construction of hybridoma and transfectoma for large-scale heterologous protein expression. To develop a metabolic model for the NS0 cell line, genomic evidence from the mouse sequence annotation, biochemical information from published literature on animal cell metabolism and mammalian cell biochemistry, metabolic reactions from existing models in a SimPheny™ database, and experimental data were compiled, reconciled, and incorporated in the metabolic network reconstruction. Using the experimental data and the reconstructed model of NS0, a physiologically representative objective function was identified, that is, maximization of nutritional uptake rates, and model-based media formulations were generated to improve productivity and growth in GS-NS0 cell culture.

Metabolic Network Reconstruction for NS0 Cell Line.

The metabolic network of NS0 cell line was reconstructed using published literature on animal cell metabolism, online databases, and existing metabolic models of mammalian cells in SimPheny™ (Waterston et al., *Nature* 420:520-562 (2002); Bronk, *Metabolism: Functional Diversity and Integration*, Addison Wesley Longman, Essex, England (1999); Devlin, *Textbook of Biochemistry with Clinical Correlations*, John Wiley and Sons, New York, N.Y. (1997); Salway, *Metabolism at a glance*, Blackwell Science, Oxford (1999); Vander et al., *Human physiology: the mechanisms of body function*, McGraw-Hill, New York (1994)). To accelerate the metabolic network reconstruction of NS0 cell line, previously published metabolic models of hybridoma were utilized to identify central metabolic pathways in mammalian cells (Sheikh et al., supra, 2005; Savinell and Palsson, supra, 1992a; Savinell and Palsson, supra, 1992b). Major metabolic pathways in central metabolism were included in the network reconstruction of NS0 cell metabolism, including glycolysis, the citric acid (TCA) cycle, pentose phosphate pathway, non-essential amino acid biosynthesis, and transport reactions including those for all essential amino acids identified in murine cell lines, that is, histidine, isoleucine, leucine, lysine, methionine, phenylalanine, threonine, tryptophan, and valine (Sheikh et al., supra, 2005; Xie and Wang, *Biotechnol Bioeng* 95:270-284 (2006); Simpson et al., *Biotechnol Bioeng* 64, 174-186 (1999); Nielsen et al., *Biotechnol Bioeng* 56:372-379 (1997); Bonarius et al., *Biotechnol Bioeng* 50:299-318 (1996)). The complete metabolic network includes a total of 470 metabolic reactions and 456 metabolites distributed in intracellular compartments including cytosol, mitochondria, endoplasmic reticulum, peroxisome, and extra-cellular space. All the metabolic reactions in this reconstructed network are elementally- and charge-balanced and none of the metabolic pathways is lumped or simplified.

To ensure that all the biosynthetic components can be synthesized in the network, additional biochemical reactions were added to the initial draft reconstruction of NS0 metabolism to account for biosynthesis of carbohydrates, RNA, DNA, phospholipids, cholesterol, and sphingolipids. Since experimental data for the NS0 cell line indicate that the uptake of essential amino acids exceeds the requirements for biomass and antibody production, degradation pathways for all essential amino acids were incorporated into the network reconstruction. Inclusion of each reaction in the network was supported by genetic, sequence, and/or biochemical evidence available through online databases or published literature, including the National Center for Biotechnology Information (NCBI), KEGG: Kyoto Encyclopedia of Genes and Genomes, UniProt (Universal Protein Resource), BRENDA: the Comprehensive Enzyme Information System, and scientific articles (Aoki-Kinoshita and Kanehisa, *Methods Mol. Biol.* 396:71-92 (2007); Pruitt et al., *Nucleic*

Figure 6A:
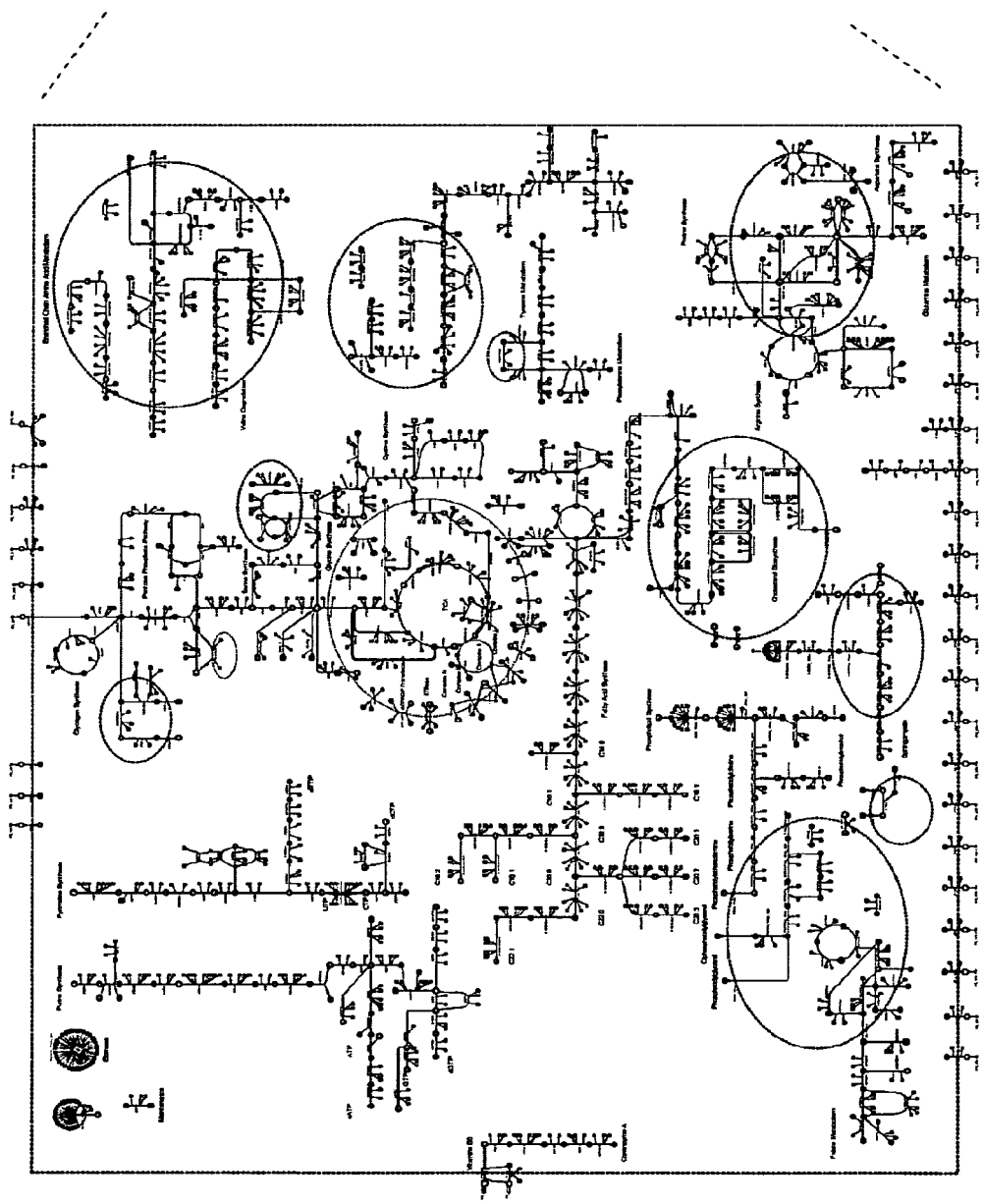
FIG. 6 shows a metabolic network for the NS0 murine myeloma cell line, containing 470 reactions and 456 metabolites, and mapping of the major metabolic pathways in the network.
Figure 6B:
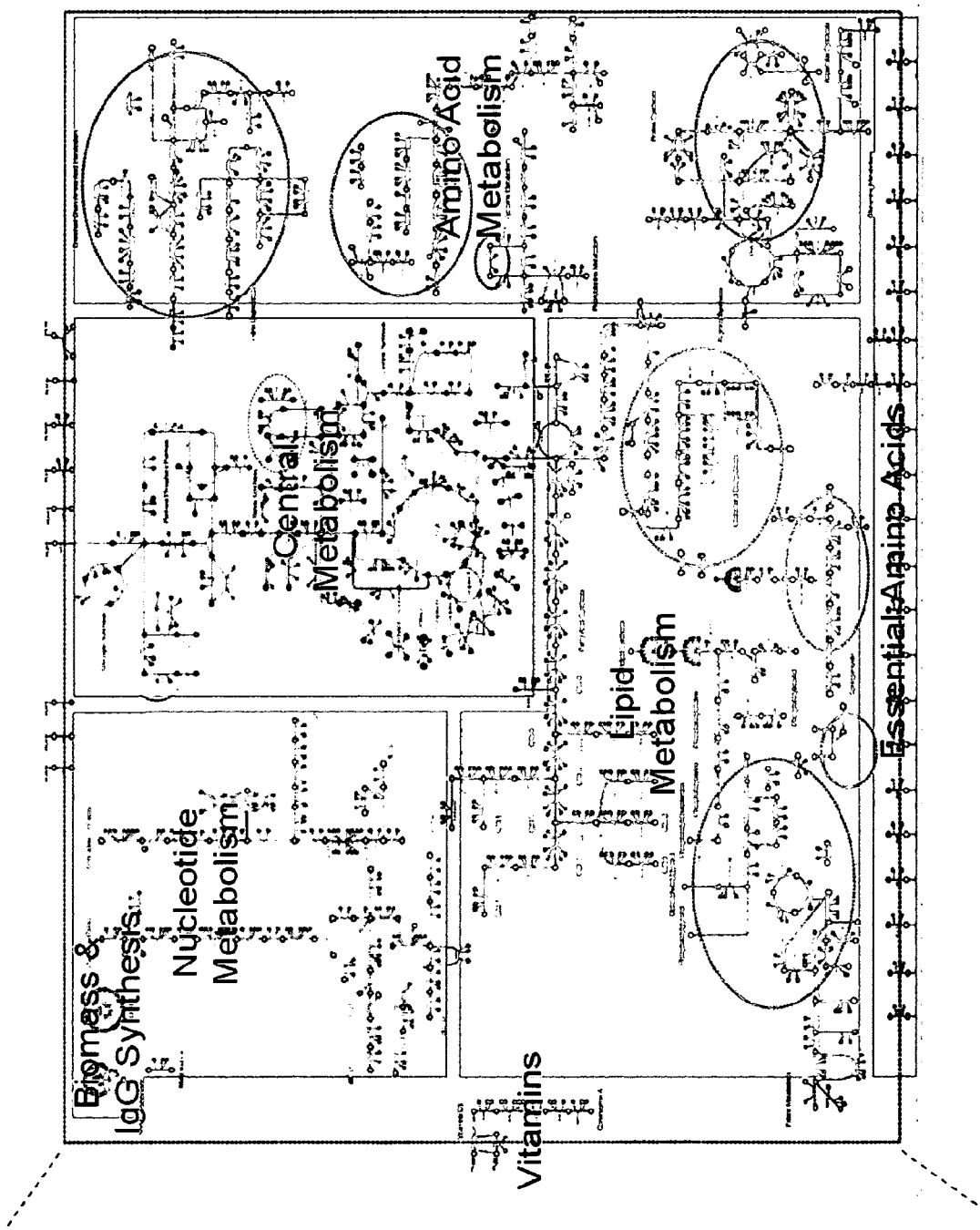

Acids Res 35:D61-D65 (2007); Boutet et al., Methods Mol. Biol. 406:89-112 (2007); Barthelmes, Nucleic Acids Res 35:D511-D514 (2007)). A snapshot of the metabolic map with 470 reactions and 456 metabolites is shown in FIG. 6.

Biomass and Monoclonal Antibody Composition.

In the absence of direct experimental measurements, the biosynthetic composition of a hybridoma cell line was adopted from the published literature and incorporated into the reconstructed network to represent the metabolic requirements of the NS0 cell line for generating one gram of dry cell (Table 1) (Sheikh et al., supra, (2005). Since both cell lines are derived from mouse, the use of hybridoma cell composition for the NS0 cell line was justified.

TABLE 1

Hybridoma biomass composition (adopted from Sheikh, supra, 2005).

| metabolite | mmol/g DW | metabolite | mmol/g DW |
|---|---|---|---|
| alanine | 0.600 | glycogen | 0.279 |
| arginine | 0.377 | dAMP | 0.0148 |
| aspartate | 0.359 | Dcmp | 0.0099 |
| asparagines | 0.288 | dGMP | 0.0099 |
| cysteine | 0.145 | dTMP | 0.0148 |
| glutamine | 0.322 | AMP | 0.0330 |
| glutamate | 0.386 | CMP | 0.0551 |
| glycine | 0.538 | GMP | 0.0624 |
| histidine | 0.143 | UMP | 0.0330 |
| isoleucine | 0.324 | cholesterol | 0.018 |
| leucine | 0.564 | phosphatidylcholine | 0.069 |
| lysine | 0.570 | phosphatidylethanolamine | 0.026 |
| methionine | 0.138 | phosphatidynositol | 0.010 |
| phenylalanine | 0.219 | phosphatidylserine | 0.003 |
| proline | 0.313 | phosphatidylglycerol | 0.001 |
| serine | 0.430 | diphosphatidylglycerol | 0.003 |
| threonine | 0.386 | sphingomyelin | 0.008 |
| tryptophan | 0.044 | ATP | 43.153 |
| tyrosine | 0.182 | | |
| valine | 0.416 | | |

The fatty acid composition was taken from previously measured values obtained from hybridoma cells (Table 2). Metabolic reactions for synthesis of all fatty acids were included in the network based on known biochemical pathways for mammalian fatty acid metabolism (Waterston et al., Nature 420:520-562 (2002); Bronk, Metabolism: Functional Diversity and Integration, Addison Wesley Longman, Essex, England (1999); Devlin, Textbook of Biochemistry with Clinical Correlations, John Wiley and Sons, New York, N.Y. (1997); Salway, Metabolism at a glance, Blackwell Science, Oxford (1999); Vander et al., Human physiology: the mechanisms of body function, McGraw-Hill, New York (1994)). Using cell-specific composition, fatty acid containing compounds such as phospholipids and steroids were also added to the model to correctly account for the lipid composition of the cell (Table 2).

TABLE 2

Fatty acid composition in the metabolic network of NS0 cell line.

| Fatty Acids | M/W (g/mol) | % (g/g lipid) | % (g/g FA) | % (g/mol) | Avg MW (mol/mol) |
|---|---|---|---|---|---|
| C14:0 | 228.4 | 1.5 | 1.538 | 3.514 | 0.019 |
| C16:1 | 254.4 | 6.3 | 6.462 | 16.438 | 0.071 |
| C16:0 | 256.4 | 14 | 14.359 | 36.816 | 0.156 |
| C18:2 | 280.4 | 0.4 | 0.410 | 1.150 | 0.004 |
| C18:1 | 282.5 | 56.6 | 58.051 | 163.995 | 0.570 |
| C18:0 | 284.4 | 10.4 | 10.667 | 30.336 | 0.104 |
| C20:3 | 306.4 | 1.1 | 1.128 | 3.457 | 0.010 |
| C20:2 | 308.4 | 1.3 | 1.333 | 4.112 | 0.012 |
| C20:1 | 310.5 | 4.7 | 4.821 | 14.968 | 0.043 |
| C20:0 | 312.5 | 0.3 | 0.308 | 0.962 | 0.003 |
| C22:1 | 338.5 | 0.9 | 0.923 | 3.125 | 0.008 |
| Total FA | | 97.5 | 100.00 | 278.872 | |

FA, fatty acid;
Avg, average;
MW, molecular weight

In addition, the amino acid composition of a human anti-rabies IgG monoclonal antibody was used to define the protein product in the network. A corresponding reaction was added to represent the formation of IgG in the NS0 cell line by incorporating the amino acid composition of IgG (Table 3) and the total energy requirement for protein synthesis and processing, that is, 4.306 mol ATP/mol IgG (Sheikh et al., supra, 2005). Production of antibody, or other products, including therapeutic products, can be simulated by maximizing an objective function (that is, uptake of nutrients alone or in combination with energy, biomass, and other network reactions) and product formation simultaneously, or maximizing an objective while imposing a constraint for product formation.

TABLE 3

Amino acid composition of a human anti-rabies IgG monoclonal antibody synthesized in NS0 cell line.

| Amino Acid | $mol_{AA}/mol_{MAb}$ |
|---|---|
| Alanine | 0.0618 |
| Arginine | 0.0253 |
| Asparagine | 0.0337 |
| Aspartate | 0.0365 |
| Cystein | 0.0253 |
| Glutamine | 0.0407 |
| Glutamate | 0.0449 |
| Glycine | 0.0843 |
| Histidine | 0.0183 |
| Isoleucine | 0.0211 |
| Leucine | 0.0815 |
| Lysine | 0.0632 |
| Methionine | 0.0126 |
| Phenylalanine | 0.0267 |
| Proline | 0.0702 |
| Serine | 0.1208 |
| Threonine | 0.0772 |
| Tryptophan | 0.0211 |
| Tyrosine | 0.0407 |
| Valine | 0.0941 |

Utilization of Hydrolysate by Mammalian Cell Line.

Figure 7:
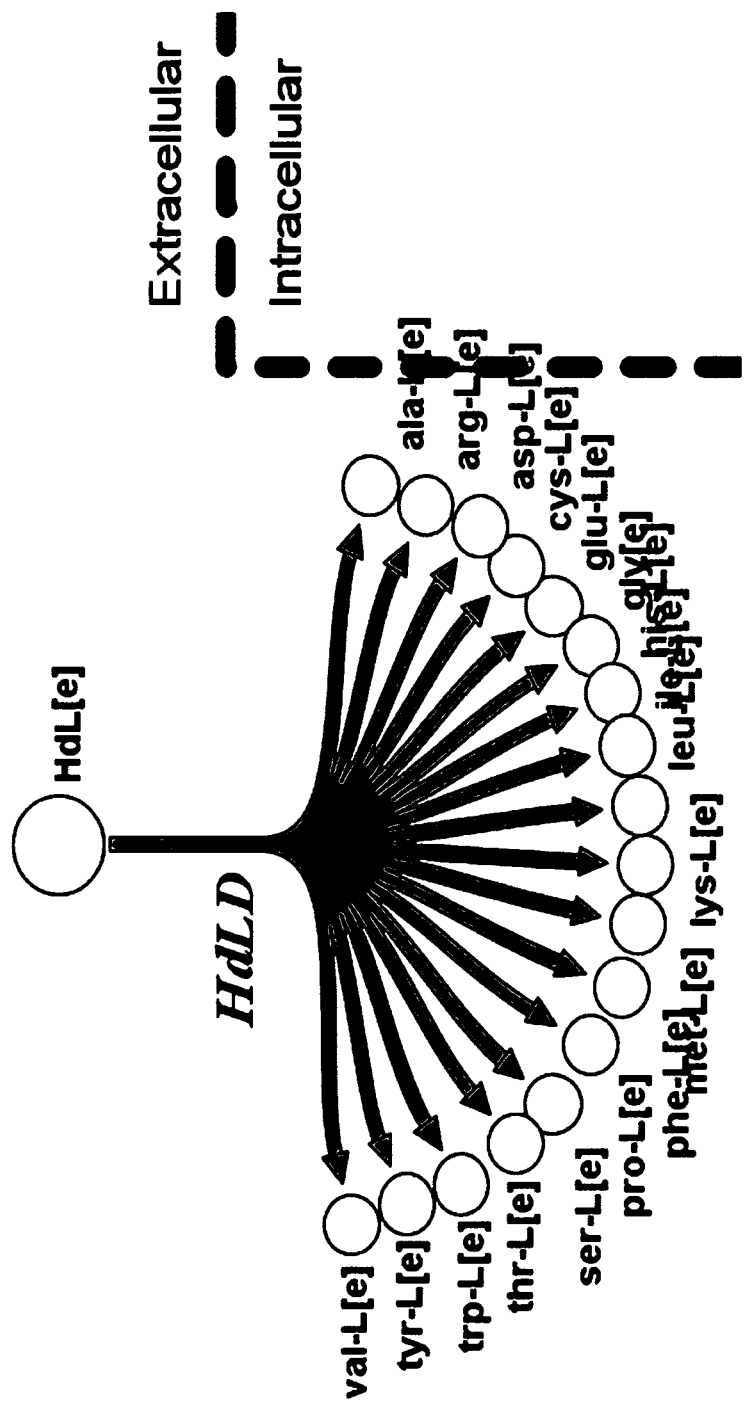
FIG. 7 shows a metabolic network representation of hydrolysate proteolysis in the extracellular space. Proteolysis is assumed to take place outside the cell where an experimentally defined ratio of amino acids (determined based on the hydrolysate's composition) are released and become available to the cell culture media for uptake.

Although the NS0 cell line used in this study did not require the use of protein hydrolysates in the cell culture media, metabolic utilization of hydrolysates can be represented in the reconstructed networks based on an experimentally determined protein composition. The exact mechanism of hydrolysate proteolysis and its utilization is still not fully understood. However, it is widely accepted that protein hydrolysates can be used as a source of amino acids and oligopeptides to enhance growth in cell culture (Schlaeger, J Immunol. Methods 194:191-199 (1996)). If present in the media, protein hydrolysates are represented in the model as an extra-cellular compound with an average amino acid composition determined experimentally. Proteolysis of the hydrolysates is assumed to take place outside the cell, where an experimentally defined ratio of amino acids composing the hydrolysate molecule is released to the extra-cellular amino acid pool (see FIG. 7). The rate of proteolysis is determined using cell culture experimental data using a material balance equation, as described below, and specified in the model.

Cell Culture Experiments and Rate Calculations.

Batch cell culture experiments for parental and an IgG producing NS0 clone grown on chemically defined media were performed. Cell and metabolite concentrations were experimentally measured. Cholesterol-dependent murine NS0 myeloma cells were kept as suspension cultures in polycarbonate shaker flasks incubated on a rotary shaker (120 rpm) at 37° C./5% $CO_2$ in a working volume of 30 mL. Routine passage was performed every third or fourth day at an inoculum density of $3-4\times10^5$ cells/mL. Inocula for experiments were taken from cultures at cell densities of $1.5-2\times10^6$ cells/mL. ExCell NS0™ chemically-defined cell culture media supplemented with 0.4% (v/v) Synthechol™ was used for all experiments. The parental NS0 cell line was cultured in the aforementioned media supplemented with 4 mM L-glutamine, and the IgG producing NS0-GS clone was cultured in the presence of 2% (v/v) GSEM™ to activate the glutamine synthetase expression system. The bioreactors were 5 L.

Braun bioreactors were operated at a working volume of 4 L. Each reactor was controlled via a BioStat DCU and the online process data collected via MFCS. The temperature was controlled at 37.0±0.5° C. with a hot water jacket. The pH was set to 7.30±0.2, and was controlled with on-demand $CO_2$ sparging and a drip addition of a sodium carbonate and sodium bicarbonate mixture. The DO (dissolved oxygen) was set to 50% and was controlled with an on-demand sparge of oxygen. Agitation was performed with dual three bladed marine impellers set to 100 rpm. All four reactors were inoculated at $0.3\times10^6$ viable cells per mL (vc/mL) from a cell stock that was in the mid-log growth phase. Two bioreactors were inoculated with parental cells, and the other two inoculated with the IgG producing clone. Each bioreactor was sampled daily for viability, cell density, offline pH, glucose, glutamine, glutamate, lactate, ammonium, sodium, potassium, amino acids, IgG, and vitamin analysis. Specific uptake and secretion rates of metabolites were calculated using the standard material balance equation during exponential growth, $S-S_o=q_s\int X_v dt$, where S is a consumed nutrient or produced metabolite concentration, $S_o$ is the initial metabolite concentration, $q_s$ is the specific rate constant, and $X_v$ is the viable cell concentration (see, for example, Blanch and Clark, *Biochemical Engineering*, CRC, New York (1997)). Negative values of qs indicate a net uptake while positive values represent a net production. To compute $q_s$, the integral of viable cells was computed using the trapezoid rule and $q_s$ was estimated using a linear regression of $S-S_o=q_s\int X_v dt$ over the exponential cell growth. Cell specific growth rate was computed using standard growth equation, $X_v=X_{v,o}e^{\mu t}$, where $X_{v,o}$ is the initial cell concentration and $\mu$ is cell specific growth rate.

Once the computational representation of metabolism is completed, the reconstructed network can be used to interrogate the network capabilities to synthesize biomass components and energy, determine metabolic network parameters such as growth and non-growth associated energy requirements, validate network behavior by comparing the simulation results to experimental measurements, and design new strategies for media optimization, process development, or cell line engineering. The reconstructed network of NS0, as described above, was used to examine the network capabilities for precursor metabolite and biomass formation. Experimental data was used to determine network parameters, including the growth and non-growth associated energy maintenance values. The accuracy of the network representation was validated by comparing the simulation results to experimental measurements and the model was used to identify media optimization strategies that result in improved cell growth and protein production and reduced byproduct formation (see below).

Example II

Precursor Metabolite, Energy, and Biomass Synthesis in the Reconstructed Metabolic Model of NS0 Cell Line This example describes characteristics of the reconstructed metabolic model of the NS0 cell line.

To assess the network's ability to synthesize biomass components, precursor metabolite formation and energy (ATP) production were simulated using glucose as the sole carbon source. The reconstructed network was able to correctly generate all the precursor metabolites at levels equal or below the maximum theoretical values from glucose, as it was expected and similar to previously reconstructed models for microbial cells such as *E. coli* and *S. cerevisiae* (Forster et al., *Genome Res* 13:244-253 (2003); Varma et al., *Appl. Environ. Microbiol.* 59:2465-2473 (1993)). In addition, using a P/O ratio of 2.5 (Sheikh et al., *Biotechnol Prog.* 21:112-121 (2005); Vo et al., *J. Biol. Chem.* 279, 39532-39540 (2004)), the metabolic model simulated ATP formation at a maximum yield of 32 mol ATP/mol glucose, consistent with a draft network reconstruction of human metabolism in SimPheny™ and previously published values for mammalian cells (Salway, *Metabolism at a glance*, Blackwell Science, Oxford (1999); Vo et al., *J. Biol. Chem.* 279:39532-39540 (2004)).

In the absence of comprehensive thermodynamic, kinetic, or localization information to constrain intracellular fluxes, groups of metabolic reactions in the reconstructed network can potentially be coupled to create cycles that erroneously generate energy and redox potential without carbon expenditure. The NS0 reconstructed metabolic model was tested for network cycles that can freely generate energy and redox potential in the form of ATP, NADH, and NADPH in all cellular compartments. Mitochondrial acyl-CoA dehydrogenase reaction in combination with a set of four other intercellular reactions in the amino acid and central metabolism was identified to generate free ATP in mitochondria. Since the reversibility of this reaction is not well known (according to BRENDA database, Barthelmes et al., *Nucleic Acids Res.* 35:D511-D514 (2007)), acyl-CoA dehydrogenase was constrained to be irreversible in the forward direction in all simulations to prevent the free formation of mitochondrial ATP.

The metabolic network was also tested for its ability to synthesize all the biosynthetic components listed in Table 1. All non-essential amino acids were correctly synthesized from glucose except for cysteine and tyrosine. Amino acids cysteine and tyrosine are considered conditionally essential since their synthesis includes incorporation of essential amino acid precursors. Cysteine is synthesized from methionine, and tyrosine is synthesized from phenylalanine, both of which are essential amino acids in mouse metabolism (see, for example, Sheikh et al., supra, 2005). When the network is supplied with methionine and phenylalanine, cysteine and tyrosine are correctly synthesized in the model. In addition, the network was also tested to verify that the essential amino acid (EAA) biosynthetic pathways are not present in the model and EAAs are available for protein synthesis only by uptake from extra-cellular space, that is, from the media.

The metabolic model requirements for cofactors and vitamins were tested and agreed well with nutritional requirements in mammalian cells. For example, fatty acyl-CoA formation in phospholipid synthesis requires Coenzyme A that is synthesized from pantothenate (vitamin B5). Pantothenate is an essential vitamin in the human and animal diet and is also supplied to mammalian cell lines in the media (Stipanuk, *Biochemical and physiological aspects of human nutrition*, W.B. Saunders Company, Philadelphia, Pa. (2000)). In the metabolic network, lipid synthesis is coupled to pantothenate supplementation, and the network is unable to make biomass in the absence of vitamin B5 intake, as expected.

Choline is another essential nutrient for mammals that is required for the formation of phosphocholine (Atwood, *Oxford Dictionary of Biochemistry and Molecular Biology*, Oxford University Press, USA (2006)). The NS0 metabolic network does not contain any of the reactions for choline synthesis, and to satisfy phospholipid bio synthetic requirements, the metabolic network must take up choline from the extra-cellular space. In the absence of choline supplementation, the NS0 metabolic network is unable to make phosphocholine and biomass, as expected.

Example III

Metabolic Growth Simulation

This example describes simulation of metabolic growth for the NS0 cell line.

To simulate growth in the reconstructed model and to validate the accuracy of the network content, metabolic network parameters including the growth and non-growth associated energy requirements were determined using experimental data, and the model predictions were validated by comparing the simulation results to experimental measurements.

Metabolite Uptake and (By)Product Secretion Rate Constraints in the NS0 Metabolic Model.

To simulate cell physiology in a bioreactor, metabolite uptake and secretion rates and protein and biomass formation rates were calculated from cell culture data, as described above. The maximum uptake of input nutrients, or the maximum limit on nutrient uptake constraints in the model, was set to the rates calculated from the experimental data and the minimum values were constrained to zero, so the uptake of nutrients could vary between zero and experimentally determined values. Similarly, the minimum growth and antibody production rates, or the minimum limit on the biomass and protein production, were constrained to experimental values and maximum production was set to be unlimited, to ensure that the model produces protein and biomass at least at rates equal to experimentally determined values.

Due to experimental error or low sensitivity of analytical methods used for detecting metabolite concentrations, uptake of essential amino acids may be lower than the required values for protein production and cell growth. A minimum uptake rate for each essential amino acid was calculated using the metabolic network by constraining the minimum growth and antibody production rates to experimental values as described above, allowing unlimited amount of all nutrients to be taken up, and minimizing the uptake of essential amino acids in the model. Where the calculated minimum uptake rates for essential amino acids exceeded experimental measurements, the calculated values were used to define the maximum limit on uptake rates in the simulations.

Energy Requirements in Parental and Antibody-producing Clone.

Figure 8:
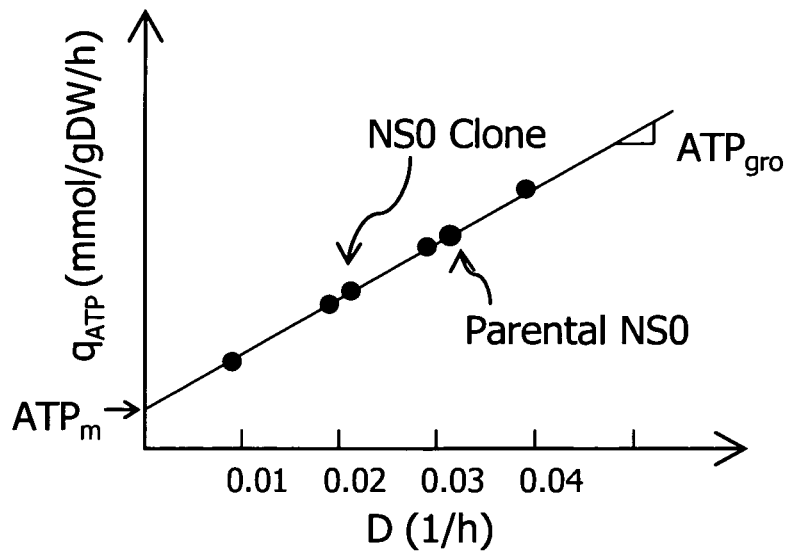
FIG. 8 shows a determination of the energy parameters in a metabolic network. The slope of ATP production ($q_{ATP}$) versus dilution rate (or growth rate) provides an estimate of the growth-associated energy requirements in the cell. The non-growth associated maintenance, or ATPm, is estimated at the y-intercept where D=0.

Procedures for calculating the energy requirements for growth and non-growth associated activities are well established (Varma et al., *Appl. Environ. Microbiol.* 59:2465-2473 (1993)). The growth associated energy requirement is the amount of energy used for all activities that result in biomass synthesis or growth. The non-growth associated requirement is the amount of energy needed for maintaining all other activities in the cell, including motility, pH and osmotic balance, and such. Growth ($ATP_{gro}$) and non-growth ($ATP_m$, for maintenance energy) associated energy requirements can be estimated from cell culture data collected at different growth rates (FIG. 8), by setting all the input/output rates equal to the experimental values in each growth experiments, and maximizing ATP hydrolysis reaction to compute $q_{ATP}$. The growth associated energy requirement is estimated from the slope of $q_{ATP}$ over growth rate, or dilution rate, and the maintenance energy is determined at the y-intercept where growth is zero.

For NS0 cell line, only one growth rate experiment was performed for the parental and IgG-producing clone (see FIG. 8, green and pink circles), and $ATP_{gro}$ and $ATP_m$ could not be determined separately. As a result, the energy requirements were lumped into one parameter represented by $ATP_{lumped}$, which was assumed not to change significantly in different media or cell culture conditions. $ATP_{lumped}$ was calculated by constraining the uptake and secretion rates in the model to experimental values and maximizing intracellular ATP hydrolysis reaction in the parental (1.782 mmol/gDW/h) and IgG-producing (1.009 mmol/gDW/h) models. The lumped energy requirements were specified respectively in each model as a fixed demand constraint and were used in all growth and media optimization simulations.

Sensitivity Analysis of Energetic Parameters.

Figure 9:
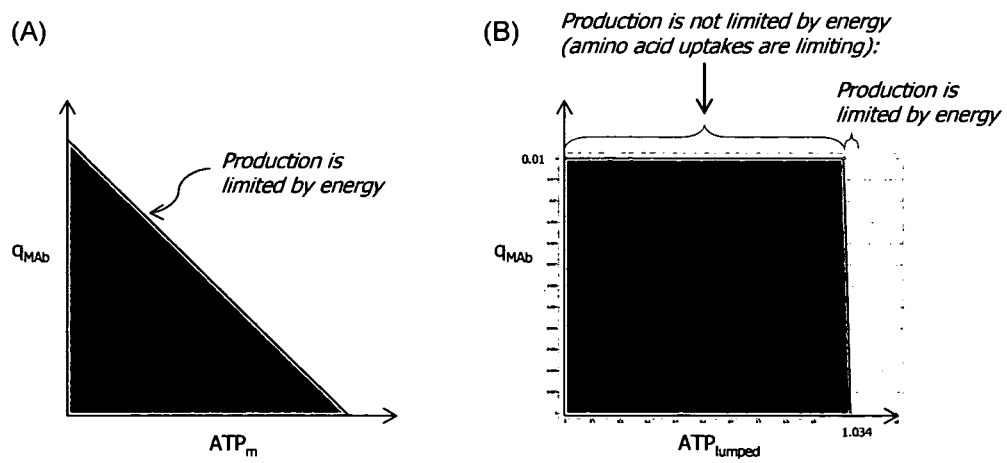
FIG. 9 shows the effect of energy parameter on product formation.

Production of a chemical or product of interest in microbes, where substrate is limiting for energy formation, can be greatly hampered by the growth and non-growth associated energy demands in the cell. If product formation is energy limited, reduction in the energetic parameters in the network can potentially improve production rates in the cell (see FIG. 9A), that is, by lowering the energy requirement of the network or increasing ATP synthesis, product formation can improve.

To determine whether product formation in NS0 is sensitive to the energetic parameters in the network, the maximum monoclonal antibody (MAb) formation rate was calculated when the amount of $ATP_{lumped}$ varied from zero to 1.034 mmol/gDW/h. Results showed that energetic of the network becomes limiting for protein production only at very high $ATP_{lumped}$ values, that is, between 1.009 and 1.034 mmol/gDW/h. For $ATP_{lumped}$ values of up to 1.009 mmol/gDW/h, protein production is limited instead by the uptake of amino acids in the media.

Bioreactor Simulation and Metabolic Objective Function During Exponential Growth.

In constraint-based modeling, an optimal metabolic flux distribution in a metabolic network is calculated by maximizing or minimizing a biologically meaningful objective function. Previously utilized objective functions in metabolic networks include optimal growth as a combination of biomass components, minimization of ATP production, minimization of the total nutrient uptake, or the minimization of system perturbations, that is, homeostasis (Savinell and Palsson, supra, 1992b; Bonarius et al., *Biotechnol Bioeng* 58:258-262 (1998); Segre et al., *Proc. Natl. Acad. Sci. USA* 99:15112-15117 (2002)). In mammalian cell line models, a variety of objective functions have been tested to simulate growth and protein production (see Table 4). In a mouse hybridoma model, the objective functions used were minimizing ATP production, minimizing moles nutrient uptake, minimizing mass nutrient uptake, and minimizing NADH production (Savinell and Palsson, supra, 1992a). Although no single objective was found to govern cell behavior, minimizing redox production gave results that were most similar to hybridoma cell behavior. A model based on Shiekh et al., supra, 2005, correctly predicted growth, lactate, and ammonia production when glucose, oxygen, and glutamine uptake was constrained to experimentally measured values. However, the model did not predict the production of alanine and did not provide any explanation for why animal cells oxidize glutamine partially.

TABLE 4

Previously tested objective functions in constraint-based mammalian cell line models.

| FBA-based Metabolic Models | Objective Functions used in the Study |
| --- | --- |
| Savinell and Palsson, supra, 1992a | Minimizing ATP production<br>Minimizing moles nutrient uptake<br>Minimizing mass nutrient uptake<br>Minimizing NADH production |
| Sheikh et. al., supra, 2005 | Maximizing growth<br>Minimizing substrate uptake rate<br>Maximizing the production of monoclonal antibody |

Figure 10:
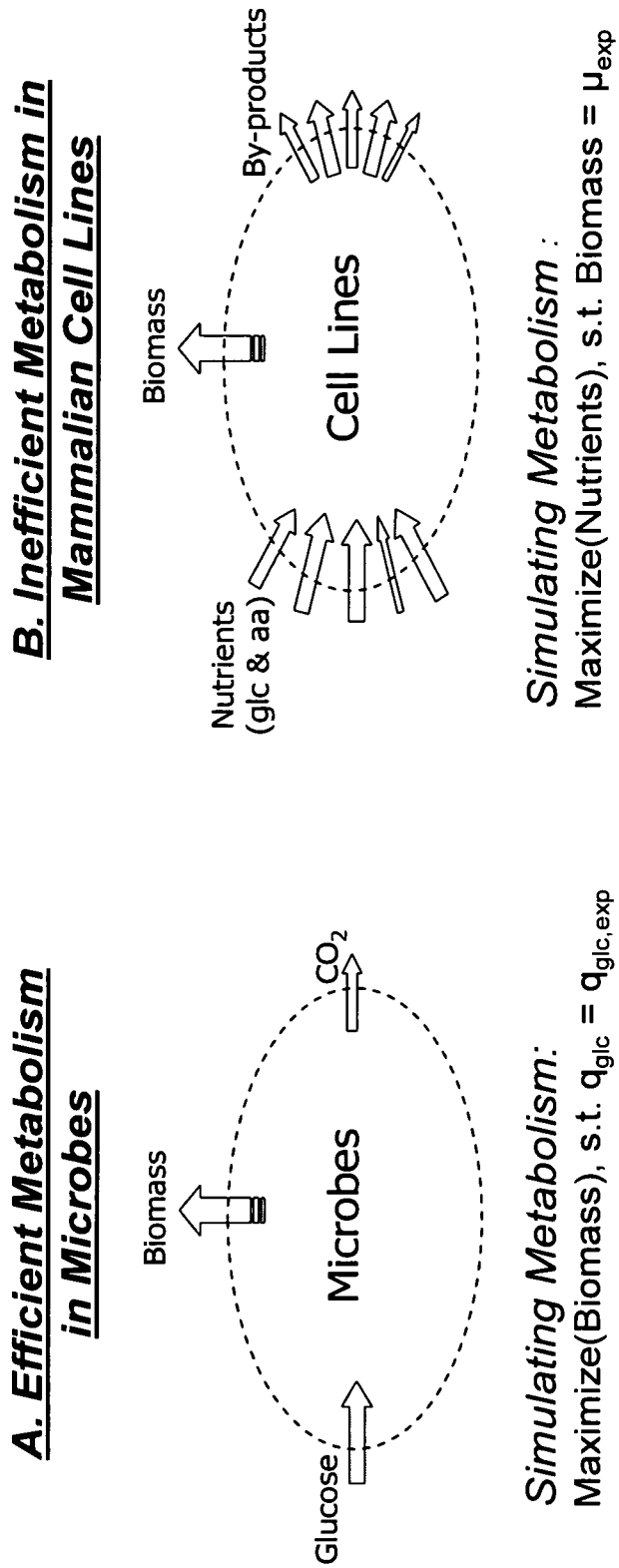

Analysis of cell culture data, in the context of metabolic network, showed that uptake of input nutrients exceeds the minimum requirements for growth, monoclonal antibody production, and energy requirements in the cell. This demonstrates that, unlike microbial cells, the doubling time and product formation in mammalian cell lines is slow and not limited by metabolic uptake. As a result, the cells exhibit an inefficient metabolism, where large amounts of nutrients are taken up and large quantities of byproducts are formed in the cell culture (FIG. 10B). This metabolic inefficiency may reflect the growth conditions mammalian cells are adapted to in cell culture or animal tissue, where ample amounts of nutrients are available for growth and energy synthesis. Thus unlike microbes, mammalian cells have not evolved to optimize their metabolism by maximizing the use of available nutrients for growth and energy production, and instead they take up more nutrients than is needed and create large amounts of byproduct wastes in the process. This metabolic inefficiency can be mathematically represented in the reconstructed model as the maximization of the nutrient uptake rates.

To validate the accuracy of this objective function, cell culture data was simulated in the model for a parental, that is, a non-producing cell line, and an IgG producing NS0 clone. The simulation results were benchmarked by comparing byproduct secretion rates to experimental measurements (Table 5). The results show that the metabolic model was able to correctly capture NS0 cell line growth and metabolite uptake and secretion rates in a batch bioreactor for both the parental and IgG producing NS0 clone. Major differences between the simulated values and experimental measurements (shown in red/italics in Table 5) resulted from the difference in essential amino acid requirements of the cell for growth and product formation. As described above, this is due to experimental error, low sensitivity of analytical methods for measuring metabolite concentrations, or inaccurate biomass composition used in the network. Other differences between the simulation results and experimental values (shown in blue/bold Table 5) may result from inaccurate representation of metabolism in the network, absence of metabolic or regulatory constraints used in the simulations, or experimental measurements.

The results for bioreactor simulations provided a demonstration for the applicability of the model to capture NS0 cell physiology and created a baseline for developing model-driven media optimization strategies to reduce byproduct formation (see Example V). It must be noted that the simulation results also showed small production of urea to balance nitrogen in the network. This may be due to experimental error, undetected uptake or secretion of nitrogen containing compounds, or incorrect representation of metabolic pathways in the model. Since elemental balance of nitrogen in the experimental data, independent of the metabolic model, indicated an imbalance in total nitrogen being used and produced in cell culture, further investigation of media components including the presence of urea should provide additional insights about the sensitivity of experimental measurements, incompleteness of experimental protocol, and/or metabolic pathways in NS0 cells.

TABLE 5

Batch bioreactor simulations for the parental (parental bioreactor) and an IgG producing clone (clone bioreactor).

| Parent Bioreactor | | Exp Data | Simulation | Clone Bioreactor | | Exp Data | Simulation |
| --- | --- | --- | --- | --- | --- | --- | --- |
| Growth Rate | | 0.033 | 0.033 | Growth Rate | | 0.028 | 0.028 |
| Glucose | | −0.774 | −0.774 | Glucose | | −0.202 | −0.202 |
| Glutamine | | −0.135 | −0.135 | Glutamine | | 0.000 | 0.000 |
| Glutamate | | 0.015 | 0.015 | Glutamate | | −0.015 | −0.015 |
| Lactate | | 1.513 | 1.499 | Lactate | | 0.311 | 0.311 |
| NH4 | | 0.084 | 0.084 | NH4 | | −0.016 | −0.016 |
| IgG | | 0.000 | 0.000 | IgG | | 0.012 | 0.012 |
| Alanine | | 0.029 | 0.029 | Alanine | | 0.015 | 0.015 |
| Arginine | | −0.019 | −0.019 | Arginine | | −0.047 | −0.047 |
| Asparagine | | −0.010 | −0.010 | Asparagine | | −0.010 | −0.010 |
| Aspartate | | 0.000 | 0.000 | Aspartate | | 0.000 | 0.000 |
| Cysteine | CE | −0.009 | −0.009 | Cysteine | CE | −0.005 | −0.005 |
| Glycine | | 0.003 | 0.003 | Glycine | | −0.002 | −0.002 |
| Histidine | E | −0.005 | −0.005 | Histidine | E | −0.003 | −0.003 |
| Isoleucine | E | −0.017 | −0.017 | Isoleucine | E | −0.020 | −0.020 |

TABLE 5-continued

Batch bioreactor simulations for the parental (parental bioreactor) and an IgG producing clone (clone bioreactor).

| Parent Bioreactor | | Exp Data | Simulation | Clone Bioreactor | | Exp Data | Simulation |
|---|---|---|---|---|---|---|---|
| Leucine | E | −0.022 | −0.022 | Leucine | E | −0.023 | −0.023 |
| Lysine | E | −0.017 | −0.017 | Lysine | E | −0.010 | *−0.014* |
| Methionine | E | −0.007 | −0.007 | Methionine | E | −0.004 | −0.004 |
| Phenylalinine | E | −0.007 | −0.007 | Phenylalinine | E | −0.004 | *−0.007* |
| Proline | | −0.002 | −0.002 | Proline | | −0.011 | −0.011 |
| Serine | | 0.001 | 0.001 | Serine | | −0.003 | −0.003 |
| Threonine | E | −0.014 | −0.014 | Threonine | E | −0.008 | *−0.011* |
| Tryptophan | E | 0.000 | *−0.002* | Tryptophan | E | 0.000 | *−0.002* |
| Tyrosine | CE | −0.005 | −0.005 | Tyrosine | CE | −0.004 | −0.004 |
| Valine | E | −0.016 | −0.016 | Valine | E | −0.017 | −0.017 |

Positive (negative) numbers correspond to production (uptake) rates.
Bold indicates values within the experimental range;
italics indicates values outside the experimental range.
Rates are shown in units of mmol/gDW/h, except for growth rate which is in unit of 1/h.
CE—conditionally essential
E—essential amino acid

Example IV

Metabolic Network Analysis for Byproduct Formation

This example describes metabolic network analysis for byproduct formation.

Figure 11:
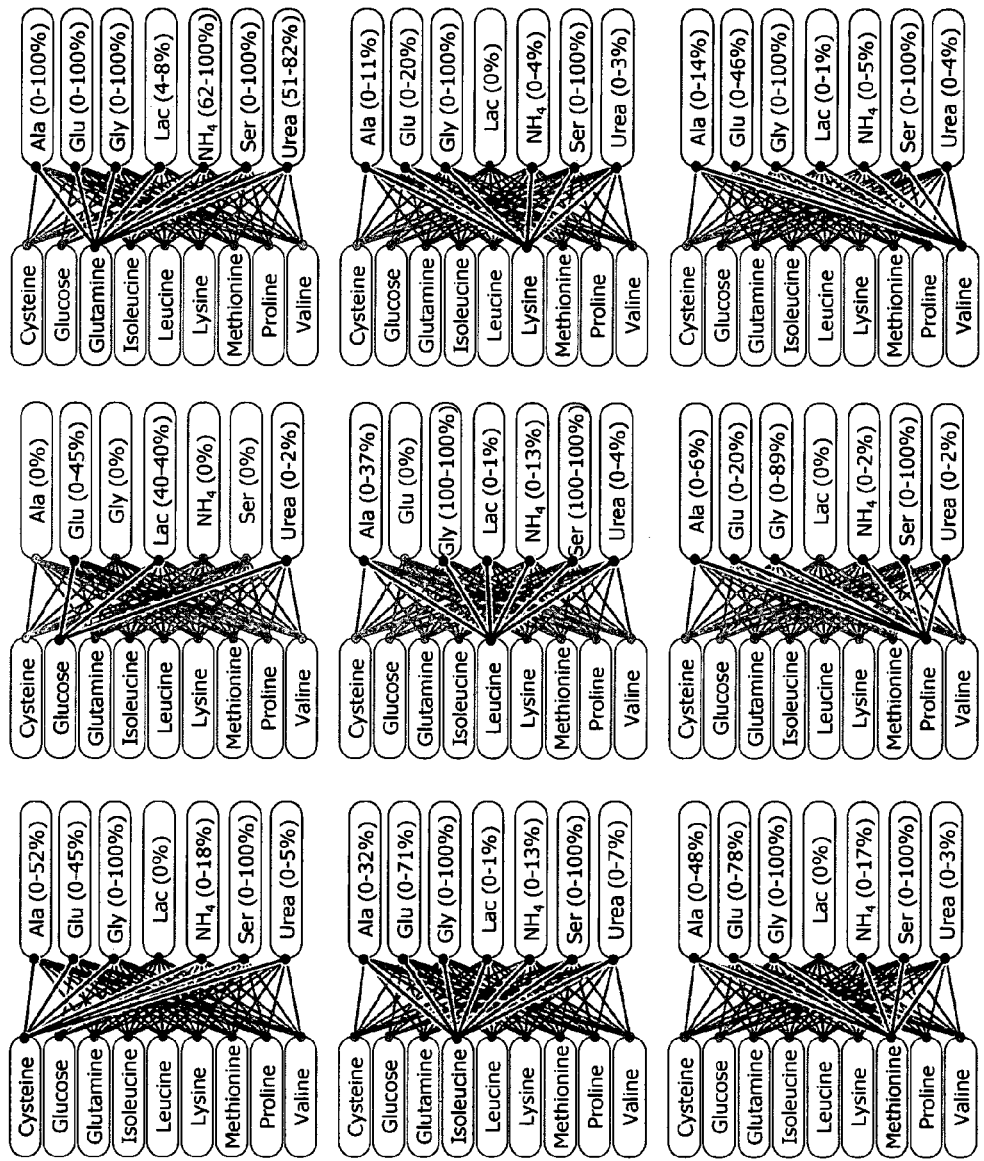
FIG. 11 shows nutrient contribution to byproducts formation in the parental GS-NS0 cell line. The highlighted nutrients (on the left hand side of the connectivity diagrams) and the corresponding byproducts formed (on the right hand side) are shown in each sub-panel. The range of minimum and maximum contribution of each byproduct formation from individual nutrients is shown in percent contribution.
Figure 12:
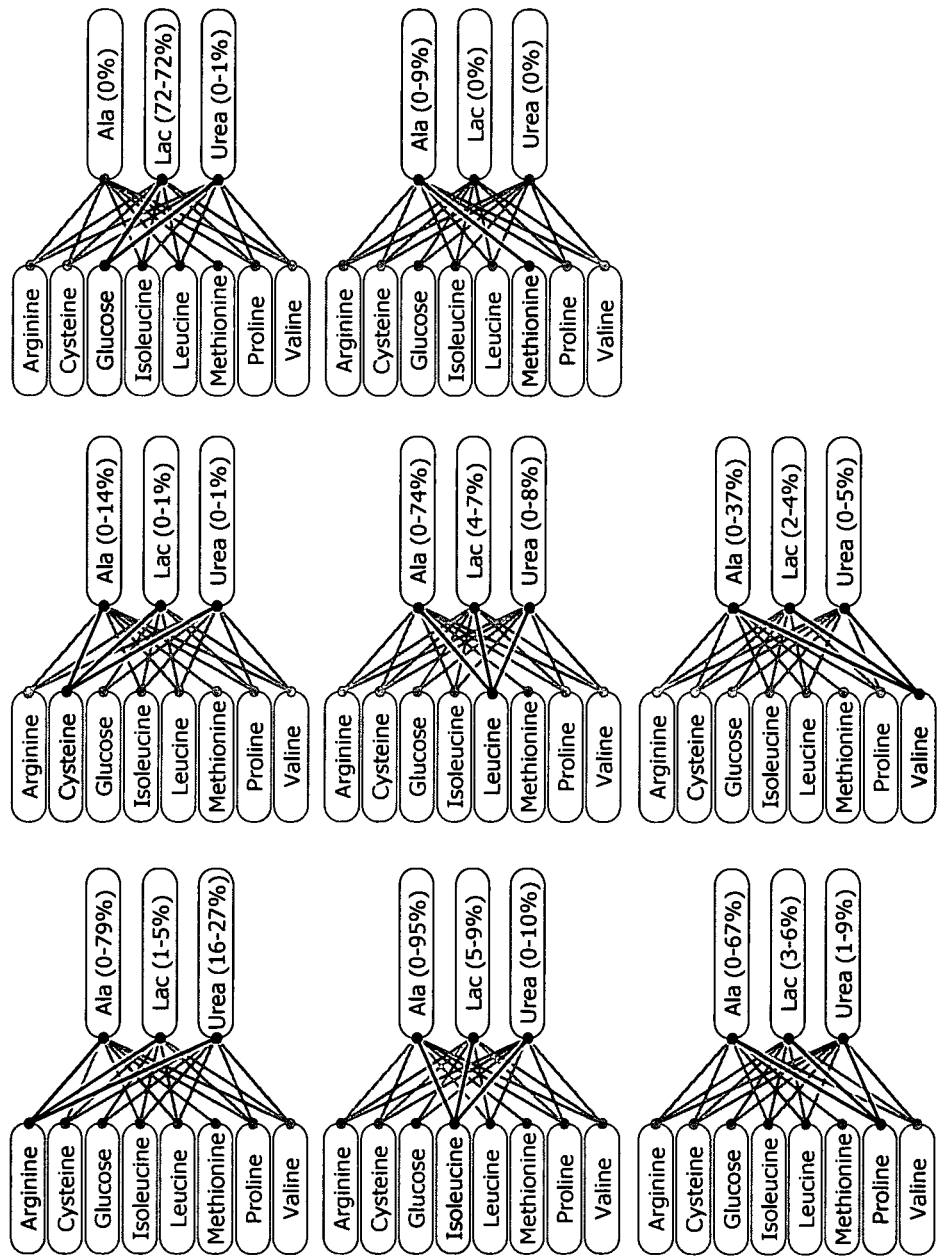
FIG. 12 shows nutrient contribution to byproducts formation in the IgG producing GS-NS0 cell line. The highlighted nutrients (on the left hand side of the connectivity diagrams) and the corresponding byproducts formed (on the right hand side) are shown in each sub-panel. The range of minimum and maximum contribution of each byproduct formation from individual nutrients is shown in percent contribution.

To gain a more in-depth understanding of metabolism in the host cell line, the reconstructed model was used to study the underlying metabolic factors that contribute to byproduct formation, growth, and protein production in NS0 cell line. Contribution of input nutrients to byproduct formation in NS0 cell culture was studied by minimizing the byproduct formation in the parental and clone simulations, identifying what nutrient uptake rates were changed compared with the results shown in Table 5, constraining all those nutrient uptake rates to the new values except for one, and determining the minimum and maximum rate of byproduct formation that result from excess uptake of one nutrient at a time (FIGS. 11 and 12). The range of byproduct formation and the maximum contribution of each nutrient to the formation of cell culture byproducts provide evidence about the mechanism and importance of nutrient overload in the metabolic network.

Non-zero lower values signify that production of a byproduct is guaranteed in the presence of excess nutrient uptake. Nutrients with non-zero lower byproduct contribution thus form a high priority list of media components that can be manipulated experimentally to lower byproduct secretion in cell culture. As an example, the results show that the main source of lactate formation in both the parental and clone cell line is excess amount of glucose uptake, which agrees well with conclusions made previously in published literature, implicating glucose as the main contributor to lactate production in NS0 cell culture (Xie et al., *Trends Biotechnol* 15:109-113 (1997)). The model also shows that the main source of ammonium formation in the parental NS0 cell line is glutamine (FIG. 11), and when glutamine synthetase is added to the NS0 model in a glutamine-free media simulation, ammonium secretion ceases (FIG. 12), agreeing again with the observed characteristics of a GS-NS0 cell culture (Barnes et al., *Cytotechnology* 32:109-123 (2000)).

Percent contribution of byproduct formation based on the results obtained from metabolic network analysis can be further investigated using isotopomer labeling experiments. Although isotopomer labeling experiments were not performed here, analysis of metabolic networks for mammalian cell culture can clearly generate testable hypotheses that further the understanding of metabolism in mammalian cell lines.

Example V

Model-Driven Media Design

This example describes the development of optimized media based on a reconstructed model of the NS0 cell line.

Metabolic simulation of the NS0 cell culture and network analysis of the NS0 cell line for byproduct formation demonstrated that the reconstructed model can correctly capture NS0 cell metabolism and thus be used to identify strategies for byproduct reduction. To develop optimized media formulations for NS0 cell line, the reconstructed model of NS0 was used to identify model-driven media formulations that support growth and antibody production with lower lactate, alanine, and urea production rates in the antibody producing clone. Bioreactor cell culture data for the IgG producing clone (Table 3) was used as the "base case" to design optimized media in silico and to benchmark the improvements in productivity in the subsequent experiments. Since lowering metabolite concentrations in the basal medium required developing a new formulation and entailed extensive effort, nutritional supplementation to the basal medium was considered only and any strategies for lowering the concentration of media components was excluded initially. In addition, media optimization was performed only for the IgG producing clone and not the parental cell line to target both byproduct reduction and antibody production.

To determine nutritional changes that lower byproduct formation in NS0 cell culture and to benchmark the model-driven media optimization approach, three media design strategies were identified using the metabolic model and experimental data: model-based formulation to minimize byproduct formation; model-based media formulation to increase growth and product formation; and data-based media formulation to add depleted nutrients derived from cell culture bioreactor data.

Using linear optimization and the reconstructed network of NS0 cell line (see Example I), media formulations that minimize byproduct formation, maximize growth rate and IgG production, with nutrient uptake rates of equal or higher than the base case values, were identified. The model was also used to determine the limiting nutrients for biomass, that is, growth, and product (IgG) formation using the metabolic model. And finally, a set of nutrients was identified that appeared to be depleted from the media solely based on the cell culture data, as it is traditionally done in a depletion analysis, to benchmark the advantage of a rational modeling approach over the existing media and process optimization techniques.

Figure 13:
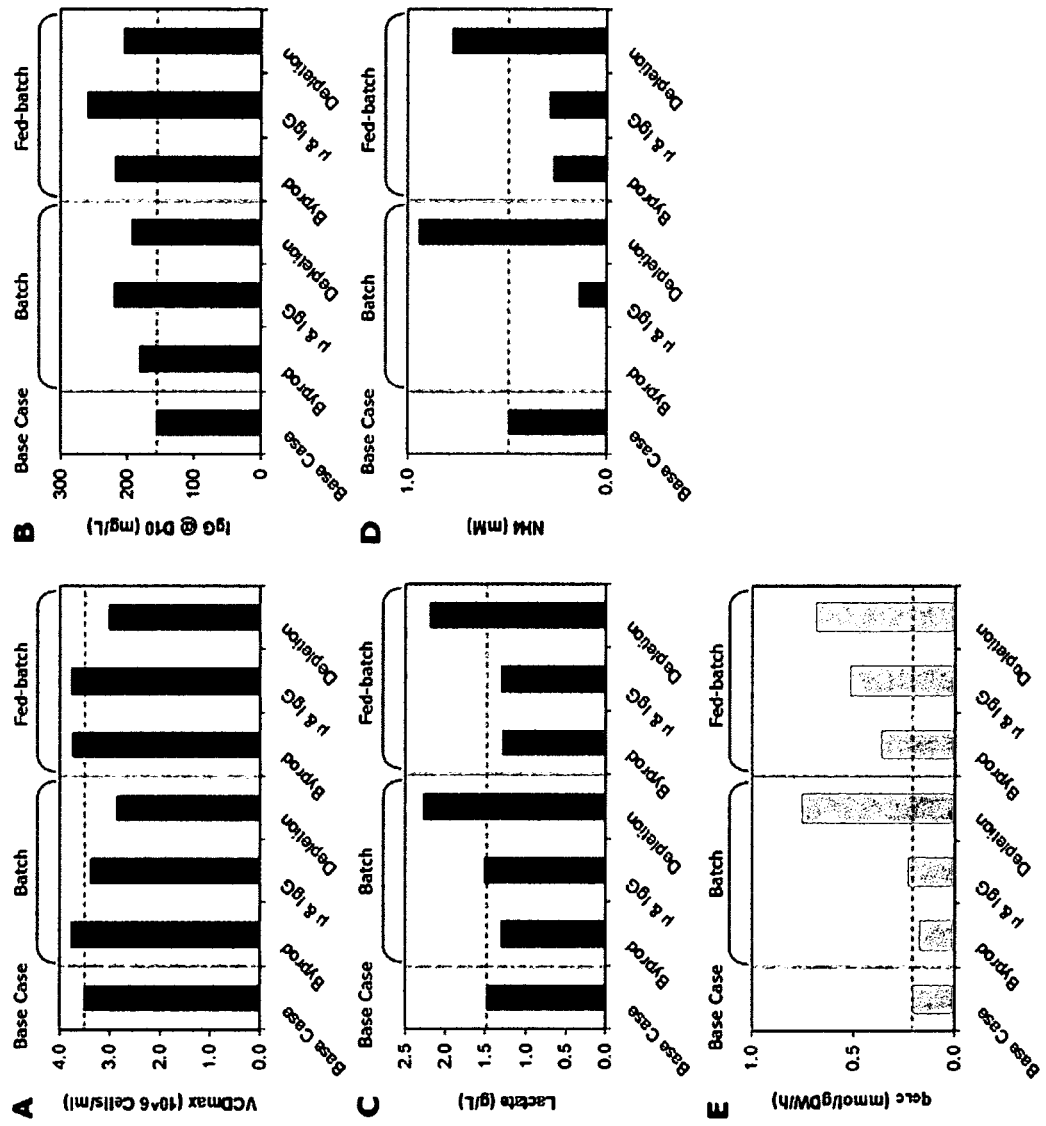
FIG. 13 shows experimental results from the validation studies. The dashed line designates the base case experimental values, that is, before media optimization. 'Byprod', media optimization for byproduct reduction; 'μ&IgG', media optimization for growth and product increase; 'Depletion', media optimization using traditional depletion analysis; VCD, viable cell density; qGLC, rate of glucose uptake. Horizontal dashed lines mark the base case values.
Figure 14:
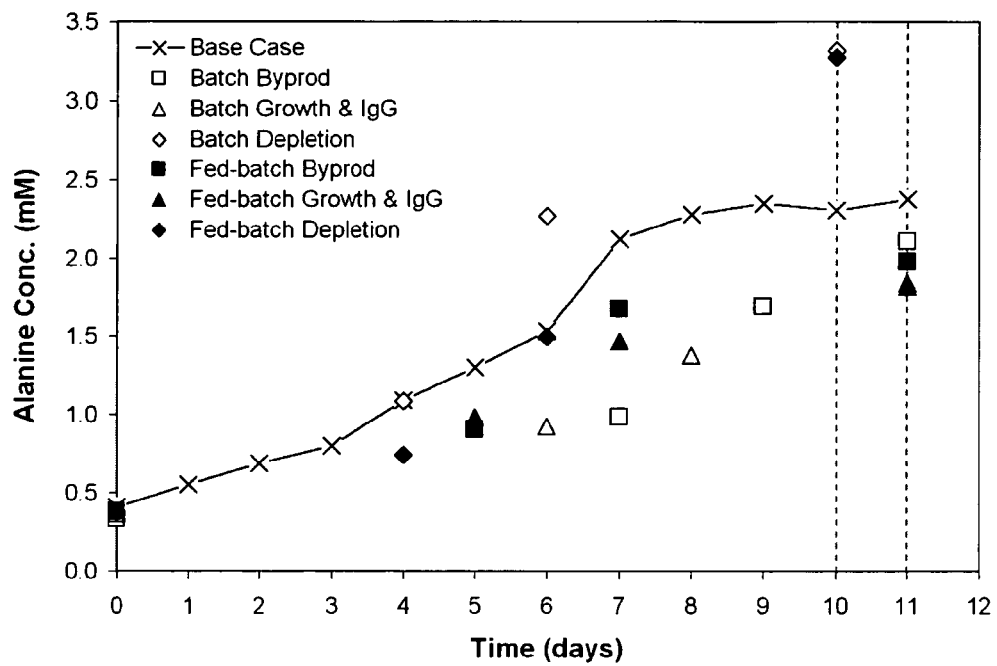
FIG. 14 shows alanine concentration from the validation studies. Amino acid analysis of cell culture media was done only on selected days (data points show measurements on the corresponding days for each bioreactor). Cumulative concentration of alanine at the end of the experiments (that is, on day 10 or 11) are highlighted by the vertical dashed lines. Compared with the 'base case', both types of model-driven media formulations showed lower alanine secretion (black and white square and triangles). However, in both the batch and fed-batch 'depletion' analysis, the total alanine concentration exceeded the 'base case' (black and white diamonds).

To test the model-driven media designs, seven cell culture experiments were performed by increasing the concentration of selected amino acids in the basal medium by three-fold (Table 6). The bioreactors were set up, controlled, and analyzed in the same manner as the previous experiments (see Example I), using only the NS0 clonal cells for cell culture. One bioreactor was used with no change in media formulation as control. Amino acids were fed to the batch bioreactors (Experiments 2-4 of Table 6) just before inoculation on day zero. The last three bioreactors (fed-batch Experiments 5-7 of Table 6) were each fed one bolus of corresponding formulation on day three. All bioreactors were stopped on day ten or eleven.

in experiments 3 and 6, respectively. The viable cell density in experiment 3 and 6 remain approximately the same as the "base case" (FIG. 13A). Also, the final lactate, ammonium, and alanine concentrations were lowered compared with the "base case" values, even though the formulation was not designed specifically for a reduced byproduct formation (FIGS. 13C and 13D and FIG. 14). A lower byproduct formation was coupled with a higher glucose uptake rate, as shown in FIG. 13E, indicating a shift in metabolic utilization of glucose towards product synthesis and away from byproduct formation. As with the model-driven media designs for reduced byproduct formation, media formulation for increased growth and productivity showed higher specific productivity compared with the "base case" (up to 86%).

Depletion analysis, commonly used in mammalian cell culture, showed the least amount of improvement in terms of byproduct reduction, maximum viable cell density, and final product titers. The product titers in the "depletion" studies did increase compared with the "base case," which explains why depletion analysis has gained popularity in cell culture

TABLE 6

Experimental set-up for in silico media validation. Plus signs refer to the added amino acids to the basal media. Byprod, byproduct; $\mu$, growth rate.

| Nutrients | No-fed Control | Batch Bioreactor | | | Fed-batch Bioreactor | | |
| --- | --- | --- | --- | --- | --- | --- | --- |
| | | Lower Byprod | Higher μ and IgG | Depleted Nutrients | Lower Byprod | Higher μ and IgG | Depleted Nutrients |
| Arginine | | | | + | | | + |
| Cysteine | | | | + | | | + |
| Glutamate | | | | + | | | + |
| Glycine | | + | | + | + | | + |
| Histidine | | + | + | | + | + | |
| Leucine | | | | + | | | + |
| Lysine | | + | + | | + | + | |
| Phenylalinine | | | + | | | + | |
| Threonine | | + | + | | + | + | |
| Tryptophan | | | + | + | | + | + |
| Tyrosine | | + | + | | + | + | |
| Experiments | 1 | 2 | 3 | 4 | 5 | 6 | 7 |

Figure 15:
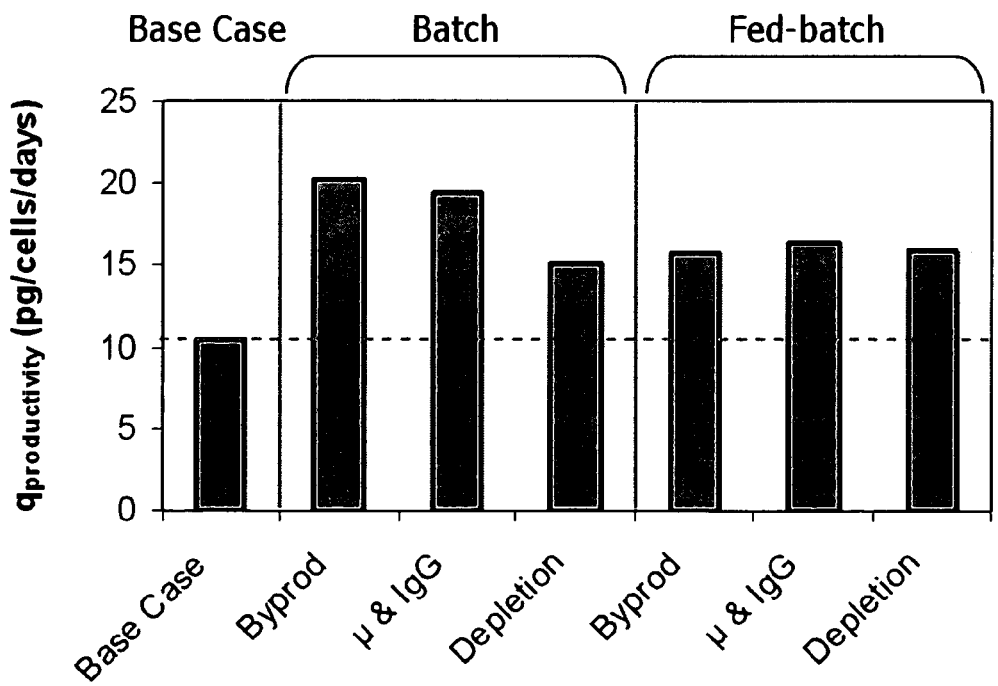
FIG. 15 shows average specific productivity in media- and data-driven optimization designs. Horizontal dashed line marks the base case value.

Results from the validation studies (FIGS. 13-15) clearly showed significant improvement in the model-driven media formulations over both the "base case" and the "depletion" analysis results. Since the implementation of media designs was done in a qualitative fashion, results are also compared qualitatively. In all the experiments, growth rate of the cell culture remained the same, that is, 0.02 l/h. An increase in growth rate was not expected to occur since, in batch culture, cells generally reach maximum growth rate (Blanch and Clark, *Biochemical Engineering*, Marcel Dekker, Inc., New York (2007)). The cell culture for "byproduct" reduction (that is, experiments 2 and 5) and higher "$\mu$ and IgG" production (that is, experiments 3 and 6) showed significant improvements compared with the "base case" and the "depletion" study. Maximum viable cell density in batch and fed-batch "byproduct" experiments increased by approximately 7% compared with the "base case" (FIG. 13A). In addition, byproduct formation of lactate, ammonium, and alanine was clearly lowered in the "byproduct" reduction experiments (FIGS. 13C and 13D and FIG. 14), while higher product titers (up to 41%) and specific productivity (up to 93%) was achieved (FIG. 13B and FIG. 15).

Similarly, media formulation for increased "$\mu$ and IgG" production showed significant increase in product titers, that is, 41% and 67% increase over the "base case" product titers protein production. Although the final product titers were improved in both of the "deletion" runs, percent increase was half as much as the designs generated for increased growth and productivity. that is, only 24% and 31% increase over the "base case" product titers were observed in experiments 4 and 7, as opposed to 41% and 67% in experiments 3 and 6. In addition, the highest byproduct concentrations were observed in the "depletion" studies among all other bioreactors (FIGS. 13C and 13D and FIG. 14). High concentrations of lactate and ammonium in the "depletion" runs correlate with a considerably higher uptake of glucose in those experiment (FIG. 13E), confirming the earlier analysis described in Example I that identified glucose as a major contributor to lactate and nitrogen secretion in the cell culture.

Although implemented in a qualitative manner, a model-driven media optimization approach clearly shows significant improvements in byproduct reduction, cell growth, and productivity over methods commonly used in mammalian cell culture. More effective implementation of this approach, however, requires quantitative formulation of media composition through a comprehensive media and process optimization framework that allows the calculation of media concentrations from model-based metabolite uptake and secretion rates.

In general, media optimization strategies can be designed for reducing byproduct formation, reducing media nutrients, increasing growth rate, increasing cell productivity, and their combinations (Table 7). As shown here, a preliminary analysis of scenario 1.B in Table 8 has been performed and experimentally tested, that is, byproduct reduction by nutrient addition. Other aspects of cell culture protein production including byproduct reduction, biomass and productivity increase, and nutrient uptake reduction as a means for improving the product yield can also be tested. Since it is generally believed that byproduct formation results from an overflow of excess nutrients, reducing nutrient concentrations may prove to be a more effective approach in improving product yield and reducing byproduct formation. Using this approach, the in silico media formulations can be rank-ordered based on the highest growth and productivity increase and byproduct reduction and tested experimentally using mammalian cell culture.

models; increased utilization of selected amino acids may increase monoclonal antibody and biomass production in the cell; high lactate formation results from excess uptake of glucose; and incomplete oxidation of supplied glutamine in the parental cell line may contribute to the large secretion of ammonium. Constraint-based modeling as applied to mammalian cell line metabolism can thus be used to quantitatively compute and analyze metabolism in production cell lines and to gain fundamental understanding of cell physiology and protein production.

Example VI

Modeling CHO Cell Lines

This example describes modeling of CHO cell lines.

Currently, most cell and process development strategies are performed using a trial and error approach where process

TABLE 7

Media optimization scenarios for NS0 cell line.

| Media Optimization Scenarios | A. Nutrient Removal | B. Nutrient Addition |
|---|---|---|
| Byproduct Reduction | $\min(q_{byproducts})$ <br> subject to: $0 \leq q_{nutrients} \leq q_{max,exp}$ | $\min(q_{byproducts})$ <br> subject to: $0 \leq q_{nutrients} \leq \infty$ |
| Nutrient Reduction | $\min(q_{nutrients})$ <br> subject to: $0 \leq q_{nutrients} \leq q_{max,exp}$ | N/A |
| Growth Increase | $\max(\mu)$ <br> subject to: $0 \leq q_{nutrients} \leq q_{max,exp}$ | $\max(\mu)$ <br> subject to: $0 \leq q_{nutrients} \leq \infty$ |
| Productivity Increase | $\max(q_{MAb})$ <br> subject to: $0 \leq q_{nutrients} \leq q_{max,exp}$ | $\max(q_{MAb})$ <br> subject to: $0 \leq q_{nutrients} \leq \infty$ |
| Growth Increase & Byproduct Reduction | $\max(\mu)$ & $\min(q_{byproducts})$ <br> subject to: $0 \leq q_{nutrients} \leq q_{max,exp}$ | $\max(\mu)$ & $\min(q_{byproducts})$ <br> subject to: $0 \leq q_{nutrients} \leq \infty$ |
| Productivity Increase & Byproduct Reduction | $\max(q_{MAb})$ & $\min(q_{byproducts})$ <br> subject to: $0 \leq q_{nutrients} \leq q_{max,exp}$ | $\max(q_{MAb})$ & $\min(q_{byproducts})$ <br> subject to: $0 \leq q_{nutrients} \leq \infty$ |
| Growth and Productivity Increase & Byproduct Reduction | $\max(\mu$ & $q_{MAb})$ & $\min(q_{byproducts})$ <br> subject to: $0 \leq q_{nutrients} \leq q_{max,exp}$ | $\max(\mu$ & $q_{MAb})$ & $\min(q_{byproducts})$ <br> subject to: $0 \leq q_{nutrients} \leq \infty$ |

Min, minimize;
max, maximize;
q, uptake or secretion rate;
MAb, monoclonal antibody;
exp, experimentally determined value from batch culture bioreactor data.

Stoichiometric analysis of microbial and mammalian cell metabolism using a constraint-based framework is well established. The first metabolic network for an NS0 cell line has been reconstructed containing 470 metabolic reactions and 456 intracellular metabolites. The reconstruction of NS0 metabolism described above correctly captures many of the metabolic behaviors of the cell under experimentally determined conditions.

Collectively, metabolic network analysis of NS0 cell lines demonstrates that the physiological behavior of mammalian cell lines can be correctly represented and predicted using linear optimization and constraint-based modeling. The work described above has shown that growth and byproduct secretion in mammalian cell culture can be correctly calculated. In addition, network analysis provided valuable insight about the underlying mechanism of byproduct formation, energy balance, and metabolic network inefficiency in metabolizing the media nutrients and resulted in the development of optimized media formulations for byproduct reduction and growth and productivity increase. Specifically, the reconstructed network has shown that: qualitative implementation of in silico media designs can reduce byproduct formation and improve cell growth and productivity; potential benefits in reducing byproduct formation can be quantitatively determined using the reconstructed outputs are improved laboriously by experimentation. These empirical optimization techniques are widely used because in most cases little is known about the underlying biological factors that impact growth and protein production in the host cell lines. A fundamental understanding of cell line response to biological and environmental changes can thus greatly improve and accelerate the development of new therapeutic proteins and production of existing protein products.

Gaining a fundamental understanding of cell function is particularly important in expression systems that are widely used for research and commercial production. The most commonly used mammalian expression systems for therapeutic protein production are Chinese hamster ovary (CHO) cells, followed by murine lymphoid cells (e.g. NS0 and SP2/0). CHO cells are widely used because: (1) they can grow both as anchorage-dependent cells and in suspension, (2) they can be cultured in serum- and even protein-free media, and (3) they perform post-translational modifications similar to human glycosylation patterns (Mols et al., *In Vitro Cell Del. Biol. Anim.* 41:83-91 (2005). In addition, platform technologies for cell transfection, gene amplification, and clone selection in CHO cells are well characterized and widely used in both research and manufacturing (Mol et al., supra).

Despite their use in the development of new proteins and the production of approved therapeutic products, little is known about the metabolism and underlying biological interactions in CHO cell lines. Even though 472 genomes have now been completely sequenced and made publicly available, the hamster genome has yet to be sequenced. Currently no plans have been made either to publish the CHO genome sequenced through a privately funded effort by the Consortium for Chinese Hamster Ovary Cells Genomic Research (Wlaschin and Hu, Biotehnol. Bioeng. 98:428-439 (2007)). Furthermore, despite a large body of literature focused on improving protein expression, media optimization, and process development in CHO cells, only a limited number of studies have focused on intracellular metabolic characterization of CHO cell lines under laboratory or scale up conditions. To build a knowledge base for CHO cells that contains the most concise representation of collective biological knowledge to date and to provide a context for analyzing biological content for the CHO cell line, an integrated and model-driven computational and experimental approach is needed. Such an integrate platform can then be used to reconcile and interrogate the existing data, and to drive media, process, and cell engineering in a way that fundamentally changes how host c ell lines are developed and therapeutic proteins are produced.

Previous efforts related to mammalian systems using the constraint-based modeling approach include development of a draft reconstruction of murine hybridoma metabolism, a metabolic model of the NS0 cell line, as well as genome-scale network reconstructions for mouse and human metabolism (refs. Sheikh et al., *Biotechnol. Prog.* 21:112-121 (2005); Duarte et al., *Proc. Natl. Acad. Sci. U.S.A.* 104: 1777-1782 (2007)). Although the metabolic network reconstruction of hybridoma and NS0 cell lines have provided valuable information, they offer limited benefits in the study and design of CHO-based protein production, mainly because cell growth and protein production vary drastically in different cell lines and culture conditions and any improvements in CHO cell line require the use of CHO cells and its cell culture data.

A comprehensive and integrated computational/experimental platform for rational design and optimization of protein production in Chinese hamster ovary cell lines has been developed. This integrated platform combines advanced modeling technologies with established experimental techniques to improve the timelines and quality of the therapeutic products in the CHO expression system.

The overall goal was to utilize an integrated computational/experimental approach to characterize the effect of sodium butyrate supplementation, which is known to enhance protein expression, on CHO cell metabolism and to identify and prioritize alternative strategies that result in similar improvements in specific productivity without the need to prevent apoptosis (an undesirable side effect of butyrate treatment). The results provide a demonstration of the feasibility of developing a rational approach for recombinant protein production in CHO cell lines that can be used to: (a) generate fundamental understanding for cell line response to environmental and genetic perturbations, and (b) develop novel metabolic interventions for improved protein production.

Described in more detail below are the following:

I: Develop a Whole-cell Metabolic Network for CHO Cells: A whole-cell metabolic network was developed for a CHO cell line using published literature, experimental data, and previously developed mammalian metabolic network reconstructions. The reconstructed metabolic network accounted for all the central catabolic and anabolic pathways in Chinese hamster cells, including the carbohydrate, amino acid, lipid, and nucleotide metabolism, as well as monoclonal antibody production and glycosylation pathways. In the absence of the Chinese hamster genome sequence and annotation, the metabolic pathways were reconstructed based on a closely related organism, *Mus musculus*, for which a metabolic network reconstruction is available. The reconstructed network contained the most comprehensive representation of the CHO metabolism available to date.

II: Generate Growth Data and Validate the Metabolic Model using Experimental Measurements: To complete and validate the CHO metabolic model, experimental data was generated for cell growth, protein production, nutrient uptake, and byproduct formation rates in a CHO cell line. The cells are grown in a chemically defined media in a glucose-limited batch culture. The experimental data obtained are used to: (a) calculate associated energy requirements in a CHO cell line, and (b) validate the accuracy of the model for capturing and simulating metabolism by comparing the modeling results to experimental values.

III: Characterize the Effect of Varying Culture Conditions on Cell Metabolism: To demonstrate the benefit of combining a modeling and experimental approach in CHO-based protein production, the reconstructed model was used to study metabolic changes in cell cultures treated with sodium butyrate, a known chemical enhancer for specific productivity. For this purpose, the metabolic exchange rates were experimentally determined in a butyrate-treated chemostat and the model used to identify the mechanism by which sodium butyrate affects metabolism and enhances protein production via the intracellular metabolic pathways.

The reconstructed network simulated the normal growth behavior of the Chinese hamster ovary cell line in comparison with experimental data and demonstrated the usefulness of the model to gain insight about the underlying effect of media supplementation on CHO metabolism and to develop alternative metabolic interventions that may circumvent the disadvantages of chemical supplementation.

Importance of Modeling CHO Cell Lines.

A number of different expression systems are used for the production of therapeutic proteins including prokaryotes, yeasts, mammalian cells, transgenic plants and animals. CHO cells however are the preferred expression system due to the advantages they offer in research and manufacturing. They can easily be genetically manipulated. They can grow both as adherent cells and in suspension. They adopt to grow in serum-, hydrolysate-, and even protein-free media. Platform technologies for cell transfection, gene amplification, and clone selection in CHO cells are well characterized and widely used (Mols et al., *In Vitro Cell Dev. Biol. Anim.* 41:83-91 (2005)) and they have an established history of regulatory approval for recombinant protein expression (Nissom et al., *Mol. Biotechnol.* 34:125-140 (2006)). And most importantly, they perform post-translational modifications similar to human glycosylation patterns (Mols et al., supra). Consequently, CHO cell lines have become the dominant host cell for protein production and account for the production of more than 70% of all US licensed therapeutic proteins as of 2004 (Birch, J. R., Mammalian cell culture: current status, future prospects 9-2-0004).

Like most mammalian cell lines, production of therapeutic proteins in Chinese hamster ovary cells is hampered by a number of challenges. CHO cells are known to have a very unstable karyotype due to chromosomal rearrangements, especially in response to amplification procedures (Barnes et al., *Biotechnol. Bioeng.* 81:631-639 (2003)). In addition, instability in product formation has been observed in CHO cells, even in the presence of an amplification marker such as methotrexate (Barnes et al., supra). Moreover, culture conditions can drastically influence productivity and growth in CHO cell cultures, including medium pH, osmolality and culture temperature (Furukawa and Ohsuye, *Cytotechnology* 26:153-164 (1998)).

Approximately 20-30% of the total cost of biopharmaceutical therapeutic production is associated with process development and clinical manufacturing (Rose et al., *Handbook of Industrial Cell Culture*, Vinci, V and Pareh, S. (eds.) Humana Press, Totowa, 2003) pp. 69-103), which is done in most cases through a trial and error approach. These empirical optimization techniques are widely used because in most cases little is known about the underlying biological factors that impact growth and protein production in the host cell lines. Process improvements that result from a fundamental understanding of cell line response to biological and environmental changes can thus greatly accelerate the discovery of new therapeutic proteins and improve production of existing products.

Impact of Metabolic Modeling in Mammalian Cell Line Protein Production.

Unlike the trial and error strategies that are commonly used in therapeutic protein production, metabolic modeling provides a clear definition for the underlying physiology and metabolism of the host cell lines and offers a rational approach for designing and optimizing protein production. Computational metabolic modeling can serve as a design and diagnostic tool to: Identify what pathways are being used under specified genetic and environmental conditions; Determine the fate of nutrients in the cell; Identify the source of waste products; Examine the effect of eliminating existing reactions or adding new pathways to the host cell line; Analyze the effect of adding nutrients to the media; Interpret process changes (e.g. scale-up) at a fundamental physiological level; and Generate rational design strategies for media optimization, process development, and cell engineering.

As evident by the success with microbial models, a whole-cell metabolic model reconstruction for commonly used mammalian cell lines will be extremely valuable for both research and product development and manufacturing. There are strong scientific and financial incentives to develop technologies that can increase the protein production in host cell lines and to reduce the cost of producing therapeutic proteins using engineering approaches. Many biological factors influence the ability to achieve high production titers, including cell density, media composition, and culture conditions, all of which are linked to metabolism which is the deriving engine of the cell for growth and product formation. Understanding metabolic changes that follow genetic and environmental perturbations in cell culture will allow for the development of more effective strategies to improve productivity and avoid unexpected variation in cell culture and protein production.

Metabolic Models for Rational Bioprocess Design.

Any attempt to improve protein production by overcoming fundamental metabolic limitations requires a platform for the comprehensive analysis of cellular metabolic systems. Genome-scale models of metabolism offer the most effective way to achieve a high-level characterization and representation of metabolism. These models reconcile all of the existing genetic, biochemical, and physiological data into a metabolic reconstruction, encompassing all of the metabolic capabilities and fitness of an organism. These in silico models serve as the most concise representation of collective biological knowledge on the metabolism of an organism. As such they become the focal point for the integrative analysis of vast amounts of experimental data and a central resource to design experiments, interpret experimental data, and drive research programs. It is now becoming recognized that the construction of genome-scale in silico models is important to integrate large amounts of diverse high-throughput datasets and to prospectively design experiments to systematically 'fill in the gaps' in knowledge base of particular organisms (Ideker et al., *Science* 292:929-934 (2001)).

The exercise of constructing and demonstrating the use of genome-scale models of metabolism began in earnest out of academic efforts in which this team was involved. Previously published in silico representations of metabolism include those for *E. coli* MG1655 (Edward and Palsson, *Proc. Natl. Acad. Sci. U.S.A.* 97:5528-5533 (2000)), *H. influenzae* Rd (Edwards and Palsson, *J. Biol. Chem.* 274: 17410-17416 (1999); Schilling and Palsson *J. Theor. Biol.* 203:249-283 (2000)), *H. pylori* (Schilling et al., *J. Bacteriol.* 184:4582-4593 (2002), and *S. cerevisiae* (Forster et al., *Genome Res.* 13:244-253 (2003)). The general process has been previously reviewed along with various applications of the in silico models (Schilling et al., *Biotechnol. Prog.* 15:288-295 (1999); Covert et al., *Trends Biochem. Sci.* 26:179-186 (2001)). It is desirable to develop much more comprehensive models maintained at higher quality control levels with industry best practices.

In combination with appropriate simulation methods these models can also be used to generate hypotheses to guide experimental design efforts and improve the efficiency of bioprocess design and optimization. When properly integrated with experimental technologies, an extremely powerful combined platform for metabolic engineering can be implemented. A focus is on the development of cellular models of metabolism for a wide range of applications within industrial biotechnology from the production of small molecule chemicals/metabolites to the production of therapeutic proteins and biologics.

Reconstructed Networks for Hybridoma. Reconstruction and simulation of metabolism within the constraint-based framework is well established for microbial organisms (Edwards and Palsson, *Proc. Natl. Acad. Sci. U.S.A.* 97:5528-5533 (2000); Edwards and Palsson, *J. Biol. Chem.* 274: 17410-17416 (1999); Schilling et al., *J. Bacteriol.* 184: 4582-4593 (2002); Forster et al., *Genome Res.* 13:244-253 (2003)), and has been extended to study mammalian cells (Sheikh et al., *Biotechnol. Prog.* 21:112-121 (2005); Duarte et al., *Proc. Natl. Acad. Sci. U.S.A.* 104:1777-1782 (2007); Savinell and Palsson, *J. Theor. Biol.* 154:455-473 (1992)). The first metabolic model for a mammalian cell line was built for an antibody producing murine hybridoma by Savinell and Palsson, herein referred to as Savinell's model (Savinell and Palsson, supra). Although the network size in this model was relatively small compared with present genome-scale reconstructions, the model correctly captured many of the metabolic behaviors of the hybridoma cell line under experimentally determined conditions. A more comprehensive reconstruction of hybridoma metabolism was recently published using a generic genome-scale metabolic network for *Mus musculus* (Sheikh et al., supra). This genome-based hybridoma model, herein referred to as Sheikh's model, accounts for 1220 reactions and 872 internal metabolites and correctly predicts growth rate, lactate secretion, and ammonia production (at higher growth rates) in a chemostat cell culture.

Using the modeling and simulation software platform SimPheny™, the Savinell and Palsson hybridoma model was reconstructed and expanded in the database (herein referred to as the small-scale hybridoma in SimPheny™).

The reconstructed network contains 234 reactions and 249 metabolites (compared to the original Savinell model with only 83 reactions and 42 metabolites) and accounts for major pathways involving energy metabolism and mass transformation in the cell. In addition to the expanded hybridoma model, a genome-based metabolic model of NS0 was completed, herein referred to as the genome-scale model of hybridoma in SimPheny™, using the sequence and annotation of the mouse genome (Waterston et al., Nature 420:520-562 (2002)) and published literature. The metabolic network of NS0 contains 469 reactions and 455 metabolites. The reconstructed model contains elementally and charge balanced reactions and provides the correct protein, reaction, and metabolite localization in the intracellular organelles. The reconstructed metabolic models of hybridoma and NS0 have been developed using industry-level high quality assurance and quality control procedures and are more comprehensive in scope and detail than previously developed models.

Small-Scale Metabolic Model of Hybridoma in SimPheny™.

For simplicity, many of the metabolic pathways in Savinell's hybridoma model were represented as a single lumped reaction and most of the metabolite co-factors in the network were excluded. For example, biosynthesis of purines and pyrimidines to form DNA and RNA was lumped into a single reaction. In addition, co-metabolites such as ADP, AMP, NAD, and NADP were not included in the network reconstruction, causing the network reactions to be elementally unbalanced.

Figure 16:
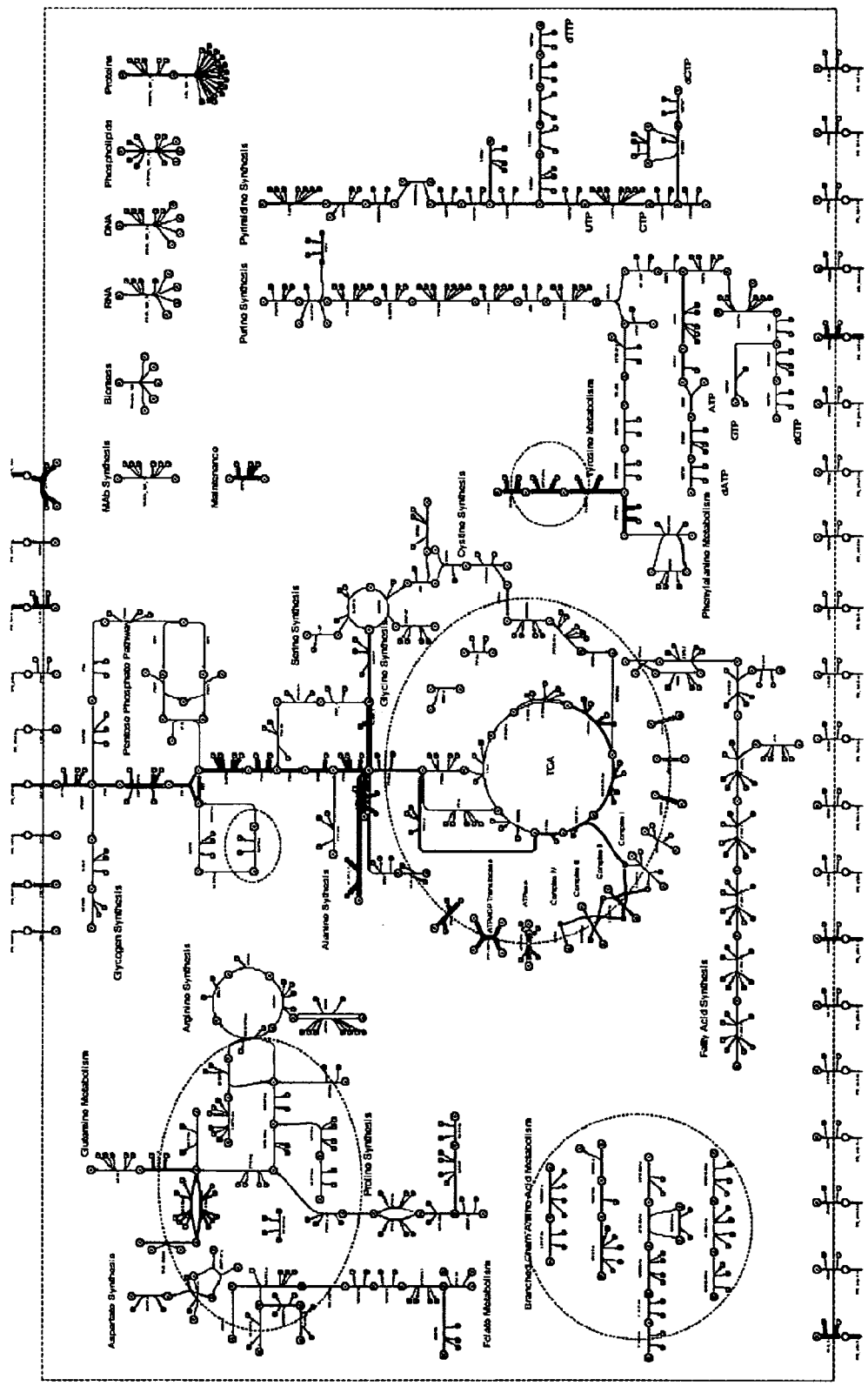
FIG. 16 shows metabolic simulation of hybridoma cell culture grown in batch bioreactor during steady exponential growth, using the expanded network reconstruction in SimPheny™. The reconstructed model contains 234 reactions (lines) and 249 metabolites (circles) and accounts for metabolite compartmentalization in cytosol and mitochondria. The color and thickness of the reactions correspond to the flux values in the metabolic simulation.

To determine whether the agreement between the model simulations and experimental data for byproduct formation was real or due to an artifact resulting from an incorrect representation of metabolic pathways, a refined and improved model of hybridoma metabolism was reconstructed in SimPheny™. The lumped reactions in Savinell's model were replaced with elementally and charged balance reactions in the refined network. Biochemical and genetic data were used to support inclusion of metabolic reactions using the mouse genome and published literature (Waterston et al., Nature 420:520-562 (2002)). Metabolite co-factors were added to the network reconstruction and additional metabolic pathways were included to accurately represent metabolism in hybridoma. Metabolic model refinement and expansion resulted in a network reconstruction containing 234 reactions and 249 metabolites (FIG. 16).

The metabolic capabilities of the small-scale hybridoma model were compared with the Savinell's model simulation for growth measurements obtained from a batch bioreactor during exponential growth (Ozturk and Palsson, Biotechnol. Prog. 7:481-494 (1991)). The experimental measurements included the uptake and secretion rates of glucose, lactate, oxygen, ammonia, and all amino acids expect proline, cysteine, and tryptophan, the antibody production rate, and growth rate. Similar to the Savinell's model, the expanded model simulated byproduct secretion of lactate, alanine, and ammonia (FIG. 16), indicating that the formation of these key byproducts was not an artifact of a reaction imbalance or pathway simplification. The calculated non-growth associated maintenance (ATPm) value in the expanded model was slightly different than the small-scale model. The quantitative difference in ATPm is a result of a more accurate representation of the energy consuming and producing reactions in the expanded network that were originally lumped in the small-scale reconstruction.

The metabolic model was also used to investigate lactate, ammonia, and alanine production in hybridoma cells and to determine the nutrient contributions to the formation of these key byproducts in cell culture. A sensitivity analysis illustrated that formation of lactate and ammonia results almost entirely from the excess amount of glucose and glutamine taken up by the cell, respectively. In contrast to lactate and ammonia, alanine formation could not be linked to excess uptake of any single nutrient and instead, uptake of several amino acids was shown to contribute to alanine production.

Taken together, network expansion of the hybridoma model provided a framework for interrogating the metabolic response of hybridoma cells to an experimentally defined growth condition and allowed for an investigation of the nutrient contributions to byproduct formation in the cell culture.

Genome-based Metabolic Model of NS0 Cell Line in SimPheny™.

Figure 17:
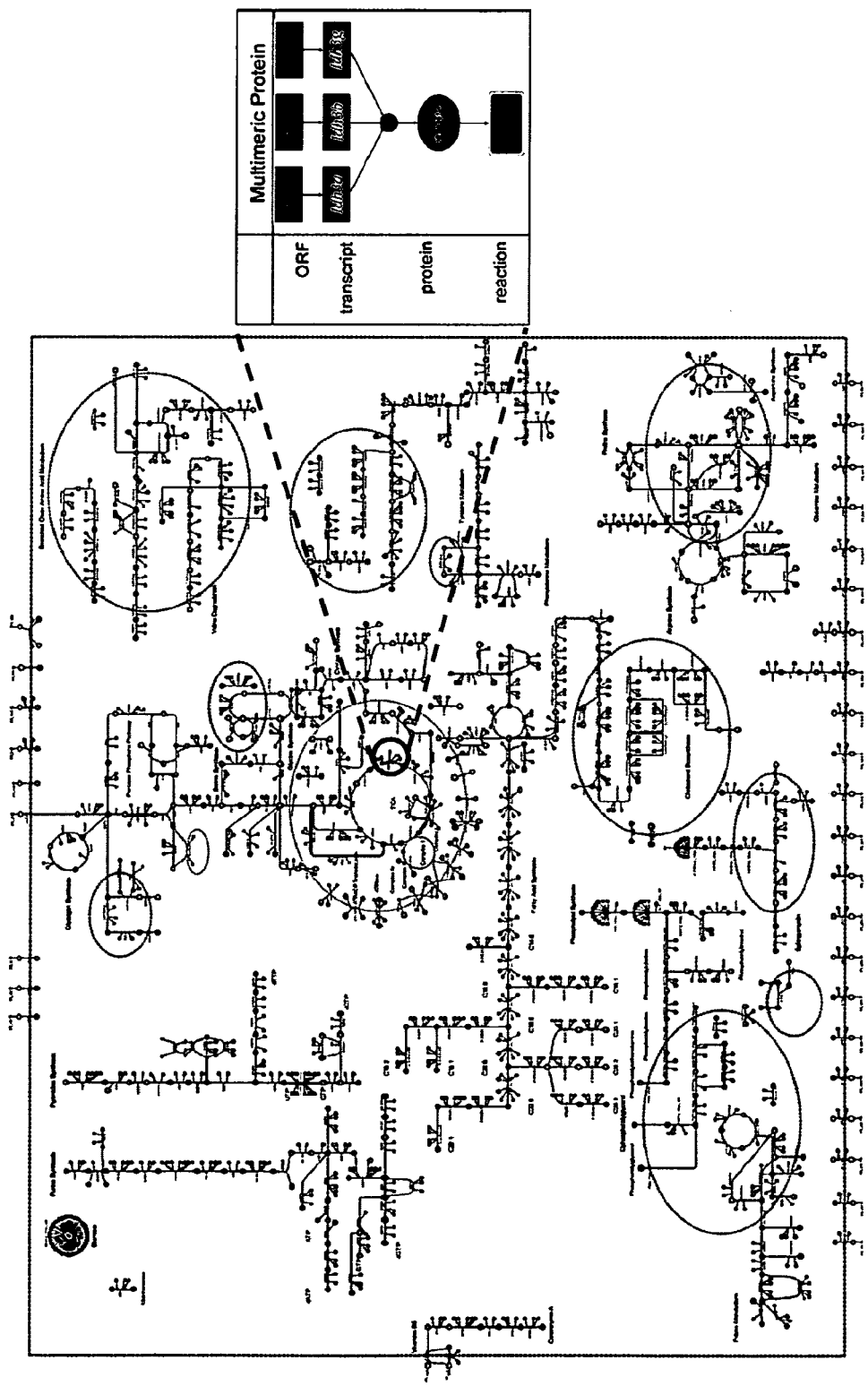
FIG. 17 shows and exemplary NS0 metabolic network and an example gene-protein-reaction association in SimPheny™ shown for a multimeric protein (isocitrate dehydrogenase).

In addition to the hybridoma metabolic network, a genome-scale metabolic model for NS0 cell line has been completed using the sequence and annotation of the mouse genome, published literature, online databases, and the available knowledge on mammalian metabolic reactions and pathways (Waterston et al., Nature 420:520-562 (2002); Bronk, J. R., Metabolism: Functional Diversity and Integration. Addison Wesley Longman, Essex, England, (1999); Devlin, T. M. Textbook of Biochemistry with Clinical Correlations. John Wiley and Sons, New York, N.Y., (1997); Salway, J. G. Metabolism at a glance. Blackwell Science, Oxford (1999); Vander et al., Human physiology: the mechanisms of body function. McGraw-Hill, New York (1994). Using the current framework in SimPheny™, the gene-protein-reaction association is fully represented in the network reconstruction of NS0 cell line (FIG. 17). All the metabolic reactions in this reconstructed network are elementally and charge balanced and none of the metabolic pathways are lumped or simplified. Metabolic enzymes are appropriately compartmentalized into extracellular, cytosolic, mitochondrial, peroxisomal, vacuolar, and other intracellular compartments and appropriate transport reactions are defined for the exchange of metabolites across microsomal and plasma membranes.

Preliminary Studies.

Reconstruction and simulation of metabolism within the constraint-based framework is well established for microbial organisms (Varma and Palsson, Bio/Technology 12:994-998 (1994); Edwards et al., Environ. Microbiol. 4:133-140 (2002); Savinell and Palsson, J. Theor. Biol. 154:455-473 (1992); Waterston et al., Nature 420:520-562 (2002)), and has been extended to study mammalian cells (Lakshmi Kamath, Drug Discovery & Development Jan. 12, 2005; Wlaschin et al., Biotechnol. Bioeng. 91:592-606 (2005); Baik et al., Biotechnol. Bioeng. 93:361-371 (2006); De Leon et al., J. Biosci. Bioeng. 103:82-91 (2007); Ernst et al., Biotechnol. J. 1:639-650 (2006)). The first constraint-based model for a mammalian cell line was built for an antibody-producing murine hybridoma cell line by Savinell and Palsson (Wlaschin et al., supra; Hayduk et al., Electrophoresis 25:2545-2556 (2004)). Although the network size in this model was relatively small compared with present genome-scale reconstructions, the model correctly captured many of the metabolic behaviors determined for the hybridoma cell line under experimental conditions. Recently, a more comprehensive reconstruction of hybridoma metabolism was published using a generic genome-scale metabolic network for Mus musculus (Baik et al., Biotechnol. Bioeng. 93:361-371 (2006)) that correctly predicted growth rate, lactate secretion, and ammonia (at higher growth rates) in a chemostat cell culture.

In addition to the published work, three reconstructed metabolic models for mammalian cells have now been completed, including a more refined model of hybridoma metabolism, a genome-based model of NS0, and a metabolic model of Chinese Hamster Ovary (CHO) cell line. Using the modeling and simulation software platform SimPheny™, a CHO cell line metabolic model was constructed. CHO cells are the most commonly used mammalian host for therapeutic protein expression; nearly 70% of all recombinant protein therapeutics produced today are made in CHO cells (Wlaschin and Hu, *Biotechnol. Bioeng.* 98:429-439 (2007)). To develop a CHO cell metabolic model, information was utilized from published literature on animal metabolism and biochemistry, CHO cell line physiology, and CHO cell-specific transcriptomics and proteomics studies. The reconstructed network contains 550 elementary and charge-balanced reactions involving 524 metabolites, and accounts for pathways of central metabolism including energy, mass transformation and biomass production. In addition, the reconstructed model also correctly accounts for reaction and metabolite localization within intracellular organelles.

Metabolic Network Reconstruction for CHO Cell Line in SimPheny™.

Figure 20:
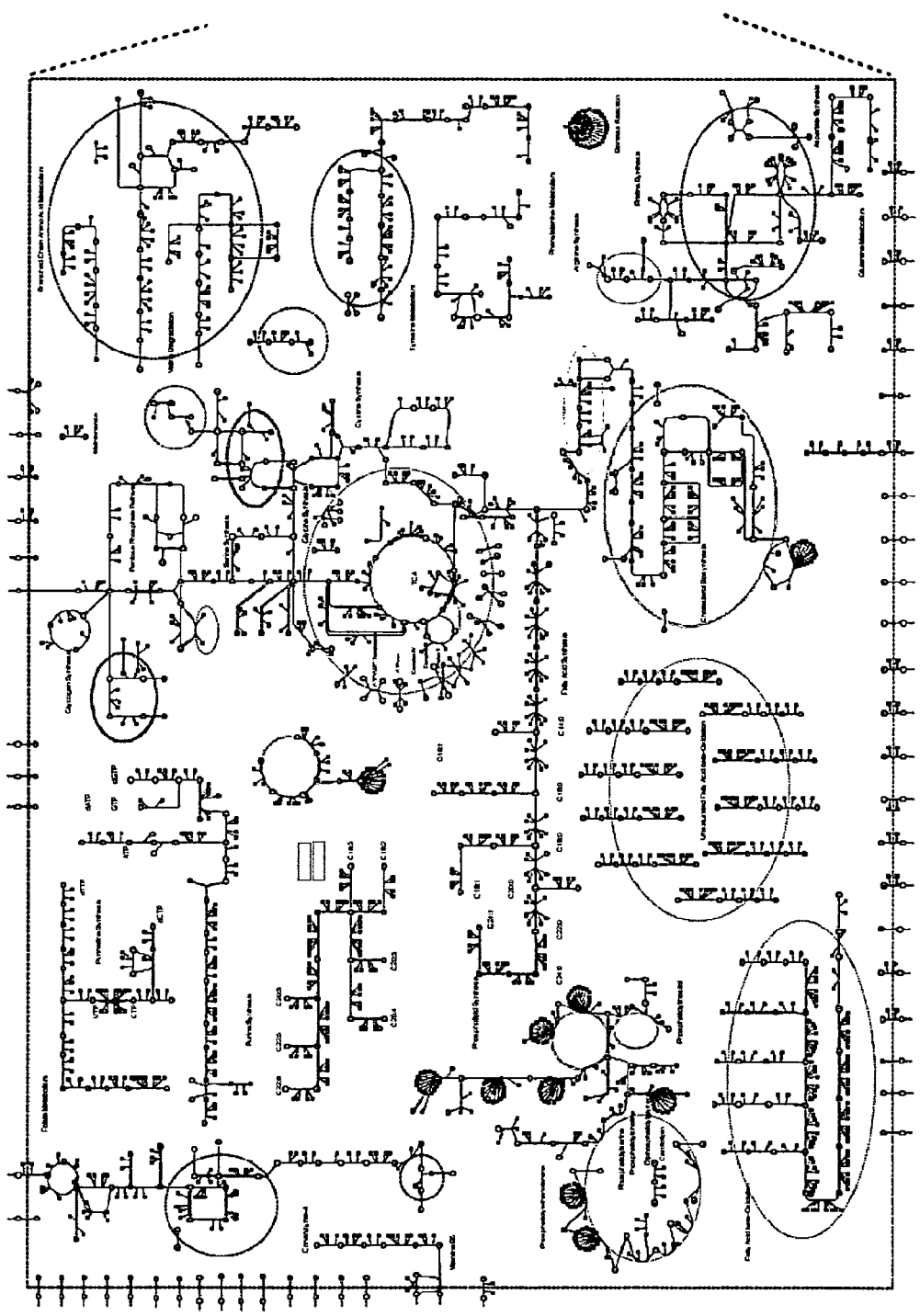
FIG. 20 shows a snapshot of CHO cell line metabolic network, containing 550 reactions and 524 metabolites and mapping of the major metabolic pathways in the network.
Figure 20:
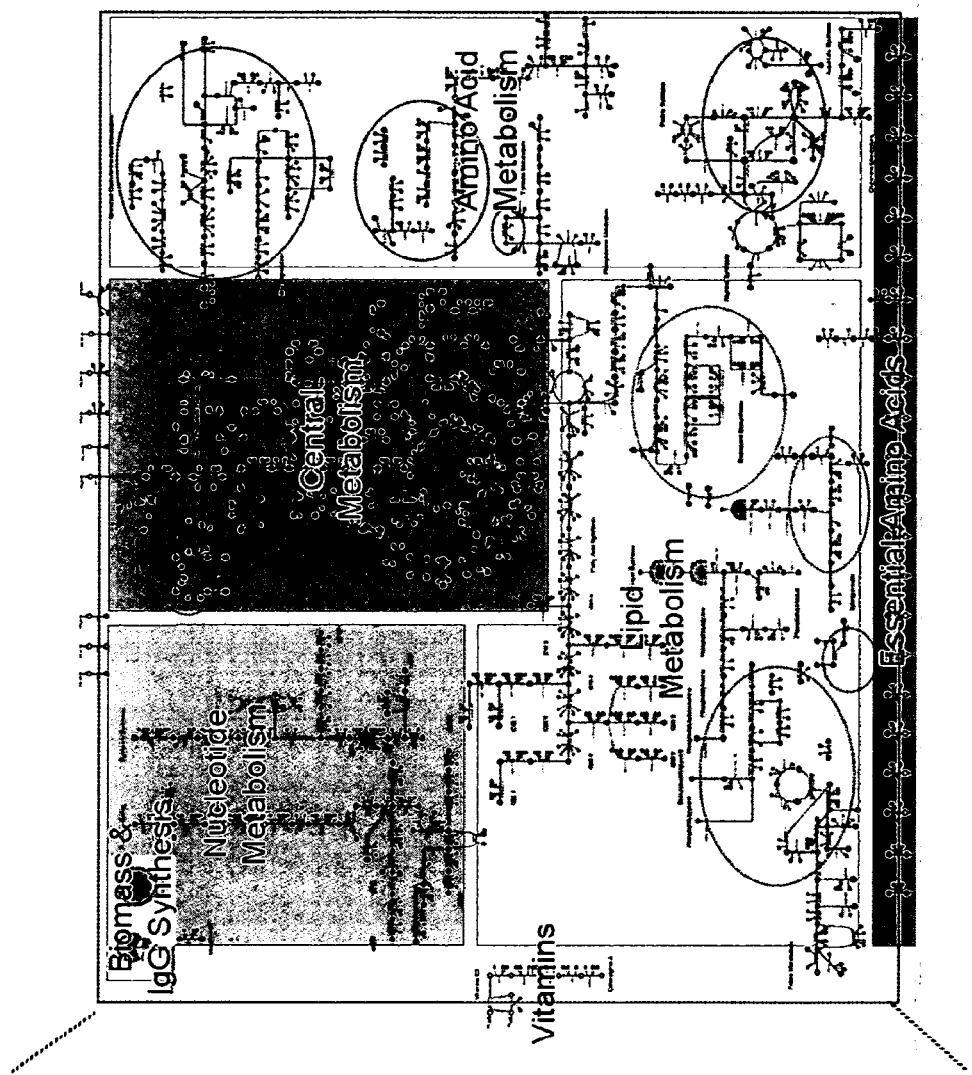

The metabolic model of CHO cell line was reconstructed in SimPheny™ using published literature and on-line databases on CHO cell line metabolism. Major pathways in central metabolism were included in the metabolic network reconstruction of the CHO cell, including glycolysis, the citric acid (TCA) cycle, pentose phosphate pathway, nonessential amino acid biosynthesis, nonessential fatty acid synthesis and fatty acid β-oxidation (Hayduk et al., *Electrophoresis* 25:2545-2556 (2004); Hayduk and Lee, *Biotechnol. Bioeng.* 90:354-364 (2005); Lee et al., *Biotechnol. Prog.* 19:1734-1741 (2003); Van Dyk et al., *Proteomics* 3:147-156 (2003); Hayter et al., *Appl. Microbiol. Biotechnol.* 34:559-564 (1991)). Transport reactions for essential amino acids (i.e. histidine, isoleucine, leucine, lysine, methionine, phenylalanine, threonine, tryptophan, and valine), essential fatty acids (i.e. α-linolenic acid, C18:2, and linoleic acid, C18:3), and other nutrient uptake were included and verified using published CHO medium composition (Kaufmann et al., *Biotechnol. Bioeng.* 63:573-582 (1999); Hayter et al., *Biotechnol. Bioeng.* 42:1077-1085 (1993)). The stoichiometry of the electron transport system was specified with a P/O ratio of 2.5 for NADH (measure of oxidative phosphorylation) based on the value determined for mammalian cells (Seewoster and Lehmann, *Appl. Microbiol. Biotechnol.* 44:344-250 91995)). To ensure that all the biosynthetic components can be synthesized in the network, reactions for biosynthesis of carbohydrates, RNA, DNA, phospholipids, cholesterol, and sphingolipids were added to the reconstructed CHO metabolic network even in the absence of direct genetic or biochemical evidence in CHO cells. Reaction reversibility and intracellular localization were verified using published literature and online databases (refs. Narkewicz et al., *Biochem. J.* 313 (Pt 3) 991-996 (1996); Lao and Toth, *Biotechnol. Prog.* 13:688-691 (1997)). The complete metabolic network includes a total of 550 metabolic reactions and 524 metabolites distributed in intracellular compartments including cytosol, mitochondria, endoplasmic reticulum, peroxisome, as well as the extra-cellular space. All the metabolic reactions in this reconstructed network are elementally and charge-balanced and none of the metabolic pathways is lumped (i.e. several consecutive pathway reactions are merged into one) or simplified. A snapshot view of the metabolic map with 550 reactions and 524 metabolites is shown in FIG. 20.

Precursor Metabolite, Energy, and Biomass Synthesis in the Reconstructed Metabolic Model of CHO Cell Line.

To assess the network's ability to synthesize biomass components, precursor metabolite formation and energy (ATP) production were simulated using glucose as a sole carbon source. The reconstructed network was able to correctly generate all precursor metabolites at values equal to or below the maximum theoretical values from glucose, similar to previously reconstructed models for microbial cells such as *E. coli* and *S. cerevisiae* (Waterston et al., *Nature* 420: 520-562 (2002); Lu et al., *Process Biochemistry* 40:1917-1921 (2005)). In addition, using a P/O ratio of 2.5 (Baik et al., *Biotechnol. Bioeng.* 93:361-371 (2006); Seewoster et al., *Appl. Microbiol. Biotechnol.* 44:344-350 (1995)), the metabolic model simulated ATP formation at a maximum yield of 32.75 mol ATP/mol glucose, consistent with a draft network reconstruction of human metabolism in SimPheny™ and previously published values for mammalian cells (Van Dyk et al., *Proteomics* 3:147-156 (2003); Seewoster et al., supra).

In the absence of comprehensive thermodynamic or kinetic constraints, groups of metabolic reactions in the reconstructed network can potentially be coupled to create cycles that erroneously generate energy and redox potential without carbon expenditure. The CHO cell reconstructed metabolic model was tested and verified that no spurious or invalid network cycles that can generate free energy in the form of ATP, NADH, NADPH and $FADH_2$.

The metabolic network was also tested for its ability to synthesize all the biosynthetic components listed in Table 9. All non-essential amino acids and fatty acids were correctly synthesized from glucose.

The conditionally essential amino acids cysteine and tyrosine were synthesized only when essential methionine and phenylalanine were supplied to the network, respectively, as expected. Conditionally essential fatty acids were synthesized when essential α-linolenic and linoleic fatty acid were supplied to the network. In addition, the network was also tested to verify that the essential amino acid (EAA) and essential fatty acid (EFA) biosynthetic pathways are not present in the model and that EAAs and EFAs are available for protein, lipid, and biomass biosynthesis only via uptake from extra-cellular space (i.e. the media).

TABLE 9

CHO cell biomass composition. Adopted from Altamirano et al. Fatty acid, phospholipid and sterol composition adopted from Hannah et al., *Metabolism* 44: 1428-1434 (1995) and Sleight and Kent, *J. Biol. Chem.* 258: 836-839 (1983).

| Macromolecule | % dry weight | Amino acid | mmol/g DW | Amino acid | mmol/g DW | Carbs, Nucleotide | mmol/g DW | Lipids | mmol/g DW | Fatty Acid | mol % Fatty Acid | Fatty Acid | mol % Fatty Acid |
|---|---|---|---|---|---|---|---|---|---|---|---|---|---|
| DNA | 1.9 | Ala | 0.529 | Leu | 0.490 | Glycogen | 0.389 | Chol | 0.060 | C14:0 | 0.274 | C20:5 | 1.797 |
| RNA | 5.8 | Arg | 0.351 | Lys | 0.496 | | | Chol Ester | 0.039 | C16:0 | 0.238 | C22:5 | 1.533 |
| Lipids | 7.7 | Asn | 0.217 | Met | 0.111 | dATP | 0.017 | PC | 0.089 | C16:1 | 0.234 | C22:6 | 1.506 |
| Carbs | 7 | Asp | 0.267 | Phe | 0.117 | dCTP | 0.011 | PE | 0.037 | C18:0 | 0.211 | C24:0 | 0.157 |

TABLE 9-continued

CHO cell biomass composition. Adopted from Altamirano et al. Fatty acid,
phospholipid and sterol composition adopted from Hannah et al., *Metabolism* 44: 1428-1434
(1995) and Sleight and Kent, *J. Biol. Chem.* 258: 836-839 (1983).

| Macro-molecule | % dry weight | Amino acid | mmol/g DW | Amino acid | mmol/g DW | Carbs, Nucleotide | mmol/g DW | Lipids | mmol/g DW | Fatty Acid | mol % Fatty Acid | Fatty Acid | mol % Fatty Acid |
|---|---|---|---|---|---|---|---|---|---|---|---|---|---|
| Proteins | 70.6 | Cys | 0.156 | Pro | 0.156 | dGTP | 0.011 | PI | 0.012 | C18:1 | 0.207 | C24:1 | 0.155 |
|  |  | Glu | 0.356 | Ser | 0.317 | dTTP | 0.017 | PS | 0.012 | C18:2 | 1 |  |  |
|  |  | Gln | 0.290 | Thr | 0.340 | ATP | 0.032 | SM | 0.017 | C18:3 | 2 |  |  |
|  |  | Gly | 0.434 | Trp | 0.033 | CTP | 0.053 | CL | 0.002 | C20:0 | 0.189 |  |  |
|  |  | His | 0.123 | Tyr | 0.111 | GTP | 0.060 | TG | 0.007 | C20:3 | 1.873 |  |  |
|  |  | Ile | 0.290 | Val | 0.329 | UTP | 0.032 |  |  | C20:4 | 1.834 |  |  |

Carbs—carbohydrate;
Chol—cholesterol;
PC—phosphatidylcholine;
PE—phosphatidylethanolamine;
PI—phosphatidylinositol;
PS—phosphatidylserine;
SM—sphingomyelin;
CL—cardiolipin;
TG—triacylglycerol.

The metabolic model requirements for cofactors and vitamins were tested and agreed well with nutritional requirements in mammalian cells. For example, fatty acyl-CoA formation in phospholipid synthesis requires Coenzyme A that is synthesized from pantothenate (vitamin B5). Pantothenate is an essential vitamin that is also supplied to mammalian cell lines in the media (Kaufmann et al., *Biotechnol. Bioeng.* 63:573-582 (1999); Hayter et al., *Biotechnol. Bioeng.* 42:1077-1085 91993); Krambeck and Betenbaugh *Biotechnol. Bioeng.* 92:711-728 (2005)). In the metabolic network, lipid synthesis is coupled to pantothenate supplementation and the network is unable to make biomass in the absence of vitamin B5 intake, as expected. Choline is another essential nutrient for mammals that is required for the formation of phosphocholine (Kaufmann et al., *Biotechnol. Bioeng.* 63:573-582 (1999); Hayter et al., *Biotechnol. Bioeng.* 42:1077-1085 91993); Hossler et al., *Biotechnol. Bioeng.* 95:946-960 (2006)). The CHO metabolic network does not contain any of the reactions for choline synthesis and to satisfy phospholipid biosynthetic requirements, the metabolic network must take up choline from the extra-cellular space. In the absence of choline supplementation, the CHO metabolic network is unable to make phosphocholine and biomass, as expected. Ethanolamine and putrescine are also precursors supplied in mammalian cell media (Kaufmann et al., *Biotechnol. Bioeng.* 63:572-582 (1999); Hayter et al., *Biotechnol. Bioeng.* 42:1077-1085 (1993)). Ethanolamine is an alternative route for the biosynthesis of phosphoethanolamine and it has been included in the CHO model. There were no evidence in the previous literature that putrescine is metabolized in CHO cells. Thus, putrescine exchange was not included in the model.

Validation and Analysis of the CHO Model:

Fatty Acid Metabolism in CHO Model. The metabolic capabilities of the reconstructed CHO model were evaluated using linear optimization and constraint-based modeling approach (see section B.5). To validate the reconstructed CHO metabolic model, the ATP production from one mole of eicosanoate (C20:0), octadecenoate (C18:1) and palmitate (C16:0) was simulated. To demonstrate how each of these fatty acids can be catabolized to produce energy, the influx of all other carbon sources including glucose was constrained to zero and internal demand for cytosolic ATP was maximized. Previously, mammalian cell simulations in SimPheny™ demonstrated that a unit of proton per fatty acid was required to balance fatty acyl CoA formation in the cell. The proton demand was also identified and supplied to the CHO metabolic network. The liable explanation for proton demand is the role of the proton electrochemical gradient across the inner membrane to energize the long-chain fatty acid transport apparatus. This has been observed in *E. coli* and has been shown to be required for optimal fatty acid transport (Nyberg et al., *Biotechnol. Bioeng.* 62:324-335 (1999)).

The energy (ATP) production was calculated to be 136.5 mol ATP/mol of eicosanoate (C20:0), 120.75 mol ATP/mol of octadecenoate (C18:1) and 108 mol ATP/mol of palmitate (C16:0). These results were compared with analogous ATP production calculations that were generated using the reconstructed myocyte model in SimPheny™ (Table 10). The calculated ATP values are slightly different between two models. Published experimental data and previous reconstructions of mitochondrial metabolism match results calculated in myocyte model and report that 106 mol of ATP is produced from one mole of palmitate, when the P/O ratio is 2.5 (Seewoster et al., *Appl. Microbiol. Biotechnol.* 44:344-350 (1995); Nyberg et al., *Biotechnol. Bioeng.* 62:336-347 (1999)).

TABLE 10

Maximum ATP produced from 1 mol of fatty acid.

| Fatty Acid | Abbreviation | Myocyte model | CHO model | CHO model with irreversible NADP-dependent malic enzyme |
|---|---|---|---|---|
| Eicosanoate | C20:0 | 134 | 136.5 | 134 |
| Octadecenoate | C18:1 | 118.5 | 120.75 | 118.5 |
| Palmitate | C16:0 | 106 | 108 | 106 |

Further evaluation of the CHO metabolic network allowed for identification of the metabolic difference, which caused a variation of 2 ATP mols. Mitochondrial and cytosolic NADP dependent malic enzymes are assigned to be irreversible in the myocyte model. In the reconstructed CHO metabolic model, reactions that are catalyzed by the NADP dependent malic enzyme are included to be reversible, based on the previous experimental evidence generated using various types of mammalian cell types and tissues (Altamirano et al., Biotechnol. Prog. 17:1032-1041 (2001); Provost and Bastin, J. Process Control 14:717-728 (2004); Provost et al., Bioprocess Biosyst. Eng. 29:349-366 (2006). In this case, cytosolic NADP-dependent malic enzyme performs in the reverse direction allowing for transfer of reducing equivalents from the cytosol into mitochondria via the shuttle mechanism (Altamirano et al., Biotechnol. Prog. 17:1032-1041 (2001)) which consequently contributes to additional production of ATP. Constraining NADP-dependent malic enzymes to be irreversible in the CHO model led to no flux distribution through the cytosolic and mitochondrial NADP dependent malic enzymes and generated maximum ATP production results that were equal to the results generated using the myocyte model in SimPheny™ (Table 10).

Simulation and Prediction of CHO Cell Metabolism in Different Growth Conditions.

To demonstrate that the CHO metabolic model can accurately simulate CHO cell line metabolism, previously generated data from the CHO cell line continuous culture experiments were used. The CHO cell line was grown in chemically defined glutamine-based glucose rich (GR) and glucose limited (GL) chemostat cultivations at a dilution rate D=0.020 h−1. The uptake and secretion rates for 20 amino acids, glucose, lactate and ammonium were experimentally determined, and O2 consumption and $CO_2$ production were computed using metabolic flux analysis (MFA) (Altamirano et al., J. Biotechnol. 125:547-556 (2006)). To ensure that adequate amounts of essential amino and essential fatty acids are supplied for cell growth, the model was used to calculate the minimum required uptake rates for all essential amino acids and fatty acids. Where calculated minimum uptake rates of essential amino acids exceeded experimental measurements, the calculated values were used in further simulations (Table 11).

To simulate CHO cell physiology in two growth conditions, the maximum uptake of input nutrients was set to the rates calculated from the experimental data, growth was constrained to be equal to dilution rate and byproduct secretion was simulated for each growth condition. The simulation results were benchmarked by comparing substrate uptake and byproduct secretion rates to experimental measurements (Table 11). Major differences between the simulated values and experimental measurements resulted from the difference in essential amino acid requirements for the cell growth (shown in bold, Table 11). Most of these differences fall within the experimentally determined standard deviation for the essential amino acid uptake rates.

TABLE 11

Experimental CHO cell culture data fitted to the CHO metabolic network. Adopted from Altamirano et al. (Lakshmi Kamath, Keeping up with Protein Demand. Drug Discovery & Development. 1-12-2005).

|  | Glucose excess | | Glucose limitation | |
|---|---|---|---|---|
|  | Exp | Model | Exp | Model |
| Growth rate | 0.020 | 0.020 | 0.020 | 0.020 |
| Ala | 0.016 | 0.016 | 0 | 0 |
| Arg | −0.005 | −0.005 | −0.007 | −0.007 |
| Asn | −0.015 | −0.015 | −0.020 | −0.020 |
| Asp | 0.007 | 0.007 | 0.003 | 0.003 |
| C18:2 | — | −0.008 | — | −0.008 |
| C18:3 | — | 0 | — | 0 |
| $CO_2$ | 0.422 | 0.413 | 0.340 | 0.340 |
| Cys | −0.004 | −0.004 | −0.003 | −0.003 |
| Gln | 0 | 0 | 0 | 0 |
| Glu | −0.055 | −0.055 | −0.075 | −0.075 |
| Glucose | −0.190 | −0.190 | −0.056 | −0.056 |
| Gly | 0.012 | 0.012 | 0.017 | 0.017 |
| His | −0.002 | −0.014 | −0.003 | −0.002 |
| Ile | −0.004 | −0.006 | −0.007 | −0.006 |
| Lactate | 0.256 | 0.256 | 0.011 | 0.011 |
| Leu | −0.007 | −0.010 | −0.011 | −0.010 |
| Lys | −0.007 | −0.010 | −0.010 | −0.010 |
| Met | −0.002 | −0.002 | −0.002 | −0.012 |
| $NH_4^+$ | 0.022 | 0.022 | 0.042 | 0.042 |
| $O_2$ | −0.371 | −0.371 | −0.318 | −0.318 |
| Phe | −0.002 | −0.003 | −0.002 | −0.003 |
| Pro | −0.002 | −0.002 | −0.003 | −0.003 |
| Ser | −0.023 | −0.023 | −0.024 | −0.024 |
| Thr | −0.006 | −0.007 | −0.006 | −0.007 |
| Trp | −0.001 | −0.001 | −0.001 | −0.001 |
| Tyr | −0.001 | −0.001 | −0.002 | −0.002 |
| Urea | — | 0 | — | 0.004 |
| Val | −0.005 | −0.007 | −0.006 | −0.007 |
| ATPM | — | 1.709 | — | 0.993 |

Validated metabolite uptake and secretion rates were used to calculate ATP maintenance in each growth condition tested (Table 11). Calculated ATP maintenance values matched previously computed ATP maintenance values in SimPheny™ for the NS0 cell line (i.e. 1.782 mmol/gDW/h and 1.009 mmol/gDW/h) and correlated well with previously determined ATP maintenance values in the literature (0.7-2.0 mmol/gDW/h) for various mammalian cell lines (Wlaschin et al., Biotechnol. Bioeng. 91:592-606 (2005); Varma and Palsson, App. Environ. Microbiol. 60:3724-3731 (1994)).

In constraint-based modeling approaches that use optimization, a cellular objective function needs to be defined to determine metabolic flux distributions in a reconstructed network. Previously, in mammalian cell line models, a variety of objective functions were tested to simulate growth (Wlaschin et al., Biotechnol. Bioeng. 91:592-606 (2005); Brorson et al., Biotechnol. Bioeng. 80:257-267 (2002); Oh et al., Biotechnol. Prog. 21:1154-1164 (2005)); however, no single objective function was found to govern cell behavior. It has been experimentally shown that mammalian cell culture exhibit an inefficient metabolism, where large amount of nutrients are taken up and large quantities of byproducts are formed in the cell culture (Schilling et al., Biotechnol. Prog. 15:288-295 (1999); Wlaschin et al, supra; Brorson et al., Biotechnol. Bioeng. 80:257-167 (2002)). This metabolic inefficiency can be mathematically represented in the reconstructed model as the maximization of nutrient uptake. Computational and experimental results also suggest that the cell's physiology might be governed by the objective to maximize ATP production (Brorson et al., supra). In addition, the objective function of maximizing growth rate can represent culture behavior in a CHO cell line under the assumption that the immortalized cell lines, like tumor cells, lose growth regulation and tend to grow uncontrollably (Rodriguez et al., Biotechnol. Prog. 21:22-30 (2005); Liu et al., J. Biosci. Bioeng. 91:71-75 (2001)). These three objective functions, i.e. maximizing growth rate (herein referred to as Sim1, Sim2 and Sim3), maximizing ATP production (Sim4) and maximizing total nutrient uptake rate (Sim5)

were tested to simulate CHO cell line culture behavior and the results were summarized in Table 12.

TABLE 12

Simulation of CHO metabolism using the reconstructed CHO model.

| | Glucose Excess (GE) | | | Glucose Limitation (GL) | | | |
|---|---|---|---|---|---|---|---|
| | Exp | Sim 1 | Sim2 | Exp | Sim3 | Sim4 | Sim5 |
| Ala | 0.016 | 0.016* | 0 | 0 | 0 | 0 | 0 |
| Asp | 0.007 | 0 | 0 | 0.003 | 0.028 | 0 | 0.002 |
| $CO_2$ | 0.422 | 0.476 | 0.451 | 0.340 | 0.345 | 0.425 | 0.353 |
| Gly | 0.012 | 0.004 | 0 | 0.017 | 0.006 | 0 | 0 |
| Growth rate | 0.020 | 0.020 | 0.020 | 0.020 | 0.020 | 0.020 | 0.020 |
| Lactate | 0.256 | 0.204 | 0.255 | 0.011 | 0.028 | 0.000 | 0.080 |
| $NH_4^+$ | 0.022 | 0.035 | 0.056 | 0.042 | 0.027 | 0.060 | 0.069 |
| Urea | — | 0 | 0 | — | 0 | 0 | 0 |
| RQ | 1.13 | 1.28 | 1.21 | 1.07 | 1.08 | 1.33 | 1.11 |

Exp—experimental data. Adopted from Altamirano et al, *Biotechnol. Prog.* 17: 1032-1041 (2001). SIm1, Sim2 and
SIm3—simulation results, when objective function is to maximize growth
Sim4—simulation results, when objective function is to maximize ATP production
Sim5—simulation results, when objective function is to maximize substrate uptake
*upper bound for alalnine production was fixed To test the CHO metabolic model for its predictive capabilities, the uptake rates of glucose, oxygen, and all other measured substrates were constrained at the measured experimental values. Secretion rates of all byproducts were left opened and only upper bound on alanine production was imposed during Sim1 (Table 12). In the two GE and GL growth conditions tested, maximization of growth rate gave the results that best mimic CHO metabolism, compared to objective functions to maximize ATP production (Sim4) or maximize substrate uptake (Sim5). In GE cultivation conditions an additional upper bound constrain on alanine production improved predictive simulation results (Sim1 versus Sim2). Though, in GL cultivation conditions, no alanine is produced and thus all byproduct production has been predicted without imposing constraints on any byproduct produced (Sim3, Table 12). It has previously been reported that a stringent relation between glucose excess and alanine formation is present and that alanine overflow metabolism is energetically wasteful (Choi et al., *Biotechnol. Bioeng.* 91:793-800 (2005); Mahadevan and Schilling, *Metab. Eng.* 5:264-276 (2003)). The CHO cell culture modeling results confirm the experimental evidences and show that imposing demand for alanine production, as an energy consuming path, is necessary to simulate CHO cell culture metabolism in glucose and energy excess growth conditions. On the other hand, in glucose limitation, CHO cells generate limited amount of energy ($ATP_{GL} < ATP_{GE}$ (Table 11)) and thus no energy is directed to wasteful alanine production.

In summary, biologically meaningful objective functions and experimentally determined constraints were identified in: (1) glucose and energy limited, and (2) glucose and energy excess growth conditions to successfully simulate and describe CHO metabolism in cell culture. These preliminary results demonstrate the ability of the reconstructed CHO metabolic model to accurately represent CHO cell line metabolism in silico.

Summary of Preliminary Studies.

Stoichiometric analysis of microbial and mammalian cell line metabolism using a constraint-based framework is well established and extends over 15 years of research and experimentation. A comprehensive reconstruction of CHO cell was developed, which contains 550 reactions and tracks the fate of 524 metabolites. Metabolic network analysis of CHO cell line demonstrates that the physiological behavior of mammalian cell lines can be correctly represented and predicted using linear optimization and constraint-based modeling. Specifically, the preliminary work has shown that energy production, growth and byproduct secretion in mammalian cell culture can be correctly recalculated by the model, and that the CHO metabolic model can be used to predict CHO cell metabolism. In addition, network analyses provided valuable insight about the underlying mechanism of byproduct formation and energy balance in glucose-rich and glucose-limited CHO cell line cultivation. Collectively, constraint-based modeling as applied to mammalian cell line metabolism can thus be used to quantitatively compute and analyze metabolism in cell lines and to gain fundamental understanding of cell physiology and metabolism that can ultimately be used to improve industrial cell processes.

Model-Driven Metabolic Characterization in Varying Culture Conditions.

To demonstrate the benefit of combining a modeling and experimental approach in CHO-based protein production, we will use the reconstructed model to study metabolic changes of CHO-K1 cells in the presence of sodium butyrate in cell culture. The effect of sodium butyrate supplementation to mammalian cell culture has been studied extensively in the past (Lamotte et al., *Cytotechnology* 29:55-64 (1999); De Leon et al., *J. Biosci. Bioeng.* 103:82-91 (2007); Van Dyk et al., *Proteomics* 3:147-156 (2003); Brorson et al., *Biotechnol. Bioeng.* 80:257-267 (2002); Oh et al., *Biotechnol. Prog.* 21:1154-1164 (2005); Rodriguez et al., *Biotechnol. Prog.* 21, 22-30 (2005)). It has been shown that addition of sodium butyrate to the culture medium enhances specific productivity of γ-glutamyl transferase, tissue type plasminogen activator (t-PA), erythropoietin (EPO), and monoclonal antibodies in CHO cell lines 68. Butyrate supplementation is thought to increase protein synthesis by inhibiting a histone deacetylase which keeps the DNA tightly wrapped around the histones (Liu et al., *J. Biosci. Bioeng.* 91:71-75 (2001)). Inhibition of histone deacetylase increases the accessibility of the deoxyribonuclease to DNA and results in an increase in the rate of DNA transcription and protein biosynthesis. However, histone deacetylation is required for the completion of the G1 phase in cell cycle and its inhibition results in apoptosis or programmed cell death (Liu et al., *J. Biosci. Bioeng.* 91:71-75 (2001)). As a consequence, butyrate supplementation has shown to reduce viable cell density and volumetric productivity in cell culture (Choi et al., *Biotechnol. Bioeng.* 91:793-800 (2005)).

To prevent the apoptotic effect of sodium butyrate in protein production, three main strategies have been implemented: (a) addition or manipulation of culture nutrients, (b) genetic engineering of the cell lines, and (c) supplementation of anti-apoptotic chemicals (Oh et al., *Biotechnol. Prog.* 21:1154-1164 (2005)). Medium supplementation has been used to replenish the depleted nutrients from the cell culture and to prolong cell survival. However it has been shown that this approach does not necessarily lead to enhanced productivity (Oh et al., supra). Genetic modification of the cells by over-expression of the Bcl-2 protein has shown to prevent apoptosis in cell culture, however with varying phenotypic outcome depending on the cell line and culture condition (Oh et al., supra). Chemical supplementation of antioxidants such as N-acetylcysteine has also shown to prevent apoptosis and enhance volumetric titers, however the cost of chemical supplementation and their effect on glycosylation pattern of the final product have raise important concerns about the applicability of this approach in protein production (Oh et al., *Biotechnol. Prog.* 21:1154-1164 (2005)).

To circumvent the drawbacks associated with sodium butyrate supplementation in cell culture, an approach that may be found useful is to study the underlying mechanism by which specific productivity increases in butyrate-treated cell culture and to study its effect on metabolism, cell growth, and protein synthesis to develop alternative metabolic interventions that mimic the effect of butyrate supplementation without the need for anti-apoptotic treatment. This can be done by studying the metabolic fluxes in butyrate-free and butyrate-treated cell culture to identify significant differences that may contribute to the observed growth and productivity differences between the two growth conditions.

To evaluate metabolic changes mediated by butyrate treatment, we measured metabolite concentrations in batch conditions treated with 0, 0.5 and 1 mM sodium butyrate, using the same protocol as described above. It has been shown that CHO cell cultures treated with 0.5 and 2 mM sodium butyrate in batch lose cell viability after about 45 and 10 hours, respectively (De Leon et al., *J. Biosci. Bioeng.* 103:82-91 (2007)). Thus the two sodium butyrate concentrations were tested to: (1) identify major changes following a high dose butyrate treatment, and (2) ensure that the observed changes are sustained in a longer culture period treated with a low dose butyrate concentration.

Experimental Work:

Chinese Hamster Ovary cells were grown in spinner-flask batch cultivations in chemically defined CHO medium with 0 mM, 0.5 mM or 1.0 mM sodium butyrate added at the 24th hour of the cultivation. Experiments were performed in duplicate. Cultivations lasted from 117 to 144 hours and data for cell growth (viability, cell count and dry cell weight), exometabolome (glucose, lactose, ammonium and 19 amino acids) and cultivation conditions (osmolality, pH, temperature and bicarbonate) was recorded every 12-24 hours. From the collated experimental data, maximum specific substrate uptake, maximum specific product production and maximum specific growth rates were calculated for CHO exponential growth phase, and specific substrate uptake and specific product production rates were calculated for stationary growth phase.

Figure 18:
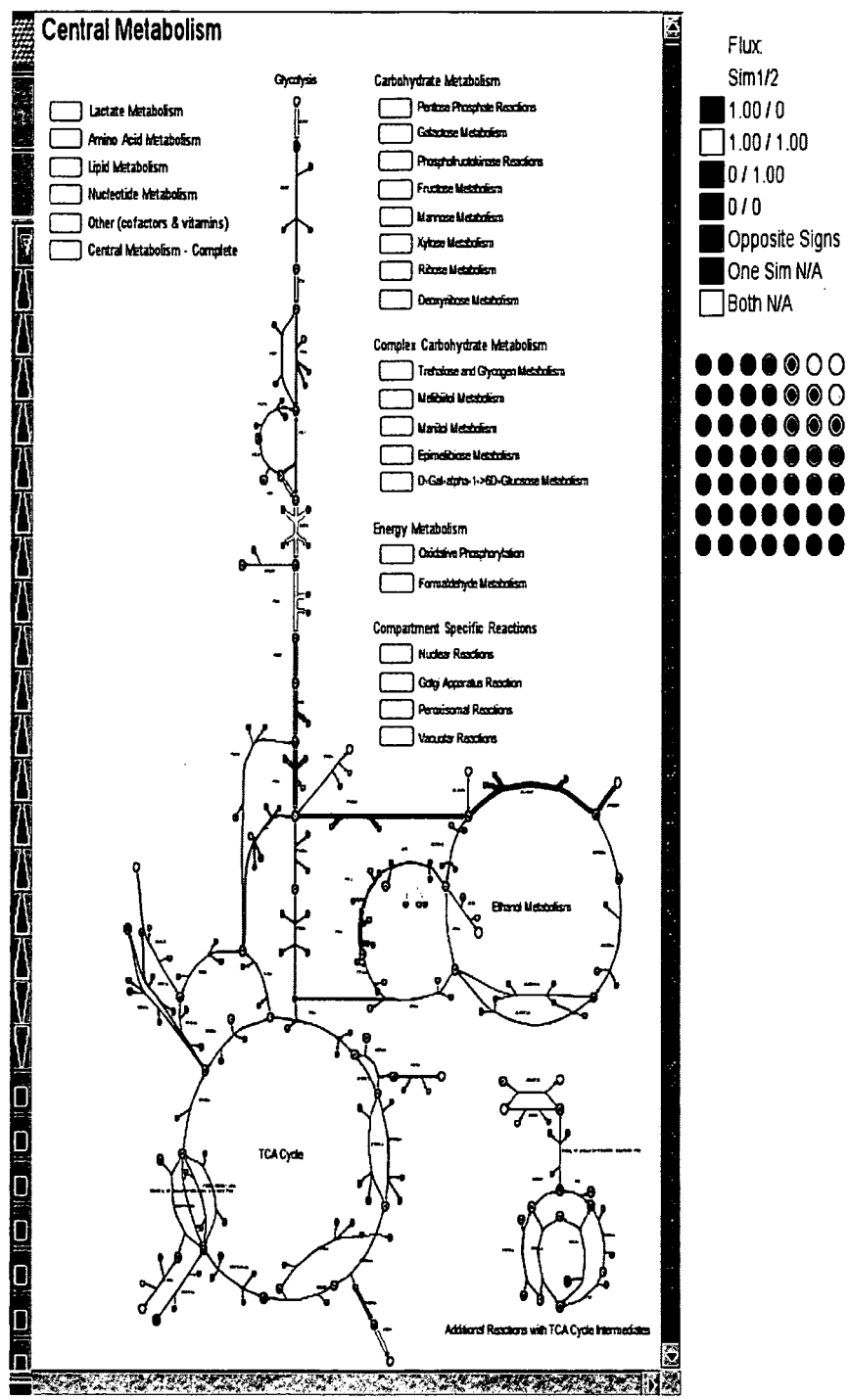
FIG. 18 shows a metabolic flux comparison between the butyrate-free and butyrate-treated simulations. (A) Simulation Module in SimPheny™ allows for the tabular and visual comparison of metabolic fluxes in two simulations. (B) The range of possible flux values can be identified using a Flux Variability Analysis (FVA), where the most significant changes are attributed to non-overlapping values. For simplicity, the most distinct flux differences are shown by the most generalized cases (I to VII), in the positive flux direction. A, butyrate-free condition; B, butyrate-treated condition; -, no change; x, single flux value; bar, range of flux values.
Figure 18B:
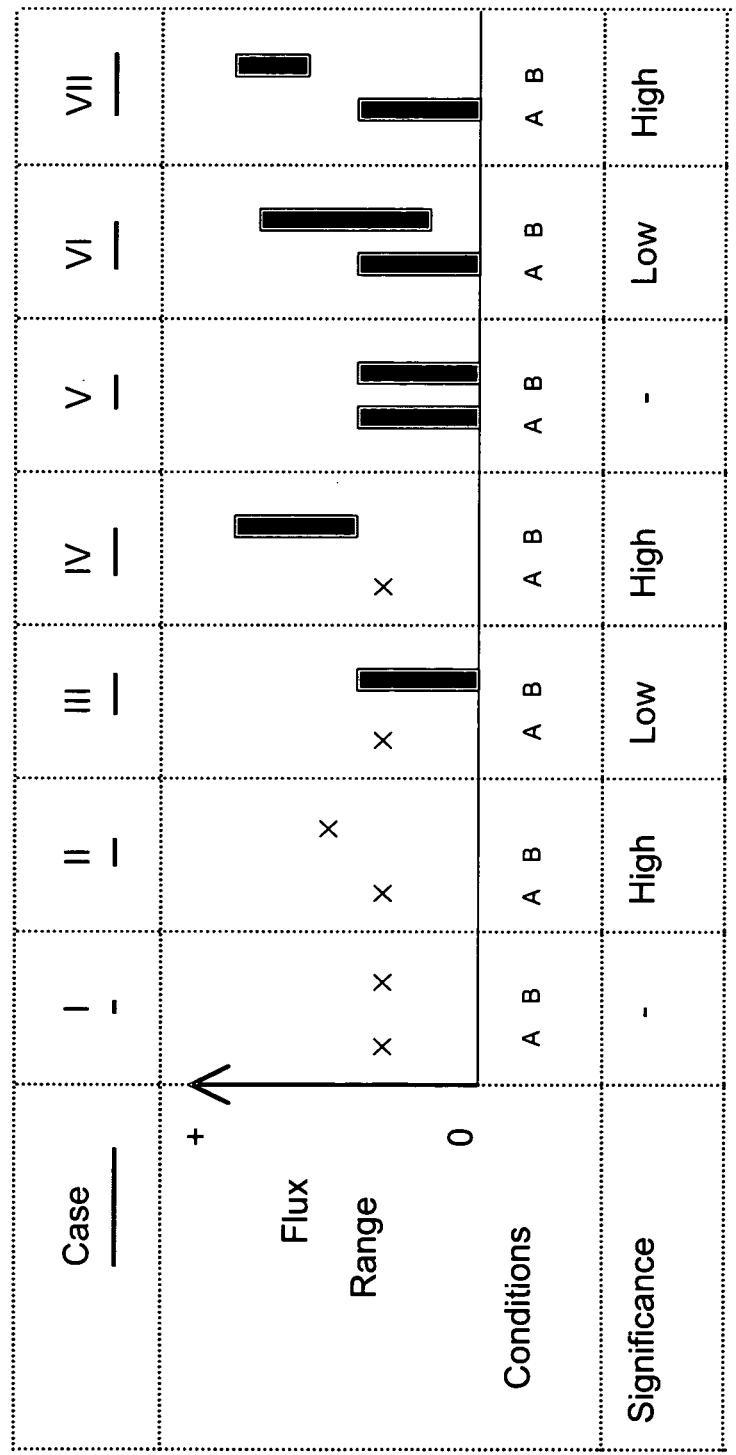
Figure 19:
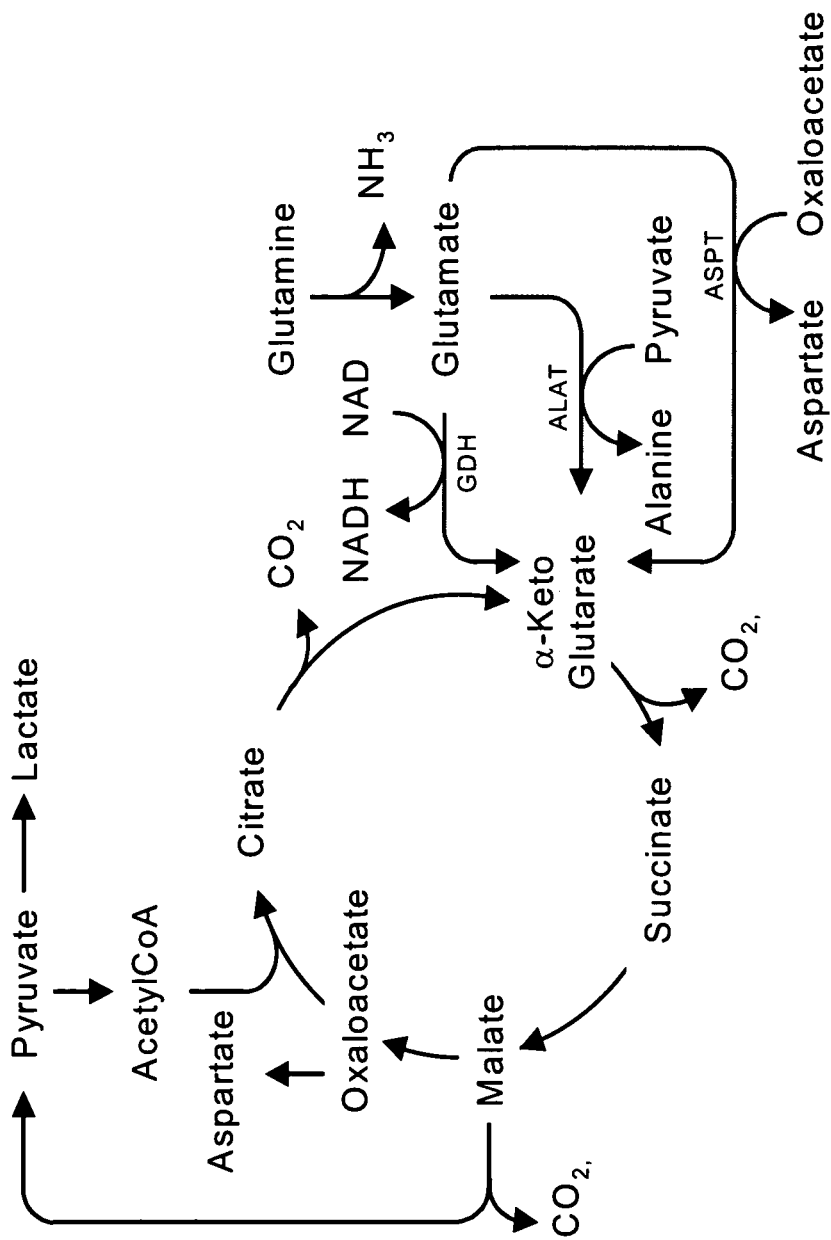
FIG. 19 shows pathways of glutamine utilization. Complete oxidation of glutamine results in the formation of $CO_2$ using glutamate dehydrogenase (GDH). Partial oxidation of glutamine can result in the formation of alanine via alanine transaminase (ALAT) reaction, or aspartate via aspartate transaminase (ASPT) reaction. Intracellular compartmentalization is not shown.

To understand the effect of butyrate supplementation on CHO cell metabolism, intracellular flux distributions between the treated and untreated simulations were compared in SimPheny™. The SimPheny™ Simulation Module allows for the comparison of metabolic fluxes in two simulations (FIG. 18A). Using this tool, we identified significant metabolic changes between the two simulations. Since the whole-cell reconstructed models are generally underdetermined (that is the number of constraints are less than the degrees of freedom in the network), a unique intracellular flux distribution cannot be calculated. However, methods have been developed to calculate the range of allowable flux values that each intracellular metabolic reaction can exhibit when an objective function is maximized or minimized (Mahadevan and Schilling, *Metab. Eng.* 5:264-276 (2003)). This approach, called flux variability analysis (FVA), was used to identify significant metabolic changes that follow sodium butyrate supplementation. To reduce uncertainty in the network analysis, the metabolic network was constrained by specifying the uptake and secretion rates of all metabolites, and growth to experimental measurements in the untreated and treated cell culture. Reactions with no overlapping values exhibited the most significant changes (FIG. 18B) and were identified as a potential mechanism to mimic the effect of sodium butyrate in protein production. The significant changes identified using the variability analysis can be tested individually and in combination with other significant metabolic changes identified in the untreated simulation to quantify their effect and to develop a list of single and multiple modifications that exhibit the same overall metabolic changes shown in the butyrate-treated case. The outcome of this analysis provided a list of metabolic interventions that can be experimentally tested in future studies.

Simulation of CHO Cell Metabolism in 6 Different Growth Conditions:

Calculated specific rates were used to simulate CHO metabolism in SimPheny™ using single optimization and the reconstructed CHO model. A total of 6 simulations that represented CHO cell line metabolism in different growth conditions were created. These simulations represented (i) exponential CHO cell growth in 0 mM NaBu, 0.5 mM NaBu, and 1.0 mM NaBu conditions, and (ii) stationary CHO cell growth in 0 mM NaBu, 0.5 mM NaBu, and 1.0 mM NaBu conditions.

NaBu Affect to CHO Cell Metabolism:

Flux Variability Analysis module in SimPheny™ was used to identify metabolic pathways and specific metabolic reactions that were significantly affected under 0.5 mM or 1 mM sodium butyrate treatment compared to control (0 mM NaBu) cultivation. (Reactions with no overlapping flux values between two conditions exhibited the significant changes.) The fluxes through 321 reactions (out of 550 reactions in the CHO model) were significantly changed under 0.5 mM and 1.0 mM sodium butyrate treatment compared to the control cultivation in exponential growth phase. The fluxes through 117 reactions were significantly changed under 0.5 mM and 1.0 mM sodium butyrate treatment in stationary growth phase. Reactions were found in which flux changed significantly in exponentially and stationary growth phases.

A total of 97 of these metabolic changes qualitatively overlapped among exponential and stationary growth phases and these metabolic reactions were identified to be markers of sodium butyrate effect on cell metabolism that is unrelated to cell growth. Hypergeometric distribution statistical test identified that overrepresentation of significant flux changes were among reactions of pentose phosphate pathway and ile-L, leu-L and val-L degradation pathway. These identified changes correlated with metabolic changes that are expected under sodium butyrate treatment. Sodium butyrate is known to induce ROS production, damage redox homeostasis, and thus induce cell death through apoptosis (Lakshmi Kamath, *Drug Discovery & Development, Jan.* 12, 2005; Wurm, *Nat. Biotechnol.* 22:1393-1398 (2004)). We propose that the found overrepresented significant higher flux through pentose phosphate pathway indicate induced production of NADPH that plays a role in maintaining the reduced cellular redox state. We expect that found overrepresented and significantly higher flux through ile-L, leu-L and val-L degradation pathway indicate cell's induced capability to produce recombinant protein under sodium butyrate treatment 1,3, since non-essential amino acids in the cell can be synthesized from branched chain amino acids ile-L, leu-L and val-L4. In addition, the experimental-computational platform indicated that more of essential amino acids were taken up by strains grown under sodium butyrate treatment than it was needed for biomass production. We propose that these changes in amino acid metabolism had happened during prolonged G1 phase under sodium butyrate treatment and it is a potential metabolic event/change that allows cells to induce recombinant protein production in sodium butyrate cultivations 3.

A total of 17 reactions were significantly changed during exponential and stationary phase in response to sodium butyrate, but had opposite effects (i.e. NaBu repressed flux through these reactions in exponential growth phase, but induced flux through these reactions during stationary phase and vice versa). The lists of these metabolic reactions (e.g. three reactions of glycolysis Hex1, Gapd and Pgk) represent potential targets that can be manipulated to maintain higher growth rate and induced specific protein production.

Metabolic Targets for Improved Protein Production:

Identified significant flux changes between sodium butyrate treated and control cultivations served as targets that could be chemically or genetically manipulated to improve specific protein productivity. At this time, we suggest that these manipulations should (i) preserve upregulated fluxes through BCAA pathway, (ii) induce, if possible, flux through pentose phosphate pathway, and (iii) induce flux through glycolysis even more during exponential phase in sodium butyrate treated culture.

The effect of sodium butyrate can also be studied using other approaches including isotopomer labeling experiments and Metabolic Flux Analysis (Stephanopoulos and Nielsen, *Metabolic Engineering: Principles and Methodologies*, Academic Press, San Diego, Calif. (1998)). The use of additional techniques, including the isotopomer labeling analysis or MFA, can be done where an integrated platform is used to engineer cell lines for improved productivity.

Example VII

Design of Novel Selection Systems

This example describes selecting cell lines for optimized production.

The need to develop new and optimized methods for host cell engineering and for selection of high-producing clones within heterogeneous populations in a timely and cost-efficient manner has become more and more crucial, particularly as regulatory constraints on development timelines remain stringent and production demands for new therapeutics continue to rise (Altamirano et al., *Biotechnol. Prog.* 17:1032-1041 (2001)).

One of the major challenges in mammalian based protein production is population heterogeneity that results following cell line transfection. Heterogeneous populations contain cells with different integration sites, copy numbers and varying specific productivities. Some of these are obviated by using clones; however, spontaneous loss of expression also happens. Low- or non-producing subpopulations can outgrow the producing population, thereby substantially lowering product yields. To enhance protein production, transfected cells must be extensively screened, often spanning over several months in the early stages of product development, to identify and select high producing clones.

Currently, the industrial production of many commercially valuable proteins predominantly involves the use of two selection markers, both of which capitalize on the use of a metabolic enzyme: dihydrofolate reductase (DHFR) (Seth et al., *Curr. Opin. Biotechnol.* 18:557-564 (2007)) and glutamine synthetase (GS) (Page and Sydenham, *Biotechnology* 9:64-68 (1991)). In both cases, simultaneous expression of these essential enzymes along with production of the recombinant protein allows for the selection of high producing clones in the cell culture. Despite their widespread and established use in cell line protein production, the use of DHFR and GS selection systems are limited by a number of disadvantages. The DHFR selection system can take more than 6 months to be implemented, it is laborious and can be leaky (i.e. it looses its selectivity over time (Cockett et al., *Biotechnology* 8:662-667 (1990)). It requires repeated rounds of selection and amplification with the expensive and toxic enzyme inhibitor methotrexate, and additional screening steps (e.g. series of limiting dilutions) to isolate clones with a high specific productivity (Wurm, *Nat. Biotechnol.* 22:1393-1398 (2004); Page and Sydenham, *Biotechnology* 9:64-68 (1991)). The GS selection system on the other hand uses only one round of selection for gene amplification, and in addition generates metabolic advantages to the cell culture, including reduction of toxic ammonia formation and increased cell viability (Page and Sydenham, *Biotechnology* 9:64-68 (1991); Urlaub and Chasin, *Proc. Natl. Acad. Sci. U.S.A.* 77:4216-4220 (1980)). It takes only 2 months for the GS selection system to generate high producing clones, however, the use of the GS system is expensive and requires substantial licensing and royalty payments (Zhang et al., *Cytotechnology* 51:21-28 (2006)).

In addition to the DHFR and GS systems, other selection markers have been tested in the past ten years. However, no significant advancements in the selection system design have been made thus far. As a result, there is a growing industrial demand for new and superior selection systems (Kingston et al., *Current Protocols in Molecular Biology* (John Wiley & sons, Inc., (1993)) that: (i) are inexpensive, scaleable, quick, and simple to use, (ii) do not require multiple rounds of selection and amplification, (iii) perform in a stringent selection manner, and (iv) preferably induce additive metabolic advantages to mammalian cell culture. As with GS and DHFR, metabolic enzymes can thus offer unique advantages for developing novel selection systems in mammalian cell lines for high producing clone selection. To identify and develop such novel selection systems, modeling and simulation technologies that capture the underlying metabolism and physiology of the host cell line can significantly accelerate the development of a superior selection system in mammalian protein production.

A computational modeling platform, called SimPheny™ (short for Simulating Phenotypes), that enables the efficient development of genome-scale models of metabolism and their simulation using a constraint-based modeling approach (Browne and Ul-Rubeai, *Trends Biotechnol.* 25:425-432 (2007); U.S. publication 20030233218). Within this platform, over a dozen bacterial and eukaryotic models have been developed that are used in strain engineering and bioprocessing for a wide range of product development applications. More recently this platform has been used for modeling mammalian systems, including for murine hybridoma, NS0, and Chinese Hamster Ovary (CHO) cell lines. The reconstructed metabolic models of the aforementioned mammalian cell lines have been extensively validated both retrospectively and prospectively for the study of growth as well as metabolite uptake and secretion profiles of batch and fed-batch cell cultures.

A systems biology approach utilizes the knowledge of a whole cell metabolism and is capable to provide rational designs for identifying new selection systems. The overall goal of this proof-of-concept study is to utilize the integrated modeling and experimental approach to computationally identify and experimentally evaluate new selection systems in CHO cell line. Novel selection system design can be done by:

I: Identification and prioritizing novel selection systems in CHO cell line using a reconstructed metabolic model: Essential metabolic reactions can be identified using the model that are candidate targets for designing novel selection systems in CHO cell line. A network-wide in silico deletion analysis can be performed using the reconstructed model of CHO metabolism, to search for essential metabolic functions that can be used as the basis for novel auxotrophic selections. Candidate targets can be prioritized based on a number of criteria, including a predicted stringent specificity of the new selection system based on an in silico deletion analysis and improved cell physiology, such as reduced byproduct formation and increased growth rate.

II: Experimentally implementing the top candidate selection system in CHO cell line: The top candidate selection system identified can be experimentally implemented by first creating a clone of the CHO cell line that is auxotrophic for a predicted media component. Disruption of the target gene(s) can done using a zinc-finger nuclease system made available for use by Sigma-Aldrich (Price et al., *Nat. Rev. Microbiol.* 2:886-897 (2004); Santiago et al., *Proc. Natl. Acad. Sci. U.S.A.* 105:5809-5814 (2008)). The generated deletion clone can then be tested for its auxotrophic characteristics. Verified auxotrophic clones can be transfected with a selection vector that includes the sequences of the genes that encode a traceable antibody to model a therapeutic protein, and an active allele of the previously disrupted gene encoding the essential enzyme(s), i.e. the selection marker. Stable antibody-producing clones will also be verified for the implemented selection system and antibody production.

III. Evaluating the development and implementation of a model-based selection system in CHO cell line: To determine the success of developing a novel selection system in a CHO cell line, we will compare experimentally generated cell culture data can be compared with those calculated by the reconstructed CHO metabolic model. The deletion and antibody producing clones created are characterized using spinner flask cultivations. Growth, metabolite uptake, and byproduct secretion patterns of the deletion and antibody producing clones can be qualitatively compared with the computationally predicted results.

Novel selection systems can thus be computationally identified and experimentally validated a novel selection system in CHO cells, focused on targets with added metabolic advantages such as reduced byproduct formation and increased growth rate. The resulting novel selection system and antibody production can be developed and improved further using existing experimental and computational techniques, and other novel targets can be identified and validated.

Therapeutic Proteins in Healthcare.

Production costs by mammalian cell culture remain high, and new methods to provide a more effective approach to optimize cell engineering, media optimization, and process development are of highest interest to the industry, particularly as regulatory constraints on development timelines remain stringent and production demands for new therapeutics rapidly rise. Production costs are a major concern for management planning, especially with intense product competition, patent expirations, introduction of second-generation therapeutics and accompanying price pressure, and pricing constraints imposed by regulators and reimbursement agencies. Reducing the cost of therapeutic protein development and manufacturing, and shortening the timelines for product development would do much to ensure that the next generation of medicines can be created in amounts large enough to meet patients' needs, and at prices low enough that patients can afford.

Current Approaches in Protein Producing Clone Selection and Screening.

Selection markers play an important role in the overall development process of therapeutic proteins in mammalian cell cultures. Selection markers are used to ensure that mammalian cells have been successfully transfected with a heterologous gene of interest. Such transfected cells can then be screened for maximal expression of the cognate heterologous protein of interest (Browne and Al-Rubeai, *Trends Biotechnol.* 25:425-432 (2007); Wurm, *Nat. Biotechnol.* 22:1393-1398 (2004)). In general, selection and screening systems for mammalian cell cultures are designed using one or a combination of the following strategies: (i) utilization of strain auxotrophic characteristics, (ii) exploitation of strain resistance to a drug, and (iii) the expression of heterologous proteins (e.g GFP) that can be physically detected using flow cytometry or other robotics tools.

In the past, production of therapeutic proteins in mammalian cell lines has been dominated by the use of selection markers that have metabolic origin, including dihydrofolate reductase (DHFR) (Page and Sydenham, *Biotechnol.* 9:64-68 (1991)), glutamine synthetase (GS) (Cockett et al., *Biotechnology* 8:662-667 (1990)), thymidylate synthase (Ayusawa et al., *Somatic. Cell Genet.* 7:523-534 (1981)) and bacterial xanthine guanine phosphorybosyl transferase (Mulligan and Berg, *Science* 209:1422-1427 (1980)). The industrial production of many commercially valuable proteins has focused largely on two markers, DHFR (Page and Sydenham, supra) and GS (Cockett et al., *Biotechnology* 8:662-667 (1990)). The DHFR system is routinely and widely used with CHO cells that are deficient in the DHFR activity and thus require hypoxanthine and thymidine in the medium for growth and nucleotide production (Page and Sydenham, supra). The DHFR selection system is sensitive to ectopic differences in expression, requiring repeated rounds of selection and amplification with the expensive and toxic enzyme inhibitor methotrexate, as well as additional screening steps (e.g. series of limiting dilutions) to isolate clones with a high specific productivity of the target protein (Jayapal et al., *Chem. Eng. Progress* 103:40-47 (2007); Cockett et al., supra). Also, spontaneous mutations within the DHFR gene can cause leakiness of the selection strategy (Urlaub and Chasin, *Proc. Natl. Acad. Sci. U.S.A.* 77:4216-4220 (1980)). Overall, this system can result in very high levels of heterologous protein amplification (1000 copies per cell) (Kingston et al., *Current Protocols in Molecular Biology*, John Wiley & Sons, Inc., (1993)), however, the extra work needed to screen for stable and highly expressing clonal strains can take 6 to 12 months (Jayapal et al., *Chem. Eng. Progress* 103:40-47 (2007)). In contrast the GS system typically requires only a single round of selection and amplification to generate maximally expressing heterologous protein producers (Cockett et al., supra). CHO cells have a low level of endogenous glutamine synthetase activity, which usually can maintain cell growth in the absence of glutamine; however, the growth is not as good as in the presence of glutamine. Upon transfection with a GS selection system, CHO cell lines gain a significant metabolic advantage—these cell lines have increased viability in glutamine-free media and they produce less ammonia, which is a toxic metabolic byproduct that can adversely affect protein glycosylation and cell growth rates (Zhang et al., *Cytotechnology* 51:21-28 (2006)). The additional selective pressure of toxic methionine sulfoximine (MSX) is used to amplify GS and heterologous protein production (Cockett et al., supra). It takes only 2 months for the GS selection system to generate stable high producing clones; however, the use of the GS system is expensive as it requires substantial licensing and royalty payments (Kingston et al., *Current Protocols in Molecular Biology* (John Wiley & Sons, Inc., (1993)).

Importance of New Selection System Development.

Selection of high-producing mammalian cell lines represents a bottleneck in process development for the production of biopharmaceuticals, both in terms of the required development time and bioreactor capacity (Browne and Al-Rubeai, *Trends Biotechnol.* 25:425-432 (2007)). The market of therapeutic proteins is expected to double between 2007 and 2010. If the biopharmaceutical industry is to meet with increasing market demand, more efficient methods of cell line selection are required (Browne and Al-Rubeai, supra). Despite a significant effort in development of new selection systems for the past 20 years, no major improvements resulting in new and superior selection system designs have been achieved. Current selection methods are hampered by a number of disadvantages and are time-consuming, expensive and not suitable for large scale production (Browne and Al-Rubeai, supra). Most selection systems require continuous addition of selective agents such as antibiotics or toxic compounds to maintain high protein production. With increasing stringency in biotherapeutic production and manufacturing regulations it is essential to ensure that the end product contains no antibiotics and no genes for antibiotic resistance (TechNote: Antibiotic-Free Systems for Production. *Genetic Engineering & Biotechnology News* 26, (2006)). Removing these selection agents from industrial protein production cultivations can cause loss of stable protein producing strains and can greatly hamper therapeutic protein production. Therefore, the industry has long been in need of new selection systems that are relatively simple, reliable and inexpensive (Browne and Al-Rubeai, supra).

In addition to the need for more reliable and less expensive selection systems, there is an increasing need to develop superior mammalian cell lines with improved metabolic characteristics. Previous cell line engineering efforts have focused on controlling metabolic flow in mammalian expression systems, including CHO cell lines, to reduce production of toxic metabolic intermediates and byproducts (e.g. lactate and ammonium). In addition to reducing metabolic efficiency of the cell for protein production, secretion of metabolic byproducts can negatively affect cell growth, cell viability, and product formation in industrial cultivations (Altamirano et al., *Biotechnol. Prog.* 17:1032-1041 (2001); Irani et al., *Biotechnol. Bioeng.* 66:238-246 (1999); Jeong et al., *Mol. Cell. Biochem.* 284:1-8 (2006)). The GS selection system, developed through a minimal and rational manipulation of cell metabolism, is an example of a selection system with beneficial metabolic characteristics. In the GS selection system, glutamine is synthesized intracellularly, allowing the transfected cells to grow in a glutamine-free media. The added advantage of the GS system is that the cell culture produces less ammonium in continuous mammalian cell line cultivation, improving the overall cell viability and productivity (Cockett et al., *Biotechnology* 8:662-667 (1990); Zhang et al., *Cytotechnology* 51:21-28 (2006)). As shown in the GS system, developing an effective and inexpensive selection system that simultaneously improves the metabolic characteristics of the cell line is of great value in the production of therapeutic proteins in mammalian cell lines.

Other metabolic enzymes could be promising alternatives with additional metabolic advantages for developing novel selection systems in mammalian cell lines for high-producing clone selection similar to the GS selection system. Identifying such selection systems, however, requires a fundamental understanding of metabolic pathways in the cell. A comprehensive knowledge of cell metabolism and the interlinking metabolic pathways allows for identifying candidate selection systems that: (i) only use media supplements, needed for biomass production, as a selective pressure, (ii) eliminate the need to use expensive additives i.e. antibiotics or enzyme inhibiting compounds in cell engineering processes, (iii) eliminate the need of multiple cloning and use of multiple selection systems in the engineering of high protein producing cell line, and (iv) cause metabolic improvement (e.g. regulation of alanine overflow, induction of cell growth or reduction of byproduct formation) in mammalian cell lines. The integrated computational and experimental platform provides a unique framework for identifying and developing such superior selection systems to select better performing mammalian cell lines.

Importance of Metabolic Modeling in Design of Selection Systems and Improved Mammalian Cell Line Culture.

Understanding cell physiology and interlinking metabolic pathways is key when designing superior selection systems. Modeling and simulation technologies that capture the underlying metabolism and physiology of the host cell line can significantly accelerate the development of a superior selection system in mammalian protein production. Computational metabolic modeling can serve as a research and design tool to: Identify what pathways are being used under specified genetic and environmental conditions; Determine the fate of nutrients in the cell; Identify the source of potentially toxic waste products; Examine the effect of eliminating existing reactions or adding new pathways to the host cell line Analyze the effect of adding nutrients to the media; Interpret process changes (e.g. scale-up) at a fundamental physiological level; Generate rational design strategies for cell engineering, media optimization and process development.

Thus, a whole-cell network reconstruction for mammalian cell line metabolism will be extremely valuable as a platform for engineering mammalian cell line culture. There are strong scientific and financial incentives to develop technology that can speed-up desired mammalian cell clone engineering and selection, while simultaneously reducing the cost of the process. Many metabolic factors influence the performance of a selection system. Understanding metabolic changes that follow genetic and environmental perturbations in the cell culture engineering processes will allow for the development of more effective selection systems to ultimately improve cell culture and avoid unexpected variation in cell culture protein production.

Metabolic Models for Rational Bioprocess Design.

Any attempt to improve protein production by overcoming fundamental metabolic limitations requires a platform for the comprehensive analysis of cellular metabolic systems. Genome-scale models of metabolism offer the most effective way to achieve a high-level characterization and representation of metabolism. These models reconcile all of the existing genetic, biochemical, and physiological data into a metabolic reconstruction encompassing all of the metabolic capabilities and fitness of an organism. These in silico models serve as the most concise representation of collective biological knowledge on the metabolism of a microorganism. As such they become the focal point for the integrative analysis of vast amounts of experimental data and a central resource to design experiments, interpret experimental data, and drive research programs. It is now becoming recognized that the construction of genome-scale in silico models is important to integrate large amounts of diverse high-throughput datasets and to prospectively design experiments to systematically "fill in the gaps" in knowledge base of particular organisms (Ideker et al., *Science* 292:929-934 (2001)).

The exercise of constructing and demonstrating the use of genome-scale models of metabolism began in earnest out of academic efforts in which this team was involved. Previously published in silico representations of metabolism include those for *Escherichia coli* MG1655 (Edwards and Palsson, *Proc. Natl. Acad. Sci. U.S.A.* 97:5528-5533 (2000)), *H. influenzae* Rd (Edwards and Palsson, *J. Biol. Chem.* 274:17410-17416 (1999); Schilling and Palsson, *J. Theor. Biol.* 203:249-283 (2000)), *H. pylori* (Schilling et al., *J. Bacteriol.* 184:4582-4593 (2002)), *S. cerevisiae* (Forster et al., *Genome Res.* 13:244-253 (2003)), and *Homo sapiens* (Duarte et al., *Proc. Natl. Acad. Sci. U.S.A.* 104:1777-1782 (2007)). More recently this platform has been used for modeling mammalian cell lines, including murine hybridoma, NS0, and Chinese Hamster Ovary (CHO) cell lines. The general process has been previously published along with various applications of the in silico models (Schilling et al., *Biotechnol. Prog.* 15:288-295 (1999); Covert et al., *Trends Biochem. Sci.* 26:179-186 (2001)). In combination with appropriate simulation methods, these models can also be used to generate hypotheses to guide experimental design efforts and to improve the design and optimization of selection systems for mammalian cell lines. When properly integrated with experimental technologies, an extremely powerful combined platform for design of selection systems and mammalian cell line engineering can be implemented for a wide range of applications within the pharmaceutical and biotechnology industries for production and development of healthcare products, therapeutic proteins, and biologics.

Deletion Analysis in Computational Modeling of Metabolism.

In silico deletion analysis has been successfully used to predict the viability of various gene knockouts in genome-scale metabolic models of *Escherichia coli* and *Sacchromyces* cerevisiae using a constraint-based modeling approach (Forster et al., *OMICS* 7:193-202 (2003); Edwards and Palsson, *BMC Bioinformatics* 1:1 (2000)). In *E. coli*, an in silico deletion analysis was carried out on the central metabolic genes. The in silico growth results under different substrate conditions were then compared with experimental data and shown to predict 86% (68 of 79 cases) correctly (Edwards and Palsson, supra). When the model made an incorrect prediction, that prediction was always conservative (i.e. the model said the cell could grow while the experiments showed no growth). A later study analyzed 13,750 growth phenotypes and the model agreed in 10,828 (78.7%) of those cases (Covert et al., *Nature* 429:92-96 (2004)). An in silico deletion analysis was also carried out in the yeast *S. cerevisiae*. In the first study, in silico growth was correctly predicted for 81.5% (93 of 114) of the cases (Famili et al., *Proc. Natl. Acad. Sci. U.S.A.* 100:13134-13139 (2003)). A later study expanded the in silico analysis to the genome-scale, correctly predicting 89.4% knockout cases (496 of 555) (Forster et al., supra). Thus, the viability of gene knockouts in genome-scale metabolic models has shown to be predicted with high accuracy. Exemplary deletions in CHO cells are shown in Tables 19 and 20.

Selection System Design: The promising preliminary results, as shown in the Preliminary Studies section, clearly demonstrate that the reconstructed CHO cell line model correctly simulates metabolism in cell culture, and thus can be used effectively for the design of novel selection systems. We will demonstrate the feasibility of identifying novel and superior selection systems using an integrated computational and experimental approach, whereby predictions based on analyses of the CHO cell line metabolic model will be tested and implemented. To accomplish this goal, the reconstructed model of CHO metabolism is used in combination with experimental capabilities to computationally identify new selection systems in CHO cell lines and experimentally implement and evaluate the top candidate in CHO cells.

Figure 21:
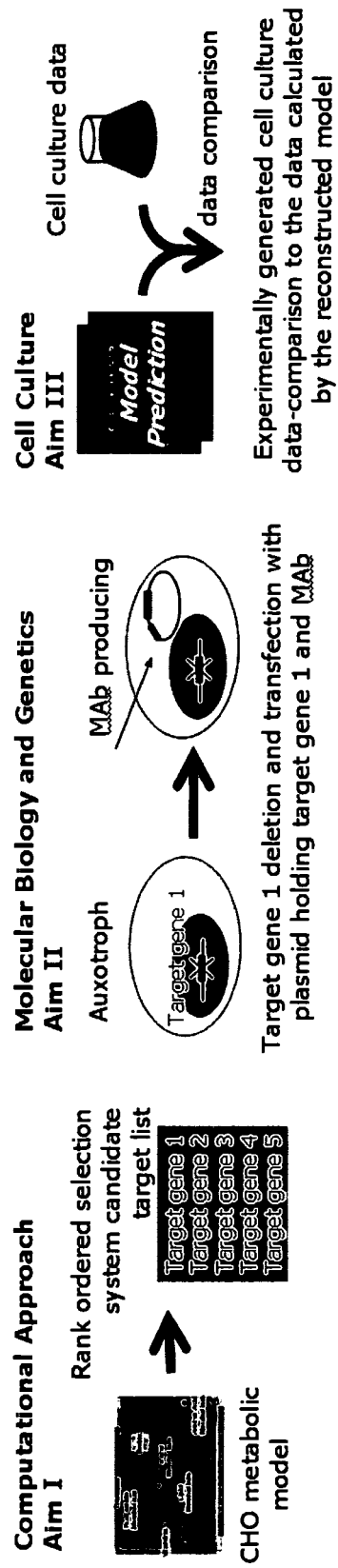
FIG. 21 shows strategy to create an improved selection system in Chinese Hamster Ovary cell line. A target selection marker gene will be identified using a computational approach with the reconstructed CHO cell metabolic model. Computationally designed selection system will be implemented by first disrupting target gene 1 and then inserting it back on a plasmid as a selection marker. By model predicted and experimentally generated cell culture data will be compared and strategies for the selection system design improvements will be created.

The experimental study is performed in three stages (FIG. 21). Essential metabolic reactions are identified that are candidate targets for designing novel and superior selection systems using network-wide deletion analysis and using our proprietary reconstructed model of CHO metabolism. The candidate targets are rank-ordered and prioritized based on a number of criteria, including the predicted stringent specificity of the new selection system and improved cell physiology using our in-house computational tools. The top candidate selection system is experimentally implemented in the CHO-S cell line by: (a) creating an auxotrophic clone, (b) transiently transfecting cells with a selection vector that includes an antibody-expressing gene, and (c) selecting protein producing cell lines based on their auxotrophy. The development and implementation of a model-based selection system is evaluated in CHO cells by comparing experimentally generated cell culture data with those calculated by the reconstructed model. Successful completion of this validation study will provide a demonstration of the scientific and technical feasibility of the integrated platform for design of new and superior metabolic selection systems in mammalian based protein production.

Identify and Prioritize Novel Selection Systems in Chinese Hamster Ovary Cell Line Using a Reconstructed Metabolic Model.

Using the reconstructed and validated model of CHO metabolism, we aim to identify essential metabolic reactions that are candidate targets for designing novel selection systems in CHO cell lines using an in silico deletion study (see above) (Altamirano et al., *Biotechnol. Prog.* 17:1032-1041 (2001); Browne and Al-Rubeai, *Trends Biotechnol.* 25:425-432 (2007)). We will perform a network-wide single- and double-reaction deletion analysis by removing the corresponding reactions from the network while simulating growth, as described in the Preliminary Studies section. The results from this in silico deletion study will provide us with a list of: (i) single target reactions, which are essential (required for growth), and (ii) two-reaction deletions that are fatal to the cell (i.e. synthetic lethals) (Step 1, FIG. 22). Only deletion of target reactions that generate true lethal deletion strains (strains with deleted essential genes and synthetic lethalities) will be further analyzed within the CHO metabolic network in SimPhenyυ.

Once a list of single and double lethal deletions are identified, we will investigate each case to identify a subset of the in silico deletion strains for which growth can be restored under an auxotrophic condition, i.e. by adding a precursor metabolite (i.e. nucleotide, vitamin or amino acid) to the chemically defined CHO cell growth medium. We will also evaluate and rank order such precursor metabolite, based on the knowledge about their transport systems, the cost, availability and safety of these metabolites to be used in industrial protein production (Step 2, FIG. 22).

In order to identify a superior selection system compared to existing ones, we will aim to find a metabolic marker, which is a selection marker of true auxotrophy (described above) and a marker of improved metabolism. An existing example of the selection system of interest is the GS selection system, the presence of which induces cell growth in the absence of glutamine and reduced production of toxic ammonia (Walsh, *Nat. Biotechnol.* 21:865-870 (2003)). To identify superior selection systems, we will perform additional computational analyses to determine the metabolic network response to the changes (i.e. increase or decrease) imposed on a flux through a particular reaction of interest. In this study we will use Robustness Analysis (Lakshmi Kamath, *Drug Discovery & Development, Jan.* 12, 2005) to identify target reactions through which constrained higher flux can improve CHO cell line metabolic properties, e.g. to reduce toxic byproduct production, reduce wasteful energy metabolism, reduce alanine overflow or improve monoclonal antibody productivity (Step 3, FIG. 22) (Altamirano et al., *Biotechnol. Prog.* 17:1032-1041 (2001); Wurm, F. M., *Nat. Biotechnol.* 22:1393-1398 (2004)). These target reactions will be rank-ordered based on their potential benefits to metabolic characteristic of cell culture. Results identified by Robustness Analysis for increasing flux through a reaction will be implemented by transfecting the auxotrophic CHO cell line with the selection marker gene that is placed on a powerful promoter, e.g. hCMV promoter that has successfully been used in mammalian cell line applications, including GS selection system design (Jayapal et al., *Chem. Eng. Progress* 103:40-47 (2007)). Alternatively, less active promoters will be used if over-expression of the gene of interest proves to be toxic to the cells.

Figure 22:
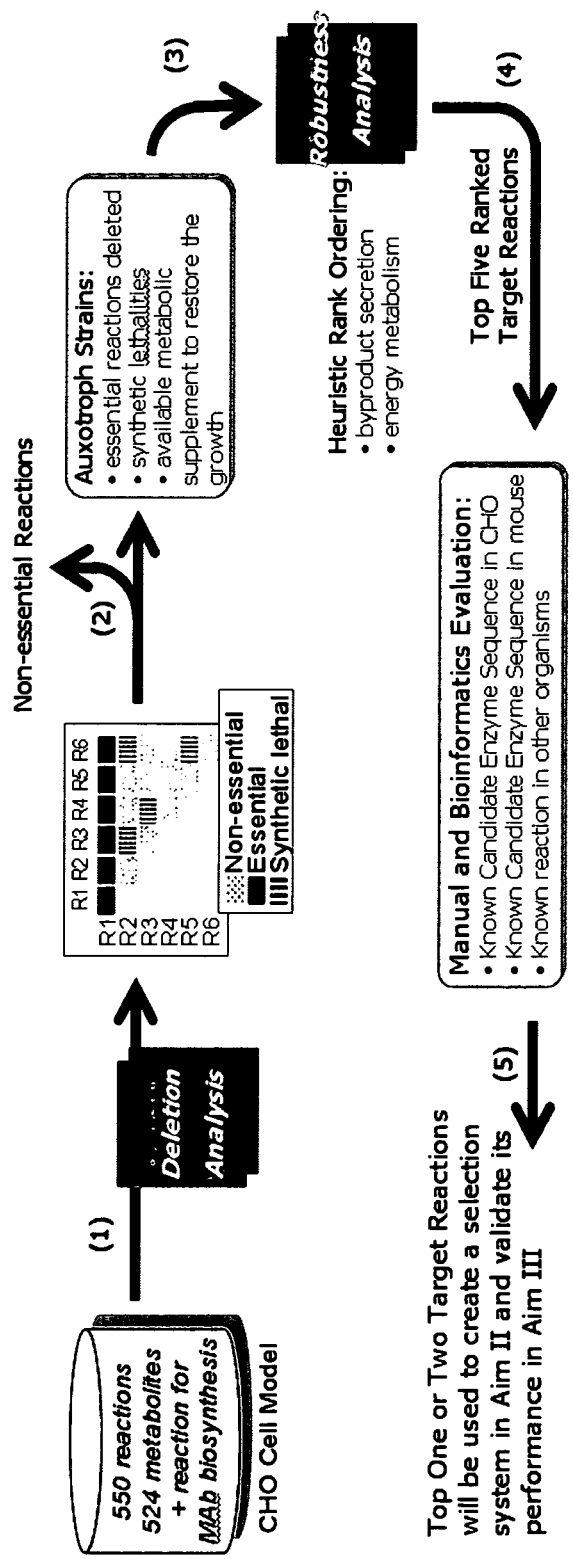
FIG. 22 shows that deletion analysis can be performed on CHO metabolism (Step 1). Metabolic target reactions, deletion of which would create true auxotrophs can be identified (Step 2). Target reactions can be analyzed using Robustness Analysis for superior selection system design in SimPheny™ (Step 3) and top five candidates can be subjected to manual and bioinformatics evaluation (Step 4). Top one or two target reactions (one essential reaction or one synthetic lethality of two target reactions) can be selected for one experimental selection system design (Step 5).

Finally, top five target metabolic reactions will be further subjected to manual and bioinformatics evaluation (Step 4, FIG. 22). First, number of (iso-)enzymes catalyzing the target reaction of interest will be identified using previous publications on CHO cell line physiology and metabolism, and CHO EST genome sequence library (Seth et al., *Curr. Opin. Biotechnol.* 18:557-564 (2007)). Chinese Hamster genome sequence annotation has not yet been published. Sequence comparison of CHO EST library to the GenBank database has shown that mouse is the best model organism with complete genetic and sequence information that can be used for comparative analysis for the CHO cell line (Seth et al., *Curr. Opin. Biotechnol.* 18:557-564 (2007)). Thus, if none of top five target gene sequences is known specifically for Chinese Hamster, or cannot be determined using bioinformatics tools, we will use mouse and hamster sequence similarity to experimentally determine sequences of Chinese Hamster target genes (see below). Using bioinformatics tools and published literature, we will also investigate the presence of multiple copies of the target genes that may be present in Chinese Hamster genome. Since CHO cells are known to be functionally hemizygous for many genes primarily due to gene inactivation (Page and Sydenham, *Biotechnology* 9:64-68 (1991); Cockett et al., *Biotechnology* 8:662-667 (1990)), we expect that experimental implementation of the candidate selection system will require deletion of only one or two genes, thus simplify the effort required in developing true auxotrophic clones. Candidate targets will be rank ordered based on the known or predicted number of target (iso-)genes and their known or predicted sequences in Chinese Hamster genome. The top candidate target identified will be experimentally implemented to create a metabolic selection system in CHO cell line. We will attempt to implement top two or top three selection systems in parallel to avoid the possibility that poor transport efficiency of a supplemental nutrient in one of auxotroph strains not predicted by the model could jumper cell growth in the timelines of this project significantly.

Experimentally Implement Top Candidate Selection System in CHO Cell Line.

To experimentally validate the computational approach, we will create the candidate selection system in CHO-S cell line. CHO-S cells are a subclone of the parental CHO cell line, which have been adopted to grow in suspension and can produce monoclonal antibodies in serum-, hydrolysate-, and protein-free chemically defined media. In addition, CHO-S is not a proprietary cell line, there are no issued patents restricting the use of CHO-S cells, and they can be purchased through Invitrogen Corp. Deletion of the target gene and insertion of the GFP tag will be done using a zinc-finger nuclease (ZFN) system available through Sigma-Aldrich (Urlaub and Chasin, *Proc. Natl. Acad. Sci. U.S.A.* 77:4216-4220 (1980)). Sigma Aldrich uses their proprietary algorithm to in silico design several ZFN candidates and does all necessary ZNF assembly and DNA binding testing to select the best ZFN pair to provide to the customer. ZFN technology uses a general solution using a combination of two fundamental biological processes: DNA recognition by C2H2 zinc-finger proteins and repair of DNA double-strand breaks using non-homologous end joining (NHEJ) or using homology dependent repair (HDR). We will use the zinc finger nuclease (ZFN) driven targeted gene disruption and sight-specific gene insertion technology to disrupt and inactivate the gene that codes for the target reaction and simultaneously introduce the GFP tag to the deletion strains (first scheme, FIG. 23) (Urlaub and Chasin, *Proc. Natl. Acad. Sci. U.S.A.* 77:4216-4220 (1980); Zhang et al., *Cytotechnology* 51:21-28 (2006)). Previous studies have shown that ZFN-mediated gene disruption or targeted gene insertion is a robust and general method for targeted and precise genome editing in mammalian cells and ZFN-targeted GFP integration in CHO cell line has a frequency of insertion of up to 13% (Kingston et al., *Current Protocols in Molecular Biology*, John Wiley & sons, Inc., (1993); Browne and Al-Rubeai, *Trends Biotechnol.* 25:425-432 (2007); Price and Palsson, *Nat. Rev. Microbiol.* 2:886-897 (2004); Santiago et al., *Proc. Natl. Acad. Sci. U.S.A.* 105:5809-5814)). ZFN-based gene deletion has proven to be more effective than temporary 'knock down' approaches based on small molecule inhibitors, zinc finger transcription factors, antibodies, antisense, or RNAi. Also, only transient ZFN expression is required to generate permanent gene deletions (Urlaub and Chasin, *Proc. Natl. Acad. Sci. U.S.A.* 77:4216-4220 (1980); Urnov et al., *Nature* 435:646-651 (2005); Polastro and Tulcinsky, *Scrip Magazine* (August 2002)). Compared with gene addition via random integration, ZFN-based technology provides robust, targeted, and precise gene insertions (Zhang et al., *Cytotechnology* 51:21-28 (2006)). Overall, ZFN-based technology should generate quicker, permanent, and higher probability gene manipulation results compared with other available mammalian cell engineering technologies.

To create a gene deletion clone for the target gene sequence selected, we will design a pair of ZFNs that specifically bind to the sequence of target gene exon, disruption of which would disrupt the target gene expression. If the results of the manual and bioinformatics evaluation were inconclusive regarding Chinese Hamster target gene sequence, we will clone genomic DNA fragment from the Chinese Hamster Ovary cell line (based on mouse genome sequence) and determine the nucleotide sequence of a stretch of DNA that encompasses the complete sequence of the target gene. The intron/exon boundaries will be identified by RT-PCR following GT/AG rule and the exon sequence will be used for the design of ZFNs. We will also engineer (or obtain from Sigma Aldrich) the homologous donor plasmid that contains GFP cDNA flanked by 750-bp stretches of sequence that are homologous to the target locus and that surround double strand break introduced by ZFN. Next, CHO cells will be transfected with the donor plasmid carrying GFP tag and ZFNs. During ZFN-induced homologous DNA repair, the GFP is inserted at the cleavage site of the target gene and the expression of the target gene is disrupted (First scheme, FIG. 11).

Following cell transfection, CHO cells will be cultivated in completely supplemented medium with all the ingredients that are required for the created auxotrophs to grow. CHO cells that express GFP will be selected using fluorescence-activated cell sorting (FACS) (Step 1, FIG. 11). Repeated rounds of selected GFP-tagged cell cultivation and FACS sorting will be performed to select for the highest levels of GFP-driven fluorescence, and clonal GFP-expressing cell lines will be produced. The GFP tag was chosen to use as a screening/selection marker rather than antibiotic resistance or limiting dilution cloning (LDC) approaches, since the GFP-based method performs faster and more cells can be screened at a time (Pissarra, Nat. Biotechnol. 22:1355-1356 (2004)). Also, GFP has no known negative impact on cell growth and metabolism. In contrast, antibiotic based selection slows down cell growth and requires additional time for cell recovery. A single FACS sorting using GFP-tag selection system can generate clonal transfected cell culture approximately 10 times faster compared with LDC selection approach (Pissarra, Nat. Biotechnol. 22:1355-1356 (2004)) and can generate a cell pool that has 38 times increased specific productivity (Rose and Ramakrishnan, Handbook of Industrial Cell Culture, Vinci, V. and Pareh, S. (eds.), Humana Press, Totowa, pp. 69-103 (2003)). The GFP-tagged FACS sorting studies have shown that the generation of clonal cell lines is not a requirement for achieving high-level expression, even though the current generation of cell sorters does allow for single-cell cloning (Ayusawa et al., Cell Genet. 7:523-534 (1981)). If found necessary clonal cell lines can be produced with equivalent ease.

Clonal GFP expressing cells selected by FACS analysis will be tested to determine whether the target gene has been successfully disrupted. To confirm that the target gene is disrupted and does not express functional enzyme, we will first sequence the cDNA or look for polymorphisms in the target gene or RNA. If the timelines and resources allows, we will also look for loss of the target protein using antisera. Non-transfected CHO cells will be used as a negative control. If available, we will use an enzymatic assay to verify that the target reaction is inactivated. Finally, we will use selective plating assays with or without supple mental nutrient to verify that the created deletion strain is a true auxotroph and grows only when supplemental nutrient is added. The results from these experiments will ensure that the target gene has been deleted, the target reaction has been inactivated and true metabolic nutrient auxotroph has been created.

Figure 23:
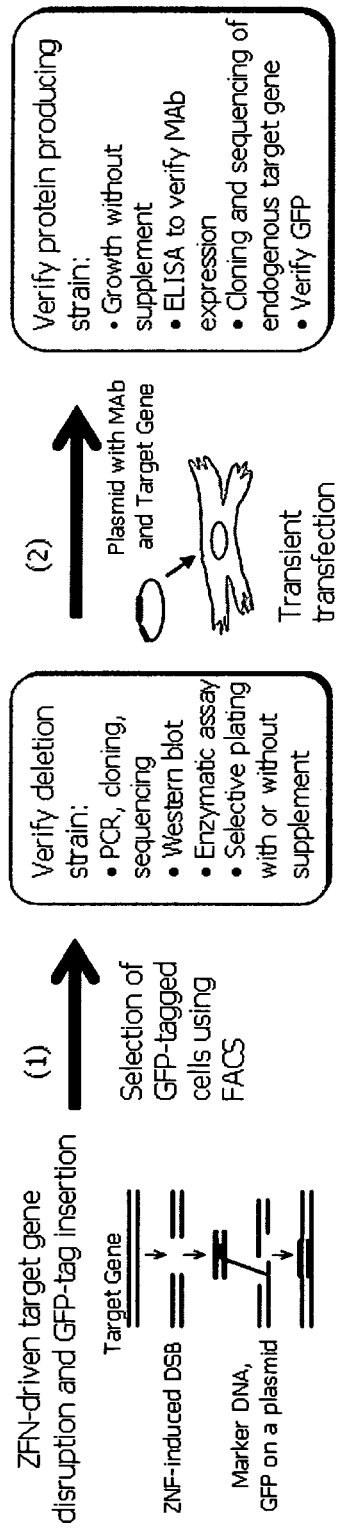
FIG. 23 shows that a metabolic auxoroph and GFP-tagged CHO cell can be created using ZFN-based technology (Zhang et al., *Cytotechnology* 51:21-28 (2006)). GFP expressing CHO cells can be selected using FACS (Step 1). The target gene disruption will be verified using various molecular biology tools, the true auxotroph can be transiently transfected with selection vector expressing target gene i.e. selection marker gene and monoclonal antibody coding genes (Step 2) and the transfected cells can be selected in CHO chemically defined media and tested for monoclonal antibody production.

Experimentally validated true auxotrophs will be transiently transfected with 2 µg of two monoclonal antibody expressing plasmids in which one contains an expression cassette for the antibody light chain and the other contains a cassette for the antibody heavy chain and a cassette for the deleted target gene expression (Step 2, FIG. 23). If Robustness Analysis predicts that amplification of the target gene benefits cell characteristics, we will use a powerful promoter to over-express the target gene, i.e. the selection marker aiming to improve metabolic properties of the cell. Based on previous results 10, CHO cells transfected with plasmids expressing both a monoclonal antibody and the target selection marker will retain co-selected in the absence of supplemental nutrient. After two weeks, stable monoclonal antibody production will be generated in this cell line and antibody expression will be verified using ELISA according to manufactures protocol (Bethyl Laboratories). Additional tests, such as screening for GFP expression and sequencing of endogenous target gene, will be performed to verify that the endogenous target gene remains disrupted in the final CHO cell culture (Step 2, FIG. 23). Alternatively to a full MAb, FaB fragment (that only coincides to the binding end of an antibody) will be expressed in CHO cells. FaB fragment may be expressed as a single gene and this will simplify experimental work and still be sufficient to validate this proof-of-concept study.

Evaluate the Development and Implementation of a Model-Based Selection System in CHO Cell Line.

Once the model-based selection system is implemented in CHO cell line, we will compare experimentally generated cell culture data with those calculated by the reconstructed model (FIG. 21). For this purpose, we will characterize the selected (deletion and protein producing) cell lines generated in batch spinner flask cultivations in a chemically defined CHO cell line medium. The only difference between these two cultivations will be a supplemental nutrient that is added to the deletion CHO cell line cultivation media. We will grow two CHO cell lines in batch-type cultivations until steady state is reached. Throughout the exponential growth phase, we will take culture samples for cell count and cell viability testing. We will measure extracellular metabolite concentrations using analytical detection capabilities, i.e. LCMS, GCMS and HPLC (see also the attached Letter of Support). Using collected experimental data, we will then calculate carbon balance, cell specific growth rate, substrate uptake and byproduct production rates for the deletion and protein producing strain. In addition, recombinant protein production will be measured throughout the range of growth by an ELISA test. Through the computational analysis, simulations that represent CHO deletion and protein producer strains are generated. Experimentally generated values will be qualitatively compared with SimPheny™-generated predictions for the deletion and protein producing CHO cell lines. These results are used to qualitatively evaluate the capability of the computational modeling approach to design selection systems and predict their effects on cell metabolism and protein production. Overall, this proof of concept study will demonstrate if computational approaches can be beneficially utilized in mammalian cell culture engineering predicting target gene deletion, transfection and gene amplification effect on cell metabolism. Based on the results of this qualitative study, we will design and propose new strategies, based on which we will aim to quantitatively improve selection system design.

Summary of the Research Design and Methods. We demonstrate the feasibility of designing novel selection systems using a combination of the computational platform in SimPheny™, and advanced ZNF-based gene deletion and cell transfection technology (Urlaub and Chasin, Proc. Natl. Acad. Sci. U.S. A 77:4216-4220 (1980); Browne and Al-Rubeai, Trends Biotechnol. 25:425-432 (2007)). The results of the method are confirmed by the ability to computationally identify and experimentally validate a novel selection system in CHO cell line, focused on targets with added metabolic advantages such as reduced byproduct formation and increased growth rate. The attainment of these goals allows further development and improvement of the best resulting novel selection system and experimentally evaluate other novel targets.

Example VIII Utilizing Biomarkers to Determine Viral Infection of Cell Cultures This example describes utilizing biomarkers to signal infection of a cell culture from a viral infection.

Adventitious Viral Contaminations in Industrial Animal Cell Culture.

Contamination in animal cell culture is of critical concern in the industry and can cause the complete loss of cell cultures in manufacturing. Thus, testing of materials and cell culture is practiced rigorously. Whereas microbial contaminations (fungi, yeasts, and bacteria) can be easily identified, detection of mycoplasma and viruses is more difficult because they are not observable by routine light microscopy and may not cause noticeable changes in a cell culture, e.g. rapid pH change or culture turbidity (Merten, Cytotechnology 39:91-116 (2002); Lincoln and Gabridge, Methods. Cell Biol. 57:49-65 (1998)). Adventitious viral contaminations present the serious threat because of the difficulty to detect some viruses, and the risk, such viruses pose on patients.

Adventitious viruses are the most dangerous contamination for the industrial animal cell culture, since these viruses might be originated from any animal or human and can be successfully amplified in an industrial animal cell cultures. The potential sources of adventitious viral contamination include: (i) cell culture reagents of animal (e.g. serum, trypsine) or even non-animal (media components) (Garnick, Dev. Biol. Stand. 88:49-56 (1996)) origin, and (ii) operator error (Merten, Cytotechnology 39:91-116 (2002); Garnick, Dev. Biol. Stand. 88:49-56 (1996)). Routine testing of cell lines of interest to biotechnology companies revealed a contamination frequency with adventitious viruses of less than 1% (Moore, Dev. Biol. Stand. 76:51-56 (1992). Today, a total of 11 bovine viruses (BAV, PI-3, BPV, BRSV, BVD-NADL, BVD-NY1, BTV-10, IBR, Rabis Virus, Reovirus-3, and VSV), which are known to be originated from bovine products (serum and albumin), has to be tested at the end of therapeutic production, based on federal regulation code 9. However, unknown and the new emerging viruses cause a large threat to animal cell culture, as these might pass undetected into production. If undetected, these viruses may cause false results in virus screening, jeopardized safety of the derived biologic, and ultimately cause infection to operator and patient (Merten, Cytotechnology 39:91-116 (2002)).

Effect of Viral Infection on Animal Cell Metabolism.

A virus is a microscopic infectious agent that uses host cell to disassemble virus particle, replicate virus genome, use host translational machinery to synthesize viral proteins, enclose itself with a lipid envelop, and maybe even modify the structure or function of host cell to suit virus needs. As it has been well established in published literature, viruses affect host cell metabolism (Munger et al., Nat. Biotechnol. 26:1179-1186 (2008); Kovas, Experientia 17:153-160 (1961); Landini, J. Gen. Virol. 65 (Pt 7):1229-1232 (1984); Maranga et al., Biotechnol. Bioeng. 90:645-655 (2005)). It has been shown that viral infection upregulates overall host cell metabolism by upregulating the consumption of essential amino acids and efflux to nucleotide and fatty acid biosynthesis (Munger et al., Nat. Biotechnol. 26:1179-1186 (2008); Landini, J. Gen. Virol. 65 (Pt 7):1229-1232 (1984); Maranga et al., Biotechnol. Bioeng. 90:645-655 (2005)) Infected cells show increased consumption of glucose and oxygen, and consequently this leads to accelerated energy metabolism (Landini, J. Gen. Virol. 65 (Pt 7):1229-1232 (1984); Maranga et al., Biotechnol. Bioeng. 90:645-655 (2005)). It has also been demonstrated that concentrations of intermediate metabolites within glycolytic, TCA cycle, and nucleotide biosynthesis pathways markedly increase following a viral infection (Munger et al., PLoS. Pathog. 2:e132 (2006)). Activities of enzymes from central metabolism have also been reported to be stimulated under viral infection, e.g. when HeLa cells were infected with poliomyelitis virus, glucose-6-phosphatase activity was stimulated within 30 min (Munger et al., Nat. Biotechnol. 26:1179-1186 (2008); Kovas, Experientia 17:153-160 (1961); (Munger et al., PLoS. Pathog. 2:e132 (2006)). Collected data provides solid evidence of detectable changes in host cell central metabolism after virus infection. In this research proposal, biomarkers of adventitious virus contamination in animal cell culture will be identified utilizing the host cell metabolism data.

Current Approaches to Prevent Adventitious Viral Infection are not Sufficient.

Industry is continuously seeking to improve methods for detection, identification, inactivation and removal of potentially contaminating pathogens in product development and manufacturing. Current methods for adventitious virus detection include (Points to Consider in the Manufacture and Testing of Monoclonal Antibody Products for Human Use, U.S. Department of Health and Human Services Food and Drug Administration Center for Biologics Evaluation Research, pp. 1-50 (1997); Viral Safety Evaluation of Biotechnology Products Derived from Cell Lines of Human or Animal Origin Q5A (R1), International Conference on Harmonisation of Technical Requirements for Registration of Pharmaceuticals for Human Use, ICH Harmonised Tripartite Guideline, pp. 1-27 (1999); Derivation and Characterisation of Cell Substrates Used for Production of Biotechnological/Biological Products Q5D, International Conference on Harmonisation of Technical Requirements for Registration of Pharmaceuticals for Human Use, ICH Harmonised Tripartite Guideline, pp. 1-13 (1997)): (1) Adventitious virus specific tests: qPCR and fluorescent antibody staining. These tests are highly sensitive, but limited to a few viruses that can be screened for in a cost effective manner; (2) Virus general (non-specific) tests: observation of cytopathogenic effect and hemadsorption tests. These assays are able to detect a broader spectrum of viruses. However, these tests are not very sensitive and are time consuming.

The therapeutics industry has employed a multifaceted approach in virus detection (Merten, Cytotechnology 39:91-116 (2002); Points to Consider in the Manufacture and Testing of Monoclonal Antibody Products for Human Use, U.S. Department of Health and Human Services Food and Drug Administration Center for Biologics Evaluation Research, pp. 1-50 (1997); Viral Safety Evaluation of Biotechnology Products Derived from Cell Lines of Human or Animal Origin Q5A (R1), International Conference on Harmonisation of Technical Requirements for Registration of Pharmaceuticals for Human Use, ICH Harmonised Tripartite Guideline, pp. 1-27 (1999); Derivation and Characterisation of Cell Substrates Used for Production of Biotechnological/Biological Products Q5D, International Conference on Harmonisation of Technical Requirements for Registration of Pharmaceuticals for Human Use, ICH Harmonised Tripartite Guideline, pp. 1-13 (1997); Ill and Dehghani, Curr. Opin. Drug Discov. Develop. 12:296-304 (2009);

Schiff, *In Vitro Cell Dev. Biol. Anim.* 41:65-70 (2005); Robertson, *Dev. Biol. Stand.* 88:37-40 (1996)). First, general (non-specific) and specific virus testing is performed at the following manufacturing process stages: master cell bank, working cell bank, raw materials, unprocessed bulk harvest, late expanded cells, and final product. Second, raw materials could be cleaned and purified (using e.g. nanofiltration, g- or UV irradiation). Third, chemical and physical purification treatments could be applied during the downstream processing to eliminate or inactivate viruses. All these practices strive to ensure safety and mitigate the risk of patient infection undergoing bio-therapeutic treatment, however, these practices still gives only limited guarantee of safety. Today, viral contaminations cannot be treated, and contaminated cultures should be discarded (Merten, *Cytotechnology* 39:91-116 (2002)). Early detection of infection can prevent loss of manufacturing runs, reduce the cost of labor and production and ensure patients safety and care. Thus, there is a critical and urgent need to develop rapid, accurate and sensitive adventitious viral detection methods that can be performed on the manufacturing floor to enable a rapid response to contain or limit adventitious contaminations.

New Biomarker Applications in Animal Cell Culture and Therapeutic Production.

There is an increasing interest in identifying and utilizing biomarkers to improve industrial animal cell culture process performance and thus improve production of therapeutics. Today, animal cell culture industry is interested in identifying biomarkers of stress, apoptosis, cell line contamination, as well as biomarker or high-producing cell lines (Kumar et al., *Biotechnol. Prog.* 24:273-278 (2008); Woolley and Al-Rubeai, *Biotechnol. Bioeng.* 104(3):590-600 (2009); Woolley and Al-Rubeai, *Biotechnol. Adv.* 27:177-184 (2009); Allison et al., *Deciphering the Mechanisms of Therapeutic Protein Production*, CHO Consortium, SBE Special Section, pp. 48-52 (2009)). Identification of such biomarkers would improve the ability to control animal cell culture, improve animal cell culture process performance, and ultimately improve production of therapeutics. It has been suggested that the animal cell culture improvements can be done through relevant process or media modification/supplementation upon biomarker identification, or through genetic engineering of cell lines (Allison et al., *Deciphering the Mechanisms of Therapeutic Protein Production*, CHO Consortium, SBE Special Section, pp. 48-52 (2009)). Attempts to identify animal cell culture biomarkers have been made using gene expression, proteome and metabolome analysis tools. Gene expression analysis tools were utilized to identify genetic pathways and distinct gene targets that are characteristics of a high-producing cell lines. After comprehensive pathway analysis and validation, these gene target biomarkers can potentially be used to improve therapeutic productivity in animal cell culture through genetic manipulation of the target gene, or through media supplementation (Allison et al., *Deciphering the Mechanisms of Therapeutic Protein Production*, CHO Consortium, SBE Special Section, pp. 48-52 (2009)). Proteomics and metabolomic footprinting tools are also being developed to identify biomarkers of animal cell culture (Kumar et al., *Biotechnol. Prog.* 24:273-278 (2008); Woolley and Al-Rubeai, *Biotechnol. Bioeng.* 104(3):590-600 (2009); Woolley and Al-Rubeai, *Biotechnol. Adv.* 27:177-184 (2009); Seagle, *Tissue Eng. Part C. Methods* 14:107-118 (2008)). Biomarkers have not been used as an early diagnostic tool for cell culture contaminations. This description, thus, is the first to present this application.

A Model-driven Approach Identifying Metabolic Biomarkers.

Figure 24:
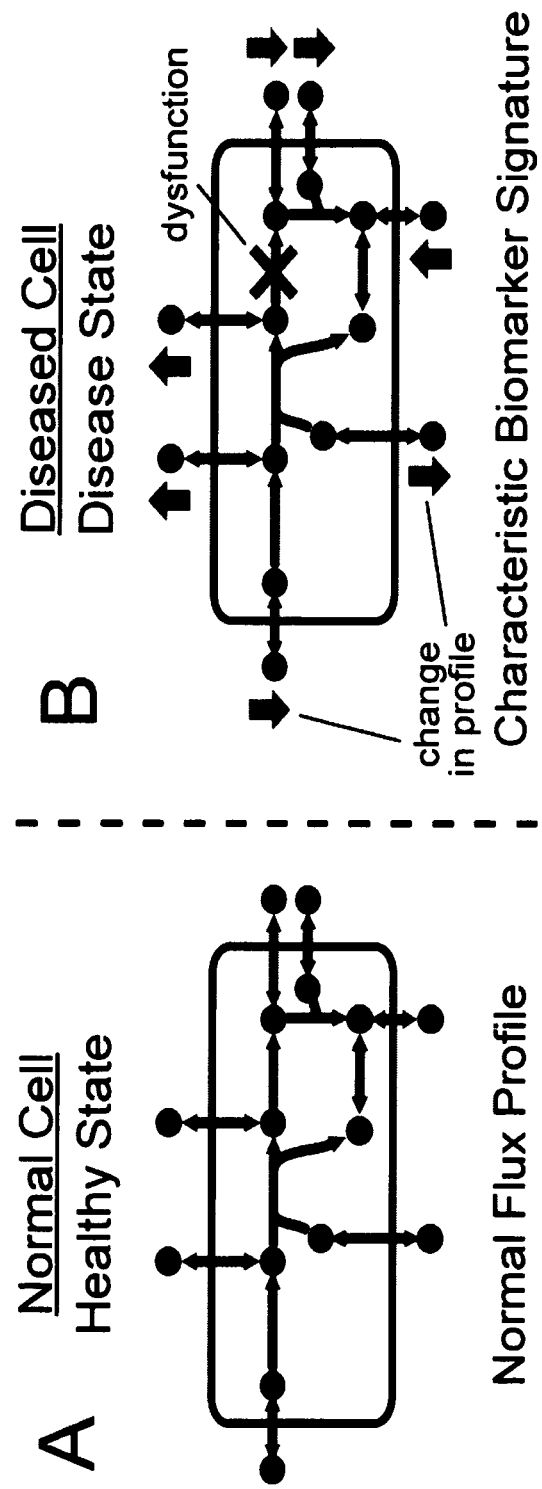
FIG. 24 shows the premise of the biomarker analysis approach. (A) Shown is a drawing of a cell for which a normal flux profile can be calculated given a model, nutrient conditions, and the constraint-based approach. (B) Shown is a similar cell, but with a dysfunctional enzyme. The model again can be used to calculate the effect on the flux distribution that this change has and a characteristic biomarker signature can be predicted by comparing inputs and outputs from the healthy and disease states. These biomarkers can help aide in the diagnosis of metabolic diseases.

A computational approach has been developed and successfully validated to predict metabolic signatures, called biomarkers that are unique to a distinct metabolic state of the cell. The premise of the constraint-based biomarker modeling approach lies in the ability of a model to accurately predict the effect of system outputs that is caused by a change in an internal component (FIG. 24). With this, by measuring the system outputs, such as biofluid metabolite levels in an individual, one can determine what is happening inside the cells of the body. This inside look into the cell will enable the determination of the health of a patient. Because of this great promise, the field of biomarkers is of significant interest to the NIH in a number of translational and basic research areas (Kaiser, *Science* 324:867 (2009)). The same principal approaches of the biomarker analysis tool can be easily translated and used in understanding animal cell culture infection, stress, cell death, etc.

Figure 25:
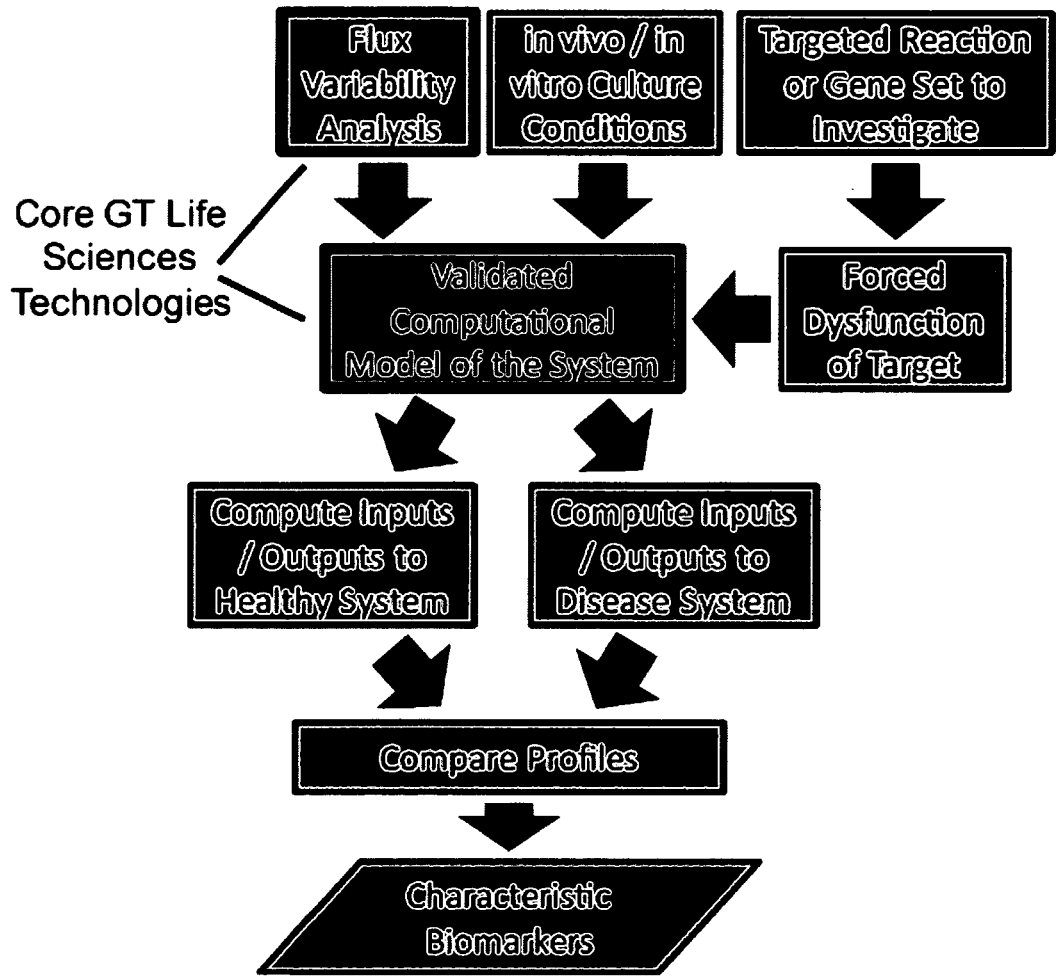
FIG. 25 shows the workflow for the computation of biomarkers. Knowledge of in vivo and in vitro conditions, sets of targeted genes, and the established algorithm of flux variability analysis are all used along with the validated computation model to compute inputs/outputs for a disease and healthy system. These input/output profiles are then computed and characteristic biomarkers are determined for the disease state being examined.
Figure 26:
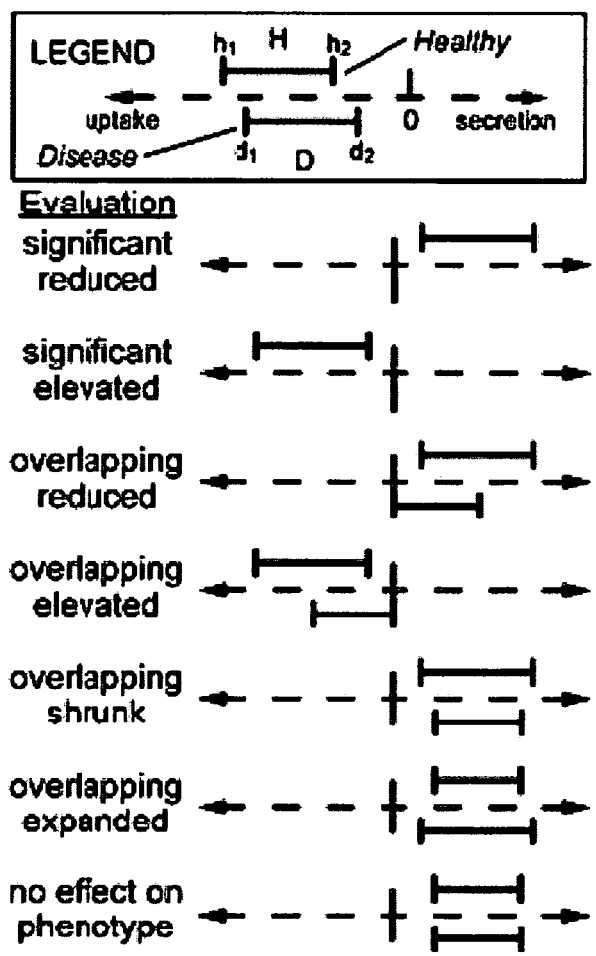
FIG. 26 shows categorization and description of different types of biomarkers. For each evaluation of a biomarker, the green (top) bar indicates the uptake/excretion interval for a healthy individual and the red (bottom) bar indicates the disease interval. 'Significant' biomarkers do not have healthy and disease intervals that overlap. H, healthy; D, disease. The divergence and overlap metrics were also developed to quantify the significance of a biomarker. Where H (h1, h2) corresponds to the healthy interval and D (d1,d2) describe the diseased state.

The method to detect biomarkers using a constraint-based approach utilizes two technologies, a reconstructed and validated model of a cell and the constraint-based computational algorithm of flux balance analysis (Price et al., *Nat. Rev. Microbiol.* 2:886-897 (2003)) (specifically, the approach of flux variability analysis (FVA), that find the minimum and maximum range of possible fluxes for each network reaction (Mahadevan and Schilling, *Metab. Eng.* 5:264-276 (2003)). These two technologies allow the computation of the biomarker profiles for both healthy and disease states, such as an enzymatic dysfunction within a cell (FIG. 25). With two profiles, characteristic biomarkers that are unique to the disease state can be determined. The advantages of this approach not only lie in the computational aspects, but also in the problem formulation to compute biomarkers in conditions that closely mimic in vivo conditions. To identify the biomarkers in the analysis, metrics to prioritize and rank the findings from the computational analysis have been generated and also a categorization of the results comparing the healthy and disease (or altered) states for the system. FIG. 26 shows the categorization of different biomarkers for the developed analysis. These categories describe the qualitative findings of the analysis. Furthermore, metrics to quantify and rank the significance of each biomarker in relation to each other, also examine the divergence and the overlap of the healthy and disease intervals. For each of these metrics, if the biomarker was elevated (see FIG. 26), the metrics were positive and vice versa for reduced biomarkers. Furthermore, when considering significance, the biomarkers with metric values that possess the greatest magnitude (positive or negative) are scored as the most significant.

Figure 27:
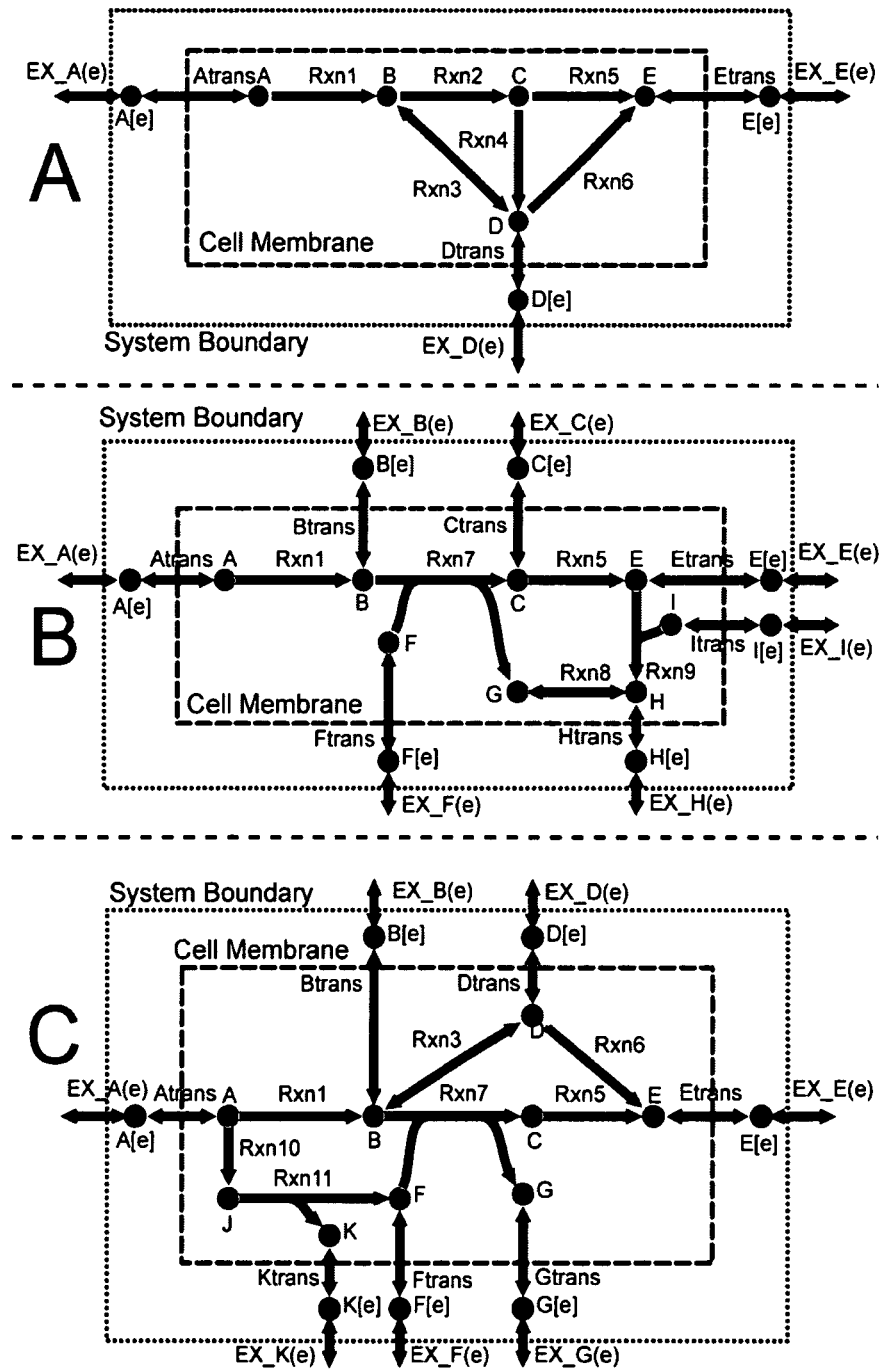
FIG. 27 show drawings of example networks or 'Toy' networks to demonstrate the biomarker analysis platform. Each of these three simple networks were examined individually as well as in combination to determine the combinatorial effects on biomarker identification.

Application to a Toy Network:

Single System. To first demonstrate the application of constraint-based modeling to identifying biomarkers in a system with internal deficiencies, toy networks were generated and implemented for the analysis. FIG. 27 shows the example toy networks for which the application was first applied. The basis of the analysis is to set the environmental conditions for a given network (i.e., set the allowable inputs), and in this case, allow up to three different inputs. Since it is a toy network, arbitrary values can be used. Following this, the normal range of biomarkers is computed for the full toy network and recorded. Finally, the network is perturbed by disabling a given reaction (or reactions) and the biomarkers are then computed through comparison of the healthy and disease ranges of outputs. This approach was first applied as an analysis of a single system.

Toy network A will be used as a demonstration tool to describe the results of the biomarker analysis and the different types of biomarkers. For this analysis, metabolites A and D each were allowed to enter the system at the rate of 1 unit of flux (a negative value indicating uptake of the metabolite) and all metabolites were allowed to leave the system to the full extent, if possible. Furthermore, the healthy state of the cell was analyzed at 25% of the maximum flux possible through the targeted reaction to represent a normal "typical" functioning state. The effect of the 25% rate, or gamma, for the normal state will be analyzed in detail later. Table 13 shows the results produced when determining the biomarkers for 'Rxn 1' (Reaction 1) when examined in the context of a totally disabled functionality in the disease state. From the analysis, it was determined that the input or output of each metabolite that can enter or leave the system is affected when Rxn 1 is disabled. For metabolite 'A', the diseased state (Rxn 1 not active) totally eliminated the uptake of 'A' and therefore, it is considered a significant reduced biomarker. For metabolites D and E, the exchange with the outside environment of the cell is also affected as metabolite 'A' can no longer be converted to 'D' or 'E'. However, as 'D' can enter the system, the intervals are overlapping and some 'E' can be produced. Therefore, metabolites 'D' and 'E' are overlapping reduced biomarkers to 'Rxn 1'. Analysis of the other reactions in Toy Network A revealed that the only other reactions which possess characteristic biomarkers are 'Rxn 4' and '5', as their necessary activity (in the healthily state) forces the production of 'E'. Therefore, metabolites D and E are an overlapping elevated biomarker and an overlapping reduced biomarker, respectively, in these cases. As only three reactions out of the six in toy network A have at least one biomarker, network A is a relatively robust network as compared to networks B and C, which will now be analyzed (see Table 15).

A biomarker analysis on Toy Networks B and C revealed that both networks possess a relatively high number of biomarkers for each reaction in the network. One example of biomarkers from this network is for the calculation of biomarkers for 'Rxn 7' in Toy Network C (Table 14), again with the healthy state being active at 25% of the maximum flux through the reaction. Reaction 7 has five biomarkers with one of these being a significant biomarker as the production of metabolite 'G' is eliminated in a diseased state for the cell. Each of the additional reactions in the network were analyzed in a similar fashion. As shown in Table 15, all five of the intracellular reactions in Network C have biomarkers and additionally, each have approximately six. Similarly, all of the reactions in Toy Network B have a biomarker and each have six out of the total possible of seven metabolites that are exchanged with the environment surrounding the "toy cell". Visual inspection of Networks B and C reveal that these networks have less alternate pathways (or routes) to achieve the same functions. Thus, when any of the reactions are disabled, the potential for each of the metabolite's exchange with the environment is directly affected. As a result, Toy Networks B and C possess reactions that have a relatively high number of biomarkers in each of their disease profiles.

With the results of the analysis of each of the toy networks calculated and key examples given to demonstrate the output, the effect of analyzing the cells together will now be evaluated to determine the impact of intercellular metabolite exchange.

Application to a Toy Network: Multi-Cell System.

Figure 28:
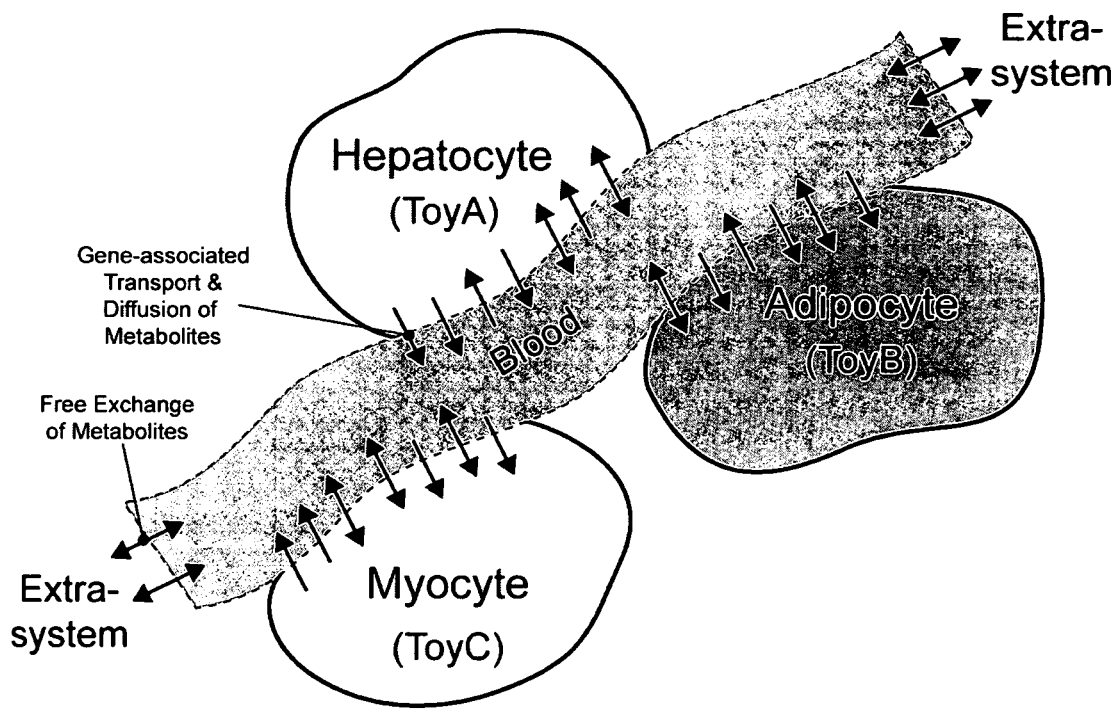
FIG. 28 shows a depiction of how the different models interact in a combined analysis. Shown are drawings of the genome-scale Hepatocyte, adipocyte, and myocyte networks and the 'Toy' networks. Each of the networks were examined individually as well as in combination to determine the combinatorial effects on biomarker identification. In the combined analysis, biomarkers are determined at the level of the blood (biofluid).

An analysis of a multi-network (or multi-cell) system revealed the combinatorial effect of interacting networks with both similar and contrasting pathways. Intuitively, the results will be dependent on the structure of the networks being examined. Nonetheless, some general conclusions can be drawn from the multi-cell system analysis. FIG. 28 shows a diagram of how both the toy and a potential set of genome-scale human cell models can be analyzed. In these analyses, all of the metabolites that enter or leave any of the networks were examined for each case. Furthermore, analyses on the level of examining a deficiency in all of the enzyme-encoded reactions catalyzed by a given gene can be executed simultaneously. This situation is relevant biologically, for example, when there is a given genetic deficiency present in multiple tissue types (approximately 70% of diseases affect multiple tissues (Jimenez-Sanchez et al., *The Metabolic & Molecular Bases of Inherited Disease*, Scriver, C. R., Beaudet, M. D., Sly, W. S. & Valle, D. (eds.), McGraw-Hill, New York, pp. 167-174 (2001)). Analysis on the level of the genes in a network is similar to deleting a single reaction in each of the individual toy network analyses as the models are set up on a one gene to one reaction basis (e.g., no isozymes). Table 16 shows the results when analyzing two input conditions: the largest value from each of the individual inputs analyzed in the single network simulations and the sum of all of the inputs from the analysis of the single networks. In total, there are 11 different gene-encoded catalyzed reactions and 10 different metabolites that can be exchanged. Nine of the 11 reactions have at least one biomarker and the average number of biomarkers per reaction is similar to that of Toy Networks B and C, approximately six. This would suggest that under these conditions, the multi-network analysis behaves similar to the less robust networks (Toy Network B and C). Furthermore, the two different input conditions did not result in a significant difference in results with only two genes having one more biomarker each with the larger amount of inputs (genes the catalyze 'Rxn5' and 'Rxn6' in the model(s)).

A more in-depth analysis on the biomarker prediction results in the context of allowing internetwork interactions revealed a change in biomarker patterns for the reactions examined. As before, the same two reactions were analyzed as in the single network analyses. Tables 17 and 18 show the results when analyzing deficiencies in the gene that catalyzes 'Rxn1' and 'Rxn 7' individually in all networks, if applicable. In the multi-cell analyses, all of the metabolites that enter and/or leave any of the toy networks were examined therefore and here we will compare the similar metabolites that are shared in the single network and these combined analyses. The inputs allowed in these analyses are given in the first entry of Table 16 and again, the healthy state of the cell was analyzed at 25% of the maximum flux possible through the targeted reaction. In examining the gene that catalyzes 'Rxn1' in all of the networks, the most striking change in the biomarker pattern is that metabolite 'A' is no longer a significantly reduced biomarker and is determined to be a overlapping elevated biomarker. This is due to the fact that in the single network analysis, 'Rxn 1' was the only pathway to which metabolite 'A' could be converted to metabolites in Toy Network 1. Whereas in the combined analysis, a pathway in Toy Network C allows the conversion of metabolite 'A' through a different pathway (initiated by 'Rxn 10'). This example demonstrates that results can change in the biomarker analysis when analyzing networks with different topologies. The other two shared metabolites between the analysis of 'Rxn1' are the exchange of metabolites 'D' and 'E', in both the single Toy Network A analysis and the combined multi-network analysis, both of these biomarkers are overlapping reduced biomarkers. However, the values of the divergence and relative size both decrease in the multi-network analysis.

Analysis of the gene that catalyses 'Rxn 7' in all of the models revealed a different outcome than those produced in the analysis of 'Rxn1'. For the multi-network analysis, only one of the metabolite biomarkers changed in terms of type of biomarker; metabolite 'E' was not a biomarker in the multi-network analysis where it was an overlapping reduced biomarker in the single network analysis of Toy Network C. This is due to metabolite 'E' having the ability to be converted to metabolite 'H' in Toy Network B after it is generated in Toy Network C. This is analogous to a situation where a metabolite is produced by one cell and taken up and metabolized by another. For the other six similar biomarkers in the analysis, all of the types of biomarkers remained the same. Notably, metabolite 'G' remained as a significant reduced biomarker, as it is eliminated in the disease state in both conditions. One last note is that where the divergence and relative size metrics decreased when analyzing the gene catalyzed 'Rxn1', the metrics increased in the analysis of 'Rxn7'. This fact is influenced by the change in the number and amounts of inputs between the analyses.

In summary, the results generated from the multi-network analysis demonstrate that network interaction can have an effect on biomarker prediction. However, results directly dependant on unique transformations of metabolites and paths to enter or leave a system can result in conserved results when comparing single networks to a combined analysis. These findings point to the importance of accurately defining and characterizing the key contributors to a phenotype in modeling analyses.

TABLE 13

Biomarker analysis results analyzing Rxn 1 in Toy Model A. DE, disease eliminated

| exchange | evaluation | divergence | relative size | h1 | h2 | H | d1 | d2 | D |
|---|---|---|---|---|---|---|---|---|---|
| A | significant reduced biomarker (DE) | 0 | 1 | -1 | -0.25 | 0.75 | 0 | 0 | 0 |
| D | overlapping reduced biomarker | 0.5 | 0.5 | -1 | 1 | 2 | -1 | 0 | 1 |
| E | overlapping reduced biomarker | 0.5 | 0.5 | 0 | 2 | 2 | 0 | 1 | 1 |

TABLE 14

Biomarker analysis results analyzing Rxn 7 in Toy Model C. DE, disease eliminated

| exchange | evaluation | divergence | relative size | h1 | h2 | H | d1 | d2 | D |
|---|---|---|---|---|---|---|---|---|---|
| A | no effect on phenotype | 0 | 0 | -1 | 0 | 1 | -1 | 0 | 1 |
| B | overlapping elevated biomarker | 0.19 | 0.19 | -1 | 0.63 | 1.63 | -1 | 1 | 2 |
| D | overlapping elevated biomarker | 0.19 | 0.19 | 0 | 1.63 | 1.63 | 0 | 2 | 2 |
| E | overlapping reduced biomarker | 0.19 | 0.19 | 0.38 | 2 | 1.63 | 0 | 2 | 2 |
| F | overlapping elevated biomarker | 0.62 | 0.38 | -1 | 0.63 | 1.63 | 0 | 1 | 1 |
| G | significant reduced biomarker (DE) | 0 | 1 | 0.38 | 1.5 | 1.13 | 0 | 0 | 0 |
| K | no effect on phenotype | 0 | 0 | 0 | 1 | 1 | 0 | 1 | 1 |

TABLE 15

Summary of the biomarker analysis analyzing the different reactions in each of the toy models.

| Network | Network Reactions (trans.) | Network Metabolites | Inputs Allowed | Exchanged Metabolites | Number of Reactions which have Biomarkers | Average Number of Biomarkers per Reaction* | Total System Biomarkers |
|---|---|---|---|---|---|---|---|
| Toy A | 6 (3) | 5 | A, D | 3 | 3 | 2.33 | 7 |
| Toy B | 5 (7) | 8 | A, B, 2F, I | 7 | 5 | 6 | 30 |
| Toy C | 7 (7) | 9 | A, B, F | 7 | 7 | 5.57 | 39 |

*Only considering reactions which have at least one biomarker.

TABLE 16

Biomarker analysis analyzing the toy models.

| Network | Network Reactions (trans.) | Network Metabolites | Inputs Allowed | Exchanged Metabolites | Number of Reactions which have Biomarkers | Average Number of Biomarkers per Reaction* | Total System Biomarkers |
|---|---|---|---|---|---|---|---|
| Toy ABC combined | 11 (10) | 11 | A, B, D, 2F, I | 10 | 9 | 5.55 | 61 |
| Toy ABC combined | 11 (10) | 11 | 3A, 2B, D, 3F, I | 10 | 9 | 5.73 | 63 |

*Only considering reactions which have at least one biomarker.

TABLE 17

Biomarker analysis results analyzing the gene that catalyzes Rxn 1 in all of the models in a combined Toy Model ABC analysis.

| exchange | evaluation | divergence | relative size | h1 | h2 | H | d1 | d2 | D |
|---|---|---|---|---|---|---|---|---|---|
| A | overlapping elevated biomarker | 0.25 | 0.25 | −1 | −0.25 | 0.75 | −1 | 0 | 1 |
| B | overlapping reduced biomarker | 0.33 | 0.33 | −1 | 2 | 3 | −1 | 1 | 2 |
| C | overlapping reduced biomarker | 0.2 | 0.2 | 0 | 2.5 | 2.5 | 0 | 2 | 2 |
| D | overlapping reduced biomarker | 0.33 | 0.33 | −1 | 2 | 3 | −1 | 1 | 2 |
| E | overlapping reduced biomarker | 0.33 | 0.33 | 0 | 3 | 3 | 0 | 2 | 2 |
| F | overlapping elevated biomarker | 0.08 | 0.08 | −2 | 0.75 | 2.75 | −2 | 1 | 3 |
| G | overlapping reduced biomarker | 0.2 | 0.2 | 0 | 2.5 | 2.5 | 0 | 2 | 2 |
| H | overlapping reduced biomarker | 0.14 | 0.14 | 0 | 3.5 | 3.5 | 0 | 3 | 3 |
| I | no effect on phenotype | 0 | 0 | −1 | 0 | 1 | −1 | 0 | 1 |
| K | overlapping elevated biomarker | 0.25 | 0.25 | 0 | 0.75 | 0.75 | 0 | 1 | 1 |

TABLE 18

Biomarker analysis results analyzing the gene that catalyzes Rxn 7 in all of the models (Toy Models B & C) in a combined Toy Model ABC analysis.

| exchange | evaluation | divergence | relative size | h1 | h2 | H | d1 | d2 | D |
|---|---|---|---|---|---|---|---|---|---|
| A | no effect on phenotype | 0 | 0 | −1 | 0 | 1 | −1 | 0 | 1 |
| B | overlapping elevated biomarker | 0.21 | 0.21 | −1 | 1.38 | 2.38 | −1 | 2 | 3 |
| C | overlapping reduced biomarker (DE) | 0 | 1 | 0 | 2.19 | 2.19 | 0 | 0 | 0 |
| D | overlapping elevated biomarker | 0.21 | 0.21 | −1 | 1.38 | 2.38 | −1 | 2 | 3 |
| E | no effect on phenotype | 0 | 0 | 0 | 3 | 3 | 0 | 3 | 3 |
| F | overlapping elevated biomarker | 0.84 | 0.58 | −2 | 0.38 | 2.38 | 0 | 1 | 1 |
| G | significant reduced biomarker (DE) | 0 | 1 | 0.31 | 2.19 | 1.88 | 0 | 0 | 0 |
| H | overlapping reduced biomarker | 0.76 | 0.65 | 0.31 | 3.19 | 2.88 | 0 | 1 | 1 |
| I | no effect on phenotype | 0 | 0 | −1 | 0 | 1 | −1 | 0 | 1 |
| K | no effect on phenotype | 0 | 0 | 0 | 1 | 1 | 0 | 1 | 1 |

A Validated Case Study in Human Hepatocyte.

Figure 29:
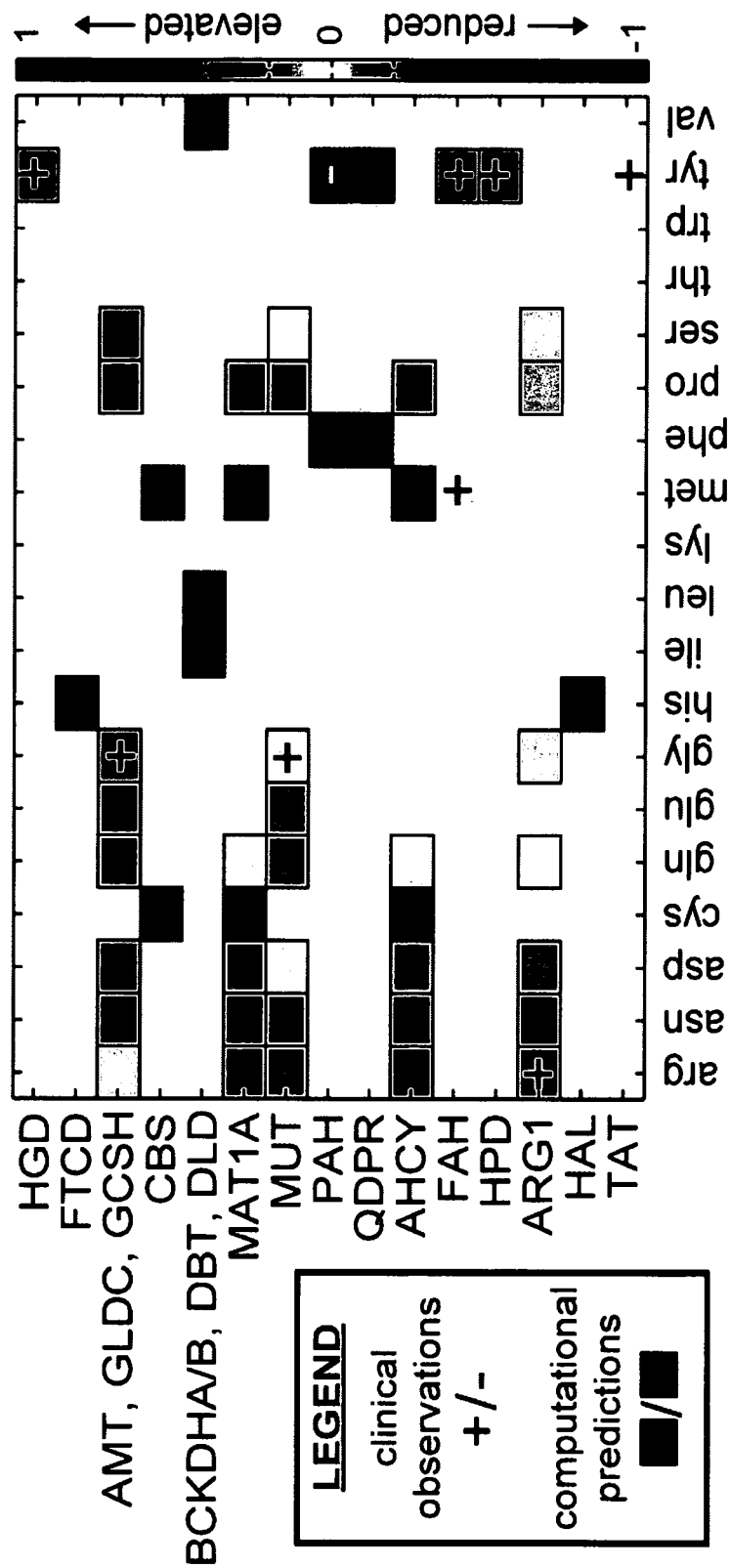
FIG. 29 shows results from an analysis of biomarkers caused from inborn errors of amino acid metabolism using a Hepatocyte model. Shown is a heatmap displaying the computational predictions for the evaluation metric 'overlap' using the hepatocyte model (red and blue boxes) overlaid with clinical diagnosis observation data from the OMIM database (Hamosh et al., *Nucleic Acids Res.* 33, D514-D517 (2005)). Each row in the heatmap corresponds to a different gene (each associated to a disease) and each row corresponds to a metabolite that is exchanged between the cell and blood (only a subset of the approximately 50 exchanged metabolites in the model is shown). A red box indicates an elevated biomarker and a blue box indicates a reduced biomarker. Gamma=25% and the baseline inputs were used.

The biomarker analysis tool (as just described) was first tested to predict biomarkers for human in-born error of metabolism (IEM) diseases using computational tools, a genome-based reconstruction of human liver, and published data. The data used for biomarker analysis tool validation was the IEM data mined from the OMIM database (Hamosh et al., *Nucleic Acids Res.* 33:D514-D517 (2005)). The IEM characteristic biomarkers were determined using hepatocyte model that was created earlier in SimPheny™ The hepatocyte model contains 705 reactions, 659 metabolites, and 947 transcripts. A total of 15 IEM diseases were examined. The analysis was performed examining dysfunctions in the genes that are associated with IEM diseases. That was possible to accomplish, since SimPheny™ models contain the necessary links (GPRs) that relate each gene to their transcript(s) to the catalyzed reaction(s), and are easily accessible and queried in computation. Results in FIG. 29 show that each of the computational predictions (blue and red for reduced and elevated biomarkers, respectively) is shown for each IEM diseased gene (each row) and the experimental data from the OMIM database is overlaid on the figure in the form of a '+' for an observed elevated biomarker and a '−' for an observed reduced biomarker. The overall agreement between the computational predictions made using the model and the observed clinically reported biomarkers (mined from the OMIM database) is 87% when matching the most significant biomarker for each disease with the reported value. The most significant biomarkers are those that are the closest to the relative value of 1 or −1 for an elevated or reduced biomarker, respectively (FIG. 29). Furthermore, there are a total of 19 biomarkers in this example set (as for some diseases, more than one biomarker has been reported) and the model was able to identify 17 of these through simulation, a 89% agreement with the experimental data sets.

An example of a correctly predicted biomarker that is difficult to infer simply by observing network topology is the homocystinuria disease, caused by the deficient activity of cystathionine beta-synthase (CBS gene). In the healthy case, when CBS is functional, methionine is taken-up from biofluids and is eventually converted to cysteine by series of enzymes that includes CBS. The method predicts that the biofluids' concentration of methionine is significantly elevated in homocystinuria as reported in OMIM (FIG. 29). Furthermore, for the CBS deficiency, cysteine (cys) is predicted to be a reduced biomarker and there is no data in the OMIM database on this potential biomarker. To further investigate the validation of this prediction, we examined the literature and found that indeed the concentration of cysteine is reduced in extracellular biofluids as reported (Lee and Briddon, *J. Inherit. Metab. Dis.* 30:35-38 (2007)). Despite the high degree of predictivity for the developed algorithm to predict biomarkers of IEM (FIG. 29), there were some diseases for which the algorithm did not perform well. For example, for the tyrosine tyrosine transaminase deficiency (TAT gene), the false prediction of elevated tyrosine is directly due to the existence of a cytosolic tyrosine transaminase enzyme catalyzed by the GOT1 gene in model. Evidence exists for this cytosolic compliment to the TAT catalyzed gene (Podglajen-Wecxsteen et al., *Ann. Dermatol. Vereol.* 120:139-142 (1993)), however removal of this activity predicts the elevated tyrosine biomarker (as presented in the OMIM data). This is a clear case of where the GOT1 gene product needs to be further evaluated for its specificity for tyrosine transaminase activity in the cytosol. In Summary, the model provides a means to understand most modes that occur and provides specific areas to look for further improvement and development.

Biomarkers for Virus Infection in CHO Cells can Thus be Calculated by:

I. Generating Growth and Metabolomics Data to Understand Virus-Infected CHO Cell Culture Metabolism.

Figure 30:
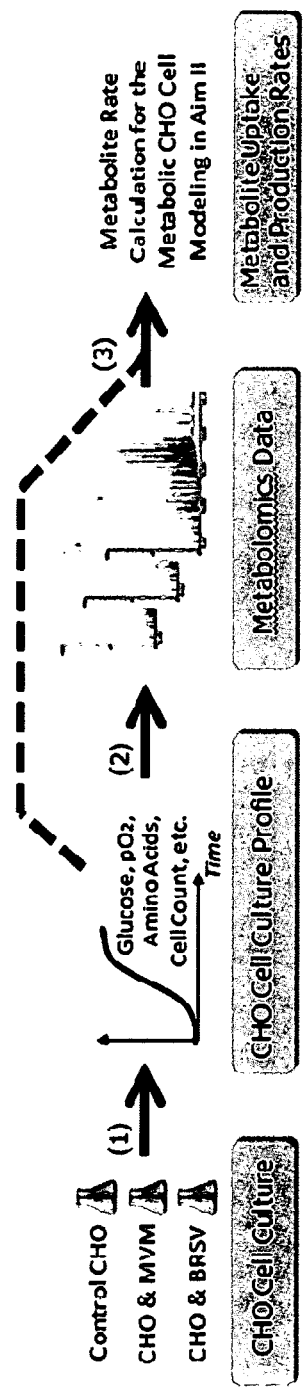
FIG. 30 shows a schematic of CHO cells cultivated in control and virus infected cultures. Samples are taken every 12 hours throughout exponential growth phase to characterize CHO cell growth and metabolism (step 1). Supernatant samples from selected sampling points are subjected to metabolomics analysis (step 2). Cell culture and metabolomics data are used for metabolic rate calculation that will be utilized in CHO cell modeling. MMV—Mouse Minute Virus; BRSV—Bovine Respiratory Syncytial Virus.

To study virus-infected CHO cell culture metabolism and ultimately identify characteristic biomarker for adventitious virus, one can collect CHO cell culture metabolomics, CHO cell growth, and virus count data from three cell culture experiments: (i) control CHO cell culture, (ii) adventitious virus MMV infected CHO cell culture and (iii) BRSV infected CHO cell culture (FIG. 30). All experiments will be performed in four biological replicas required for metabolomics analysis, to ensure good reproducibility of the generated data. The two adventitious viruses MMV and BRSV are chosen for initial study because they are more frequently observed in industrial animal cell contaminations. Both cell cultures will be infected with 1000 virus/mL titer that is detectable with existing common virus detection tests. Collected CHO cell growth, virus count and large-scale metabolite profiling would benefit the modeling approach for two reasons. First, a whole-cell analysis of metabolic requirements will provide a systems level overview of a broad range of metabolites that are important for growth in CHO, allowing us to validate/improve reconstructed CHO metabolic model. Second, by accounting for the more complete set of metabolic inputs and outputs to/from the cell, we will more accurately calculate the carbon and nitrogen balance in the system that would improve the in silico flux calculation that is required for the biomarker identification using the modeling approach. Consequently, the identified biomarkers are a clear representation of the metabolic changes in the cell that potentially can be used for an accurate biomarker analysis.

CHO Cell Culture.

CHO-S cells (Invitrogen, Inc.) will be grown in 0.5 L shake flasks with a 150 ml working volume using 100 rpm in 5% $CO_2$ incubators. MMV and BRSV infections will be introduced at $24^{th}$ hour after CHO cell inoculation. CHO cell culture will be performed in four biological replicas, in a serum-free protein-free OptiCHO chemically defined media (Invitrogen, Inc). All twelve cell cultures will be maintained at temperature of 37.1±1° C. and pH of 7.2. Cell cultures will be terminated at the end of exponential growth phase.

CHO Cell Culture Profile.

Culture samples for metabolite and cell growth analysis will be collected every 12 hours from control CHO cell culture, MMV-infected CHO cell culture and BRSV-infected CHO cell culture. Cell number and cell viability will be determined using Improved Neubauer hemacytometer and trypan blue dye exclusion, respectively. Bioreactor pH, temperature and osmolality will be recorded at each sampling time point. Glucose, lactate, ammonium, $pCO_2$, $pO_2$ and other element concentrations will be determined using Nova BioProfile 400 gas analyzer. To validate viral amplification in infected CHO cell cultures and sensitivity of available virus-specific and common detection methods, viral detection tests will be performed at each 12-hour sampling point (Charles River Laboratories International, Inc.).

Biochemical Analysis.

In addition to the on-line biochemical analysis data collected using NOVA 400 gas analyzer, at each sampling point (every 12 hours), samples for metabolome analysis will be collected and frozen in −20° C. Amino acids and organic acids will be analyzed in house using HPLC and GCMS capabilities. Generated cell growth and metabolic profile data is analyzed within CHO metabolic model to identify exponential growth time points, during which the more extensive metabolome profiling is useful for the model-based simulation of CHO cell and identification of adventitious virus biomarkers. Supernatant samples from selected 5 exponential growth phase data points for control and virus-infected cell cultures will then be subjected to global metabolite analysis. A total of 60 samples will be analyzed: 3 cell cultures×5 time points in each cell culture×4 sample replicates.) Metabolite extraction will be performed, and ultra high performance liquid chromatography/tandem mass spectrometry, and gas chromatography/mass spectrometry are used to detect, determine relative ion concentrations, and match ion features to compound identities.

Specific Metabolite Uptake, Production and Specific Growth Rate Calculation.

To further analyze CHO cell metabolism using the computational approach and understand CHO cell metabolic changes caused by viral-infection, we will determine metabolite uptake/secretion rates using generated cell culture and metabolomics dataset. Nutrient uptake and byproduct secretion rates will be estimated using bioreactor data in SimPheny™ to study the three CHO cell cultures. Bioreactor data will be imported into the Fermentation Module in SimPheny™, and reconciled based on the elemental balance of the input and output metabolites, to estimate the experimental error. The maximum specific growth rate will be determined using measurement of cell count as a function of time. The specific substrate uptake ($r_s$) and byproduct secretion rates ($r_p$) for exponential growth phase will be calculated using graphically determined values of maximum specific growth rate ($\mu$) and the biomass yield on substrate ($Y_{SX}$), or the byproduct yield on biomass ($Y_{XP}$), respectively ($r_s = \mu/Y_{SX}$; $r_p = \mu Y_{XP}$). In addition, carbon and nitrogen balance will be calculated for each dataset to ensure that mass balance for all metabolites is correctly accounted for.

Taken together, cell culture and metabolomics data will provide a comprehensive overview of the metabolite utilization and byproduct production during exponential and stationary phase in three cultivation conditions. Data generated in this part will be used to simulate CHO cell culture metabolism in the reconstructed and previously validated CHO metabolic model and to identify adventitious virus characteristic biomarkers in Part II.

II. Identifying Biomarkers of CHO Cell Culture Infected with Adventitious Viruses using Constraint-based Modeling and Biomarker Analysis Tool.

Figure 31:
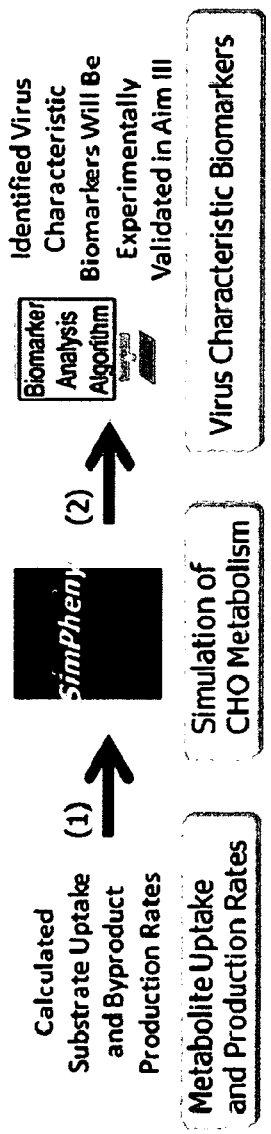
FIG. 31 shows that calculated substrate uptake and byproduct production rates are used to simulate CHO cell metabolism in control and virus-infected growth conditions in SimPheny™ (step 1). Output of Flux Variability Analysis (FVA) in SimPheny™ will be used together with Biomarker Analysis Algorithm to identify adventitious virus characteristic biomarkers that are confirmed experimentally.

To identify adventitious virus characteristic biomarkers, we will first update CHO cell model, based on metabolomics data generated. Second, we will simulate CHO cell metabolism during exponential growth phase in control and virus-infected growth conditions. Third, the model simulation results will then be utilized in Biomarker Analysis Algorithm to identify true characteristic biomarkers for adventitious virus contamination. The characteristic biomarkers identified using metabolic network analysis will be experimentally validated using a larger set of adventitious viruses (FIG. 31).

CHO Cell Metabolic Model Improvement in SimPheny™.

Metabolomics data generated will be utilized to improve the reconstructed CHO metabolic model content in SimPheny™, and to develop a more comprehensive understanding of CHO cell culture metabolism under viral infection. Metabolon Inc. has a library of approximately 2000 known and more than 5000 unknown compounds that c an be traced throughout the cell culture samples. For this initial screening, only the library of known compounds will be screened. It is expected that about 500 known metabolites will be identified from the supernatant samples of CHO cell culture. The known metabolites will be incorporated into CHO metabolic network in SimPheny™, along with the appropriate metabolic reactions. Inclusion of new metabolites and reactions will be supported based on published literature, if available.

Simulation of Virus-infected and Virus-non-infected CHO Cell Metabolism.

To understand the CHO cell metabolic response to the viral infection, metabolites identified from metabolomics analysis, along with the cell culture data will be used to simulate CHO cell metabolism in control and virus-infected cell cultures by maximizing uptake of nutrients, alone or in combination with other network reactions and functions including energy production, biomass production, and the like. Flux Variability Analysis will be performed for each cultivation condition (that is, control and infected conditions) to identify range of flux values for each reaction in CHO metabolic model. Next, significantly reduced or significantly elevated fluxes in the infected cultivation conditions compared with control will be identified (FIG. 30). From this comparison, we will be able to identify significant metabolic changes that are common to some, most or all adventitious virus infections, or that are specific to each adventitious virus. The knowledge obtained by analyzing the data in the context of the reconstructed CHO model will be further used to identify characteristic adventitious virus biomarkers, as described next.

Adventitious Virus Characteristic Biomarker Identification.

Using the Flux Variability Analysis (FVA) results, we will perform Biomarker Analysis to identify adventitious virus characteristic biomarkers in CHO cell culture. The description of the biomarker analysis framework has been described above. Briefly, generated metric system within biomarker analysis algorithm will quantify, prioritize, rank and categorize significance of each metabolic biomarker profiles. After computational identification of the biomarkers, the biomarkers with the metric values of the greatest magnitude will be determined to be the most significant and characteristic biomarkers of a viral infection. The overlap between the most significant and characteristic biomarkers identified for some, most or all virus infections will be identified as characteristic adventitious virus biomarkers of interest. These characteristic adventitious virus biomarkers that were identified for both viral contaminations will be validated and their sensitivity tested experimentally.

III. Experimentally Validating Adventitious Virus Biomarkers Identified Using A Model-Based Approach.

Figure 32:
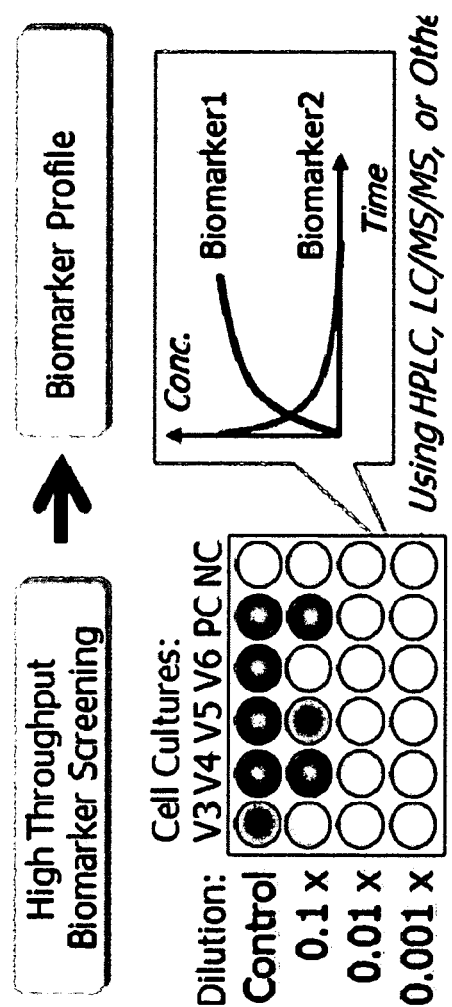
FIG. 32 shows that model-based identified viral biomarkers are validated in high throughput biomarker screening assay, where 4 adventitious viruses not previously tested and 4 different dilutions are tested. In silico identified viral biomarkers are monitored in each well through exponential growth phase using advanced liquid chromatography or mass spectrometry tools. V3, V4, V5, V6—adventitious viruses different from the ones previously tested. PC—positive control. NC—negative control.

To evaluate the accuracy of the model-based and experimental approach that was applied to identify adventitious virus biomarkers, we will perform a medium throughput analysis with the two following goals. First, we will test, if the identified characteristic markers of viral contamination are common among other adventitious viruses, and thus, can be applied to detect other adventitious virus contaminations in CHO cell culture. Second, we will attempt to evaluate the sensitivity of such viral biomarkers by performing a medium throughput dilution test. The metabolic biomarkers will be detected using available advanced liquid chromatography and mass spectrometry approaches (FIG. 32).

Preliminary High Throughput Biomarker Screening.

To evaluate if in silico identified biomarkers are applicable to detect other adventitious viruses in CHO cell culture, the 24-well biomarker screening assay will be performed. Four adventitious viruses (not previously tested), e.g. Vesivirus, BAV, BPV and PI-3, will be screened in CHO cell cultures in 24-well plate assay. The 24-well plate will be used to grow CHO cell cultures. Adventitious viruses will be inoculated in each of the wells at the $24^{th}$ hour after the start of cell culture. In addition, 4 different virus infection dilutions will be tested to evaluate sensitivity of biomarker analysis method (FIG. 11, scheme on the left). In 'control' condition for titer, 1000 virus/mL will be inoculated in CHO cell cultures, the same titer that was used in studies discussed above. 10×, 100× and 1000× viral infection dilutions will be performed (assuring the presence of at least 1 virus per well) for all of the tested viruses to determine the sensitivity of viral biomarker approach. Alternatively, we will modify viral infection dilution range to be used based on the results generated as described above. Samples for cell growth, productivity, existing viral screening methods and biomarker analysis will be collected and analyzed throughout the exponential growth phase in each well.

Biomarker Profiling.

Depending on which metabolites will be identified to be the biomarkers, in-house available advanced mass spectrometry (MS) or liquid chromatography (LC) tools will be utilized. We will utilize in-house available, or develop metabolite (biomarker) detection assays. We will use these metabolite detection tools throughout the cell culture in the high throughput biomarker screening. This biomarker screening assay will allow us to validate: (i) if in silico identified biomarkers are applicable to detect broader range of animal cell culture infectious adventitious viruses, (ii) if sensitivity of the biomarker analysis tool is compatible or better to the existing viral infection detection tools considering time, expense and sensitivity, and (iii) if in silico identified biomarkers may serve as an instantaneous detection tool for viral contamination. The overall success in this study will be measured by identifying adventitious virus characteristic biomarkers in silico and validating their applicability in testing various adventitious virus contaminations in CHO cell culture.

Summary of the Research and Design Methods.

Completion of these outlined steps will provide a validation of a model-based approach to discover metabolic biomarkers for adventitious virus contamination in animal cell culture. Successful completion of the work will allow the full development of a biomarker analysis for viral cell culture contamination in subsequent work by more comprehensively validating the predicted (virus specific and virus non-specific) biomarker signatures on a larger set of viruses and cell lines, and developing a standard biomarker assay for virus detection. Beyond this, the successful completion of the outlined studies supports the experimental-modeling approach that can be applied to: (i) identify biomarkers for other infectious agents, e.g. mycoplasma, or cross-contamination of cell lines, (ii) identify biomarkers of other animal cell culture important features, e.g. apoptosis, stress, or (iii) to develop cell line engineering or media supplementation designs to create virus resistant CHO cell lines.

Example IX

Metabolic Engineering of Mammalian Cell Lines

Superior Expression Cell Line

This example describes metabolic engineering of a cell line to produce a cell line with improved expression of product.

The example describes generating a superior mammalian cell line for production of a desired protein product such as therapeutic proteins. A superior mammalian cell line can be developed by designing genetic modifications (including gene deletion, insertion, over-expression, inhibition, and others, alone or in combination) in a parental or product producing cell line. The metabolic engineering targets can be identified by first simulating cell metabolism (i.e. by maximizing uptake of nutrients, alone or in combination with other network reactions and functions including energy production, biomass production, and such), followed by computationally deleting single or multiple gene/proteins/reactions, adding single or multiple genes/proteins/reactions, increasing or reducing the gene/protein/reaction activity, alone or in combination, to increase product formation, cell growth, or to reduce byproduct formation, or combination of those together.

Developing a Superior Parental CHO Cell Line.

A superior parental CHO cell line is generated for production of therapeutic proteins. To accomplish this, a computational modeling approach, CHO cell molecular biology and cell culture capabilities, are combined with advanced technologies, such as zinc finger nuclease gene deletion and whole transcriptome sequencing to design, implement, and characterize a superior parental CHO cell line. These technologies are used to systematically compute gene knockout targets in the CHO cell line to eliminate byproduct formation. These cell line engineering designs can be characterized and evaluated for their increased performance over the starting baseline values.

In addition, iterative cell line design and analysis, along with the ability to incorporate the additional experimental metabolic engineering tools for gene over-expression and gene knock-ins allow for the construction of cell lines that have better productivity and less byproduct secretion. The computational model can also be continually updated with new content from different 'omics' data types to increase accuracy in predictability and interpretation of cell line performance. The ability to add new heterologous genetic content, as well as improve the expression and function of native content (e.g., promoter engineering), will allow the development of a CHO cell line with increased productivity and less wasteful byproduct formation.

Computational Cell Line Engineering Design and Selection of Designs

Computational Design for the Elimination of Wasteful Byproduct Formation.

Figure 33:
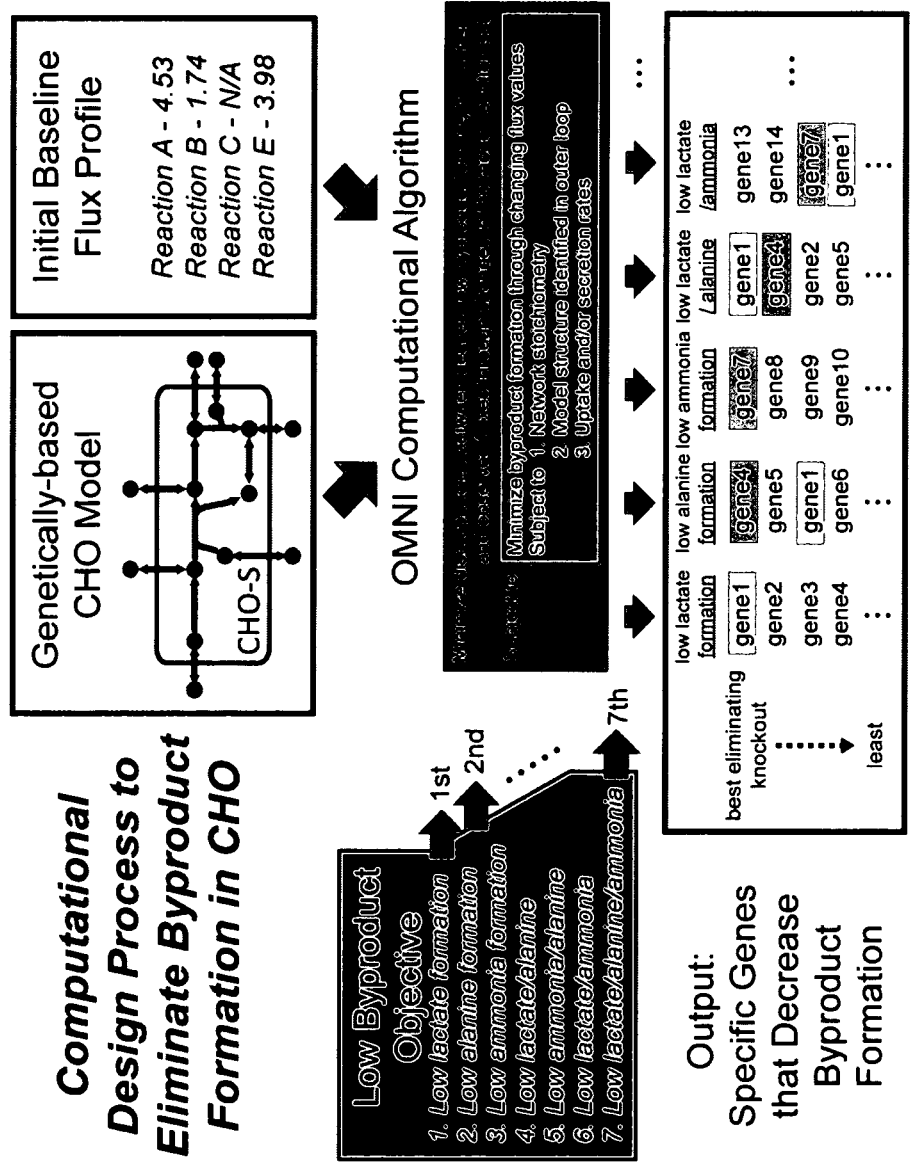
FIG. 33 shows the computational design process for calculating byproduct eliminating gene knockouts in CHO. The input to the OMNI algorithm is the genetically-based CHO model and the initial performance of the strain in the form of flux values from $^{13}C$ flux experiments. Using the OMNI algorithm, different low byproduct objectives are analyzed and the output is specific gene knockouts that can be made to shift flux towards a low byproduct formation phenotype (from the baseline performance). The results are used to determine the most promising knockouts. It is expected that similar genes will be found for different objectives and these are likely strong candidates (shaded boxes).

The reconstructed CHO metabolic model and the initial characterization of the baseline performance of the CHO cell line will be inputs to a computational analysis to identify the most beneficial knockouts for byproduct elimination (FIG. 33). The desired cellular objective of minimizing byproduct formation will be used as the design criteria in the inner-objective of the algorithm and lists of changes (i.e., knockouts) that will shift the observed baseline production phenotype towards this phenotype will be generated, along with relative scores that rank the most influential change that can be made 35. For the analysis, different low byproduct formation objectives will be used to rapidly compute the best genes to eliminate in each case. The different cases that will be analyzed will be, for example, all of the three major byproducts lactate, ammonia, and alanine individually, and in combination. The selection of designs will be discussed in the following section.

A second computational effort will be used to not only suggest the best knockouts to make in the baseline CHO cell, but to determine which native reaction(s) in the cell should be over-expressed to eliminate byproduct formation or help to maintain a desirable growth rate. This will be done by allowing the model to over-express genes (by forcing higher flux through their corresponding reactions) and not just knock them out. These targets will be examined subsequently in an experimental implementation. Furthermore, in subsequent computational design, the algorithm and model will be utilized to examine the addition of heterologous content 102 to the cell (i.e., new genes and resulting reactions) and the effect on the production phenotype. In this approach, the content that will be allowed to be added to the cell will be compiled to from a set of genes that have been successfully expressed in mammalian cells (as similarly demonstrated in an earlier study (Kim and Lee, *Appl. Microbiol. Biotechnol.* 76:659-665 (2007)).

Selection of the Most Promising Cell Line Engineering Designs to Implement.

The computational results from the cell line engineering design process are manually reviewed and the most promising designs to eliminate byproduct formation are determined. The goal is to generate different cell lines (e.g. three cell lines) that have lower byproduct formation than the parent CHO line. In the case of a promising design having isozymes for a targeted reaction, multiple cell lines (e.g. two cell lines) will be made. In this situation, one design will have up to two different genes knocked out to eliminate all (or nearly all) of the function of any isozymes that perform the same reaction in the CHO cell. The presence of isozymes will be determined, for example, by the whole transcriptome sequencing and annotation. Preference will be given to promising gene targets that have two or less isozymes in the cell so that the metabolic function being targeted will likely be eliminated and the desired effect can then be evaluated. In the case that none of the best gene functions to eliminate have less than two highly-expressed isozymes for a reaction, the top two isozymes (in terms of mRNA expression levels) will be targeted for deletion. If the most promising knockout cell lines to make only require one gene knockout in each case, up to three cell lines, in this example, will be made. This situation could arise in the case of a single gene accounting for the critical functionality of an enzyme (Boyer, Nature 402(6759):247, 249 (1999)), if the active enzyme is a product of a single gene (e.g., pyruvate carboxylase (Carbone and Robinson, Biochem. J. 370(Pt 1):275-282 (2003)); Jitrapakdee and Wallace 1-16), or if there are no isozymes present in the cell for the targeted reaction (e.g., NAD+-dependent glutamate dehydrogenase (Deluna et al., J. Biol. Chem. 276(47):43775-43783 (2001)).

The knockouts that will be selected for this study will be those that are predicted to eliminate byproduct formation the greatest. This process will be done manually for the top, for example, 10 scoring reactions that eliminate byproduct formation. Selecting the targets that will most eliminate byproduct formation will demonstrate the power of a model-driven metabolic engineering approach over an inference trial-and-error approach. The most promising obvious genes to knockout that can be expected might be lactate dehydrogenase (Jeong et al., Biochem. Biophys. Res. Commun. 28(5):1141-1149 (2001); Kim and Lee, Appl. Microbiol. Biotechnol. 74(1):152-159 (2007)) or alanine transaminase (Rognstad and Wals, Biochim. Biophys. Acta. 437(1):16-21 (1976)), but non-intuitive and not previously identified genes are likely to appear in the analysis. Specifically, the elimination of ammonia production will likely result in non-intuitive, previously not-identified designs as ammonia can be created through multiple pathways in the cell (e.g., through metabolism of multiple amino acids). Up to three cell line engineering designs will then be made in this example, using the newly available and efficient zinc figure nuclease (ZFN) technology as described below. Further development of the cell lines may involve generating multiple reaction knockout/knockin/overexpression designs.

Cell Line Development, Characterization, and Comparison to Baseline Performance.

Figure 34:
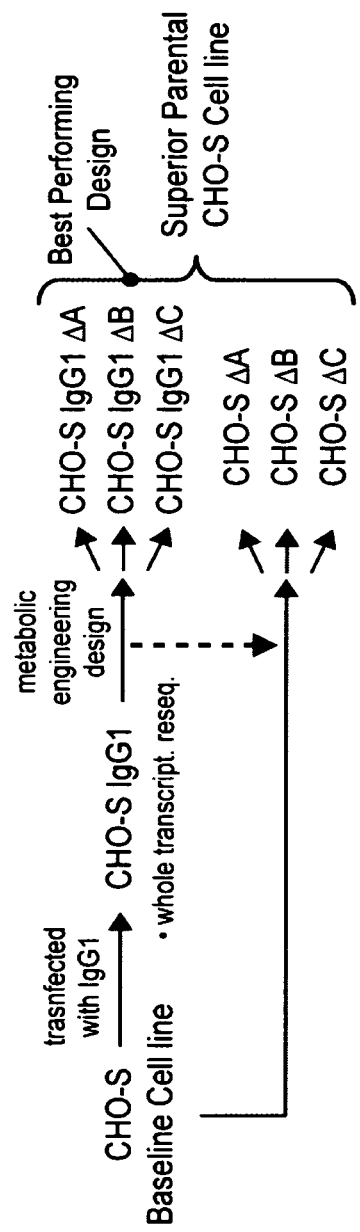
FIG. 34 shows generation of a superior parental CHO-S cell line.

The plan for generating a superior parental CHO cell line is presented in FIG. 34. Optimal cell line designs will be computed on the baseline performance of a CHO-S cell expressing IgG1, three different cell line designs (each in the CHO-S IgG1 and CHO-S cell line with no expressing vector) will then be constructed and characterized, to generate a superior low byproduct parental CHO-S cell line. Details for the implementation and execution are described below.

Zinc-Finger Nuclease Design and Execution.

We will use the ZFN targeted gene disruption technology to delete and inactivate the genes that code for the target reactions identified as discussed above (Moehle et al., Proc. Natl. Acad. Sci. U.S.A 104(9):3055-3060 (2007); Santiago et al., Proc. Natl. Acad. Sci. U.S.A 105(15):5809-5814 (2008)). If necessary, gene deletion will be performed sequentially if more than one gene is targeted in one strain. After each gene disruption, clonal cell lines will be isolated and gene disruption will be verified using known protocols and chemistry. Shake flask cell cultivations will be performed after each gene disruption to characterize cell growth and verify reduced byproduct formation. In addition, small interfering RNA (siRNA) (Fire et al., Nature 391:806-811 (1998); Sung et al. Metab. Eng. 9:452-464 (2007); Sung et al., Metab. Eng. 7:457-466 (2005); Bertrand et al., 296(4):1000-1004 (2002)) gene silencing approaches will be used, as an alternative method for the zinc-finger nuclease system. Results from this function-silencing technique will be used to determine the effect that a given gene has on the cell and, although transient, the results can be used to further attempt stable gene mutants for the desired cell lines with an alternate knockout approach than ZFN. To create a gene deletion clone for a targeted gene, the ZFN knockout systems will be used. CHO genomic sequence and computational algorithms are commercially available (Sigma-Aldrich, St. Louis Mo.) to design pairs of ZFNs that specifically bind to the sequence of target gene exon, disruption of which would disrupt the target gene expression. After preliminary experimental validation in CHO, we will then transfect the CHO-S cells with the pair of ZFNs, validate gene deletion and select desired clones. During ZFN-induced non-homologous DNA repair, the expression of the target gene will be disrupted.

PCR reagents will be used to validate targeted gene elimination. CHO cells that will have gene deletions, will be selected using limiting dilution cloning (LDC) approach. It is expected that a 1-20% probability that a target gene of interest will be deleted using ZFNs approach. Thus, there is a high chance to identify one or more clones with deleted gene per one 96-well plate. To confirm that the target gene is disrupted and does not express functional enzyme, we will first sequence the cDNA or look for polymorphisms in the target gene or RNA. Non-transfected CHO-S cells will be used as a negative control. If available, we will use an enzymatic assay to verify that the target reaction is inactivated. The results from these experiments will ensure that the target gene has been deleted. In the case of multiple deletions (up to two gene deletions for one cell line), targeted gene knockouts will be implemented by sequential deletion using the described ZFN approach. After each target gene deletion, the resulting CHO cell line will be characterized in shake-flask cultivations and banked. The final clone that contains all deletions implemented will be characterized according to the procedure outlined in the following section. All of the cell line designs will likely be implemented in parallel for efficient parallelization in the cell line construction process.

Growth Screens, Profiling, and Quantification of Improvement for the Engineered Cell Line.

Final characterization of the engineered cell lines will be performed to determine the extent of byproduct elimination. The final clones will be grown in identical conditions as the baseline CHO-S cell line so the change in genetic content is the only variable changing in the process and a straightforward evaluation of byproduct elimination can be made. For the engineered cell lines, percent improvement, as well as quantitative values, for lactate, ammonia, and L-alanine formation and protein production will be determined and reported. The best performing cell line in terms of increased protein productivity and titer will be selected as the superior parental CHO cell line.

In addition to decreasing byproduct forming cell lines, it will be established as to what degree of quantitative agreement is found between model predictions and experimental results to ensure that the model has captured the mechanism behind the improved production. Thus, we will examine the external and internal flux measurements such as the substrate, byproduct formation, and growth rates within the context of the constraint-based model to which the knockout prediction strategies were applied. Byproduct yields calculated at the end of the exponential growth phase as well as the end of fed-batch cultures will also be calculated. We will directly compare the measured byproduct fluxes with the in silico predictions for each experiment.

Finally, based on the initial decrease in byproduct formation, agreements with predictions and effectiveness of the computational approaches, second generation modifications to the generated cell lines will be determined. This process will be similar to the approach outlined above except instead of comparison of the theoretical minimum byproduct forming phenotype(s) with the baseline CHO-S cell line, it will be with the newly generated cell lines. These new designs will also be computed with the knowledge gained from algorithm performance in the predictability for the initial designs. Second generation modifications will be suggested for all of the generated cell lines, regardless of performance, and will feed directly into future iterations.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

TABLE 19

Selection System Designs - Single Deletion Results

| | | |
|---|---|---|
| 3DSPHR | [c]: 3dsphgn + h + nadph --> nadp + sphgn | Sphingolipid Metabolism |
| 6PGCter | 6pgc[c] <==> 6pgc[r] | Transport, Endoplasmic Reticular |
| ACACT1r | [c]: (2) accoa <==> aacoa + coa | Fatty Acid Metabolism |
| ACCOAC | [c]: accoa + atp + hco3 --> adp + h + malcoa + pi | Fatty Acid Biosynthesis |
| ADK1 | [c]: amp + atp <==> (2) adp | Purine Metabolism |
| ADNK1 | [c]: adn + atp --> adp + amp + h | Purine Metabolism |
| ADSL2r | [c]: 25aics <==> aicar + fum | Purine Metabolism |
| AGAT_CHO | [c]: (0.001) 1ag3p_CHO + (0.025) arachdcoa + (0.016) clpndcoa + (0.01) cvncoa + (0.002) ecsacoa + (0.003) ecspecoa + (0.004) estcoa + (0.064) hdcoa + (0.007) lgnccoa + (0.003) lnlecoa + (0.008) nrvnccoa + (0.042) ocdycacoa + (0.404) odecoa + (0.253) pmtc | Phospholipid Metabolism |
| AHC | [c]: ahcys + h2o <==> adn + hcys-L | Methionine Metabolism |
| AICART | [c]: 10fthf + aicar <==> fprica + thf | Purine Metabolism |
| AIRCr | [c]: air + co2 <==> 5aizc + h | Purine Metabolism |
| AKBDHm | [m]: 2obut + coa + nad --> co2 + nadh + ppcoa | Cysteine Metabolism |
| AKBtm | 2obut[m] <==> 2obut[c] | Transport, Mitochondrial |
| ARGSL | [c]: argsuc <==> arg-L + fum | Arginine Metabolism |
| ARGSS | [c]: asp-L + atp + citr-L --> amp + argsuc + h + ppi | Arginine Metabolism |
| ASNS1 | [c]: asp-L + atp + gln-L + h2o --> amp + asn-L + glu-L + h + ppi | Alanine and Aspartate Metabolism |
| ASPCTr | [c]: asp-L + cbp <==> cbasp + h + pi | Pyrimidine Biosynthesis |
| ATP/ADPtp | adp[c] + atp[x] <==> adp[x] + atp[c] | Sterol Biosynthesis |
| C14STRer | [r]: 44mctr + h + nadph --> 44mzym + nadp | Sterol Biosynthesis |
| C3STKR2er | [r]: h + nadph + zym_int2 --> nadp + zymst | Sterol Biosynthesis |
| C4STMO1er | [r]: 44mzym + (2) h + (3) nadph + (3) o2 --> 4mzym_int1 + (4) h2o + (3) nadp | Sterol Biosynthesis |
| CBPS | [c]: (2) atp + gln-L + h2o + hco3 --> (2) adp + cbp + glu-L + (2) h + pi | Pyrimidine Biosynthesis |
| CBPSAm | [m]: (2) atp + co2 + h2o + nh4 --> (2) adp + cbp + (3) h + pi | Glutamate Metabolism |
| CDPDGPm_CHO | [m]: (0.001) cdpdag_CHO + glyc3p <==> cmp + h + (0.001) pgp_CHO | Phospholipid Metabolism |
| CERPT2_CHO | [c]: (0.001) cer_CHO + h + (0.001) pc_CHO --> (0.001) 12dgr_CHO + (0.001) sphgmy_CHO | Sphingolipid Metabolism |
| CERS_CHO | [c]: (0.001) facoa_avg_CHO + sphgn --> coa + (0.001) dcer_CHO + h | Sphingolipid Metabolism |
| CHLPCTD | [c]: cholp + ctp + h --> cdpchol + ppi | Phospholipid Metabolism |
| CHOLK | [c]: atp + chol --> adp + cholp + h | Phospholipid Metabolism |
| CHOLtu | chol[e] <==> chol[c] | Transport, Extracellular |
| CHSTEROLter | chsterol[c] <==> chsterol[r] | Transport, Endoplasmic Reticular |
| CITL2 | [c]: atp + cit + coa --> accoa + adp + oaa + pi | Fatty Acid Metabolism |
| CLPNtm_CHO | clpn_CHO[m] <==> clpn_CHO[c] | Transport, Mitochondrial |
| CLSm_CHO | [m]: (0.001) cdpdag_CHO + (0.001) pg_CHO --> (0.001) clpn_CHO + cmp + h | Phospholipid Metabolism |

TABLE 19-continued

Selection System Designs - Single Deletion Results

| | | |
|---|---|---|
| CO2ter | co2[c] <==> co2[r] | Transport, Endoplasmic Reticular |
| CO2tp | co2[c] <==> co2[x] | Transport, Peroxisomal |
| CYOO4m | (4) focytcc[m] + (8) h[m] + o2[m] --> (4) ficytcc[m] + (4) h[c] + (2) h2o[m] | Oxidative Phosphorylation |
| CYOR4m-ubq10 | (2) ficytcc[m] + (2) h[m] + q10h2[m] --> (2) focytcc[m] + (4) h[c] + ubq10[m] | Oxidative Phosphorylation |
| CYSTGL | [c]: cysth-L + h2o --> 2obut + cys-L + nh4 | Methionine Metabolism |
| CYSTS | [c]: hcys-L + ser-L --> cysth-L + h2o | Methionine Metabolism |
| CYTK1 | [c]: atp + cmp <==> adp + cdp | Pyrimidine Metabolism |
| CYTK1m | [m]: atp + cmp <==> adp + cdp | Pyrimidine Metabolism |
| DAGCPT_CHO | [c]: (0.001) 12dgr_CHO + cdpchol --> cmp + h + (0.001) pc_CHO | Phospholipid Metabolism |
| DAGPYP_CHO | [c]: h2o + (0.001) pa_CHO --> (0.001) 12dgr_CHO + pi | Phospholipid Metabolism |
| DASYN_CHO | [c]: ctp + h + (0.001) pa_CHO <==> (0.001) cdpdag_CHO + ppi | Phospholipid Metabolism |
| DASYNm_CHO | [m]: ctp + h + (0.001) pa_CHO <==> (0.001) cdpdag_CHO + ppi | Phospholipid Metabolism |
| DCERDS_CHO | [c]: (0.001) dcer_CHO + h + nadph + o2 --> (0.001) cer_CHO + (2) h2o + nadp | Sphingolipid Metabolism |
| DESAT161 | [c]: h + nadph + o2 + pmtcoa --> (2) h2o + hdcoa + nadp | Fatty Acid Desaturation |
| DESAT181 | [c]: h + nadph + o2 + strcoa --> (2) h2o + nadp + odecoa | Fatty Acid Desaturation |
| DESAT205g | [c]: arachdcoa + h + nadph + o2 --> ecspecoa + (2) h2o + nadp | Fatty Acid Synthesis |
| DESAT226g | [c]: clpndcoa + h + nadph + o2 --> cvncoa + (2) h2o + nadp | Fatty Acid Synthesis |
| DESAT241 | [c]: h + lgnccoa + nadph + o2 --> (2) h2o + nadp + nrvnccoa | Fatty Acid Synthesis |
| DHFR | [c]: dhf + h + nadph <==> nadp + thf | Folate Metabolism |
| DHORD3m-ubq10 | dhor-S[c] + ubq10[m] <==> orot[c] + q10h2[m] | Pyrimidine Biosynthesis |
| DHORTS | [c]: dhor-S + h2o <==> cbasp + h | Pyrimidine Metabolism |
| DHPRx | [c]: dhbpt + h + nadh <==> nad + thbpt | Folate Metabolism |
| DMATT | [c]: dmpp + ipdp --> grdp + ppi | Sterol Biosynthesis |
| DMPPtp | dmpp[x] <==> dmpp[c] | Transport, Peroxisomal |
| DPMVDp | [x]: 5dpmev + atp --> adp + co2 + ipdp + pi | Sterol Biosynthesis |
| DTMPK | [c]: atp + dtmp <==> adp + dtdp | Pyrimidine Metabolism |
| FACOAL182 | [c]: atp + coa + ocdcya <==> amp + ocdycacoa + ppi | Fatty Acid Metabolism |
| FACOAL240 | [c]: atp + coa + ttc <==> amp + lgnccoa + ppi | Fatty Acid Metabolism |
| FACOAavg_CHO | [c]: (0.025) arachda + atp + coa + (0.01) dcshea + (0.016) dcspea + (0.002) ecsa + (0.003) ecspea + (0.004) ecstea + (0.253) hdca + (0.064) hdcea + (0.003) lnlne + (0.008) nrvnc + (0.13) ocdca + (0.404) ocdcea + (0.042) ocdcya + (0.007) ttc + (0.029) ttd | Sphingolipid Metabolism |
| FAEL203 | [c]: (5) h + lnlecoa + malcoa + (4) nadph + o2 --> co2 + coa + estcoa + (3) h2o + (4) nadp | Fatty acid elongation |
| FAEL225 | [c]: ecspecoa + (5) h + malcoa + (4) nadph + o2 --> clpndcoa + co2 + coa + (3) h2o + (4) nadp | Fatty acid elongation |
| FALDtp | fald[c] <==> fald[x] | Transport, Peroxisomal |
| FAS100 | [c]: (3) h + malcoa + (2) nadph + octa --> co2 + coa + dca + h2o + (2) nadp | Fatty Acid Biosynthesis |
| FAS120 | [c]: dca + (3) h + malcoa + (2) nadph --> co2 + coa + h2o + ddca + (2) nadp | Fatty Acid Biosynthesis |
| FAS140 | [c]: ddca + (3) h + malcoa + (2) nadph --> co2 + coa + h2o + (2) nadp + ttdca | Fatty Acid Biosynthesis |
| FAS160 | [c]: (3) h + malcoa + (2) nadph + ttdca --> co2 + coa + h2o + hdca + (2) nadp | Fatty Acid Biosynthesis |
| FAS180 | [c]: (3) h + hdca + malcoa + (2) nadph --> co2 + coa + h2o + (2) nadp + ocdca | Fatty Acid Biosynthesis |
| FAS200 | [c]: (3) h + malcoa + (2) nadph + ocdca --> co2 + coa + ecsa + h2o + (2) nadp | Fatty Acid Biosynthesis |
| FAS220 | [c]: ecsa + (3) h + malcoa + (2) nadph --> co2 + coa + dcsa + h2o + (2) nadp | Fatty Acid Biosynthesis |
| FAS240 | [c]: dcsa + (3) h + malcoa + (2) nadph --> co2 + coa + h2o + (2) nadp + ttc | Fatty Acid Biosynthesis |
| FAS80_L | [c]: accoa + (8) h + (3) malcoa + (6) nadph --> (3) co2 + (4) coa + (2) h2o + (6) nadp + octa | Fatty Acid Biosynthesis |
| FORter | for[c] <==> for[r] | Transport, Endoplasmic Reticular |
| FRDPter | frdp[c] <==> frdp[r] | Transport, Endoplasmic Reticular |
| FTHFLr | [c]: atp + for + thf <==> 10fthf + adp + pi | Folate Metabolism |

TABLE 19-continued

Selection System Designs - Single Deletion Results

| | | |
|---|---|---|
| FldAct | [c]: fald + thf --> h2o + mlthf | Folate Metabolism |
| G3PD1 | [c]: glyc3p + nad <==> dhap + h + nadh | Glycolysis/Gluconeogeneis |
| G5SADs | [c]: glu5sa <==> 1pyr5c + h + h2o | Arginine and Proline Metabolism |
| G5SDm | [m]: glu5p + h + nadph --> glu5sa + nadp + pi | Proline Biosynthesis |
| G6PASEer | [r]: g6p + h2o --> glc-D + pi | Glycolysis/Gluconeogenesis |
| G6PDH2er | [r]: g6p + nadp --> 6pgl + h + nadph | Pentose Phosphate Pathway |
| G6Pter | g6p[c] <==> g6p[r] | Transport, Endoplasmic Reticular |
| GALU | [c]: g1p + h + utp <==> ppi + udpg | Carbohydrate Metabolism |
| GARFTi | [c]: 10fthf + gar --> fgam + h + thf | Purine Metabolism |
| GAT_CHO | [c]: (0.025) arachdcoa + (0.016) clpndcoa + (0.01) cvncoa + (0.002) ecsacoa + (0.003) ecspecoa + (0.004) estcoa + glyc3p + (0.064) hdcoa + (0.007) lgnccoa + (0.003) lnlecoa + (0.008) nrvnccoa + (0.042) ocdycacoa + (0.404) odecoa + (0.253) pmtcoa + (0.13) | Phospholipid Metabolism |
| GK1 | [c]: atp + gmp <==> adp + gdp | Purine Metabolism |
| GL3Ptrm | glyc3p[c] <==> glyc3p[m] | Transport, Mitochondrial |
| GLCter | glc-D[c] <==> glc-D[r] | Transport, Endoplasmic Reticular |
| GLNS | [c]: atp + glu-L + nh4 --> adp + gln-L + h + pi | Glutamate Metabolism |
| GLU5Km | [m]: atp + glu-L --> adp + glu5p | Proline Biosynthesis |
| GLUPRT | [c]: gln-L + h2o + prpp --> glu-L + ppi + pram | Purine Metabolism |
| GLUSAtm | glu5sa[c] <==> glu5sa[m] | Transport, Mitochondrial |
| GLYGS | [c]: udpg --> glycogen + h + udp | Carbohydrate Metabolism |
| GLYtp | gly[c] <==> gly[x] | Transport, Peroxisomal |
| GMPS2 | [c]: atp + gln-L + h2o + xmp --> amp + glu-L + gmp + (2) h + ppi | Purine Metabolism |
| GMTR | [c]: amet + gly --> ahcys + h + sarcs | Glycine, Serine, and Threonine Metabolism |
| GRTT | [c]: grdp + ipdp --> frdp + ppi | Sterol Biosynthesis |
| H2Oter | h2o[c] <==> h2o[r] | Transport, Endoplasmic Reticular |
| HCO3E | [c]: co2 + h2o <==> h + hco3 | Other |
| HCO3Em | [m]: co2 + h2o <==> h + hco3 | Other |
| HEX1 | [c]: atp + glc-D --> adp + g6p + h | Glycolysis/Gluconeogenesis |
| HISt4r | his-L[e] + na1[e] <==> his-L[c] + na1[c] | Transport, Extracellular |
| HMGCOAR | [c]: coa + mev-R + (2) nadp <==> (2) h + hmgcoa + (2) nadph | Steroid Metabolism |
| HMGCOASi | [c]: aacoa + accoa + h2o --> coa + h + hmgcoa | Sterol Biosynthesis |
| ILEtec | ile-L[e] <==> ile-L[c] | Transport, Extracellular |
| IMPC | [c]: h2o + imp <==> fprica | Purine Metabolism |
| IMPD | [c]: h2o + imp + nad --> h + nadh + xmp | Purine Metabolism |
| IPDDIp | [x]: ipdp <==> dmpp | Sterol Biosynthesis |
| IPDPtp | ipdp[x] <==> ipdp[c] | Transport, Peroxisomal |
| LEUtec | leu-L[e] <==> leu-L[c] | Transport, Extracellular |
| LNS14DMer | [r]: (2) h + lanost + (3) nadph + (3) o2 --> 44mctr + for + (4) h2o + (3) nadp | Sterol Biosynthesis |
| LNSTLSer | [r]: Ssq23epx --> lanost | Sterol Biosynthesis |
| LYSt | lys-L[e] <==> lys-L[c] | Transport, Extracellular |
| METAT | [c]: atp + h2o + met-L --> amet + pi + ppi | Methionine Metabolism |
| MEt4r | met-L[e] + na1[e] <==> met-L[c] + na1[c] | Transport, Extracellular |
| MEVK1p | [x]: atp + mev-R --> 5pmev + adp + h | Sterol Biosynthesis |
| MEVtp | mev-R[x] <==> mev-R[c] | Sterol Biosynthesis |
| MMEm | [m]: mmcoa-S <==> mmcoa-R | Valine, Leucine, and Isoleucine Degradation |
| MMMrm | [m]: mmcoa-R <==> succoa | Valine, Leucine, and Isoleucine Degradation |
| NDP8 | [c]: dudp + h2o --> dump + h + pi | Pyrimidine Metabolism |
| NDPK1 | [c]: atp + gdp <==> adp + gtp | Purine Metabolism |
| NDPK2 | [c]: atp + udp <==> adp + utp | Purine Metabolism |
| NDPK3 | [c]: atp + cdp <==> adp + ctp | Purine Metabolism |
| NDPK3m | [m]: atp + cdp <==> adp + ctp | Purine Metabolism |
| NDPK4 | [c]: atp + dtdp <==> adp + dttp | Pyrimidine Metabolism |
| NDPK5 | [c]: atp + dgdp <==> adp + dgtp | Pyrimidine Metabolism |
| NDPK7 | [c]: atp + dcdp <==> adp + dctp | Pyrimidine Metabolism |
| NDPK8 | [c]: atp + dadp <==> adp + datp | Pyrimidine Metabolism |
| O2t | o2[e] <==> o2[c] | Transport, Extracellular |
| O2ter | o2[c] <==> o2[r] | Transport, Endoplasmic Reticular |
| OCBTm | [m]: cbp + orn-L <==> citr-L + h + pi | Arginine and Proline Metabolism |
| OCDCYAtr | ocdcya[e] <==> ocdcya[c] | Transport, Extracellular |

TABLE 19-continued

Selection System Designs - Single Deletion Results

| | | |
|---|---|---|
| OMPDC | [c]: h + orot5p --> co2 + ump | Pyrimidine Metabolism |
| ORNCITRtm | citr-L[m] + h[m] + orn-L[c] <==> citr-L[c] + h[c] + orn-L[m] | Transport, Mitochondrial |
| ORNTAm | [m]: akg + orn-L <==> glu-L + glu5sa | Arginine and Proline Metabolism |
| ORNtrm | h[m] + orn-L[c] <==> h[c] + orn-L[m] | Transport, Mitochondrial |
| ORPT | [c]: orot5p + ppi <==> orot + prpp | Pyrimidine Metabolism |
| PAtm_CHO | pa_CHO[c] <==> pa_CHO[m] | Transport, Mitochondrial |
| PGDH | [c]: 6pgc + nadp --> co2 + nadph + ru5p-D | Pentose Phosphate Pathway |
| PGLer | [r]: 6pgl + h2o --> 6pgc + h | Pentose Phosphate Pathway |
| PGMT | [c]: g1p <==> g6p | Glycolysis/Gluconeogenesis |
| PGPPAm_CHO | [m]: h2o + (0.001) pgp_CHO --> (0.001) pg_CHO + pi | Phospholipid Metabolism |
| PHE4MO | [c]: o2 + phe-L + thbpt --> dhbpt + h2o + tyr-L | Phenylalanine, Tyrosine, and Tryptophan Biosynthesis |
| PHEtec | phe-L[e] <==> phe-L[c] | Transport, Extracellular |
| PINOS_CHO | [c]: (0.001) cdpdag_CHO + inost <==> cmp + h + (0.001) pino_CHO | Phospholipid Metabolism |
| PIt2p | h[c] + pi[c] <==> h[x] + pi[x] | Transport, Peroxisomal |
| PIter | h[c] + pi[c] <==> h[r] + pi[r] | Transport, Endoplasmic Reticular |
| PMEVKrp | [x]: 5pmev + atp <==> 5dpmev + adp | Sterol Biosynthesis |
| PPA | [c]: h2o + ppi --> h + (2) pi | Purine Metabolism |
| PPAer | [r]: h2o + ppi --> h + (2) pi | Sterol Biosynthesis |
| PPAm | [m]: h2o + ppi --> h + (2) pi | Other |
| PPCOACrm | [m]: atp + hco3 + ppcoa <==> adp + h + mmcoa-S + pi | Valine, Leucine, and Isoleucine Degradation |
| PRAGS | [c]: atp + gly + pram --> adp + gar + h + pi | Purine Metabolism |
| PRAIS | [c]: atp + fpram --> adp + air + h + pi | Purine Metabolism |
| PRASCS | [c]: 5aizc + asp-L + atp <==> 25aics + adp + h + pi | Purine Metabolism |
| PRFGS | [c]: atp + fgam + gln-L + h2o --> adp + fpram + glu-L + (2) h + pi | Purine Metabolism |
| PRPPS | [c]: atp + r5p <==> amp + h + prpp | Purine Metabolism |
| PTDSS1_CHO | [c]: chol + (0.001) ps_CHO <==> (0.001) pc_CHO + ser-L | Phospholipid Metabolism |
| RNDR1 | [c]: adp + trdrd --> dadp + h2o + trdox | Purine and Pyrimidine Metabolism |
| RNDR2 | [c]: gdp + trdrd --> dgdp + h2o + trdox | Purine and Pyrimidine Metabolism |
| RNDR3 | [c]: cdp + trdrd --> dcdp + h2o + trdox | Purine and Pyrimidine Metabolism |
| RNDR4 | [c]: trdrd + udp --> dudp + h2o + trdox | Purine and Pyrimidine Metabolism |
| RPI | [c]: r5p <==> ru5p-D | Pentose Phosphate Pathway |
| SARCOp | [x]: h2o + o2 + sarcs --> fald + gly + h2o2 | Glycine, Serine, and Threonine Metabolism |
| SARCStrp | sarcs[c] <==> sarcs[x] | Transport, Peroxisomal |
| SERPT | [c]: h + pmtcoa + ser-L --> 3dsphgn + co2 + coa | Sphingolipid Metabolism |
| SQLEer | [r]: h + nadph + o2 + sql --> Ssq23epx + h2o + nadp | Sterol Biosynthesis |
| SQLSer | [r]: (2) frdp + h + nadph --> nadp + (2) ppi + sql | Sterol Biosynthesis |
| SUCD1m-ubq10 | [m]: succ + ubq10 <==> fum + q10h2 | Citrate Cycle (TCA) |
| TAL | [c]: g3p + s7p <==> e4p + f6p | Pentose Phosphate Pathway |
| THRt4r | na1[e] + thr-L[e] <==> na1[c] + thr-L[c] | Transport, Extracellular |
| TKT1 | [c]: r5p + xu5p-D <==> g3p + s7p | Pentose Phosphate Pathway |
| TKT2 | [c]: e4p + xu5p-D <==> f6p + g3p | Pentose Phosphate Pathway |
| TMDSr | [c]: dump + mlthf <==> dhf + dtmp | Pyrimidine Metabolism |
| TRDRr | [c]: h + nadph + trdox <==> nadp + trdrd | Pyrimidine Metabolism |
| TRIGS_CHO | [c]: (0.001) 12dgr_CHO + (0.001) facoa_avg_CHO --> coa + (0.001) triglyc_CHO | Triglycerol Synthesis |
| TRPt | trp-L[e] <==> trp-L[c] | Transport, Extracellular |
| UMPK | [c]: atp + ump <==> adp + udp | Pyrimidine Metabolism |
| VALtec | val-L[e] <==> val-L[c] | Transport, Extracellular |
| PIt6 | h[e] + pi[e] <==> h[c] + pi[c] | Transport, Extracellular |

TABLE 19-continued

Selection System Designs - Single Deletion Results

| | | |
|---|---|---|
| RPE | [c]: ru5p-D <==> xu5p-D | Pentose Phosphate Pathway |
| ADSL1r | [c]: dcamp <==> amp + fum | Purine Metabolism |
| ADSS | [c]: asp-L + gtp + imp --> dcamp + gdp + (2) h + pi | Purine Metabolism |

TABLE 20

Selection System Designs - Double Deletion Results

| | | | | |
|---|---|---|---|---|
| ACACT1rm | [m]: (2) accoa <==> aacoa + coa | and | ALATA_L | [c]: akg + ala-L <==> glu-L + pyr |
| ACGK_CHO | [c]: atp + (0.001) mglyc_CHO --> (0.001) 1ag3p_CHO + adp + h | and | FACOAL203 | [c]: atp + coa + ecstea <==> amp + estcoa + ppi |
| ACGK_CHO | [c]: atp + (0.001) mglyc_CHO --> (0.001) 1ag3p_CHO + adp + h | and | FACOAL205 | [c]: atp + coa + ecspea <==> amp + ecspecoa + ppi |
| ACMUCD | [c]: acmucsal + h --> amucsal + co2 | and | ALATA_L | [c]: akg + ala-L <==> glu-L + pyr |
| ACMUCD | [c]: acmucsal + h --> amucsal + co2 | and | MTHFC | [c]: h2o + methf <==> 10fthf + h |
| ACONT | [c]: cit <==> icit | and | CSm | [m]: accoa + h2o + oaa --> cit + coa + h |
| AKGD2m | [m]: 2oxoadp + coa + nad --> co2 + glutcoa + nadh | and | ALATA_L | [c]: akg + ala-L <==> glu-L + pyr |
| AKGD2m | [m]: 2oxoadp + coa + nad --> co2 + glutcoa + nadh | and | MTHFC | [c]: h2o + methf <==> 10fthf + h |
| ALATA_L | [c]: akg + ala-L <==> glu-L + pyr | and | 2OXOADPTm | 2oxoadp[c] + akg[m] <==> 2oxoadp[m] + akg[c] |
| ALATA_L | [c]: akg + ala-L <==> glu-L + pyr | and | AMCOXO | [c]: 2amuc + h + h2o + nadph --> 2oxoadp + nadp + nh4 |
| ALATA_L | [c]: akg + ala-L <==> glu-L + pyr | and | CSm | [m]: accoa + h2o + oaa --> cit + coa + h |
| ALATA_L | [c]: akg + ala-L <==> glu-L + pyr | and | GCOADrm | [m]: fad + glutcoa + h <==> b2coa + co2 + fadh2 |
| ALATA_L | [c]: akg + ala-L <==> glu-L + pyr | and | HANTHDOr | [c]: 3hanthrn + o2 <==> acmucsal |
| ALATA_L | [c]: akg + ala-L <==> glu-L + pyr | and | SUCD3m-ubq10 | [m]: fadh2 + ubq10 <==> fad + q10h2 |
| AMUCD | [c]: amucsal + h2o + nad --> 2amuc + (2) h + nadh | and | ALATA_L | [c]: akg + ala-L <==> glu-L + pyr |
| AMUCD | [c]: amucsal + h2o + nad --> 2amuc + (2) h + nadh | and | MTHFC | [c]: h2o + methf <==> 10fthf + h |
| ASPTA1 | [c]: akg + asp-L <==> glu-L + oaa | and | GACm | asp-L[m] + glu-L[c] + h[c] --> asp-L[c] + glu-L[m] + h[m] |
| ASPTA1m | [m]: akg + asp-L <==> glu-L + oaa | and | ASPTA1 | [c]: akg + asp-L <==> glu-L + oaa |
| ATP/ADPtm | adp[c] + atp[m] <==> adp[m] + atp[c] | and | GAPD | [c]: g3p + nad + pi <==> 13dpg + h + nadh |
| ATP/ADPtm | adp[c] + atp[m] <==> adp[m] + atp[c] | and | GLCt1r | glc-D[e] <==> glc-D[c] |
| ATP/ADPtm | adp[c] + atp[m] <==> adp[m] + atp[c] | and | PGM | [c]: 3pg <==> 2pg |
| ATP/ADPtm | adp[c] + atp[m] <==> adp[m] + atp[c] | and | PYK | [c]: adp + h + pep --> atp + pyr |
| C3STDH1xer | [r]: 4mzym_int1 + nad --> 4mzym_int2 + co2 + nadh | and | C3STDH1yer | [r]: 4mzym_int1 + nadp --> 4mzym_int2 + co2 + nadph |
| C4STMO2yer | [r]: 4mzym_int2 + nadp + o2 --> co2 + h + nadph + zym_int2 | and | C3STDH1yer | [r]: 4mzym_int1 + nadp --> 4mzym_int2 + co2 + nadph |
| C4STMO2yer | [r]: 4mzym_int2 + nadp + o2 --> co2 + h + nadph + zym_int2 | and | C4STMO2xer | [r]: 4mzym_int2 + nad + o2 --> co2 + h + nadh + zym_int2 |

TABLE 20-continued

Selection System Designs - Double Deletion Results

| | | | | |
|---|---|---|---|---|
| C4STMO2yer | [r]: 4mzym_int2 + nadp + o2 --> co2 + h + nadph + zym_int2 | and | DHCR72er | [r]: 7dhchsterol + h + nadph --> chsterol + nadp |
| C4STMO2yer | [r]: 4mzym_int2 + nadp + o2 --> co2 + h + nadph + zym_int2 | and | LATHSTOxer | [r]: h + lathost + nadh + o2 --> 7dhchsterol + (2) h2o + nad |
| CATm | [m]: (2) h2o2 --> (2) h2o + o2 | and | O2trm | o2[c] <==> o2[m] |
| CATp | [x]: (2) h2o2 --> (2) h2o + o2 | and | O2tp | o2[c] <==> o2[x] |
| CHOLSE_CHO | [c]: (0.025) arachda + chsterol + (0.01) dcshea + (0.016) dcspea + (0.002) ecsa + (0.003) ecspea + (0.004) ecstea + h + (0.253) hdca + (0.064) hdcea + (0.003) lnlne + (0.008) nrvnc + (0.13) ocdca + (0.404) ocdcea + (0.042) ocdcya + (0.007) ttc + (0.029) | and | ACAT_CHO | [c]: chsterol + (0.001) facoa_avg_CHO --> (0.001) cholse_CHO + coa |
| CHSTNIer | [r]: zymst <==> cholsd | and | EBP2rer | [r]: zymstnl <==> lathost |
| CHSTNIer | [r]: zymst <==> cholsd | and | STRR2er | [r]: h + nadph + zymst --> nadp + zymstnl |
| CITMALtm | cit[c] + h[c] + mal-L[m] <==> cit[m] + h[m] + mal-L[c] | and | ACONT | [c]: cit <==> icit |
| CRNOTtm | crn[m] + strcrn[c] <==> crn[c] + strcrn[m] | and | FACOAL180 | [c]: atp + coa + ocdca <==> amp + ppi + strcoa |
| CRNPTtm | crn[m] + pmtcrn[c] <==> crn[c] + pmtcrn[m] | and | FACOAL160 | [c]: atp + coa + hdca <==> amp + pmtcoa + ppi |
| CRNTDT | [c]: crn + tdcoa <==> coa + tdcrn | and | FACOAL140 | [c]: atp + coa + ttdca <==> amp + ppi + tdcoa |
| CRNTTtm | crn[m] + tdcrn[c] <==> crn[c] + tdcrn[m] | and | FACOAL140 | [c]: atp + coa + ttdca <==> amp + ppi + tdcoa |
| CSm | [m]: accoa + h2o + oaa --> cit + coa + h | and | FACOAL140 | [c]: atp + coa + ttdca <==> amp + ppi + tdcoa |
| CSm | [m]: accoa + h2o + oaa --> cit + coa + h | and | MTHFD | [c]: mlthf + nadp <==> methf + nadph |
| CSm | [m]: accoa + h2o + oaa --> cit + coa + h | and | PSP_L | [c]: h2o + pser-L --> pi + ser-L |
| CTPS1 | [c]: atp + nh4 + utp --> adp + ctp + (2) h + pi | and | CTPS2 | [c]: atp + gln-L + h2o + utp --> adp + ctp + glu-L + (2) h + pi |
| DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 | and | FACOAL181 | [c]: atp + coa + ocdcea <==> amp + odecoa + ppi |
| DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 | and | FACOAL203 | [c]: atp + coa + ecstea <==> amp + estcoa + ppi |
| DAGH_CHO | [c]: (0.001) 12dgr_CHO + h2o --> (0.025) arachda + (0.01) dcshea + (0.016) dcspea + | and | FACOAL205 | [c]: atp + coa + ecspea <==> amp + ecspecoa + ppi |

TABLE 20-continued

Selection System Designs - Double Deletion Results

| | | | | |
|---|---|---|---|---|
| | (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 | | | |
| DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 | and | FACOAL226 | [c]: atp + coa + dcshea <==> amp + cvncoa + ppi |
| DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 | and | FACOAL241 | [c]: atp + coa + nrvnc <==> amp + nrvnccoa + ppi |
| DESAT183 | [c]: h + nadph + o2 + ocdycacoa --> (2) h2o + lnlecoa + nadp | and | LNLNEtr | lnlne[e] <==> lnlne[c] |
| DESAT184 | [c]: h + lnlecoa + nadph + o2 --> (2) h2o + nadp + strdnccoa | and | DESAT204 | [c]: estcoa + h + nadph + o2 --> arachdcoa + (2) h2o + nadp |
| DESAT204 | [c]: estcoa + h + nadph + o2 --> arachdcoa + (2) h2o + nadp | and | FAEL204g | [c]: (5) h + malcoa + (4) nadph + o2 + strdnccoa --> arachdcoa + co2 + coa + (3) h2o + (4) nadp |
| DHCR72er | [r]: 7dhchsterol + h + nadph --> chsterol + nadp | and | C3STDH1yer | [r]: 4mzym_int1 + nadp --> 4mzym_int2 + co2 + nadph |
| DHCR72er | [r]: 7dhchsterol + h + nadph --> chsterol + nadp | and | CHSTNIer | [r]: zymst <==> cholsd |
| DHCR72er | [r]: 7dhchsterol + h + nadph --> chsterol + nadp | and | DHCR71er | [r]: ddsmsterol + h + nadph --> dsmsterol + nadp |
| DHCR72er | [r]: 7dhchsterol + h + nadph --> chsterol + nadp | and | LSTO1er | [r]: cholsd + h + nadph + o2 --> ddsmsterol + (2) h2o + nadp |
| DHCR72er | [r]: 7dhchsterol + h + nadph --> chsterol + nadp | and | STRR3er | [r]: dsmsterol + h + nadph --> chsterol + nadp |
| ECOAH1am | [m]: 3hbycoa <==> b2coa + h2o | and | ALATA_L | [c]: akg + ala-L <==> glu-L + pyr |
| ECOAH1am | [m]: 3hbycoa <==> b2coa + h2o | and | MTHFC | [c]: h2o + methf <==> 10fthf + h |
| ENO | [c]: 2pg <==> h2o + pep | and | ATP/ADPtm | adp[c] + atp[m] <==> adp[m] + atp[c] |
| ENO | [c]: 2pg <==> h2o + pep | and | GLCt1r | glc-D[e] <==> glc-D[c] |
| ETAPCTr | [c]: ctp + ethap + h <==> cdpea + ppi | and | PSERD_CHO | [c]: h + (0.001) ps_CHO --> co2 + (0.001) pe_CHO |
| ETHAMK | [c]: atp + etha --> adp + ethap + h | and | PSERD_CHO | [c]: h + (0.001) ps_CHO --> co2 + (0.001) pe_CHO |
| ETHAPT_CHO | [c]: (0.01) 12dgr_CHO + cdpea <==> cmp + h + (0.01) pe_CHO | and | PSERD_CHO | [c]: h + (0.001) ps_CHO --> co2 + (0.001) pe_CHO |
| ETHAt | etha[e] <==> etha[c] | and | PSERD_CHO | [c]: h + (0.001) ps_CHO --> co2 + (0.001) pe_CHO |

TABLE 20-continued

Selection System Designs - Double Deletion Results

| | | | | |
|---|---|---|---|---|
| FACOAL140 | [c]: atp + coa + ttdca <==> amp + ppi + tdcoa | and | CRNTDm | [m]: coa + tdcrn <==> crn + tdcoa |
| FACOAL140 | [c]: atp + coa + ttdca <==> amp + ppi + tdcoa | and | FAOXC160m | [m]: coa + fad + h2o + nad + pmtcoa --> accoa + fadh2 + h + nadh + tdcoa |
| FACOAL140 | [c]: atp + coa + ttdca <==> amp + ppi + tdcoa | and | SUCD3m-ubq10 | [m]: fadh2 + ubq10 <==> fad + q10h2 |
| FACOAL160 | [c]: atp + coa + hdca <==> amp + pmtcoa + ppi | and | CRNPT | [c]: crn + pmtcoa <==> coa + pmtcrn |
| FACOAL160 | [c]: atp + coa + hdca <==> amp + pmtcoa + ppi | and | CRNPTm | [m]: coa + pmtcrn <==> crn + pmtcoa |
| FACOAL160 | [c]: atp + coa + hdca <==> amp + pmtcoa + ppi | and | CSm | [m]: accoa + h2o + oaa --> cit + coa + h |
| FACOAL160 | [c]: atp + coa + hdca <==> amp + pmtcoa + ppi | and | FAOXC180m | [m]: coa + fad + h2o + nad + strcoa --> accoa + fadh2 + h + nadh + pmtcoa |
| FACOAL160 | [c]: atp + coa + hdca <==> amp + pmtcoa + ppi | and | SUCD3m-ubq10 | [m]: fadh2 + ubq10 <==> fad + q10h2 |
| FACOAL161 | [c]: atp + coa + hdcea <==> amp + hdcoa + ppi | and | ACGK_CHO | [c]: atp + (0.001) mglyc_CHO --> (0.001) 1ag3p_CHO + adp + h |
| FACOAL161 | [c]: atp + coa + hdcea <==> amp + hdcoa + ppi | and | DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 |
| FACOAL180 | [c]: atp + coa + ocdca <==> amp + ppi + strcoa | and | CRNOT | [c]: crn + strcoa <==> coa + strcrn |
| FACOAL180 | [c]: atp + coa + ocdca21 ==> amp + ppi + strcoa | and | CRNOTm | [m]: coa + strcrn <==> crn + strcoa |
| FACOAL180 | [c]: atp + coa + ocdca21 ==> amp + ppi + strcoa | and | CSm | [m]: accoa + h2o + oaa --> cit + coa + h |
| FACOAL180 | [c]: atp + coa + ocdca <==> amp + ppi + strcoa | and | FAOXC200m | [m]: coa + ecsacoa + fad + h2o + nad --> accoa + fadh2 + h + nadh + strcoa |
| FACOAL180 | [c]: atp + coa + ocdca <==> amp + ppi + strcoa | and | SUCD3m-ubq10 | [m]: fadh2 + ubq10 <==> fad + q10h2 |
| FACOAL181 | [c]: atp + coa + ocdcea <==> amp + odecoa + ppi | and | ACGK_CHO | [c]: atp + (0.001) mglyc_CHO --> (0.001) 1ag3p_CHO + adp + h |
| FACOAL183 | [c]: atp + coa + lnlne <==> amp + lnlecoa + ppi | and | DESAT183 | [c]: h + nadph + o2 + ocdycacoa --> (2) h2o + lnlecoa + nadp |
| FACOAL200 | [c]: atp + coa + ecsa <==> amp + ecsacoa + ppi | and | CRNET | [c]: crn + ecsacoa <==> coa + ecsacrn |
| FACOAL200 | [c]: atp + coa + ecsa <==> amp + ecsacoa + ppi | and | CRNETm | [m]: coa + ecsacrn <==> crn + ecsacoa |
| FACOAL200 | [c]: atp + coa + ecsa <==> amp + ecsacoa + ppi | and | CRNETtm | crn[m] + ecsacrn[c] <==> crn[c] + ecsacrn[m] |
| FACOAL200 | [c]: atp + coa + ecsa <==> amp + ecsacoa + ppi | and | CRNTC | [c]: crn + lgnccoa <==> coa + lgnccrn |

TABLE 20-continued

Selection System Designs - Double Deletion Results

| | | | | |
|---|---|---|---|---|
| FACOAL200 | [c]: atp + coa + ecsa <==> amp + ecsacoa + ppi | and | CRNTCm | [m]: crn + lgnccoa <==> coa + lgnccrn |
| FACOAL200 | [c]: atp + coa + ecsa <==> amp + ecsacoa + ppi | and | CRNTCtm | crn[m] + lgnccrn[c] <==> crn[c] + lgnccrn[m] |
| FACOAL200 | [c]: atp + coa + ecsa <==> amp + ecsacoa + ppi | and | FAOXC240m | [m]: (2) coa + (2) fad + (2) h2o + lgnccoa + (2) nad --> (2) accoa + ecsacoa + (2) fadh2 + (2) h + (2) nadh |
| FACOAL200 | [c]: atp + coa + ecsa <==> amp + ecsacoa + ppi | and | SUCD3m-ubq10 | [m]: fadh2 + ubq10 <==> fad + q10h2 |
| FACOAL204 | [c]: arachda + atp + coa <==> amp + arachdcoa + ppi | and | ACGK_CHO | [c]: atp + (0.001) mglyc_CHO --> (0.001) 1ag3p_CHO + adp + h |
| FACOAL204 | [c]: arachda + atp + coa <==> amp + arachdcoa + ppi | and | DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 |
| FACOAL225 | [c]: atp + coa + dcspea <==> amp + clpndcoa + ppi | and | ACGK_CHO | [c]: atp + (0.001) mglyc_CHO --> (0.001) 1ag3p_CHO + adp + h |
| FACOAL225 | [c]: atp + coa + dcspea <==> amp + clpndcoa + ppi | and | DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0 |
| FACOAL226 | [c]: atp + coa + dcshea <==> amp + cvncoa + ppi | and | ACGK_CHO | [c]: atp + (0.001) mglyc_CHO --> (0.001) 1ag3p_CHO + adp + h |
| FACOAL241 | [c]: atp + coa + nrvnc <==> amp + nrvnccoa + ppi | and | ACGK_CHO | [c]: atp + (0.001) mglyc_CHO --> (0.001) 1ag3p_CHO + adp + h |
| FBA | [c]: fdp <==> dhap + g3p | and | GLCt1r | glc-D[e] <==> glc-D[c] |
| FBP | [c]: fdp + h2o --> f6p + pi | and | GLCt1r | glc-D[e] <==> glc-D[c] |
| FKYNH | [c]: Lfmkynr + h2o --> for + h + kynr-L | and | ALATA_L | [c]: akg + ala-L <==> glu-L + pyr |
| FKYNH | [c]: Lfmkynr + h2o --> for + h + kynr-L | and | MTHFC | [c]: h2o + methf <==> 10fthf + h |
| FMETDH | [c]: 10fthf + h2o + nadp --> co2 + h + nadph + thf | and | CSm | [m]: accoa + h2o + oaa --> cit + coa + h |
| FMETDH | [c]: 10fthf + h2o + nadp --> co2 + h + nadph + thf | and | GLYATm | [m]: accoa + gly <==> 2aobut + coa |
| FMETDH | [c]: 10fthf + h2o + nadp --> co2 + h + nadph + thf | and | THRt2m | h[c] + thr-L[c] <==> h[m] + thr-L[m] |
| FUM | [c]: fum + h2o <==> mal-L | and | FUMm | [m]: fum + h2o <==> mal-L |
| FUM2tm | fum[c] + mal-L[m] <==> fum[m] + mal-L[c] | and | FUM | [c]: fum + h2o <==> mal-L |

TABLE 20-continued

Selection System Designs - Double Deletion Results

| | | | | |
|---|---|---|---|---|
| FUM2tm | fum[c] + mal-L[m] <==> fum[m] + mal-L[c] | and | FUMm | [m]: fum + h2o <==> mal-L |
| GLCt1r | glc-D[e] <==> glc-D[c] | and | GAPD | [c]: g3p + nad + pi <==> 13dpg + h + nadh |
| GLYATm | [m]: accoa + gly <==> 2aobut + coa | and | MTHFC | [c]: h2o + methf <==> 10fthf + h |
| GLYATm | [m]: accoa + gly <==> 2aobut + coa | and | MTHFD | [c]: mlthf + nadp <==> methf + nadph |
| GLYATm | [m]: accoa + gly <==> 2aobut + coa | and | PSERTr | [c]: 3php + glu-L <==> akg + pser-L |
| GLYATm | [m]: accoa + gly <==> 2aobut + coa | and | PSP_L | [c]: h2o + pser-L --> pi + ser-L |
| GLYtm | gly[c] <==> gly[m] | and | GHMT | [c]: ser-L + thf <==> gly + h2o + mlthf |
| H2O2tm | h2o2[c] <==> h2o2[m] | and | O2trm | o2[c] <==> o2[m] |
| H2O2tp | h2o2[c] <==> h2o2[x] | and | CATp | [x]: (2) h2o2 --> (2) h2o + o2 |
| H2O2tp | h2o2[c] <==> h2o2[x] | and | O2tp | o2[c] <==> o2[x] |
| H2O2tp | h2o2[c] <==> h2o2[x] | and | O2trm | o2[c] <==> o2[m] |
| H2Otp | h2o[c] <==> h2o[x] | and | CATp | [x]: (2) h2o2 --> (2) h2o + o2 |
| H2Otp | h2o[c] <==> h2o[x] | and | O2tp | o2[c] <==> o2[x] |
| H2Otp | h2o[c] <==> h2o[x] | and | O2trm | o2[c] <==> o2[m] |
| HACD1m | [m]: aacoa + h + nadh <==> 3hbycoa + nad | and | ALATA_L | [c]: akg + ala-L <==> glu-L + pyr |
| HACD1m | [m]: aacoa + h + nadh <==> 3hbycoa + nad | and | MTHFC | [c]: h2o + methf <==> 10fthf + h |
| ICDHy | [c]: icit + nadp <==> akg + co2 + nadph | and | CITMALtm | cit[c] + h[c] + mal-L[m] <==> cit[m] + h[m] + mal-L[c] |
| ICDHy | [c]: icit + nadp <==> akg + co2 + nadph | and | CSm | [m]: accoa + h2o + oaa --> cit + coa + h |
| INSTt2r | h[e] + inost[e] <==> h[c] + inost[c] | and | MI1PS | [c]: g6p --> mi1p-D |
| KYNASE3 | [c]: h2o + hkyn --> 3hanthrn + ala-L + h | and | ALATA_L | [c]: akg + ala-L <==> glu-L + pyr |
| KYNASE3 | [c]: h2o + hkyn --> 3hanthrn + ala-L + h | and | MTHFC | [c]: h2o + methf <==> 10fthf + h |
| KYNMOr | [c]: h + kynr-L + nadph + o2 <==> h2o + hkyn + nadp | and | ALATA_L | [c]: akg + ala-L <==> glu-L + pyr |
| KYNMOr | [c]: h + kynr-L + nadph + o2 <==> h2o + hkyn + nadp | and | MTHFC | [c]: h2o + methf <==> 10fthf + h |
| LATHSTOxer | [r]: h + lathost + nadh + o2 --> 7dhchsterol + (2) h2o + nad | and | C3STDH1yer | [r]: 4mzym_int1 + nadp --> 4mzym_int2 + co2 + nadph |
| METFR | [c]: 5mthf + nadp <==> (2) h + mlthf + nadph | and | O2trm | o2[c] <==> o2[m] |
| METS | [c]: 5mthf + hcys-L --> h + met-L + thf | and | O2trm | o2[c] <==> o2[m] |
| MI1PP | [c]: h2o + mi1p-D --> inost + pi | and | INSTt2r | h[e] + inost[e] <==> h[c] + inost[c] |
| MTHFC | [c]: h2o + methf <==> 10fthf + h | and | 2OXOADPTm | 2oxoadp[c] + akg[m] <==> 2oxoadp[m] + akg[c] |
| MTHFC | [c]: h2o + methf <==> 10fthf + h | and | AMCOXO | [c]: 2amuc + h + h2o + nadph --> 2oxoadp + nadp + nh4 |
| MTHFC | [c]: h2o + methf <==> 10fthf + h | and | GCOADrm | [m]: fad + glutcoa + h <==> b2coa + co2 + fadh2 |
| MTHFC | [c]: h2o + methf <==> 10fthf + h | and | HANTHDOr | [c]: 3hanthrn + o2 <==> acmucsal |
| MTHFC | [c]: h2o + methf <==> 10fthf + h | and | SUCD3m-ubq10 | [m]: fadh2 + ubq10 <==> fad + q10h2 |
| O2tp | o2[c] <==> o2[x] | and | O2trm | o2[c] <==> o2[m] |
| P5CRx | [c]: 1pyr5c + (2) h + nadh --> nad + pro-L | and | P5CRy | [c]: 1pyr5c + (2) h + nadph --> nadp + pro-L |
| PFK | [c]: atp + f6p --> adp + fdp + h | and | TPI | [c]: dhap <==> g3p |
| PGCDr | [c]: 3pg + nad <==> 3php + h + nadh | and | CSm | [m]: accoa + h2o + oaa --> cit + coa + h |
| PGCDr | [c]: 3pg + nad <==> 3php + h + nadh | and | GLYATm | [m]: accoa + gly <==> 2aobut + coa |

TABLE 20-continued

Selection System Designs - Double Deletion Results

| | | | | |
|---|---|---|---|---|
| PGCDr | [c]: 3pg + nad <==> 3php + h + nadh | and | THRt2m | h[c] + thr-L[c] <==> h[m] + thr-L[m] |
| PGI | [c]: g6p <==> f6p | and | GLCt1r | glc-D[e] <==> glc-D[c] |
| PGK | [c]: 13dpg + adp <==> 3pg + atp | and | ATP/ADPtm | adp[c] + atp[m] <==> adp[m] + atp[c] |
| PGK | [c]: 13dpg + adp <==> 3pg + atp | and | GLCt1r | glc-D[e] <==> glc-D[c] |
| PGM | [c]: 3pg <==> 2pg | and | GLCt1r | glc-D[e] <==> glc-D[c] |
| PPCKG | [c]: gtp + oaa --> co2 + gdp + pep | and | GLCt1r | glc-D[e] <==> glc-D[c] |
| PSERTr | [c]: 3php + glu-L <==> akg + pser-L | and | CSm | [m]: accoa + h2o + oaa --> cit + coa + h |
| THRDm | [m]: nad + thr-L --> 2aobut + h + nadh | and | FMETDH | [c]: 10fthf + h2o + nadp --> co2 + h + nadph + thf |
| THRDm | [m]: nad + thr-L --> 2aobut + h + nadh | and | MTHFC | [c]: h2o + methf <==> 10fthf + h |
| THRDm | [m]: nad + thr-L --> 2aobut + h + nadh | and | MTHFD | [c]: mlthf + nadp <==> methf + nadph |
| THRDm | [m]: nad + thr-L --> 2aobut + h + nadh | and | PGCDr | [c]: 3pg + nad <==> 3php + h + nadh |
| THRDm | [m]: nad + thr-L --> 2aobut + h + nadh | and | PSERTr | [c]: 3php + glu-L <==> akg + pser-L |
| THRDm | [m]: nad + thr-L --> 2aobut + h + nadh | and | PSP_L | [c]: h2o + pser-L --> pi + ser-L |
| THRt2m | h[c] + thr-L[c] <==> h[m] + thr-L[m] | and | MTHFC | [c]: h2o + methf <==> 10fthf + h |
| THRt2m | h[c] + thr-L[c] <==> h[m] + thr-L[m] | and | MTHFD | [c]: mlthf + nadp <==> methf + nadph |
| THRt2m | h[c] + thr-L[c] <==> h[m] + thr-L[m] | and | PSERTr | [c]: 3php + glu-L <==> akg + pser-L |
| THRt2m | h[c] + thr-L[c] <==> h[m] + thr-L[m] | and | PSP_L | [c]: h2o + pser-L --> pi + ser-L |
| TPI | [c]: dhap <==> g3p | and | FBA | [c]: fdp <==> dhap + g3p |
| TPI | [c]: dhap <==> g3p | and | GLCt1r | glc-D[e] <==> glc-D[c] |
| TRPO2 | [c]: o2 + trp-L --> Lfmkynr | and | ALATA_L | [c]: akg + ala-L <==> glu-L + pyr |
| TRPO2 | [c]: o2 + trp-L --> Lfmkynr | and | MTHFC | [c]: h2o + methf <==> 10fthf + h |
| MTHFC | [c]: h2o + methf <==> 10fthf + h | and | CSm | [m]: accoa + h2o + oaa --> cit + coa + h |
| CSm | [m]: accoa + h2o + oaa --> cit + coa + h | and | GLUFT | [c]: 5fthf + glu-L <==> forglu + thf |
| FORTHFC | [c]: 5fthf + (2) h <==> methf + nh4 | and | CSm | [m]: accoa + h2o + oaa --> cit + coa + h |
| HISD1r | [c]: his-L <==> nh4 + urcan | and | CSm | [m]: accoa + h2o + oaa --> cit + coa + h |
| IZPN | [c]: 4izp + h2o --> forglu | and | CSm | [m]: accoa + h2o + oaa --> cit + coa + h |
| URCN | [c]: h2o + urcan --> 4izp | and | CSm | [m]: accoa + h2o + oaa --> cit + coa + h |
| PGI | [c]: g6p <==> f6p | and | FBA | [c]: fdp <==> dhap + g3p |
| PGK | [c]: 13dpg + adp <==> 3pg + atp | and | TPI | [c]: dhap <==> g3p |
| TPI | [c]: dhap <==> g3p | and | GAPD | [c]: g3p + nad + pi <==> 13dpg + h + nadh |
| TPI | [c]: dhap <==> g3p | and | PGI | [c]: g6p <==> f6p |
| PFK | [c]: atp + f6p --> adp + fdp + h | and | PGI | [c]: g6p <==> f6p |
| PGI | [c]: g6p <==> f6p | and | GAPD | [c]: g3p + nad + pi <==> 13dpg + h + nadh |
| PGK | [c]: 13dpg + adp <==> 3pg + atp | and | PGI | [c]: g6p <==> f6p |
| FBP | [c]: fdp + h2o --> f6p + pi | and | GAPD | [c]: g3p + nad + pi <==> 13dpg + h + nadh |
| PGK | [c]: 13dpg + adp <==> 3pg + atp | and | FBP | [c]: fdp + h2o --> f6p + pi |
| ACACT1rm | [m]: (2) accoa <==> aacoa + coa | and | MTHFC | [c]: h2o + methf <==> 10fthf + h |
| FACOAL200 | [c]: atp + coa + ecsa <==> amp + ecsacoa + ppi | and | CSm | [m]: accoa + h2o + oaa --> cit + coa + h |

TABLE 20-continued

Selection System Designs - Double Deletion Results

| | | | | |
|---|---|---|---|---|
| FBA | [c]: fdp <==> dhap + g3p | and | GAPD | [c]: g3p + nad + pi <==> 13dpg + h + nadh |
| PGK | [c]: 13dpg + adp <==> 3pg + atp | and | FBA | [c]: fdp <==> dhap + g3p |

TABLE 21

Reactions and Metabolites in Hybridoma Model

| Abbreviation | Equation | EC Number |
|---|---|---|
| ARGN | [c]: arg-L + h2o --> orn-L + urea | 3.5.3.1 |
| ORNTAm | [m]: akg + orn-L <==> glu-L + glu5sa | 2.6.1.13 |
| ASNN | [c]: asn-L + h2o --> asp-L + nh4 | 3.5.1.1 |
| ASNS1 | [c]: asp-L + atp + gln-L + h2o --> amp + asn-L + glu-L + h + ppi | 6.3.5.4 |
| GLYGS | [c]: udpg --> glycogen + h + udp | 2.4.1.11 |
| PGMT | [c]: glp <==> g6p | 5.4.2.2 |
| ACONTm | [m]: cit <==> icit | 4.2.1.3 |
| AKGDm | [m]: akg + coa + nad --> co2 + nadh + succoa | |
| CITL2 | [c]: atp + cit + coa --> accoa + adp + oaa + pi | 4.1.3.8 |
| CSm | [m]: accoa + h2o + oaa --> cit + coa + h | 4.1.3.7 |
| FUMm | [m]: fum + h2o <==> mal-L | 4.2.1.2 |
| ICDHxm | [m]: icit + nad --> akg + co2 + nadh | 1.1.1.41 |
| ICDHym | [m]: icit + nadp --> akg + co2 + nadph | 1.1.1.42 |
| MDH | [c]: mal-L + nad <==> h + nadh + oaa | 1.1.1.37 |
| MDHm | [m]: mal-L + nad <==> h + nadh + oaa | 1.1.1.37 |
| PCm | [m]: atp + hco3 + pyr --> adp + h + oaa + pi | 6.4.1.1 |
| PDHm | [m]: coa + nad + pyr --> accoa + co2 + nadh | 1.2.1.51 |
| SUCD1m | [m]: succ + ubq <==> fum + qh2 | 1.3.5.1 |
| SUCOASAm | [m]: atp + coa + succ <==> adp + pi + succoa | 6.2.1.5 |
| CYSTGL | [c]: cysth-L + h2o --> 2obut + cys-L + nh4 | 4.4.1.1 |
| CYSTS | [c]: hcys-L + ser-L --> cysth-L + h2o | 4.2.1.22 |
| ATPS4m | adp[m] + (4) h[c] + pi[m] --> atp[m] + (3) h[m] + h2o[m] | 3.6.3.14 |
| CYOO4m | (4) focytcc[m] + (8) h[m] + o2[m] --> (4) ficytcc[m] + (4) h[c] + (2) h2o[m] | 1.9.3.1 |
| CYOR4m | (2) ficytcc[m] + (2) h[m] + qh2[m] --> (2) focytcc[m] + (4) h[c] + ubq[m] | 1.10.2.2 |
| NADH4m | (5) h[m] + nadh[m] + ubq[m] --> (4) h[c] + nad[m] + qh2[m] | 1.6.99.3 |
| ACS | [c]: ac + atp + coa --> accoa + amp + ppi | 6.2.1.1 |
| ACCOAC | [c]: accoa + atp + hco3 --> adp + h + malcoa + pi | 6.4.1.2 |
| FAS100 | [c]: (3) h + malcoa + (2) nadph + octa --> co2 + coa + dca + h2o + (2) nadp | 2.3.1.85 |
| FAS120 | [c]: dca + (3) h + malcoa + (2) nadph --> co2 + coa + ddca + h2o + (2) nadp | 2.3.1.85 |
| FAS140 | [c]: ddca + (3) h + malcoa + (2) nadph --> co2 + coa + h2o + (2) nadp + ttdca | 2.3.1.85 |
| FAS160 | [c]: (3) h + malcoa + (2) nadph + ttdca --> co2 + coa + h2o + hdca + (2) nadp | 2.3.1.85 |
| FAS80_L | [c]: accoa + (8) h + (3) malcoa + (6) nadph --> (3) co2 + (4) coa + (2) h2o + (6) nadp + octa | 2.3.1.85 |
| DHFRi | [c]: dhf + h + nadph --> nadp + thf | 1.5.1.3 |
| FldAct | [c]: fald + thf --> h2o + mlthf | |
| GHMT | [c]: ser-L + thf <==> gly + h2o + mlthf | 2.1.2.1 |
| MTHFC | [c]: h2o + methf <==> 10fthf + h | 3.5.4.9 |
| MTHFD | [c]: mlthf + nadp <==> methf + nadph | 1.5.1.5 |
| ASPTA1 | [c]: akg + asp-L <==> glu-L + oaa | 2.6.1.1 |
| ASPTA1m | [m]: akg + asp-L <==> glu-L + oaa | 2.6.1.1 |
| GLUDxm | [m]: glu-L + h2o + nad <==> akg + h + nadh + nh4 | 1.4.1.3 |
| ALATA_L | [c]: akg + ala-L <==> glu-L + pyr | 2.6.1.2 |
| GLNS | [c]: atp + glu-L + nh4 --> adp + gln-L + h + pi | 6.3.1.2 |
| GLUDym | [m]: glu-L + h2o + nadp <==> akg + h + nadph + nh4 | 1.4.1.3 |
| GLUNm | [m]: gln-L + h2o --> glu-L + nh4 | 3.5.1.2 |
| GHMT2m | [m]: ser-L + thf <==> gly + h2o + mlthf | 2.1.2.1 |
| GLYCLm | [m]: gly + nad + thf --> co2 + mlthf + nadh + nh4 | 2.1.2.10 |
| GMTR | [c]: amet + gly --> ahcys + h + sarcs | 2.1.1.20 |
| PGCDr | [c]: 3pg + nad <==> 3php + h + nadh | 1.1.1.95 |
| PSERTr | [c]: 3php + glu-L <==> akg + pser-L | 2.6.1.52 |
| PSP_L | [c]: h2o + pser-L --> pi + ser-L | 3.1.3.3 |
| SARCO | [c]: h2o + o2 + sarcs --> fald + gly + h2o2 | 1.5.3.1 |
| SERD_L | [c]: ser-L --> nh4 + pyr | 4.3.1.17 |

TABLE 21-continued

Reactions and Metabolites in Hybridoma Model

| | | |
|---|---|---|
| GALU | [c]: g1p + h + utp <==> ppi + udpg | 2.7.7.9 |
| ENO | [c]: 2pg <==> h2o + pep | 4.2.1.11 |
| FBA | [c]: fdp <==> dhap + g3p | 4.1.2.13 |
| FBP | [c]: fdp + h2o --> f6p + pi | 3.1.3.11 |
| GAPD | [c]: g3p + nad + pi <==> 13dpg + h + nadh | 1.2.1.12 |
| HEX1 | [c]: atp + glc-D --> adp + g6p + h | 2.7.1.2 |
| PFK | [c]: atp + f6p --> adp + fdp + h | 2.7.1.11 |
| PGI | [c]: g6p <==> f6p | 5.3.1.9 |
| PGK | [c]: 13dpg + adp <==> 3pg + atp | 2.7.2.3 |
| PGM | [c]: 3pg <==> 2pg | 5.4.2.1 |
| PYK | [c]: adp + h + pep --> atp + pyr | 2.7.1.40 |
| TPI | [c]: dhap <==> g3p | 5.3.1.1 |
| FTHFLr | [c]: atp + for + thf <==> 10fthf + adp + pi | 6.3.4.3 |
| G3PD | [c]: dhap + h + nadh --> glyc3p + nad | 1.1.1.8 |
| G3PDm | [m]: fad + glyc3p --> dhap + fadh2 | 1.1.99.5 |
| AHC | [c]: ahcys + h2o <==> adn + hcys-L | 3.3.1.1 |
| METAT | [c]: atp + h2o + met-L --> amet + pi + ppi | 2.5.1.6 |
| ADK1 | [c]: amp + atp <==> (2) adp | 2.7.4.3 |
| ADK1m | [m]: amp + atp <==> (2) adp | 2.7.4.3 |
| ADNK1 | [c]: adn + atp --> adp + amp + h | 2.7.1.20 |
| ADSL1 | [c]: dcamp --> amp + fum | 4.3.2.2 |
| ADSL2r | [c]: 25aics <==> aicar + fum | 4.3.2.2 |
| ADSS | [c]: asp-L + gtp + imp --> dcamp + gdp + (2) h + pi | 6.3.4.4 |
| AICART | [c]: 10fthf + aicar <==> fprica + thf | 2.1.2.3 |
| AIRC | [c]: air + co2 --> 5aizc + h | 4.1.1.21 |
| ASPCT | [c]: asp-L + cbp --> cbasp + h + pi | 2.1.3.2 |
| CBPS | [c]: (2) atp + gln-L + h2o + hco3 --> (2) adp + cbp + glu-L + (2) h + pi | 6.3.5.5 |
| CTPS2 | [c]: atp + gln-L + h2o + utp --> adp + ctp + glu-L + (2) h + pi | 6.3.4.2 |
| CYTK1 | [c]: atp + cmp <==> adp + cdp | 2.7.4.14 |
| DHORD3m | dhor-S[c] + ubq[m] <==> orot[c] + qh2[m] | |
| DHORTS | [c]: dhor-S + h2o <==> cbasp + h | 3.5.2.3 |
| DTMPK | [c]: atp + dtmp <==> adp + dtdp | 2.7.4.9 |
| GARFTi | [c]: 10fthf + gar --> fgam + h + thf | 2.1.2.2 |
| GK1 | [c]: atp + gmp <==> adp + gdp | 2.7.4.8 |
| GLUPRT | [c]: gln-L + h2o + prpp --> glu-L + ppi + pram | 2.4.2.14 |
| GMPS2 | [c]: atp + gln-L + h2o + xmp --> amp + glu-L + gmp + (2) h + ppi | 6.3.5.2 |
| IMPC | [c]: h2o + imp <==> fprica | 3.5.4.10 |
| IMPD | [c]: h2o + imp + nad --> h + nadh + xmp | 1.1.1.205 |
| NDPK1 | [c]: atp + gdp <==> adp + gtp | 2.7.4.6 |
| NDPK2 | [c]: atp + udp <==> adp + utp | 2.7.4.6 |
| NDPK3 | [c]: atp + cdp <==> adp + ctp | 2.7.4.6 |
| NDPK4 | [c]: atp + dtdp <==> adp + dttp | 2.7.4.6 |
| NDPK5 | [c]: atp + dgdp <==> adp + dgtp | 2.7.4.6 |
| NDPK7 | [c]: atp + dcdp <==> adp + dctp | 2.7.4.6 |
| NDPK8 | [c]: atp + dadp <==> adp + datp | 2.7.4.6 |
| OMPDC | [c]: h + orot5p --> co2 + ump | 4.1.1.23 |
| ORPT | [c]: orot5p + ppi <==> orot + prpp | 2.4.2.10 |
| PRAGS | [c]: atp + gly + pram --> adp + gar + h + pi | 6.3.4.13 |
| PRAIS | [c]: atp + fpram --> adp + air + h + pi | 6.3.3.1 |
| PRASCS | [c]: 5aizc + asp-L + atp <==> 25aics + adp + h + pi | 6.3.2.6 |
| PRFGS | [c]: atp + fgam + gln-L + h2o --> adp + fpram + glu-L + (2) h + pi | 6.3.5.3 |
| PRPPS | [c]: atp + r5p <==> amp + h + prpp | 2.7.6.1 |
| RNDR1 | [c]: adp + trdrd --> dadp + h2o + trdox | 1.17.4.1 |
| RNDR2 | [c]: gdp + trdrd --> dgdp + h2o + trdox | 1.17.4.1 |
| RNDR3 | [c]: cdp + trdrd --> dcdp + h2o + trdox | 1.17.4.1 |
| RNDR4 | [c]: trdrd + udp --> dudp + h2o + trdox | 1.17.4.1 |
| TMDS | [c]: dump + mlthf --> dhf + dtmp | 2.1.1.45 |
| UMPK | [c]: atp + ump <==> adp + udp | 2.7.4.14 |
| URIDK3 | [c]: atp + dump <==> adp + dudp | 2.7.4.9 |
| URIK1 | [c]: atp + uri --> adp + h + ump | 2.7.1.48 |
| AAS_Hyb_bs | [c]: (9) ala-L + (4.7) arg-L + (4.4) asn-L + (5.5) asp-L + (2.8) cys-L + (3.9) gln-L + (4.6) glu-L + (7.5) gly + (2.1) his-L + (4.6) ile-L + (7.5) leu-L + (7) lys-L + (1.7) met-L + (3.5) phe-L + (4.6) pro-L + (7.1) ser-L + (6) thr-L + (1.1) trp-L + (3.5) tyr-L + (6.9) val-L --> aa_hyb | |
| ATPM | [c]: atp + h2o --> adp + h + pi | 3.6.1.15 |
| ATPS | atp[c] + h2o[c] --> adp[c] + h[e] + pi[c] | 3.6.3.6 |
| Biomass_Hyb | [c]: (6.9) dna_hyb + (117.3) glycogen + (61.8) plipid_hyb + (1584) protein_hyb + (29.2) rna_hyb --> biomass_hyb | |
| CAT | [c]: (2) h2o2 --> (2) h2o + o2 | 1.11.1.6 |
| DNAS_Hyb_bs | [c]: (2) atp + datp + dctp + dgtp + dttp + (2) h2o --> (2) adp + dna_hyb + (2) h + (2) pi | 2.7.7.7 |

TABLE 21-continued

Reactions and Metabolites in Hybridoma Model

| | | |
|---|---|---|
| HCO3E | [c]: co2 + h2o <==> h + hco3 | 4.2.1.1 |
| HCO3Em | [m]: co2 + h2o <==> h + hco3 | 4.2.1.1 |
| MAbS_Hyb_bs | [c]: aa_hyb + (0.049) atp + (0.02) g6p + (0.049) h2o --> (0.049) adp + (0.049) h + mab_hyb + (0.049) pi | |
| PLIPIDS_Hyb_bs | [c]: (6) atp + dhap + (6) h2o + hdca + nadh + ser-L --> (6) adp + (5) h + nad + (6) pi + plipid_hyb | |
| PPA | [c]: h2o + ppi --> h + (2) pi | 3.6.1.1 |
| PPAm | [m]: h2o + ppi --> h + (2) pi | 3.6.1.1 |
| PROTS_Hyb_bs | [c]: aa_hyb + (4.1) atp + (4.1) h2o --> (4.1) adp + (4.1) h + (4.1) pi + protein_hyb | |
| RNAS_Hyb_bs | [c]: (3) atp + ctp + gtp + (2) h2o + utp --> (2) adp + (2) h + (2) pi + rna_hyb | 2.7.7.6 |
| TRDR | [c]: h + nadph + trdox --> nadp + trdrd | 1.8.1.9 |
| SUCD3m | [m]: fadh2 + ubq <==> fad + qh2 | |
| G6PDH | [c]: g6p + nadp --> 6pgl + h + nadph | 1.1.1.49 |
| PGDH | [c]: 6pgc + nadp --> co2 + nadph + ru5p-D | 1.1.1.44 |
| PGL | [c]: 6pgl + h2o --> 6pgc + h | 3.1.1.31 |
| RPE | [c]: ru5p-D <==> xu5p-D | 5.1.3.1 |
| RPI | [c]: r5p <==> ru5p-D | 5.3.1.6 |
| TAL | [c]: g3p + s7p <==> e4p + f6p | 2.2.1.2 |
| TKT1 | [c]: r5p + xu5p-D <==> g3p + s7p | 2.2.1.1 |
| TKT2 | [c]: e4p + xu5p-D <==> f6p + g3p | 2.2.1.1 |
| G5SDm | [m]: glu5p + h + nadph --> glu5sa + nadp + pi | 1.2.1.41 |
| P5CRx | [c]: 1pyr5c + (2) h + nadh --> nad + pro-L | 1.5.1.2 |
| P5CRy | [c]: 1pyr5c + (2) h + nadph --> nadp + pro-L | 1.5.1.2 |
| G5SADs | [c]: glu5sa <==> 1pyr5c + h + h2o | |
| G5SADsm | [m]: glu5sa <==> 1pyr5c + h + h2o | |
| G5SD | [c]: glu5p + h + nadph --> glu5sa + nadp + pi | 1.2.1.41 |
| GLU5K | [c]: atp + glu-L --> adp + glu5p | 2.7.2.11 |
| GLU5Km | [m]: atp + glu-L --> adp + glu5p | 2.7.2.11 |
| P5CDm | [m]: 1pyr5c + (2) h2o + nad --> glu-L + h + nadh | 1.5.1.12 |
| PRO1xm | [m]: nad + pro-L --> 1pyr5c + (2) h + nadh | 1.5.1.2 |
| AKBDHm | [m]: 2obut + coa + nad --> co2 + nadh + ppcoa | |
| PPCOACm | [m]: atp + hco3 + ppcoa --> adp + h + mmcoa-S + pi | 6.4.1.3 |
| LDH_L | [c]: lac-L + nad <==> h + nadh + pyr | 1.1.1.27 |
| ME2 | [c]: mal-L + nadp --> co2 + nadph + pyr | 1.1.1.40 |
| ME2m | [m]: mal-L + nadp --> co2 + nadph + pyr | 1.1.1.40 |
| PPCKG | [c]: gtp + oaa --> co2 + gdp + pep | 4.1.1.32 |
| H2Ot5 | h2o[e] <==> h2o[c] | |
| ALA_Lt6 | ala-L[e] + h[e] <==> ala-L[c] + h[c] | |
| ARGt | arg-L[e] + h[e] <==> arg-L[c] + h[c] | |
| ASNt6 | asn-L[e] + h[e] <==> asn-L[c] + h[c] | |
| ASPt6 | asp-L[e] + h[e] <==> asp-L[c] + h[c] | |
| CO2t | co2[e] <==> co2[c] | |
| CYSt6 | cys-L[e] + h[e] <==> cys-L[c] + h[c] | |
| GLCt1 | glc-D[e] --> glc-D[c] | |
| GLNt | gln-L[e] + h[e] <==> gln-L[c] + h[c] | |
| GLUt6 | glu-L[e] + h[e] <==> glu-L[c] + h[c] | |
| GLYt6 | gly[e] + h[e] <==> gly[c] + h[c] | |
| HISt2 | h[e] + his-L[e] --> h[c] + his-L[c] | |
| ILEt2 | h[e] + ile-L[e] --> h[c] + ile-L[c] | |
| L-LACt2 | h[e] + lac-L[e] <==> h[c] + lac-L[c] | |
| LEUt6 | h[e] + leu-L[e] <==> h[c] + leu-L[c] | |
| LYSt2 | h[e] + lys-L[e] --> h[c] + lys-L[c] | |
| METt6 | h[e] + met-L[e] <==> h[c] + met-L[c] | |
| NH4t | nh4[e] <==> nh4[c] | |
| O2t | o2[e] <==> o2[c] | |
| PHEt2 | h[e] + phe-L[e] --> h[c] + phe-L[c] | |
| PIt6 | h[e] + pi[e] <==> h[c] + pi[c] | |
| PROt6 | h[e] + pro-L[e] <==> h[c] + pro-L[c] | |
| SERt6 | h[e] + ser-L[e] <==> h[c] + ser-L[c] | |
| THRt6 | h[e] + thr-L[e] <==> h[c] + thr-L[c] | |
| TRPt2 | h[e] + trp-L[e] --> h[c] + trp-L[c] | |
| TYRt6 | h[e] + tyr-L[e] <==> h[c] + tyr-L[c] | |
| UREAt | urea[e] <==> urea[c] | |
| VALt6 | h[e] + val-L[e] <==> h[c] + val-L[c] | |
| 34HPPt2m | 34hpp[c] + h[c] <==> 34hpp[m] + h[m] | |
| AKBtm | 2obut[m] <==> 2obut[c] | |
| ATP/ADPtm | adp[c] + atp[m] <==> adp[m] + atp[c] | |
| CITtam | cit[c] + mal-L[m] <==> cit[m] + mal-L[c] | |
| CO2tm | co2[c] <==> co2[m] | |
| DHAPtm | dhap[m] --> dhap[c] | |
| GACm | asp-L[m] + glu-L[c] + h[c] --> asp-L[c] + glu-L[m] + h[m] | |

TABLE 21-continued

Reactions and Metabolites in Hybridoma Model

| | | |
|---|---|---|
| GL3Ptm | glyc3p[c] --> glyc3p[m] | |
| GLUt2m | glu-L[c] + h[c] <==> glu-L[m] + h[m] | |
| GLYt2m | gly[c] + h[c] <==> gly[m] + h[m] | |
| H2Otm | h2o[c] <==> h2o[m] | |
| MALAKGtm | akg[m] + mal-L[c] --> akg[c] + mal-L[m] | |
| MALtm | mal-L[c] + pi[m] <==> mal-L[m] + pi[c] | |
| MLTHFtm | mlthf[c] <==> mlthf[m] | |
| NH4tm | nh4[c] <==> nh4[m] | |
| O2tm | o2[c] <==> o2[m] | |
| OAtm | h[c] + oaa[c] <==> h[m] + oaa[m] | |
| ORNtm | h[m] + orn-L[c] --> h[c] + orn-L[m] | |
| PItm | h[c] + pi[c] <==> h[m] + pi[m] | |
| PROtm | pro-L[c] <==> pro-L[m] | |
| PYRtm | h[c] + pyr[c] <==> h[m] + pyr[m] | |
| SERt2m | h[c] + ser-L[c] <==> h[m] + ser-L[m] | |
| THFtm | thf[c] <==> thf[m] | |
| TYRt6m | h[c] + tyr-L[c] <==> h[m] + tyr-L[m] | |
| VALt6m | h[c] + val-L[c] <==> h[m] + val-L[m] | |
| ASPTA5m | [m]: akg + tyr-L <==> 34hpp + glu-L | 2.6.1.1 |
| DHPR | [c]: dhbpt + h + nadph <==> nadp + thbpt | 1.5.1.34 |
| FUMACA | [c]: 4fumacac + h2o --> acac + fum + h | 3.7.1.2 |
| HGENDO | [c]: hgentis + o2 --> 4mlacac + h | 1.13.11.5 |
| HPPDO1 | [c]: 34hpp + o2 --> co2 + hgentis | 1.13.11.27 |
| MLACI | [c]: 4mlacac --> 4fumacac | 5.2.1.2 |
| PHE4MO | [c]: o2 + phe-L + thbpt --> dhbpt + h2o + tyr-L | 1.14.16.1 |
| TYRTA | [c]: akg + tyr-L <==> 34hpp + glu-L | 2.6.1.5 |
| ARGSL | [c]: argsuc <==> arg-L + fum | 4.3.2.1 |
| ARGSS | [c]: asp-L + atp + citr-L --> amp + argsuc + h + ppi | 6.3.4.5 |
| CBPSAm | [m]: (2) atp + co2 + h2o + nh4 --> (2) adp + cbp + (3) h + pi | 6.3.4.16 |
| FUM | [c]: fum + h2o <==> mal-L | 4.2.1.2 |
| OCBTm | [m]: cbp + orn-L <==> citr-L + h + pi | 2.1.3.3 |
| ORNCITRtm | citr-L[m] + h[m] + orn-L[c] <==> citr-L[c] + h[c] + orn-L[m] | |
| ORNTA | [c]: akg + orn-L --> glu-L + glu5sa | 2.6.1.13 |
| ACOAD2m | [m]: fad + ibcoa <==> 2mp2coa + fadh2 | 1.3.99.3 |
| ALDD4xm | [m]: h2o + mmalsa-S + nad --> (2) h + mmal + nadh | 1.2.1.3 |
| ECOAH2m | [m]: 2mp2coa + h + h2o <==> hibcoa | 4.2.1.17 |
| HACOADm | [m]: 3hmp + nad --> h + mmalsa-S + nadh | 1.1.1.31 |
| HMGLm | [m]: hmgcoa --> acac + accoa | 4.1.3.4 |
| LEUTAm | [m]: akg + leu-L <==> 4mop + glu-L | 2.6.1.42 |
| MCCCm | [m]: 3mb2coa + atp + hco3 --> 3mgcoa + adp + h + pi | 6.4.1.4 |
| MGCHm | [m]: 3mgcoa + h2o <==> hmgcoa | 4.2.1.18 |
| MMCOAHm | [m]: coa + h + mmal --> h2o + mmcoa-S | 3.1.2.17 |
| MMEm | [m]: mmcoa-S <==> mmcoa-R | 5.1.99.1 |
| MMMm | [m]: mmcoa-R --> succoa | 5.4.99.2 |
| MOBD1m | [m]: 4mop + coa + nad --> co2 + ivcoa + nadh | |
| MOBD2m | [m]: 3mob + coa + nad --> co2 + ibcoa + nadh | |
| VALTAm | [m]: akg + val-L <==> 3mob + glu-L | 2.6.1.42 |
| EX_ala-L(e) | [e]: ala-L <==> | |
| EX_arg-L(e) | [e]: arg-L <==> | |
| EX_asn-L(e) | [e]: asn-L <==> | |
| EX_asp-L(e) | [e]: asp-L <==> | |
| EX_co2(e) | [e]: co2 <==> | |
| EX_cys-L(e) | [e]: cys-L <==> | |
| EX_glc(e) | [e]: glc-D <==> | |
| EX_gln-L(e) | [e]: gln-L <==> | |
| EX_glu-L(e) | [e]: glu-L <==> | |
| EX_gly(e) | [e]: gly <==> | |
| EX_h(e) | [e]: h <==> | |
| EX_h2o(e) | [e]: h2o <==> | |
| EX_his-L(e) | [e]: his-L <==> | |
| EX_ile-L(e) | [e]: ile-L <==> | |
| EX_lac-L(e) | [e]: lac-L <==> | |
| EX_leu-L(e) | [e]: leu-L <==> | |
| EX_lys-L(e) | [e]: lys-L <==> | |
| EX_met-L(e) | [e]: met-L <==> | |
| EX_nh4(e) | [e]: nh4 <==> | |
| EX_o2(e) | [e]: o2 <==> | |
| EX_phe-L(e) | [e]: phe-L <==> | |
| EX_pi(e) | [e]: pi <==> | |
| EX_pro-L(e) | [e]: pro-L <==> | |
| EX_ser-L(e) | [e]: ser-L <==> | |
| EX_thr-L(e) | [e]: thr-L <==> | |

TABLE 21-continued

Reactions and Metabolites in Hybridoma Model

| | |
|---|---|
| EX_trp-L(e) | [e]: trp-L <==> |
| EX_tyr-L(e) | [e]: tyr-L <==> |
| EX_urea(e) | [e]: urea <==> |
| EX_val-L(e) | [e]: val-L <==> |

| Metab Abbreviation | Name | Compartment |
|---|---|---|
| 10fthf | 10-Formyltetrahydrofolate | Cytosol |
| 13dpg | 3-Phospho-D-glyceroyl phosphate | Cytosol |
| 1pyr5c | 1-Pyrroline-5-carboxylate | Cytosol |
| 1pyr5c | 1-Pyrroline-5-carboxylate | Mitochondria |
| 25aics | (S)-2-[5-Amino-1-(5-phospho-D-ribosyl)imidazole-4-carboxamido]succinate | Cytosol |
| 2mp2coa | 2-Methylprop-2-enoyl-CoA | Mitochondria |
| 2obut | 2-Oxobutanoate | Cytosol |
| 2obut | 2-Oxobutanoate | Mitochondria |
| 2pg | D-Glycerate 2-phosphate | Cytosol |
| 34hpp | 3-(4-Hydroxyphenyl)pyruvate | Cytosol |
| 34hpp | 3-(4-Hydroxyphenyl)pyruvate | Mitochondria |
| 3hmp | (S)-3-hydroxyisobutyrate | Mitochondria |
| 3mb2coa | 3-Methylbut-2-enoyl-CoA | Mitochondria |
| 3mgcoa | 3-Methylglutaconyl-CoA | Mitochondria |
| 3mob | 3-Methyl-2-oxobutanoate | Mitochondria |
| 3pg | 3-Phospho-D-glycerate | Cytosol |
| 3php | 3-Phosphohydroxypyruvate | Cytosol |
| 4fumacac | 4-Fumarylacetoacetate | Cytosol |
| 4mlacac | 4-Maleylacetoacetate | Cytosol |
| 4mop | 4-Methyl-2-oxopentanoate | Mitochondria |
| 5aizc | 5-amino-1-(5-phospho-D-ribosyl)imidazole-4-carboxylate | Cytosol |
| 6pgc | 6-Phospho-D-gluconate | Cytosol |
| 6pgl | 6-phospho-D-glucono-1,5-lactone | Cytosol |
| aa_hyb | Lumped amino acid, hybridoma | Cytosol |
| ac | Acetate | Cytosol |
| acac | Acetoacetate | Cytosol |
| acac | Acetoacetate | Mitochondria |
| accoa | Acetyl-CoA | Cytosol |
| accoa | Acetyl-CoA | Mitochondria |
| adn | Adenosine | Cytosol |
| adp | ADP | Cytosol |
| adp | ADP | Mitochondria |
| ahcys | S-Adenosyl-L-homocysteine | Cytosol |
| aicar | 5-Amino-1-(5-Phospho-D-ribosyl)imidazole-4-carboxamide | Cytosol |
| air | 5-amino-1-(5-phospho-D-ribosyl)imidazole | Cytosol |
| akg | 2-Oxoglutarate | Cytosol |
| akg | 2-Oxoglutarate | Mitochondria |
| ala-L | L-Alanine | Cytosol |
| ala-L | L-Alanine | Extra-organism |
| amet | S-Adenosyl-L-methionine | Cytosol |
| amp | AMP | Cytosol |
| amp | AMP | Mitochondria |
| arg-L | L-Arginine | Cytosol |
| arg-L | L-Arginine | Extra-organism |
| argsuc | N(omega)-(L-Arginino)succinate | Cytosol |
| asn-L | L-Asparagine | Cytosol |
| asn-L | L-Asparagine | Extra-organism |
| asp-L | L-Aspartate | Cytosol |
| asp-L | L-Aspartate | Extra-organism |
| asp-L | L-Aspartate | Mitochondria |
| atp | ATP | Cytosol |
| atp | ATP | Mitochondria |
| biomass_hyb | Biomass, hybridoma | Cytosol |
| cbasp | N-Carbamoyl-L-aspartate | Cytosol |
| cbp | Carbamoyl phosphate | Cytosol |
| cbp | Carbamoyl phosphate | Mitochondria |
| cdp | CDP | Cytosol |
| cit | Citrate | Cytosol |
| cit | Citrate | Mitochondria |
| citr-L | L-Citrulline | Cytosol |
| citr-L | L-Citrulline | Mitochondria |
| cmp | CMP | Cytosol |
| co2 | CO2 | Cytosol |

TABLE 21-continued

Reactions and Metabolites in Hybridoma Model

| | | |
|---|---|---|
| co2 | CO2 | Extra-organism |
| co2 | CO2 | Mitochondria |
| coa | Coenzyme A | Cytosol |
| coa | Coenzyme A | Mitochondria |
| ctp | CTP | Cytosol |
| cys-L | L-Cysteine | Cytosol |
| cys-L | L-Cysteine | Extra-organism |
| cysth-L | L-Cystathionine | Cytosol |
| dadp | dADP | Cytosol |
| datp | dATP | Cytosol |
| dca | Decanoate | Cytosol |
| dcamp | N6-(1,2-Dicarboxyethyl)-AMP | Cytosol |
| dcdp | dCDP | Cytosol |
| dctp | dCTP | Cytosol |
| ddca | dodecanoate (C12:0) | Cytosol |
| dgdp | dGDP | Cytosol |
| dgtp | dGTP | Cytosol |
| dhap | Dihydroxyacetone phosphate | Cytosol |
| dhap | Dihydroxyacetone phosphate | Mitochondria |
| dhbpt | 6,7-Dihydrobiopterin | Cytosol |
| dhf | 7,8-Dihydrofolate | Cytosol |
| dhor-S | (S)-Dihydroorotate | Cytosol |
| dna_hyb | Lumped DNA, hybridoma | Cytosol |
| dtdp | dTDP | Cytosol |
| dtmp | dTMP | Cytosol |
| dttp | dTTP | Cytosol |
| dudp | dUDP | Cytosol |
| dump | dUMP | Cytosol |
| e4p | D-Erythrose 4-phosphate | Cytosol |
| f6p | D-Fructose 6-phosphate | Cytosol |
| fad | FAD | Mitochondria |
| fadh2 | FADH2 | Mitochondria |
| fald | Formaldehyde | Cytosol |
| fdp | D-Fructose 1,6-bisphosphate | Cytosol |
| fgam | N2-Formyl-N1-(5-phospho-D-ribosyl)glycinamide | Cytosol |
| ficytcc | Ferricytochrome c | Mitochondria |
| focytcc | Ferrocytochrome c | Mitochondria |
| for | Formate | Cytosol |
| fpram | 2-(Formamido)-N1-(5-phospho-D-ribosyl)acetamidine | Cytosol |
| fprica | 5-Formamido-1-(5-phospho-D-ribosyl)imidazole-4-carboxamide | Cytosol |
| fum | Fumarate | Cytosol |
| fum | Fumarate | Mitochondria |
| g1p | D-Glucose 1-phosphate | Cytosol |
| g3p | Glyceraldehyde 3-phosphate | Cytosol |
| g6p | D-Glucose 6-phosphate | Cytosol |
| gar | N1-(5-Phospho-D-ribosyl)glycinamide | Cytosol |
| gdp | GDP | Cytosol |
| glc-D | D-Glucose | Cytosol |
| glc-D | D-Glucose | Extra-organism |
| gln-L | L-Glutamine | Cytosol |
| gln-L | L-Glutamine | Extra-organism |
| gln-L | L-Glutamine | Mitochondria |
| glu-L | L-Glutamate | Cytosol |
| glu-L | L-Glutamate | Extra-organism |
| glu-L | L-Glutamate | Mitochondria |
| glu5p | L-Glutamate 5-phosphate | Cytosol |
| glu5p | L-Glutamate 5-phosphate | Mitochondria |
| glu5sa | L-Glutamate 5-semialdehyde | Cytosol |
| glu5sa | L-Glutamate 5-semialdehyde | Mitochondria |
| gly | Glycine | Cytosol |
| gly | Glycine | Extra-organism |
| gly | Glycine | Mitochondria |
| glyc3p | sn-Glycerol 3-phosphate | Cytosol |
| glyc3p | sn-Glycerol 3-phosphate | Mitochondria |
| glycogen | glycogen | Cytosol |
| gmp | GMP | Cytosol |
| gtp | GTP | Cytosol |
| h | H+ | Cytosol |
| h | H+ | Extra-organism |

TABLE 21-continued

Reactions and Metabolites in Hybridoma Model

| | | |
|---|---|---|
| h | H+ | Mitochondria |
| h2o | H2O | Cytosol |
| h2o | H2O | Extra-organism |
| h2o | H2O | Mitochondria |
| h2o2 | Hydrogen peroxide | Cytosol |
| hco3 | Bicarbonate | Cytosol |
| hco3 | Bicarbonate | Mitochondria |
| hcys-L | L-Homocysteine | Cytosol |
| hdca | hexadecanoate (n-C16:0) | Cytosol |
| hgentis | Homogentisate | Cytosol |
| hibcoa | (S)-3-Hydroxyisobutyryl-CoA | Mitochondria |
| his-L | L-Histidine | Cytosol |
| his-L | L-Histidine | Extra-organism |
| hmgcoa | Hydroxymethylglutaryl-CoA | Mitochondria |
| ibcoa | Isobutyryl-CoA | Mitochondria |
| icit | Isocitrate | Mitochondria |
| ile-L | L-Isoleucine | Cytosol |
| ile-L | L-Isoleucine | Extra-organism |
| imp | IMP | Cytosol |
| ivcoa | Isovaleryl-CoA | Mitochondria |
| lac-L | L-Lactate | Cytosol |
| lac-L | L-Lactate | Extra-organism |
| leu-L | L-Leucine | Cytosol |
| leu-L | L-Leucine | Extra-organism |
| leu-L | L-Leucine | Mitochondria |
| lys-L | L-Lysine | Cytosol |
| lys-L | L-Lysine | Extra-organism |
| mab_hyb | Monoclonal antibody, hybridoma | Cytosol |
| mal-L | L-Malate | Cytosol |
| mal-L | L-Malate | Mitochondria |
| malcoa | Malonyl-CoA | Cytosol |
| met-L | L-Methionine | Cytosol |
| met-L | L-Methionine | Extra-organism |
| methf | 5,10-Methenyltetrahydrofolate | Cytosol |
| mlthf | 5,10-Methylenetetrahydrofolate | Cytosol |
| mlthf | 5,10-Methylenetetrahydrofolate | Mitochondria |
| mmal | Methylmalonate | Mitochondria |
| mmalsa-S | (S)-Methylmalonate semialdehyde | Mitochondria |
| mmcoa-R | (R)-Methylmalonyl-CoA | Mitochondria |
| mmcoa-S | (S)-Methylmalonyl-CoA | Mitochondria |
| nad | Nicotinamide adenine dinucleotide | Cytosol |
| nad | Nicotinamide adenine dinucleotide | Mitochondria |
| nadh | Nicotinamide adenine dinucleotide - reduced | Cytosol |
| nadh | Nicotinamide adenine dinucleotide - reduced | Mitochondria |
| nadp | Nicotinamide adenine dinucleotide phosphate | Cytosol |
| nadp | Nicotinamide adenine dinucleotide phosphate | Mitochondria |
| nadph | Nicotinamide adenine dinucleotide phosphate - reduced | Cytosol |
| nadph | Nicotinamide adenine dinucleotide phosphate - reduced | Mitochondria |
| nh4 | Ammonium | Cytosol |
| nh4 | Ammonium | Extra-organism |
| nh4 | Ammonium | Mitochondria |
| o2 | O2 | Cytosol |
| o2 | O2 | Extra-organism |
| o2 | O2 | Mitochondria |
| oaa | Oxaloacetate | Cytosol |
| oaa | Oxaloacetate | Mitochondria |
| octa | octanoate | Cytosol |
| orn-L | L-Ornithine | Cytosol |
| orn-L | L-Ornithine | Mitochondria |
| orot | Orotate | Cytosol |
| orot5p | Orotidine 5'-phosphate | Cytosol |
| pep | Phosphoenolpyruvate | Cytosol |
| phe-L | L-Phenylalanine | Cytosol |
| phe-L | L-Phenylalanine | Extra-organism |

TABLE 21-continued

Reactions and Metabolites in Hybridoma Model

| | | |
|---|---|---|
| pi | Phosphate | Cytosol |
| pi | Phosphate | Extra-organism |
| pi | Phosphate | Mitochondria |
| plipid_hyb | Phospholipid, hybridoma | Cytosol |
| ppcoa | Propanoyl-CoA (C3:0CoA) | Mitochondria |
| ppi | Diphosphate | Cytosol |
| ppi | Diphosphate | Mitochondria |
| pram | 5-Phospho-beta-D-ribosylamine | Cytosol |
| pro-L | L-Proline | Cytosol |
| pro-L | L-Proline | Extra-organism |
| pro-L | L-Proline | Mitochondria |
| protein_hyb | Lumped protein, hybridoma | Cytosol |
| prpp | 5-Phospho-alpha-D-ribose 1-diphosphate | Cytosol |
| pser-L | O-Phospho-L-serine | Cytosol |
| pyr | Pyruvate | Cytosol |
| pyr | Pyruvate | Mitochondria |
| qh2 | Ubiquinol | Mitochondria |
| r5p | alpha-D-Ribose 5-phosphate | Cytosol |
| rna_hyb | Lumped RNA, hybridoma | Cytosol |
| ru5p-D | D-Ribulose 5-phosphate | Cytosol |
| s7p | Sedoheptulose 7-phosphate | Cytosol |
| sarcs | Sarcosine | Cytosol |
| ser-L | L-Serine | Cytosol |
| ser-L | L-Serine | Extra-organism |
| ser-L | L-Serine | Mitochondria |
| succ | Succinate | Mitochondria |
| succoa | Succinyl-CoA | Mitochondria |
| thbpt | Tetrahydrobiopterin | Cytosol |
| thf | 5,6,7,8-Tetrahydrofolate | Cytosol |
| thf | 5,6,7,8-Tetrahydrofolate | Mitochondria |
| thr-L | L-Threonine | Cytosol |
| thr-L | L-Threonine | Extra-organism |
| trdox | Oxidized thioredoxin | Cytosol |
| trdrd | Reduced thioredoxin | Cytosol |
| trp-L | L-Tryptophan | Cytosol |
| trp-L | L-Tryptophan | Extra-organism |
| ttdca | tetradecanoate (C14:0) | Cytosol |
| tyr-L | L-Tyrosine | Cytosol |
| tyr-L | L-Tyrosine | Extra-organism |
| tyr-L | L-Tyrosine | Mitochondria |
| ubq | Ubiquinone | Mitochondria |
| udp | UDP | Cytosol |
| udpg | UDPglucose | Cytosol |
| ump | UMP | Cytosol |
| urea | Urea | Cytosol |
| urea | Urea | Extra-organism |
| uri | Uridine | Cytosol |
| utp | UTP | Cytosol |
| val-L | L-Valine | Cytosol |
| val-L | L-Valine | Extra-organism |
| val-L | L-Valine | Mitochondria |
| xmp | Xanthosine 5'-phosphate | Cytosol |
| xu5p-D | D-Xylulose 5-phosphate | Cytosol |

TABLE 22

Reactions and Metabolites in NS0 Model

| Abbreviation | Equation | EC Number |
|---|---|---|
| AGTip | [x]: ala-L + glx --> gly + pyr | 2.6.1.44 |
| ALATA_L | [c]: akg + ala-L <==> glu-L + pyr | 2.6.1.2 |
| ALATA_Lm | [m]: akg + ala-L <==> glu-L + pyr | 2.6.1.2 |
| ASNS1 | [c]: asp-L + atp + gln-L + h2o --> amp + asn-L + glu-L + h + ppi | 6.3.5.4 |
| ASNTA | [c]: akg + asn-L <==> asm + glu-L | 2.6.1.14 |
| ASPCT | [c]: asp-L + cbp --> cbasp + h + pi | 2.1.3.2 |

TABLE 22-continued

Reactions and Metabolites in NS0 Model

| | | |
|---|---|---|
| ASPDC | [c]: asp-L + h --> ala-L + co2 | 4.1.1.15 |
| ASPDCm | [m]: asp-L + h --> ala-L + co2 | 4.1.1.15 |
| ASPTA1 | [c]: akg + asp-L <==> glu-L + oaa | 2.6.1.1 |
| ASPTA1m | [m]: akg + asp-L <==> glu-L + oaa | 2.6.1.1 |
| DASPOp | [x]: asp-D + h2o + o2 --> h2o2 + nh4 + oaa | 1.4.3.1 |
| GLUDCm | [m]: glu-L + h --> 4abut + co2 | 4.1.1.15 |
| THRD_L | [c]: thr-L --> 2obut + nh4 | 4.3.1.19 |
| G5SADs | [c]: glu5sa <==> 1pyr5c + h + h2o | |
| ORNTAm | [m]: akg + orn-L <==> glu-L + glu5sa | 2.6.1.13 |
| P5CRx | [c]: 1pyr5c + (2) h + nadh --> nad + pro-L | 1.5.1.2 |
| P5CRy | [c]: 1pyr5c + (2) h + nadph --> nadp + pro-L | 1.5.1.2 |
| PRO1xm | [m]: nad + pro-L --> 1pyr5c + (2) h + nadh | 1.5.1.2 |
| PYR5CDxm | [m]: glu5sa + h2o + nad --> glu-L + (2) h + nadh | 1.5.1.12 |
| GALU | [c]: g1p + h + utp <==> ppi + udpg | 2.7.7.9 |
| GLCP | [c]: glycogen + pi --> g1p | 2.4.1.1 |
| GLYGS | [c]: udpg --> glycogen + h + udp | 2.4.1.11 |
| CRNPT | [c]: crn + pmtcoa --> coa + pmtcrn | 2.3.1.21 |
| CRNPT_Mmu_Hyb | [c]: crn + (0.001) facoa_avg_Mmu_Hyb --> coa + (0.001) facrn_avg_Mmu_Hyb | 2.3.1.21 |
| CRNPTer | [r]: coa + pmtcrn --> crn + pmtcoa | 2.3.1.7 |
| CRNPTer_Mmu_Hyb | [r]: coa + (0.001) facrn_avg_Mmu_Hyb --> crn + (0.001) facoa_avg_Mmu_Hyb | 2.3.1.21 |
| FACRNter_Mmu_Hyb | facrn_avg_Mmu_Hyb[c] <==> facrn_avg_Mmu_Hyb[r] | |
| SUCD3m | [m]: fadh2 + ubq <==> fad + qh2 | |
| ACONTm | [m]: cit <==> icit | 4.2.1.3 |
| AKGDm | [m]: akg + coa + nad --> co2 + nadh + succoa | |
| CITL2 | [c]: atp + cit + coa --> accoa + adp + oaa + pi | 4.1.3.8 |
| CSm | [m]: accoa + h2o + oaa --> cit + coa + h | 4.1.3.7 |
| FUM | [c]: fum + h2o <==> mal-L | 4.2.1.2 |
| FUMm | [m]: fum + h2o <==> mal-L | 4.2.1.2 |
| ICDHxm | [m]: icit + nad --> akg + co2 + nadh | 1.1.1.41 |
| ICDHy | [c]: icit + nadp <==> akg + co2 + nadph | 1.1.1.42 |
| ICDHym | [m]: icit + nadp --> akg + co2 + nadph | 1.1.1.42 |
| MDH | [c]: mal-L + nad <==> h + nadh + oaa | 1.1.1.37 |
| MDHm | [m]: mal-L + nad <==> h + nadh + oaa | 1.1.1.37 |
| SUCD1m | [m]: succ + ubq <==> fum + qh2 | 1.3.5.1 |
| SUCOASAm | [m]: atp + coa + succ <==> adp + pi + succoa | 6.2.1.5 |
| SUCOASGm | [m]: coa + gtp + succ <==> gdp + pi + succoa | 6.2.1.4 |
| PDHm | [m]: coa + nad + pyr --> accoa + co2 + nadh | 1.2.1.51 |
| AKBDHm | [m]: 2obut + coa + nad --> co2 + nadh + ppcoa | |
| ASPTA3 | [c]: 3sala + akg --> glu-L + spyr | 2.6.1.1 |
| ASPTA3m | [m]: 3sala + akg --> glu-L + spyr | 2.6.1.1 |
| ASPTA4 | [c]: akg + cys-L <==> glu-L + mercppyr | 2.6.1.1 |
| ASPTA4m | [m]: akg + cys-L <==> glu-L + mercppyr | 2.6.1.1 |
| CDO | [c]: cys-L + o2 --> 3sala | 1.13.11.20 |
| MCPST | [c]: mercppyr + so3 --> pyr + tsul | 2.8.1.2 |
| MCPSTm | [m]: mercppyr + so3 --> pyr + tsul | 2.8.1.2 |
| SPYR | [c]: h2o + spyr --> (2) h + pyr + so3 | |
| SPYRm | [m]: h2o + spyr --> (2) h + pyr + so3 | |
| ACCOAC | [c]: accoa + atp + hco3 --> adp + h + malcoa + pi | 6.4.1.2 |
| FAS100 | [c]: (3) h + malcoa + (2) nadph + octa --> co2 + coa + dca + h2o + (2) nadp | 2.3.1.85 |
| FAS120 | [c]: dca + (3) h + malcoa + (2) nadph --> co2 + coa + ddca + h2o + (2) nadp | 2.3.1.85 |
| FAS140 | [c]: ddca + (3) h + malcoa + (2) nadph --> co2 + coa + h2o + (2) nadp + ttdca | 2.3.1.85 |
| FAS160 | [c]: (3) h + malcoa + (2) nadph + ttdca --> co2 + coa + h2o + hdca + (2) nadp | 2.3.1.85 |
| FAS180 | [c]: (3) h + hdca + malcoa + (2) nadph --> co2 + coa + h2o + (2) nadp + ocdca | 2.3.1.85 |
| FAS200 | [c]: (3) h + malcoa + (2) nadph + ocdca --> co2 + coa + ecsa + h2o + (2) nadp | 2.3.1.85 |

TABLE 22-continued

| Reactions and Metabolites in NS0 Model | | |
|---|---|---|
| FAS220 | [c]: ecsa + (3) h + malcoa + (2) nadph --> co2 + coa + dcsa + h2o + (2) nadp | 2.3.1.85 |
| FAS80_L | [c]: accoa + (8) h + (3) malcoa + (6) nadph --> (3) co2 + (4) coa + (2) h2o + (6) nadp + octa | 2.3.1.85 |
| DESAT161 | [c]: h + nadph + o2 + pmtcoa --> (2) h2o + hdcoa + nadp | 1.14.19.1 |
| DESAT181 | [c]: h + nadph + o2 + strcoa --> (2) h2o + nadp + odecoa | 1.14.19.1 |
| DESAT182 | [c]: h + nadph + o2 + odecoa --> (2) h2o + nadp + ocdycacoa | 1.14.19.1 |
| DESAT201 | [c]: ecsacoa + h + nadph + o2 --> esecoa + (2) h2o + nadp | 1.14.19.1 |
| DESAT202 | [c]: ecsacoa + (2) h + (2) nadph + (2) o2 --> esdcoa + (4) h2o + (2) nadp | 1.14.19.1 |
| DESAT203 | [c]: ecsacoa + (3) h + (3) nadph + (3) o2 --> estcoa + (6) h2o + (3) nadp | 1.14.19.1 |
| DESAT221 | [c]: dcsacoa + h + nadph + o2 --> dsecoa + (2) h2o + nadp | 1.14.19.1 |
| FACOAavg_Mmu_Hyb | [c]: atp + coa + (0.008) dcsea + (0.003) ecsa + (0.012) ecsdea + (0.043) ecsea + (0.01) ecstea + (0.156) hdca + (0.071) hdcea + (0.104) ocdca + (0.57) ocdcea + (0.004) ocdcya + (0.019) ttdca <==> amp + (0.001) facoa_avg_Mmu_Hyb + ppi | |
| FACOAL140 | [c]: atp + coa + ttdca <==> amp + ppi + tdcoa | 6.2.1.3 |
| FACOAL160 | [c]: atp + coa + hdca <==> amp + pmtcoa + ppi | 6.2.1.3 |
| FACOAL161 | [c]: atp + coa + hdcea <==> amp + hdcoa + ppi | 6.2.1.3 |
| FACOAL180 | [c]: atp + coa + ocdca <==> amp + ppi + strcoa | 6.2.1.3 |
| FACOAL181 | [c]: atp + coa + ocdcea <==> amp + odecoa + ppi | 6.2.1.3 |
| FACOAL182 | [c]: atp + coa + ocdcya <==> amp + ocdycacoa + ppi | 6.2.1.3 |
| FACOAL200 | [c]: atp + coa + ecsa <==> amp + ecsacoa + ppi | 6.2.1.3 |
| FACOAL201 | [c]: atp + coa + ecsea <==> amp + esecoa + ppi | 6.2.1.3 |
| FACOAL202 | [c]: atp + coa + ecsdea <==> amp + esdcoa + ppi | 6.2.1.3 |
| FACOAL203 | [c]: atp + coa + ecstea <==> amp + estcoa + ppi | 6.2.1.3 |
| FACOAL220 | [c]: atp + coa + dcsa <==> amp + dcsacoa + ppi | 6.2.1.3 |
| FACOAL221 | [c]: atp + coa + dcsea <==> amp + dsecoa + ppi | 6.2.1.3 |
| DHFR | [c]: dhf + h + nadph <==> nadp + thf | 1.5.1.3 |
| DHPRx | [c]: dhbpt + h + nadh <==> nad + thbpt | 1.5.1.34 |
| FldAct | [c]: fald + thf --> h2o + mlthf | |
| FMETDH | [c]: 10fthf + h2o + nadp --> co2 + h + nadph + thf | 1.5.1.6 |
| FORTHFC | [c]: 5fthf + (2) h <==> methf + nh4 | 4.3.1.4 |
| FTHFLm | [m]: atp + for + thf <==> 10fthf + adp + pi | 6.3.4.3 |
| FTHFLr | [c]: atp + for + thf <==> 10fthf + adp + pi | 6.3.4.3 |
| METFR | [c]: 5mthf + nadp <==> (2) h + mlthf + nadph | 1.5.1.20 |
| MTHFC | [c]: h2o + methf <==> 10fthf + h | 3.5.4.9 |
| MTHFCm | [m]: h2o + methf <==> 10fthf + h | 3.5.4.9 |
| MTHFD | [c]: mlthf + nadp <==> methf + nadph | 1.5.1.5 |
| MTHFDm | [m]: mlthf + nadp <==> methf + nadph | 1.5.1.5 |
| SAMMT_hypothetical | [c]: amet + thf --> 5mthf + ahcys | |
| ABTArm | [m]: 4abut + akg <==> glu-L + sucsal | 2.6.1.19 |
| AKAM2 | [c]: nh4 + oaa <==> asm + h2o | 3.5.1.3 |
| CBPS | [c]: (2) atp + gln-L + h2o + hco3 --> (2) adp + cbp + glu-L + (2) h + pi | 6.3.5.5 |
| CBPSAm | [m]: (2) atp + co2 + h2o + nh4 --> (2) adp + cbp + (3) h + pi | 6.3.4.16 |
| G5SADsm | [m]: glu5sa <==> 1pyr5c + h + h2o | |
| GLNS | [c]: atp + glu-L + nh4 --> adp + gln-L + h + pi | 6.3.1.2 |
| GLNSm | [m]: atp + glu-L + nh4 --> adp + gln-L + h + pi | 6.3.1.2 |

TABLE 22-continued

Reactions and Metabolites in NS0 Model

| | | |
|---|---|---|
| GLUCYSL | [c]: atp + cys-L + glu-L --> adp + glucys + h + pi | 6.3.2.2 |
| GLUDC | [c]: glu-L + h --> 4abut + co2 | 4.1.1.15 |
| GLUDxm | [m]: glu-L + h2o + nad <==> akg + h + nadh + nh4 | 1.4.1.3 |
| GLUDym | [m]: glu-L + h2o + nadp <==> akg + h + nadph + nh4 | 1.4.1.3 |
| GLUNm | [m]: gln-L + h2o --> glu-L + nh4 | 3.5.1.2 |
| P5CDm | [m]: 1pyr5c + (2) h2o + nad --> glu-L + h + nadh | 1.5.1.12 |
| SSALxm | [m]: h2o + nad + sucsal --> (2) h + nadh + succ | 1.2.1.24 |
| GTHO | [c]: gthox + h + nadph --> (2) gthrd + nadp | 1.8.1.7 |
| GTHS | [c]: atp + glucys + gly --> adp + gthrd + h + pi | 6.3.2.3 |
| G3PD | [c]: dhap + h + nadh --> glyc3p + nad | 1.1.1.8 |
| G3PDcm | fad[m] + glyc3p[c] --> dhap[c] + fadh2[m] | 1.1.99.5 |
| PSERDm_Mmu_Hyb | [m]: h + (0.001) ps_Mmu_Hyb --> co2 + (0.001) pe_Mmu_Hyb | 4.1.1.65 |
| THRD | [c]: nad + thr-L --> 2aobut + h + nadh | 1.1.1.103 |
| AAO3p | [x]: gly + h2o + o2 --> glx + h2o2 + nh4 | 1.4.3.3 |
| GCCam | [m]: gly + h + lpro <==> alpro + co2 | 1.4.4.2 |
| GCCbm | [m]: alpro + thf --> dhlpro + mlthf + nh4 | 2.1.2.10 |
| GCCcm | [m]: dhlpro + nad <==> h + lpro + nadh | 1.8.1.4 |
| GHMT | [c]: ser-L + thf <==> gly + h2o + mlthf | 2.1.2.1 |
| GHMT2m | [m]: ser-L + thf <==> gly + h2o + mlthf | 2.1.2.1 |
| GLYATm | [m]: accoa + gly <==> 2aobut + coa | 2.3.1.29 |
| GLYCLm | [m]: gly + nad + thf --> co2 + mlthf + nadh + nh4 | 2.1.2.10 |
| GMTR | [c]: amet + gly --> ahcys + h + sarcs | 2.1.1.20 |
| PGCDr | [c]: 3pg + nad <==> 3php + h + nadh | 1.1.1.95 |
| PSERTr | [c]: 3php + glu-L <==> akg + pser-L | 2.6.1.52 |
| PSP_L | [c]: h2o + pser-L --> pi + ser-L | 3.1.3.3 |
| SARCOp | [x]: h2o + o2 + sarcs --> fald + gly + h2o2 | 1.5.3.1 |
| SERD_L | [c]: ser-L --> nh4 + pyr | 4.3.1.17 |
| THRA | [c]: thr-L <==> acald + gly | 4.1.2.5 |
| ENO | [c]: 2pg <==> h2o + pep | 4.2.1.11 |
| FBA | [c]: fdp <==> dhap + g3p | 4.1.2.13 |
| FBP | [c]: fdp + h2o --> f6p + pi | 3.1.3.11 |
| G6PASEer | [r]: g6p + h2o --> glc-D + pi | 3.1.3.9 |
| GAPD | [c]: g3p + nad + pi <==> 13dpg + h + nadh | 1.2.1.12 |
| HEX1 | [c]: atp + glc-D --> adp + g6p + h | 2.7.1.2 |
| PFK | [c]: atp + f6p --> adp + fdp + h | 2.7.1.11 |
| PGI | [c]: g6p <==> f6p | 5.3.1.9 |
| PGK | [c]: 13dpg + adp <==> 3pg + atp | 2.7.2.3 |
| PGM | [c]: 3pg <==> 2pg | 5.4.2.1 |
| PGMT | [c]: g1p <==> g6p | 5.4.2.2 |
| PYK | [c]: adp + h + pep --> atp + pyr | 2.7.1.40 |
| TPI | [c]: dhap <==> g3p | 5.3.1.1 |
| GLUFT | [c]: 5fthf + glu-L <==> forglu + thf | 2.1.2.5 |
| HISD1r | [c]: his-L <==> nh4 + urcan | 4.3.1.3 |
| IZPN | [c]: 4izp + h2o --> forglu | 3.5.2.7 |
| URCN | [c]: h2o + urcan --> 4izp | 4.2.1.49 |
| MI1PP | [c]: h2o + mi1p-D --> inost + pi | 3.1.3.25 |
| AASAD3m | [m]: ampsal + h2o + nad --> 2aadp + (2) h + nadh | 1.2.1.31 |
| AKGD2m | [m]: 2oxoadp + coa + nad --> co2 + glutcoa + nadh | |
| ASEMDm | [m]: ampsal + h2o + nadp --> 2aadp + (2) h + nadph | 1.2.1.31 |
| GCOADm | [m]: fad + glutcoa + h --> b2coa + co2 + fadh2 | 1.3.99.7 |
| HACD1m | [m]: aacoa + h + nadh <==> 3hbycoa + nad | 1.1.1.35 |
| OXOATm | [m]: 2aadp + akg <==> 2oxoadp + glu-L | 2.6.1.39 |
| SACCDGm | [m]: Lsacchrp + h2o + nad <==> ampsal + glu-L + h + nadh | 1.5.1.9 |
| SACCDym | [m]: akg + h + lys-L + nadph --> Lsacchrp + h2o + nadp | 1.5.1.8 |
| AHC | [c]: ahcys + h2o <==> adn + hcys-L | 3.3.1.1 |
| CTL2 | [c]: cyst-L + h2o --> nh4 + pyr + tcys | 4.4.1.1 |

TABLE 22-continued

Reactions and Metabolites in NS0 Model

| | | |
|---|---|---|
| CYSRx | [c]: (2) cys-L + nad <==> cyst-L + h + nadh | 1.8.1.6 |
| CYSTGL | [c]: cysth-L + h2o --> 2obut + cys-L + nh4 | 4.4.1.1 |
| CYSTS | [c]: hcys-L + ser-L --> cysth-L + h2o | 4.2.1.22 |
| METAT | [c]: atp + h2o + met-L --> amet + pi + ppi | 2.5.1.6 |
| METS | [c]: 5mthf + hcys-L --> h + met-L + thf | 2.1.1.13 |
| THD5m | [m]: nad + nadph --> nadh + nadp | 1.6.1.2 |
| DHORD3m | dhor-S[c] + ubq[m] <==> orot[c] + qh2[m] | |
| ATPM | [c]: atp + h2o --> adp + h + pi | 3.6.1.15 |
| CATp | [x]: (2) h2o2 --> (2) h2o + o2 | 1.11.1.6 |
| HCO3E | [c]: co2 + h2o <==> h + hco3 | 4.2.1.1 |
| HCO3Em | [m]: co2 + h2o <==> h + hco3 | 4.2.1.1 |
| MAbS_NS0 | [c]: (0.0618) ala-L + (0.0253) arg-L + (0.0337) asn-L + (0.0365) asp-L + (4.306) atp + (0.0253) cys-L + (0.0407) gln-L + (0.0449) glu-L + (0.0843) gly + (4.306) h2o + (0.0183) his-L + (0.0211) ile-L + (0.0815) leu-L + (0.0632) lys-L + (0.0126) met-L + (0.0267) phe-L + (0.0702) pro-L + (0.1208) ser-L + (0.0772) thr-L + (0.0211) trp-L + (0.0407) tyr-L + (0.0941) val-L --> (0.0001) MAb_NS0 + (4.306) adp + (4.306) h + (4.306) pi | |
| PPA | [c]: h2o + ppi --> h + (2) pi | 3.6.1.1 |
| PPAer | [r]: h2o + ppi --> h + (2) pi | 3.6.1.1 |
| PPAm | [m]: h2o + ppi --> h + (2) pi | 3.6.1.1 |
| ATPS | atp[c] + h2o[c] --> adp[c] + h[e] + pi[c] | 3.6.3.6 |
| ATPS4m | adp[m] + (4) h[c] + pi[m] --> atp[m] + (3) h[m] + h2o[m] | 3.6.3.14 |
| CYOO4m | (4) focytcc[m] + (8) h[m] + o2[m] --> (4) ficytcc[m] + (4) h[c] + (2) h2o[m] | 1.9.3.1 |
| CYOR4m | (2) ficytcc[m] + (2) h[m] + qh2[m] --> (2) focytcc[m] + (4) h[c] + ubq[m] | 1.10.2.2 |
| NADH4m | (5) h[m] + nadh[m] + ubq[m] --> (4) h[c] + nad[m] + qh2[m] | 1.6.99.3 |
| DPCOAK | [c]: atp + dpcoa --> adp + coa + h | 2.7.1.24 |
| PNTK | [c]: atp + pnto-R --> 4ppan + adp + h | 2.7.1.33 |
| PPCDC | [c]: 4ppcys + h --> co2 + pan4p | 4.1.1.36 |
| PPNCL | [c]: 4ppan + ctp + cys-L --> 4ppcys + cdp + h + pi | 6.3.2.5 |
| PTPAT | [c]: atp + h + pan4p <==> dpcoa + ppi | 2.7.7.3 |
| G6PDH2er | [r]: g6p + nadp --> 6pgl + h + nadph | 1.1.1.49 |
| G6PDHy | [c]: g6p + nadp <==> 6pgl + h + nadph | 1.1.1.49 |
| PGDH | [c]: 6pgc + nadp --> co2 + nadph + ru5p-D | 1.1.1.44 |
| PGL | [c]: 6pgl + h2o --> 6pgc + h | 3.1.1.31 |
| PGLer | [r]: 6pgl + h2o --> 6pgc + h | 3.1.1.31 |
| RBK | [c]: atp + rib-D --> adp + h + r5p | 2.7.1.15 |
| RPE | [c]: ru5p-D <==> xu5p-D | 5.1.3.1 |
| RPI | [c]: r5p <==> ru5p-D | 5.3.1.6 |
| TAL | [c]: g3p + s7p <==> e4p + f6p | 2.2.1.2 |
| TKT1 | [c]: r5p + xu5p-D <==> g3p + s7p | 2.2.1.1 |
| TKT2 | [c]: e4p + xu5p-D <==> f6p + g3p | 2.2.1.1 |
| ASPTA6m | [m]: akg + phe-L <==> glu-L + phpyr | 2.6.1.1 |
| PHETA1 | [c]: akg + phe-L <==> glu-L + phpyr | 2.6.1.58 |
| PHE4MO | [c]: o2 + phe-L + thbpt --> dhbpt + h2o + tyr-L | 1.14.16.1 |
| MI1PS | [c]: g6p --> mi1p-D | 5.5.1.4 |
| AGAT_Mmu_Hyb | [c]: (0.001) 1ag3p_Mmu_Hyb + (0.008) dsecoa + (0.003) ecsacoa + (0.012) esdcoa + (0.043) esecoa + (0.01) estcoa + (0.071) hdcoa + (0.004) ocdycacoa + (0.57) odecoa + (0.156) pmtcoa + (0.104) strcoa + (0.019) tdcoa --> coa + (0.001) pa_Mmu_Hyb | 2.3.1.51 |
| CDPDGPm_Mmu_Hyb | [m]: (0.001) cdpdag_Mmu_Hyb + glyc3p <==> cmp + h + (0.001) pgp_Mmu_Hyb | 2.7.8.8 |
| CHLPCTD | [c]: cholp + ctp + h --> cdpchol + ppi | 2.7.7.15 |
| CHOLK | [c]: atp + chol --> adp + cholp + h | 2.7.1.32 |
| DAGCPT_Mmu_Hyb | [c]: (0.001) 12dgr_Mmu_Hyb + cdpchol --> cmp + h + (0.001) pc_Mmu_Hyb | 2.7.8.2 |

TABLE 22-continued

Reactions and Metabolites in NS0 Model

| | | |
|---|---|---|
| DAGPYP__Mmu__Hyb | [c]: h2o + (0.001) pa__Mmu__Hyb --> (0.001) 12dgr__Mmu__Hyb + pi | 3.1.3.4 |
| DASYN__Mmu__Hyb | [c]: ctp + h + (0.001) pa__Mmu__Hyb <==> (0.001) cdpdag__Mmu__Hyb + ppi | 2.7.7.41 |
| DASYNm__Mmu__Hyb | [m]: ctp + h + (0.001) pa__Mmu__Hyb <==> (0.001) cdpdag__Mmu__Hyb + ppi | 2.7.7.41 |
| GAT__Mmu__Hyb | [c]: (0.008) dsecoa + (0.003) ecsacoa + (0.012) esdcoa + (0.043) esecoa + (0.01) estcoa + glyc3p + (0.071) hdcoa + (0.004) ocdycacoa + (0.57) odecoa + (0.156) pmtcoa + (0.104) strcoa + (0.019) tdcoa --> (0.001) 1ag3p__Mmu__Hyb + coa | 2.3.1.15 |
| PGPPAm__Mmu__Hyb | [m]: h2o + (0.001) pgp__Mmu__Hyb --> (0.001) pg__Mmu__Hyb + pi | 3.1.3.27 |
| PGPTm__Mmu__Hyb | [m]: (0.001) cdpdag__Mmu__Hyb + (0.001) pg__Mmu__Hyb <==> cmp + (0.001) dpg__Mmu__Hyb + h | |
| PINOS__Mmu__Hyb | [c]: (0.001) cdpdag__Mmu__Hyb + inost --> cmp + h + (0.001) pino__Mmu__Hyb | 2.7.8.11 |
| PTDSS1__Mmu__Hyb | [c]: chol + (0.001) ps__Mmu__Hyb <==> (0.001) pc__Mmu__Hyb + ser-L | |
| RNDR1 | [c]: adp + trdrd --> dadp + h2o + trdox | 1.17.4.1 |
| RNDR2 | [c]: gdp + trdrd --> dgdp + h2o + trdox | 1.17.4.1 |
| RNDR3 | [c]: cdp + trdrd --> dcdp + h2o + trdox | 1.17.4.1 |
| RNDR4 | [c]: trdrd + udp --> dudp + h2o + trdox | 1.17.4.1 |
| ADK1 | [c]: amp + atp <==> (2) adp | 2.7.4.3 |
| ADK1m | [m]: amp + atp <==> (2) adp | 2.7.4.3 |
| ADNK1 | [c]: adn + atp --> adp + amp + h | 2.7.1.20 |
| ADSL1r | [c]: dcamp <==> amp + fum | 4.3.2.2 |
| ADSL2r | [c]: 25aics <==> aicar + fum | 4.3.2.2 |
| ADSS | [c]: asp-L + gtp + imp --> dcamp + gdp + (2) h + pi | 6.3.4.4 |
| AICART | [c]: 10fthf + aicar <==> fprica + thf | 2.1.2.3 |
| AIRC | [c]: air + co2 --> 5aizc + h | 4.1.1.21 |
| GARFTi | [c]: 10fthf + gar --> fgam + h + thf | 2.1.2.2 |
| GK1 | [c]: atp + gmp <==> adp + gdp | 2.7.4.8 |
| GLUPRT | [c]: gln-L + h2o + prpp --> glu-L + ppi + pram | 2.4.2.14 |
| GMPR | [c]: gmp + (2) h + nadph --> imp + nadp + nh4 | 1.7.1.7 |
| GMPS2 | [c]: atp + gln-L + h2o + xmp --> amp + glu-L + gmp + (2) h + ppi | 6.3.5.2 |
| GTPA | [c]: gtp + (2) h2o --> gmp + (2) h + (2) pi | 3.6.1.5 |
| GUAPRT | [c]: gua + prpp --> gmp + ppi | 2.4.2.8 |
| IMPC | [c]: h2o + imp <==> fprica | 3.5.4.10 |
| IMPD | [c]: h2o + imp + nad --> h + nadh + xmp | 1.1.1.205 |
| NDP3 | [c]: gdp + h2o --> gmp + h + pi | 3.6.1.6 |
| NDPK1 | [c]: atp + gdp <==> adp + gtp | 2.7.4.6 |
| NDPK1m | [m]: atp + gdp <==> adp + gtp | 2.7.4.6 |
| NDPK2 | [c]: atp + udp <==> adp + utp | 2.7.4.6 |
| NDPK3 | [c]: atp + cdp <==> adp + ctp | 2.7.4.6 |
| NDPK3m | [m]: atp + cdp <==> adp + ctp | 2.7.4.6 |
| NDPK9 | [c]: atp + idp <==> adp + itp | 2.7.4.6 |
| NTD9 | [c]: gmp + h2o --> gsn + pi | 3.1.3.5 |
| NTPP2 | [c]: gtp + h2o --> gmp + h + ppi | 3.6.1.19 |
| NTPP9 | [c]: h2o + itp --> h + imp + ppi | 3.6.1.19 |
| PRAGS | [c]: atp + gly + pram --> adp + gar + h + pi | 6.3.4.13 |
| PRAIS | [c]: atp + fpram --> adp + air + h + pi | 6.3.3.1 |
| PRASCS | [c]: 5aizc + asp-L + atp <==> 25aics + adp + h + pi | 6.3.2.6 |
| PRFGS | [c]: atp + fgam + gln-L + h2o --> adp + fpram + glu-L + (2) h + pi | 6.3.5.3 |
| PRPPS | [c]: atp + r5p <==> amp + h + prpp | 2.7.6.1 |
| PUNP3 | [c]: gsn + pi <==> gua + r1p | 2.4.2.1 |
| CTPS1 | [c]: atp + nh4 + utp --> adp + ctp + (2) h + pi | 6.3.4.2 |
| CTPS2 | [c]: atp + gln-L + h2o + utp --> adp + ctp + glu-L + (2) h + pi | 6.3.4.2 |
| CYTK1 | [c]: atp + cmp <==> adp + cdp | 2.7.4.14 |
| CYTK1m | [m]: atp + cmp <==> adp + cdp | 2.7.4.14 |
| DHORTS | [c]: dhor-S + h2o <==> cbasp + h | 3.5.2.3 |
| DTMPK | [c]: atp + dtmp <==> adp + dtdp | 2.7.4.9 |
| NDPK4 | [c]: atp + dtdp <==> adp + dttp | 2.7.4.6 |
| NDPK5 | [c]: atp + dgdp <==> adp + dgtp | 2.7.4.6 |

TABLE 22-continued

Reactions and Metabolites in NS0 Model

| | | |
|---|---|---|
| NDPK7 | [c]: atp + dcdp <==> adp + dctp | 2.7.4.6 |
| NDPK8 | [c]: atp + dadp <==> adp + datp | 2.7.4.6 |
| OMPDC | [c]: h + orot5p --> co2 + ump | 4.1.1.23 |
| ORPT | [c]: orot5p + ppi <==> orot + prpp | 2.4.2.10 |
| TMDS | [c]: dump + mlthf --> dhf + dtmp | 2.1.1.45 |
| TRDR | [c]: h + nadph + trdox --> nadp + trdrd | 1.8.1.9 |
| UMPK | [c]: atp + ump <==> adp + udp | 2.7.4.14 |
| URIDK3 | [c]: atp + dump <==> adp + dudp | 2.7.4.9 |
| URIK1 | [c]: atp + uri --> adp + h + ump | 2.7.1.48 |
| URIK2 | [c]: gtp + uri --> gdp + h + ump | 2.7.1.48 |
| URIK3 | [c]: itp + uri --> h + idp + ump | 2.7.1.48 |
| ACOAH | [c]: accoa + h2o --> ac + coa + h | 3.1.2.1 |
| ACS | [c]: ac + atp + coa --> accoa + amp + ppi | 6.2.1.1 |
| ACSm | [m]: ac + atp + coa --> accoa + amp + ppi | 6.2.1.1 |
| ALCD2x | [c]: etoh + nad <==> acald + h + nadh | 1.1.1.1 |
| ALCD2y | [c]: etoh + nadp <==> acald + h + nadph | 1.1.1.2 |
| ALDD2x | [c]: acald + h2o + nad --> ac + (2) h + nadh | 1.2.1.3 |
| LDH_L | [c]: lac-L + nad <==> h + nadh + pyr | 1.1.1.27 |
| ME1m | [m]: mal-L + nad --> co2 + nadh + pyr | 1.1.1.38 |
| ME2 | [c]: mal-L + nadp --> co2 + nadph + pyr | 1.1.1.40 |
| ME2m | [m]: mal-L + nadp --> co2 + nadph + pyr | 1.1.1.40 |
| PCm | [m]: atp + hco3 + pyr --> adp + h + oaa + pi | 6.4.1.1 |
| PPCKG | [c]: gtp + oaa --> co2 + gdp + pep | 4.1.1.32 |
| PPCKGm | [m]: gtp + oaa --> co2 + gdp + pep | 4.1.1.32 |
| 3DSPHRer | [r]: 3dsphgn + h + nadph --> nadp + sphgn | 1.1.1.102 |
| CERPT_Mmu_Hyb | [c]: cdpchol + (0.001) cer_Mmu_Hyb --> cmp + (0.001) sphgmy_Mmu_Hyb | 2.7.8.3 |
| CERSaer_Mmu_Hyb | [r]: (0.001) facoa_avg_Mmu_Hyb + sphgn --> coa + (0.001) dcer_Mmu_Hyb | 2.3.1.24 |
| DCERDSer_Mmu_Hyb | [r]: (0.001) dcer_Mmu_Hyb + h + nadph + o2 --> (0.001) cer_Mmu_Hyb + (2) h2o + nadp | |
| SERPTer | [r]: h + pmtcoa + ser-L --> 3dsphgn + co2 + coa | 2.3.1.50 |
| 7DCHSTRer | [r]: 7dchsterol + h + nadph --> chsterol + nadp | 1.3.1.21 |
| C14STRer | [r]: 44mctr + h + nadph --> 44mzym + nadp | 1.3.1.70 |
| C3STDH1xer | [r]: 4mzym_int1 + nad --> 4mzym_int2 + co2 + nadh | 1.1.1.170 |
| C3STDH1yer | [r]: 4mzym_int1 + nadp --> 4mzym_int2 + co2 + nadph | 1.1.1.170 |
| C3STKR2er | [r]: h + nadph + zym_int2 --> nadp + zymst | 1.1.1.270 |
| C4STMO1er | [r]: 44mzym + (2) h + (3) nadph + (3) o2 --> 4mzym_int1 + (4) h2o + (3) nadp | 1.14.13.72 |
| C4STMO2xer | [r]: 4mzym_int2 + nad + o2 --> co2 + h + nadh + zym_int2 | 1.14.13.72 |
| C4STMO2yer | [r]: 4mzym_int2 + nadp + o2 --> co2 + h + nadph + zym_int2 | 1.14.13.72 |
| CHSTNIer | [r]: zymst <==> cholsd | 5.3.3.5 |
| DMATT | [c]: dmpp + ipdp --> grdp + ppi | 2.5.1.1 |
| DPMVD | [c]: 5dpmev + atp --> adp + co2 + ipdp + pi | 4.1.1.33 |
| GRTT | [c]: grdp + ipdp --> frdp + ppi | 2.5.1.10 |
| HMGCOARi | [c]: (2) h + hmgcoa + (2) nadph --> coa + mev-R + (2) nadp | 1.1.1.34 |
| HMGCOASi | [c]: aacoa + accoa + h2o --> coa + h + hmgcoa | 4.1.3.5 |
| HMGCOASim | [m]: aacoa + accoa + h2o --> coa + h + hmgcoa | 4.1.3.5 |
| IPDDI | [c]: ipdp <==> dmpp | 5.3.3.2 |
| LATHSTOxer | [r]: h + lathost + nadh + o2 --> 7dchsterol + (2) h2o + nad | |
| LATHSTOyer | [r]: h + lathost + nadph + o2 --> 7dchsterol + (2) h2o + nadp | |
| LNS14DMer | [r]: (2) h + lanost + (3) nadph + (3) o2 --> 44mctr + for + (4) h2o + (3) nadp | 1.14.13.70 |
| LNSTLSer | [r]: Ssq23epx --> lanost | 5.4.99.7 |
| MEVK | [c]: atp + mev-R --> 5pmev + adp + h | 2.7.1.36 |
| PMEVK | [c]: 5pmev + atp --> 5dpmev + adp | 2.7.4.2 |

TABLE 22-continued

Reactions and Metabolites in NS0 Model

| | | |
|---|---|---|
| SQLEer | [r]: h + nadph + o2 + sql --> Ssq23epx + h2o + nadp | 1.14.99.7 |
| SQLSer | [r]: (2) frdp + h + nadph --> nadp + (2) ppi + sql | 2.5.1.21 |
| STRRer | [r]: cholsd + h + nadph --> lathost + nadp | 1.3.1.72 |
| 6PGCter | 6pgc[c] <==> 6pgc[r] | |
| CERter_Mmu_Hyb | cer_Mmu_Hyb[c] <==> cer_Mmu_Hyb[r] | |
| CHSTEROLter | chsterol[c] <==> chsterol[r] | |
| CO2ter | co2[c] <==> co2[r] | |
| CRNter | crn[c] <==> crn[r] | |
| FORter | for[c] <==> for[r] | |
| FRDPter | frdp[c] <==> frdp[r] | |
| O2ter | o2[c] <==> o2[r] | |
| PMTCRNter | pmtcrn[c] <==> pmtcrn[r] | |
| SERt2er | h[c] + ser-L[c] <==> h[r] + ser-L[r] | |
| G6Pter | g6p[c] <==> g6p[r] | |
| GLCter | glc-D[c] <==> glc-D[r] | |
| H2Oter | h2o[c] <==> h2o[r] | |
| PIter | h[c] + pi[c] <==> h[r] + pi[r] | |
| ALA_Lt6 | ala-L[e] + h[e] <==> ala-L[c] + h[c] | |
| ARGtr | arg-L[e] <==> arg-L[c] | |
| ASNt6 | asn-L[e] + h[e] <==> asn-L[c] + h[c] | |
| ASPt6 | asp-L[e] + h[e] <==> asp-L[c] + h[c] | |
| CHLt6 | chol[e] + h[e] <==> chol[c] + h[c] | |
| CO2t | co2[e] <==> co2[c] | |
| CYSt6 | cys-L[e] + h[e] <==> cys-L[c] + h[c] | |
| GLCt1r | glc-D[e] <==> glc-D[c] | |
| GLNt | gln-L[e] + h[e] <==> gln-L[c] + h[c] | |
| GLUt6 | glu-L[e] + h[e] <==> glu-L[c] + h[c] | |
| GLYt6 | gly[e] + h[e] <==> gly[c] + h[c] | |
| H2Ot5 | h2o[e] <==> h2o[c] | |
| HISt6 | h[e] + his-L[e] <==> h[c] + his-L[c] | |
| ILEtec | ile-L[e] <==> ile-L[c] | |
| L-LACt2 | h[e] + lac-L[e] <==> h[c] + lac-L[c] | |
| LEUtec | leu-L[e] <==> leu-L[c] | |
| LYSt | lys-L[e] <==> lys-L[c] | |
| MAbt_NS0 | (0.0001) MAb_NS0[c] --> MAb_NS0[e] | |
| METt6 | h[e] + met-L[e] <==> h[c] + met-L[c] | |
| NAt7 | h[e] + na1[c] <==> h[c] + na1[e] | |
| NH4t | nh4[e] <==> nh4[c] | |
| O2t | o2[e] <==> o2[c] | |
| PHEtec | phe-L[e] <==> phe-L[c] | |
| PIt6 | h[e] + pi[e] <==> h[c] + pi[c] | |
| PNTOt4 | na1[e] + pnto-R[e] --> na1[c] + pnto-R[c] | |
| PROt6 | h[e] + pro-L[e] <==> h[c] + pro-L[c] | |
| SERt6 | h[e] + ser-L[e] <==> h[c] + ser-L[c] | |
| SO3t | h[e] + so3 [e] <==> h[c] + so3 [c] | |
| THRt6 | h[e] + thr-L[e] <==> h[c] + thr-L[c] | |
| TRPt | trp-L[e] <==> trp-L[c] | |
| TYRt | tyr-L[e] <==> tyr-L[c] | |
| UREAt | urea[e] <==> urea[c] | |
| VALtec | val-L[e] <==> val-L[c] | |
| 2OXOADPTm | 2oxoadp[c] + akg[m] <==> 2oxoadp[m] + akg[c] | |
| 34HPPtm | 34hpp[c] <==> 34hpp[m] | |
| 4ABUTtm | 4abut[c] <==> 4abut[m] | |
| ACACt2m | acac[c] + h[c] <==> acac[m] + h[m] | |
| ACtm | ac[c] <==> ac[m] | |
| AKBtm | 2obut[m] <==> 2obut[c] | |
| ATP/ADPtm | adp[c] + atp[m] <==> adp[m] + atp[c] | |
| CITRtm | citr-L[c] <==> citr-L[m] | |
| CITtam | cit[c] + mal-L[m] <==> cit[m] + mal-L[c] | |
| CO2tm | co2[c] <==> co2[m] | |
| DPGtm_Mmu_Hyb | dpg_Mmu_Hyb[c] <==> dpg_Mmu_Hyb[m] | |
| GACm | asp-L[m] + glu-L[c] + h[c] --> asp-L[c] + glu-L[m] + h[m] | |
| GL3PPtm | glyc3p[c] + pi[m] <==> glyc3p[m] + pi[c] | |
| GLUSAtm | glu5sa[c] <==> glu5sa[m] | |
| GLUt2m | glu-L[c] + h[c] <==> glu-L[m] + h[m] | |
| GLYtm | gly[c] <==> gly[m] | |
| GTPt2m | gdp[c] + gtp[m] + (2) h[c] + pi[c] --> gdp[m] + gtp[c] + (2) h[m] + pi[m] | |

TABLE 22-continued

Reactions and Metabolites in NS0 Model

| | | |
|---|---|---|
| H2Otm | h2o[c] <==> h2o[m] | |
| HMGCOAtm | hmgcoa[c] <==> hmgcoa[m] | |
| ILEt5m | ile-L[c] <==> ile-L[m] | |
| LEUtm | leu-L[c] <==> leu-L[m] | |
| LYSt6m | h[c] + lys-L[c] <==> h[m] + lys-L[m] | |
| MALAKGtm | akg[m] + mal-L[c] <==> akg[c] + mal-L[m] | |
| MALtm | mal-L[c] + pi[m] <==> mal-L[m] + pi[c] | |
| MLTHFtm | mlthf[c] <==> mlthf[m] | |
| MMALSAtm | mmalsa-S[m] <==> mmalsa-S[c] | |
| MMALtm | mmal[m] <==> mmal[c] | |
| NH4tm | nh4[c] <==> nh4[m] | |
| O2trm | o2[c] <==> o2[m] | |
| OAtm | h[c] + oaa[c] <==> h[m] + oaa[m] | |
| ORNCITRtm | citr-L[m] + h[m] + orn-L[c] <==> citr-L[c] + h[c] + orn-L[m] | |
| ORNtrm | h[m] + orn-L[c] <==> h[c] + orn-L[m] | |
| PAtm_Mmu_Hyb | pa_Mmu_Hyb[c] <==> pa_Mmu_Hyb[m] | |
| PEtm_Mmu_Hyb | pe_Mmu_Hyb[c] <==> pe_Mmu_Hyb[m] | |
| PGtm_Mmu_Hyb | pg_Mmu_Hyb[c] <==> pg_Mmu_Hyb[m] | |
| PHEtdm | phe-L[c] <==> phe-L[m] | |
| PItm | h[c] + pi[c] <==> h[m] + pi[m] | |
| PROtm | pro-L[c] <==> pro-L[m] | |
| PStm_Mmu_Hyb | ps_Mmu_Hyb[c] <==> ps_Mmu_Hyb[m] | |
| PYRtm | h[c] + pyr[c] <==> h[m] + pyr[m] | |
| SERtm | ser-L[c] <==> ser-L[m] | |
| THFtm | thf[c] <==> thf[m] | |
| TYRtm | tyr-L[c] <==> tyr-L[m] | |
| VALtm | val-L[c] <==> val-L[m] | |
| GLYtp | gly[c] <==> gly[x] | |
| H2O2tp | h2o2[c] <==> h2o2[x] | |
| H2Otp | h2o[c] <==> h2o[x] | |
| O2tp | o2[c] <==> o2[x] | |
| SARCStp | sarcs[c] --> sarcs[x] | |
| ACMUCD | [c]: acmucsal + h --> amucsal + co2 | 4.1.1.45 |
| AMCOXO | [c]: 2amuc + h + h2o + nadph --> 2oxoadp + nadp + nh4 | |
| AMUCD | [c]: amucsal + h2o + nad --> 2amuc + (2) h + nadh | 1.2.1.32 |
| FKYNH | [c]: Lfmkynr + h2o --> for + h + kynr-L | 3.5.1.9 |
| HANTHDO | [c]: 3hanthrn + o2 --> acmucsal | 1.13.11.6 |
| KYNASE3 | [c]: h2o + hkyn --> 3hanthrn + ala-L + h | 3.7.1.3 |
| TRPO2 | [c]: o2 + trp-L --> Lfmkynr | 1.13.11.11 |
| ASPTA5m | [m]: akg + tyr-L <==> 34hpp + glu-L | 2.6.1.1 |
| FUMACA | [c]: 4fumacac + h2o --> acac + fum + h | 3.7.1.2 |
| HGENDO | [c]: hgentis + o2 --> 4mlacac + h | 1.13.11.5 |
| HPPDO1 | [c]: 34hpp + o2 --> co2 + hgentis | 1.13.11.27 |
| MLACI | [c]: 4mlacac --> 4fumacac | 5.2.1.2 |
| TYRTA | [c]: akg + tyr-L <==> 34hpp + glu-L | 2.6.1.5 |
| ECOAH1am | [m]: 3hbycoa <==> b2coa + h2o | 4.2.1.17 |
| KYNAKGT1b | [c]: ahpoxbut --> h2o + xanth | |
| KYNAKGT1c | [c]: akg + hkyn --> ahpoxbut + glu-L | 2.6.1.7 |
| KYNAKGT2a | [c]: akg + kynr-L --> 4aphdob + glu-L | 2.6.1.7 |
| KYNAKGT2b | [c]: 4aphdob --> h2o + kynrt | |
| KYNASE2 | [c]: h2o + kynr-L --> ala-L + anth + h | 3.7.1.3 |
| KYNMO | [c]: h + kynr-L + nadph + o2 --> h2o + hkyn + nadp | 1.14.13.9 |
| LFORKYNHYD | [c]: Lfmkynr + h2o --> ala-L + fanth + h | 3.7.1.3 |
| QULNS2 | [c]: acmucsal --> h + h2o + quln | |
| TYRMOX | [c]: o2 + thbpt + tyr-L --> Ldopa + dhbpt + h2o | 1.14.16.2 |
| AGMT | [c]: agm + h2o --> ptrc + urea | 3.5.3.11 |
| ARGDC | [c]: arg-L + h --> agm + co2 | 4.1.1.19 |
| ARGN | [c]: arg-L + h2o --> orn-L + urea | 3.5.3.1 |
| ARGNm | [m]: arg-L + h2o --> orn-L + urea | 3.5.3.1 |
| ARGSL | [c]: argsuc <==> arg-L + fum | 4.3.2.1 |
| ARGSS | [c]: asp-L + atp + citr-L --> amp + argsuc + h + ppi | 6.3.4.5 |
| G5SDm | [m]: glu5p + h + nadph --> glu5sa + nadp + pi | 1.2.1.41 |
| GLU5Km | [m]: atp + glu-L --> adp + glu5p | 2.7.2.11 |
| OCBTm | [m]: cbp + orn-L <==> citr-L + h + pi | 2.1.3.3 |
| ORNDC | [c]: h + orn-L --> co2 + ptrc | 4.1.1.17 |

TABLE 22-continued

| Reactions and Metabolites in NS0 Model | | |
|---|---|---|
| ACACT10rm | [m]: 2maacoa + coa <==> accoa + ppcoa | 2.3.1.16 |
| ACACT1r | [c]: (2) accoa <==> aacoa + coa | 2.3.1.9 |
| ACACT1rm | [m]: (2) accoa <==> aacoa + coa | 2.3.1.9 |
| ACOAD1m | [m]: fad + ivcoa <==> 3mb2coa + fadh2 | 1.3.99.3 |
| ACOAD2m | [m]: fad + ibcoa <==> 2mp2coa + fadh2 | 1.3.99.3 |
| ACOAD3m | [m]: 2mbcoa + fad <==> 2mb2coa + fadh2 | 1.3.99.3 |
| ALDD4xm | [m]: h2o + mmalsa-S + nad --> (2) h + mmal + nadh | 1.2.1.3 |
| ALDOX1 | [c]: h2o + mmalsa-S + o2 --> h + h2o2 + mmal | 1.2.3.1 |
| ECOAH1m | [m]: 3mb2coa + h2o <==> hivcoa | 4.2.1.17 |
| ECOAH2m | [m]: 2mp2coa + h2o <==> hibcoa | 4.2.1.17 |
| ECOAH3m | [m]: 2mb2coa + h2o <==> 3hmbcoa | 4.2.1.17 |
| HACD8m | [m]: 3hmbcoa + nad <==> 2maacoa + h + nadh | 1.1.1.178 |
| HACOADrm | [m]: 3hmp + nad --> h + mmalsa-S + nadh | 1.1.1.31 |
| HIBHm | [m]: h2o + hibcoa --> 3hmp + coa + h | 3.1.2.4 |
| HMGLm | [m]: hmgcoa --> acac + accoa | 4.1.3.4 |
| ILETAm | [m]: akg + ile-L <==> 3mop + glu-L | 2.6.1.42 |
| LEUTA | [c]: akg + leu-L <==> 4mop + glu-L | 2.6.1.42 |
| LEUTAm | [m]: akg + leu-L <==> 4mop + glu-L | 2.6.1.42 |
| MCCCm | [m]: 3mb2coa + atp + hco3 --> 3mgcoa + adp + h + pi | 6.4.1.4 |
| MGCHm | [m]: 3mgcoa + h2o <==> hmgcoa | 4.2.1.18 |
| MMCOAHm | [m]: coa + h + mmal --> h2o + mmcoa-S | 3.1.2.17 |
| MMEm | [m]: mmcoa-S <==> mmcoa-R | 5.1.99.1 |
| MMMm | [m]: mmcoa-R --> succoa | 5.4.99.2 |
| MMSDHim | [m]: coa + mmalsa-S + nad --> co2 + nadh + ppcoa | 1.2.1.27 |
| MOBD1m | [m]: 4mop + coa + nad --> co2 + ivcoa + nadh | |
| MOBD2m | [m]: 3mob + coa + nad --> co2 + ibcoa + nadh | |
| MOBD3m | [m]: 3mop + coa + nad --> 2mbcoa + co2 + nadh | |
| OCOAT1m | [m]: acac + succoa --> aacoa + succ | 2.8.3.5 |
| PPCOACm | [m]: atp + hco3 + ppcoa --> adp + h + mmcoa-S + pi | 6.4.1.3 |
| VALTA | [c]: akg + val-L <==> 3mob + glu-L | 2.6.1.42 |
| VALTAm | [m]: akg + val-L <==> 3mob + glu-L | 2.6.1.42 |
| ACOAD8m | [m]: ivcoa + nad --> 3mb2coa + h + nadh | 1.3.99.10 |
| EX_ala-L(e) | [e]: ala-L <==> | |
| EX_arg-L(e) | [e]: arg-L <==> | |
| EX_asn-L(e) | [e]: asn-L <==> | |
| EX_asp-L(e) | [e]: asp-L <==> | |
| EX_chol(e) | [e]: chol <==> | |
| EX_co2(e) | [e]: co2 <==> | |
| EX_cys-L(e) | [e]: cys-L <==> | |
| EX_glc(e) | [e]: glc-D <==> | |
| EX_gln-L(e) | [e]: gln-L <==> | |
| EX_glu-L(e) | [e]: glu-L <==> | |
| EX_gly(e) | [e]: gly <==> | |
| EX_h(e) | [e]: h <==> | |
| EX_h2o(e) | [e]: h2o <==> | |
| EX_his-L(e) | [e]: his-L <==> | |
| EX_ile-L(e) | [e]: ile-L <==> | |
| EX_lac-L(e) | [e]: lac-L <==> | |
| EX_leu-L(e) | [e]: leu-L <==> | |
| EX_lys-L(e) | [e]: lys-L <==> | |
| EX_MAb_NS0(e) | [e]: MAb_NS0 <==> | |
| EX_met-L(e) | [e]: met-L <==> | |
| EX_na1(e) | [e]: na1 <==> | |
| EX_nh4(e) | [e]: nh4 <==> | |
| EX_o2(e) | [e]: o2 <==> | |
| EX_phe-L(e) | [e]: phe-L <==> | |
| EX_pi(e) | [e]: pi <==> | |
| EX_pnto-R(e) | [e]: pnto-R <==> | |
| EX_pro-L(e) | [e]: pro-L <==> | |
| EX_ser-L(e) | [e]: ser-L <==> | |
| EX_so3(e) | [e]: so3 <==> | |
| EX_thr-L(e) | [e]: thr-L <==> | |
| EX_trp-L(e) | [e]: trp-L <==> | |

TABLE 22-continued

Reactions and Metabolites in NS0 Model

| | | |
|---|---|---|
| EX__tyr-L(e) | [e]: tyr-L <==> | |
| EX__urea(e) | [e]: urea <==> | |
| EX__val-L(e) | [e]: val-L <==> | |

| Metab Abbreviation | Name | Compartment |
|---|---|---|
| 10fthf | 10-Formyltetrahydrofolate | Cytosol |
| 10fthf | 10-Formyltetrahydrofolate | Mitochondria |
| 12dgr__Mmu__Hyb | 1,2-Diacylglycerol, Hybridoma | Cytosol |
| 13dpg | 3-Phospho-D-glyceroyl phosphate | Cytosol |
| 1ag3p__Mmu__Hyb | 1-Acyl-sn-glycerol 3-phosphate, Hybridoma | Cytosol |
| 1pyr5c | 1-Pyrroline-5-carboxylate | Cytosol |
| 1pyr5c | 1-Pyrroline-5-carboxylate | Mitochondria |
| 25aics | (S)-2-[5-Amino-1-(5-phospho-D-ribosyl)imidazole-4-carboxamido]succinate | Cytosol |
| 2aadp | L-2-Aminoadipate | Mitochondria |
| 2amuc | 2-Aminomuconate | Cytosol |
| 2aobut | L-2-Amino-3-oxobutanoate | Cytosol |
| 2aobut | L-2-Amino-3-oxobutanoate | Mitochondria |
| 2maacoa | 2-Methyl-3-acetoacetyl-CoA | Mitochondria |
| 2mb2coa | trans-2-Methylbut-2-enoyl-CoA | Mitochondria |
| 2mbcoa | 2-Methylbutanoyl-CoA | Mitochondria |
| 2mp2coa | 2-Methylprop-2-enoyl-CoA | Mitochondria |
| 2obut | 2-Oxobutanoate | Cytosol |
| 2obut | 2-Oxobutanoate | Mitochondria |
| 2oxoadp | 2-Oxoadipate | Cytosol |
| 2oxoadp | 2-Oxoadipate | Mitochondria |
| 2pg | D-Glycerate 2-phosphate | Cytosol |
| 34hpp | 3-(4-Hydroxyphenyl)pyruvate | Cytosol |
| 34hpp | 3-(4-Hydroxyphenyl)pyruvate | Mitochondria |
| 3dsphgn | 3-Dehydrosphinganine | Endoplasmic Reticulum |
| 3hanthrn | 3-Hydroxyanthranilate | Cytosol |
| 3hbycoa | (S)-3-Hydroxybutyryl-CoA | Mitochondria |
| 3hmbcoa | (S)-3-Hydroxy-2-methylbutyryl-CoA | Mitochondria |
| 3hmp | (S)-3-hydroxyisobutyrate | Mitochondria |
| 3mb2coa | 3-Methylbut-2-enoyl-CoA | Mitochondria |
| 3mgcoa | 3-Methylglutaconyl-CoA | Mitochondria |
| 3mob | 3-Methyl-2-oxobutanoate | Cytosol |
| 3mob | 3-Methyl-2-oxobutanoate | Mitochondria |
| 3mop | (S)-3-Methyl-2-oxopentanoate | Mitochondria |
| 3pg | 3-Phospho-D-glycerate | Cytosol |
| 3php | 3-Phosphohydroxypyruvate | Cytosol |
| 3sala | 3-Sulfino-L-alanine | Cytosol |
| 3sala | 3-Sulfino-L-alanine | Mitochondria |
| 44mctr | 4,4-dimethylcholesta-8,14,24-trienol | Endoplasmic Reticulum |
| 44mzym | 4,4-dimethylzymosterol | Endoplasmic Reticulum |
| 4abut | 4-Aminobutanoate | Cytosol |
| 4abut | 4-Aminobutanoate | Mitochondria |
| 4aphdob | 4-(2-Aminophenyl)-2,4-dioxobutanoate | Cytosol |
| 4fumacac | 4-Fumarylacetoacetate | Cytosol |
| 4izp | 4-Imidazolone-5-propanoate | Cytosol |
| 4mlacac | 4-Maleylacetoacetate | Cytosol |
| 4mop | 4-Methyl-2-oxopentanoate | Cytosol |
| 4mop | 4-Methyl-2-oxopentanoate | Mitochondria |
| 4mzym__int1 | 4-Methylzymosterol intermediate 1 | Endoplasmic Reticulum |
| 4mzym__int2 | 4-Methylzymosterol intermediate 2 | Endoplasmic Reticulum |
| 4ppan | D-4'-Phosphopantothenate | Cytosol |
| 4ppcys | N-((R)-4-Phosphopantothenoyl)-L-cysteine | Cytosol |
| 5aizc | 5-amino-1-(5-phospho-D-ribosyl)imidazole-4-carboxylate | Cytosol |
| 5dpmev | (R)-5-Diphosphomevalonate | Cytosol |
| 5fthf | 5-Formiminotetrahydrofolate | Cytosol |
| 5mthf | 5-Methyltetrahydrofolate | Cytosol |
| 5pmev | (R)-5-Phosphomevalonate | Cytosol |
| 6pgc | 6-Phospho-D-gluconate | Cytosol |
| 6pgc | 6-Phospho-D-gluconate | Endoplasmic Reticulum |
| 6pgl | 6-phospho-D-glucono-1,5-lactone | Cytosol |
| 6pgl | 6-phospho-D-glucono-1,5-lactone | Endoplasmic Reticulum |

TABLE 22-continued

Reactions and Metabolites in NS0 Model

| | | |
|---|---|---|
| 7dchsterol | 7-Dehydrocholesterol | Endoplasmic Reticulum |
| aacoa | Acetoacetyl-CoA | Cytosol |
| aacoa | Acetoacetyl-CoA | Mitochondria |
| ac | Acetate | Cytosol |
| ac | Acetate | Mitochondria |
| acac | Acetoacetate | Cytosol |
| acac | Acetoacetate | Mitochondria |
| acald | Acetaldehyde | Cytosol |
| accoa | Acetyl-CoA | Cytosol |
| accoa | Acetyl-CoA | Mitochondria |
| acmucsal | 2-Amino-3-carboxymuconate semialdehyde | Cytosol |
| adn | Adenosine | Cytosol |
| adp | ADP | Cytosol |
| adp | ADP | Mitochondria |
| agm | Agmatine | Cytosol |
| ahcys | S-Adenosyl-L-homocysteine | Cytosol |
| ahpoxbut | 4-(2-Amino-3-hydroxyphenyl)-2,4-dioxobutanoate | Cytosol |
| aicar | 5-Amino-1-(5-Phospho-D-ribosyl)imidazole-4-carboxamide | Cytosol |
| air | 5-amino-1-(5-phospho-D-ribosyl)imidazole | Cytosol |
| akg | 2-Oxoglutarate | Cytosol |
| akg | 2-Oxoglutarate | Mitochondria |
| ala-L | L-Alanine | Cytosol |
| ala-L | L-Alanine | Extra-organism |
| ala-L | L-Alanine | Mitochondria |
| ala-L | L-Alanine | Peroxisome |
| alpro | S-Aminomethyldihydrolipoylprotein | Mitochondria |
| amet | S-Adenosyl-L-methionine | Cytosol |
| amp | AMP | Cytosol |
| amp | AMP | Mitochondria |
| ampsal | L-2-Aminoadipate 6-semialdehyde | Mitochondria |
| amucsal | 2-Aminomuconate semialdehyde | Cytosol |
| anth | Anthranilate | Cytosol |
| arg-L | L-Arginine | Cytosol |
| arg-L | L-Arginine | Extra-organism |
| arg-L | L-Arginine | Mitochondria |
| argsuc | N(omega)-(L-Arginino)succinate | Cytosol |
| asm | 2-Oxosuccinamate | Cytosol |
| asn-L | L-Asparagine | Cytosol |
| asn-L | L-Asparagine | Extra-organism |
| asp-D | D-Aspartate | Peroxisome |
| asp-L | L-Aspartate | Cytosol |
| asp-L | L-Aspartate | Extra-organism |
| asp-L | L-Aspartate | Mitochondria |
| atp | ATP | Cytosol |
| atp | ATP | Mitochondria |
| b2coa | trans-But-2-enoyl-CoA | Mitochondria |
| cbasp | N-Carbamoyl-L-aspartate | Cytosol |
| cbp | Carbamoyl phosphate | Cytosol |
| cbp | Carbamoyl phosphate | Mitochondria |
| cdp | CDP | Cytosol |
| cdp | CDP | Mitochondria |
| cdpchol | CDPcholine | Cytosol |
| cdpdag_Mmu_Hyb | CDPdiacylglycerol | Cytosol |
| cdpdag_Mmu_Hyb | CDPdiacylglycerol | Mitochondria |
| cer_Mmu_Hyb | Ceramide, Hybridoma | Cytosol |
| cer_Mmu_Hyb | Ceramide, Hybridoma | Endoplasmic Reticulum |
| chol | Choline | Cytosol |
| chol | Choline | Extra-organism |
| cholp | Choline phosphate | Cytosol |
| cholsd | 5alpha-Cholesta-7,24-dien-3beta-ol | Endoplasmic Reticulum |
| chsterol | Cholesterol | Cytosol |
| chsterol | Cholesterol | Endoplasmic Reticulum |
| cit | Citrate | Cytosol |
| cit | Citrate | Mitochondria |
| citr-L | L-Citrulline | Cytosol |
| citr-L | L-Citrulline | Mitochondria |
| cmp | CMP | Cytosol |
| cmp | CMP | Mitochondria |
| co2 | CO2 | Cytosol |

TABLE 22-continued

| Reactions and Metabolites in NS0 Model | | |
|---|---|---|
| co2 | CO2 | Endoplasmic Reticulum |
| co2 | CO2 | Extra-organism |
| co2 | CO2 | Mitochondria |
| coa | Coenzyme A | Cytosol |
| coa | Coenzyme A | Endoplasmic Reticulum |
| coa | Coenzyme A | Mitochondria |
| crn | L-Carnitine | Cytosol |
| crn | L-Carnitine | Endoplasmic Reticulum |
| ctp | CTP | Cytosol |
| ctp | CTP | Mitochondria |
| cys-L | L-Cysteine | Cytosol |
| cys-L | L-Cysteine | Extra-organism |
| cys-L | L-Cysteine | Mitochondria |
| cyst-L | L-Cystine | Cytosol |
| cysth-L | L-Cystathionine | Cytosol |
| dadp | dADP | Cytosol |
| datp | dATP | Cytosol |
| dca | Decanoate | Cytosol |
| dcamp | N6-(1,2-Dicarboxyethyl)-AMP | Cytosol |
| dcdp | dCDP | Cytosol |
| dcer_Mmu_Hyb | Dihydroceramide, Hybridoma | Endoplasmic Reticulum |
| dcsa | docosanoate (n-C22:0) | Cytosol |
| dcsacoa | docosanoyl-CoA (C22:0CoA) | Cytosol |
| dcsea | docosenoate (C22:1) | Cytosol |
| dctp | dCTP | Cytosol |
| ddca | dodecanoate (C12:0) | Cytosol |
| dgdp | dGDP | Cytosol |
| dgtp | dGTP | Cytosol |
| dhap | Dihydroxyacetone phosphate | Cytosol |
| dhbpt | 6,7-Dihydrobiopterin | Cytosol |
| dhf | 7,8-Dihydrofolate | Cytosol |
| dhlpro | Dihydrolipolprotein | Mitochondria |
| dhor-S | (S)-Dihydroorotate | Cytosol |
| dmpp | Dimethylallyl diphosphate | Cytosol |
| dpcoa | Dephospho-CoA | Cytosol |
| dpg_Mmu_Hyb | Diphosphatidylglycerol, | Cytosol |
| dpg_Mmu_Hyb | Diphosphatidylglycerol, | Mitochondria |
| dsecoa | docosenoyl-CoA (C22:1CoA) | Cytosol |
| dtdp | dTDP | Cytosol |
| dtmp | dTMP | Cytosol |
| dttp | dTTP | Cytosol |
| dudp | dUDP | Cytosol |
| dump | dUMP | Cytosol |
| e4p | D-Erythrose 4-phosphate | Cytosol |
| ecsa | Eicosanoate (n-C20:0) | Cytosol |
| ecsacoa | Eicosanoyl-CoA (n-C20:0CoA) | Cytosol |
| ecsdea | eicosadienoate (C20:2) | Cytosol |
| ecsea | eicosenoate (C20:1) | Cytosol |
| ecstea | eicosatrienoate (C20:3) | Cytosol |
| esdcoa | eicosadienoyl-CoA (C20:2CoA) | Cytosol |
| esecoa | eicosenoyl-CoA (C20:1CoA) | Cytosol |
| estcoa | eicosatrienoyl-CoA (C20:3CoA) | Cytosol |
| etoh | Ethanol | Cytosol |
| f6p | D-Fructose 6-phosphate | Cytosol |
| facoa_avg_Mmu_Hyb | Average fatty acyl-coa, Hybridoma | Cytosol |
| facoa_avg_Mmu_Hyb | Average fatty acyl-coa, Hybridoma | Endoplasmic Reticulum |
| facrn_avg_Mmu_Hyb | Average fatty acylcarnitine, | Cytosol |
| facrn_avg_Mmu_Hyb | Average fatty acylcarnitine, | Endoplasmic Reticulum |
| fad | FAD | Mitochondria |
| fadh2 | FADH2 | Mitochondria |
| fald | Formaldehyde | Cytosol |
| fald | Formaldehyde | Peroxisome |
| fanth | Formylanthranilate | Cytosol |
| fdp | D-Fructose 1,6-bisphosphate | Cytosol |
| fgam | N2-Formyl-N1-(5-phospho-D-ribosyl)glycinamide | Cytosol |
| ficytcc | Ferricytochrome c | Mitochondria |
| focytcc | Ferrocytochrome c | Mitochondria |
| for | Formate | Cytosol |
| for | Formate | Endoplasmic Reticulum |
| for | Formate | Mitochondria |

TABLE 22-continued

Reactions and Metabolites in NS0 Model

| | | |
|---|---|---|
| forglu | N-Formimidoyl-L-glutamate | Cytosol |
| fpram | 2-(Formamido)-N1-(5-phospho-D-ribosyl)acetamidine | Cytosol |
| fprica | 5-Formamido-1-(5-phospho-D-ribosyl)imidazole-4-carboxamide | Cytosol |
| frdp | Farnesyl diphosphate | Cytosol |
| frdp | Farnesyl diphosphate | Endoplasmic Reticulum |
| fum | Fumarate | Cytosol |
| fum | Fumarate | Mitochondria |
| g1p | D-Glucose 1-phosphate | Cytosol |
| g3p | Glyceraldehyde 3-phosphate | Cytosol |
| g6p | D-Glucose 6-phosphate | Cytosol |
| g6p | D-Glucose 6-phosphate | Endoplasmic Reticulum |
| gar | N1-(5-Phospho-D-ribosyl)glycinamide | Cytosol |
| gdp | GDP | Cytosol |
| gdp | GDP | Mitochondria |
| glc-D | D-Glucose | Cytosol |
| glc-D | D-Glucose | Endoplasmic Reticulum |
| glc-D | D-Glucose | Extra-organism |
| gln-L | L-Glutamine | Cytosol |
| gln-L | L-Glutamine | Extra-organism |
| gln-L | L-Glutamine | Mitochondria |
| glu-L | L-Glutamate | Cytosol |
| glu-L | L-Glutamate | Extra-organism |
| glu-L | L-Glutamate | Mitochondria |
| glu5p | L-Glutamate 5-phosphate | Mitochondria |
| glu5sa | L-Glutamate 5-semialdehyde | Cytosol |
| glu5sa | L-Glutamate 5-semialdehyde | Mitochondria |
| glucys | gamma-L-Glutamyl-L-cysteine | Cytosol |
| glutcoa | Glutaryl-CoA | Mitochondria |
| glx | Glyoxylate | Peroxisome |
| gly | Glycine | Cytosol |
| gly | Glycine | Extra-organism |
| gly | Glycine | Mitochondria |
| gly | Glycine | Peroxisome |
| glyc3p | sn-Glycerol 3-phosphate | Cytosol |
| glyc3p | sn-Glycerol 3-phosphate | Mitochondria |
| glycogen | glycogen | Cytosol |
| gmp | GMP | Cytosol |
| grdp | Geranyl diphosphate | Cytosol |
| gsn | Guanosine | Cytosol |
| gthox | Oxidized glutathione | Cytosol |
| gthrd | Reduced glutathione | Cytosol |
| gtp | GTP | Cytosol |
| gtp | GTP | Mitochondria |
| gua | Guanine | Cytosol |
| h | H+ | Cytosol |
| h | H+ | Endoplasmic Reticulum |
| h | H+ | Extra-organism |
| h | H+ | Mitochondria |
| h2o | H2O | Cytosol |
| h2o | H2O | Endoplasmic Reticulum |
| h2o | H2O | Extra-organism |
| h2o | H2O | Mitochondria |
| h2o | H2O | Peroxisome |
| h2o2 | Hydrogen peroxide | Cytosol |
| h2o2 | Hydrogen peroxide | Peroxisome |
| hco3 | Bicarbonate | Cytosol |
| hco3 | Bicarbonate | Mitochondria |
| hcys-L | L-Homocysteine | Cytosol |
| hdca | hexadecanoate (n-C16:0) | Cytosol |
| hdcea | hexadecenoate (n-C16:1) | Cytosol |
| hdcoa | Hexadecenoyl-CoA (n-C16:1CoA) | Cytosol |
| hgentis | Homogentisate | Cytosol |
| hibcoa | (S)-3-Hydroxyisobutyryl-CoA | Mitochondria |
| his-L | L-Histidine | Cytosol |
| his-L | L-Histidine | Extra-organism |
| hivcoa | 3-Hydroxyisovaleryl-CoA | Mitochondria |
| hkyn | 3-Hydroxy-L-kynurenine | Cytosol |
| hmgcoa | Hydroxymethylglutaryl-CoA | Cytosol |
| hmgcoa | Hydroxymethylglutaryl-CoA | Mitochondria |
| ibcoa | Isobutyryl-CoA | Mitochondria |
| icit | Isocitrate | Cytosol |

TABLE 22-continued

Reactions and Metabolites in NS0 Model

| | | |
|---|---|---|
| icit | Isocitrate | Mitochondria |
| idp | IDP | Cytosol |
| ile-L | L-Isoleucine | Cytosol |
| ile-L | L-Isoleucine | Extra-organism |
| ile-L | L-Isoleucine | Mitochondria |
| imp | IMP | Cytosol |
| inost | myo-Inositol | Cytosol |
| ipdp | Isopentenyl diphosphate | Cytosol |
| itp | ITP | Cytosol |
| ivcoa | Isovaleryl-CoA | Mitochondria |
| kynr-L | L-Kynurenine | Cytosol |
| kynrt | Kynurenate | Cytosol |
| lac-L | L-Lactate | Cytosol |
| lac-L | L-Lactate | Extra-organism |
| lanost | Lanosterol | Endoplasmic Reticulum |
| lathost | Lathosterol | Endoplasmic Reticulum |
| Ldopa | 3,4-Dihydroxy-L-phenylalanine | Cytosol |
| leu-L | L-Leucine | Cytosol |
| leu-L | L-Leucine | Extra-organism |
| leu-L | L-Leucine | Mitochondria |
| Lfmkynr | L-Formylkynurenine | Cytosol |
| lpro | Lipoylprotein | Mitochondria |
| Lsacchrp | L-Saccharopine | Mitochondria |
| lys-L | L-Lysine | Cytosol |
| lys-L | L-Lysine | Extra-organism |
| lys-L | L-Lysine | Mitochondria |
| MAb_NS0 | Monoclonal antibody, NS0 | Cytosol |
| MAb_NS0 | Monoclonal antibody, NS0 | Extra-organism |
| mal-L | L-Malate | Cytosol |
| mal-L | L-Malate | Mitochondria |
| malcoa | Malonyl-CoA | Cytosol |
| mercppyr | Mercaptopyruvate | Cytosol |
| mercppyr | Mercaptopyruvate | Mitochondria |
| met-L | L-Methionine | Cytosol |
| met-L | L-Methionine | Extra-organism |
| methf | 5,10-Methenyltetrahydrofolate | Cytosol |
| methf | 5,10-Methenyltetrahydrofolate | Mitochondria |
| mev-R | (R)-Mevalonate | Cytosol |
| mi1p-D | 1D-myo-Inositol 1-phosphate | Cytosol |
| mlthf | 5,10-Methylenetetrahydrofolate | Cytosol |
| mlthf | 5,10-Methylenetetrahydrofolate | Mitochondria |
| mmal | Methylmalonate | Cytosol |
| mmal | Methylmalonate | Mitochondria |
| mmalsa-S | (S)-Methylmalonate semialdehyde | Cytosol |
| mmalsa-S | (S)-Methylmalonate semialdehyde | Mitochondria |
| mmcoa-R | (R)-Methylmalonyl-CoA | Mitochondria |
| mmcoa-S | (S)-Methylmalonyl-CoA | Mitochondria |
| na1 | Sodium | Cytosol |
| na1 | Sodium | Extra-organism |
| nad | Nicotinamide adenine dinucleotide | Cytosol |
| nad | Nicotinamide adenine dinucleotide | Endoplasmic Reticulum |
| nad | Nicotinamide adenine dinucleotide | Mitochondria |
| nadh | Nicotinamide adenine dinucleotide - reduced | Cytosol |
| nadh | Nicotinamide adenine dinucleotide - reduced | Endoplasmic Reticulum |
| nadh | Nicotinamide adenine dinucleotide - reduced | Mitochondria |
| nadp | Nicotinamide adenine dinucleotide phosphate | Cytosol |
| nadp | Nicotinamide adenine dinucleotide phosphate | Endoplasmic Reticulum |
| nadp | Nicotinamide adenine dinucleotide phosphate | Mitochondria |
| nadph | Nicotinamide adenine dinucleotide phosphate - reduced | Cytosol |
| nadph | Nicotinamide adenine dinucleotide phosphate - reduced | Endoplasmic Reticulum |
| nadph | Nicotinamide adenine dinucleotide phosphate - reduced | Mitochondria |
| nh4 | Ammonium | Cytosol |
| nh4 | Ammonium | Extra-organism |
| nh4 | Ammonium | Mitochondria |
| nh4 | Ammonium | Peroxisome |
| o2 | O2 | Cytosol |

TABLE 22-continued

Reactions and Metabolites in NS0 Model

| | | |
|---|---|---|
| o2 | O2 | Endoplasmic Reticulum |
| o2 | O2 | Extra-organism |
| o2 | O2 | Mitochondria |
| o2 | O2 | Peroxisome |
| oaa | Oxaloacetate | Cytosol |
| oaa | Oxaloacetate | Mitochondria |
| oaa | Oxaloacetate | Peroxisome |
| ocdca | octadecanoate (n-C18:0) | Cytosol |
| ocdcea | octadecenoate (n-C18:1) | Cytosol |
| ocdcya | octadecdienoate (n-C18:2) | Cytosol |
| ocdycacoa | octadecadienoyl-CoA (n-C18:2CoA) | Cytosol |
| octa | octanoate | Cytosol |
| odecoa | Octadecenoyl-CoA (n-C18:1CoA) | Cytosol |
| orn-L | L-Ornithine | Cytosol |
| orn-L | L-Ornithine | Mitochondria |
| orot | Orotate | Cytosol |
| orot5p | Orotidine 5'-phosphate | Cytosol |
| pa__Mmu__Hyb | Phosphatidate, Hybridoma | Cytosol |
| pa__Mmu__Hyb | Phosphatidate, Hybridoma | Mitochondria |
| pan4p | Pantetheine 4'-phosphate | Cytosol |
| pc__Mmu__Hyb | Phosphatidylcholine, Hybridoma | Cytosol |
| pe__Mmu__Hyb | Phosphatidylethanolamine, Hybridoma | Cytosol |
| pe__Mmu__Hyb | Phosphatidylethanolamine, Hybridoma | Mitochondria |
| pep | Phosphoenolpyruvate | Cytosol |
| pep | Phosphoenolpyruvate | Mitochondria |
| pg__Mmu__Hyb | Phosphatidylglycerol, Hybridoma | Cytosol |
| pg__Mmu__Hyb | Phosphatidylglycerol, Hybridoma | Mitochondria |
| pgp__Mmu__Hyb | Phosphatidylglycerophosphate, Hybridoma | Mitochondria |
| phe-L | L-Phenylalanine | Cytosol |
| phe-L | L-Phenylalanine | Extra-organism |
| phe-L | L-Phenylalanine | Mitochondria |
| phpyr | Phenylpyruvate | Cytosol |
| phpyr | Phenylpyruvate | Mitochondria |
| pi | Phosphate | Cytosol |
| pi | Phosphate | Endoplasmic Reticulum |
| pi | Phosphate | Extra-organism |
| pi | Phosphate | Mitochondria |
| pino__Mmu__Hyb | phosphatidyl-1D-myo-inositol, Hybridoma | Cytosol |
| pmtcoa | Palmitoyl-CoA (n-C16:0CoA) | Cytosol |
| pmtcoa | Palmitoyl-CoA (n-C16:0CoA) | Endoplasmic Reticulum |
| pmtcrn | L-Palmitoylcarnitine (C16:0Crn) | Cytosol |
| pmtcrn | L-Palmitoylcarnitine (C16:0Crn) | Endoplasmic Reticulum |
| pnto-R | (R)-Pantothenate | Cytosol |
| pnto-R | (R)-Pantothenate | Extra-organism |
| ppcoa | Propanoyl-CoA (C3:0CoA) | Mitochondria |
| ppi | Diphosphate | Cytosol |
| ppi | Diphosphate | Endoplasmic Reticulum |
| ppi | Diphosphate | Mitochondria |
| pram | 5-Phospho-beta-D-ribosylamine | Cytosol |
| pro-L | L-Proline | Cytosol |
| pro-L | L-Proline | Extra-organism |
| pro-L | L-Proline | Mitochondria |
| prpp | 5-Phospho-alpha-D-ribose 1-diphosphate | Cytosol |
| ps__Mmu__Hyb | Phosphatidylserine, Hybridoma | Cytosol |
| ps__Mmu__Hyb | Phosphatidylserine, Hybridoma | Mitochondria |
| pser-L | O-Phospho-L-serine | Cytosol |
| ptrc | Putrescine | Cytosol |
| pyr | Pyruvate | Cytosol |
| pyr | Pyruvate | Mitochondria |
| pyr | Pyruvate | Peroxisome |
| qh2 | Ubiquinol | Mitochondria |
| quln | Quinolinate | Cytosol |
| r1p | alpha-D-Ribose 1-phosphate | Cytosol |
| r5p | alpha-D-Ribose 5-phosphate | Cytosol |
| rib-D | D-Ribose | Cytosol |
| ru5p-D | D-Ribulose 5-phosphate | Cytosol |
| s7p | Sedoheptulose 7-phosphate | Cytosol |
| sarcs | Sarcosine | Cytosol |
| sarcs | Sarcosine | Peroxisome |
| ser-L | L-Serine | Cytosol |

TABLE 22-continued

Reactions and Metabolites in NS0 Model

| | | |
|---|---|---|
| ser-L | L-Serine | Endoplasmic Reticulum |
| ser-L | L-Serine | Extra-organism |
| ser-L | L-Serine | Mitochondria |
| so3 | Sulfite | Cytosol |
| so3 | Sulfite | Extra-organism |
| so3 | Sulfite | Mitochondria |
| sphgmy_Mmu_Hyb | Sphingomyelin, Hybridoma | Cytosol |
| sphgn | Sphinganine | Endoplasmic Reticulum |
| spyr | 3-Sulfinylpyruvate | Cytosol |
| spyr | 3-Sulfinylpyruvate | Mitochondria |
| sql | Squalene | Endoplasmic Reticulum |
| Ssq23epx | (S)-Squalene-2,3-epoxide | Endoplasmic Reticulum |
| strcoa | Stearyl-CoA (n-C18:0CoA) | Cytosol |
| succ | Succinate | Mitochondria |
| succoa | Succinyl-CoA | Mitochondria |
| sucsal | Succinic semialdehyde | Mitochondria |
| tcys | Thiocysteine | Cytosol |
| tdcoa | Tetradecanoyl-CoA (n-C14:0CoA) | Cytosol |
| thbpt | Tetrahydrobiopterin | Cytosol |
| thf | 5,6,7,8-Tetrahydrofolate | Cytosol |
| thf | 5,6,7,8-Tetrahydrofolate | Mitochondria |
| thr-L | L-Threonine | Cytosol |
| thr-L | L-Threonine | Extra-organism |
| trdox | Oxidized thioredoxin | Cytosol |
| trdrd | Reduced thioredoxin | Cytosol |
| trp-L | L-Tryptophan | Cytosol |
| trp-L | L-Tryptophan | Extra-organism |
| tsul | Thiosulfate | Cytosol |
| tsul | Thiosulfate | Mitochondria |
| ttdca | tetradecanoate (C14:0) | Cytosol |
| tyr-L | L-Tyrosine | Cytosol |
| tyr-L | L-Tyrosine | Extra-organism |
| tyr-L | L-Tyrosine | Mitochondria |
| ubq | Ubiquinone | Mitochondria |
| udp | UDP | Cytosol |
| udpg | UDPglucose | Cytosol |
| ump | UMP | Cytosol |
| urcan | Urocanate | Cytosol |
| urea | Urea | Cytosol |
| urea | Urea | Extra-organism |
| urea | Urea | Mitochondria |
| uri | Uridine | Cytosol |
| utp | UTP | Cytosol |
| val-L | L-Valine | Cytosol |
| val-L | L-Valine | Extra-organism |
| val-L | L-Valine | Mitochondria |
| xanth | Xanthurenate | Cytosol |
| xmp | Xanthosine 5'-phosphate | Cytosol |
| xu5p-D | D-Xylulose 5-phosphate | Cytosol |
| zym_int2 | zymosterone | Endoplasmic Reticulum |
| zymst | Zymosterol | Endoplasmic Reticulum |

TABLE 23

Reactions and Metabolites in CHO Model

| Rxn Abbreviation | Equation | EC Number |
|---|---|---|
| 2OXOADPTm | 2oxoadp[c] + akg[m] <==> 2oxoadp[m] + akg[c] | |
| 3DSPHR | [c]: 3dsphgn + h + nadph --> nadp + sphgn | 1.1.1.102 |
| 3SALAASPm | 3sala[m] + asp-L[c] <==> 3sala[c] + asp-L[m] | |
| 4ABUTtm | 4abut[c] <==> 4abut[m] | |
| 5AOPtm | 5aop[c] <==> 5aop[m] | |
| 6PGCter | 6pgc[c] <==> 6pgc[r] | |
| AASAD3m | [m]: ampsal + h2o + nad --> 2aadp + (2) h + nadh | 1.2.1.31 |
| ABTArm | [m]: 4abut + akg <==> glu-L + sucsal | 2.6.1.19 |

TABLE 23-continued

Reactions and Metabolites in CHO Model

| | | |
|---|---|---|
| ABUTD | [c]: 4abutn + h2o + nad --> 4abut + (2) h + nadh | 1.2.1.19 |
| ACACT10rm | [m]: 2maacoa + coa <==> accoa + ppcoa | 2.3.1.16 |
| ACACT1r | [c]: (2) accoa <==> aacoa + coa | 2.3.1.9 |
| ACACT1rm | [m]: (2) accoa <==> aacoa + coa | 2.3.1.9 |
| ACACt2m | acac[c] + h[c] <==> acac[m] + h[m] | |
| ACAT_CHO | [c]: chsterol + (0.001) facoa_avg_CHO --> (0.001) cholse_CHO + coa | 2.3.1.26 |
| ACCOAC | [c]: accoa + atp + hco3 --> adp + h + malcoa + pi | 6.4.1.2 |
| ACGK_CHO | [c]: atp + (0.001) mglyc_CHO --> (0.001) 1ag3p_CHO + adp + h | |
| ACMUCD | [c]: acmucsal + h --> amucsal + co2 | 4.1.1.45 |
| ACOAD1m | [m]: fad + ivcoa <==> 3mb2coa + fadh2 | 1.3.99.3 |
| ACOAD2m | [m]: fad + ibcoa <==> 2mp2coa + fadh2 | 1.3.99.3 |
| ACOAD3m | [m]: 2mbcoa + fad <==> 2mb2coa + fadh2 | 1.3.99.3 |
| ACONT | [c]: cit <==> icit | 4.2.1.3 |
| ACONTm | [m]: cit <==> icit | 4.2.1.3 |
| ADK1 | [c]: amp + atp <==> (2) adp | 2.7.4.3 |
| ADK1m | [m]: amp + atp <==> (2) adp | 2.7.4.3 |
| ADMDCi | [c]: amet + h --> ametam + co2 | 4.1.1.50 |
| ADNK1 | [c]: adn + atp --> adp + amp + h | 2.7.1.20 |
| ADSL1r | [c]: dcamp <==> amp + fum | 4.3.2.2 |
| ADSL2r | [c]: 25aics <==> aicar + fum | 4.3.2.2 |
| ADSS | [c]: asp-L + gtp + imp --> dcamp + gdp + (2) h + pi | 6.3.4.4 |
| AGAT_CHO | [c]: (0.001) 1ag3p_CHO + (0.025) arachdcoa + (0.016) clpndcoa + (0.01) cvncoa + (0.002) ecsacoa + (0.003) ecspecoa + (0.004) estcoa + (0.064) hdcoa + (0.007) lgnccoa + (0.003) lnlecoa + (0.008) nrvnccoa + (0.042) ocdycacoa + (0.404) odecoa + (0.253) pmtcoa + (0.13) strcoa + (0.029) tdcoa --> coa + (0.001) pa_CHO | 2.3.1.51 |
| AGMTm | [m]: agm + h2o --> ptrc + urea | 3.5.3.11 |
| AHC | [c]: ahcys + h2o <==> adn + hcys-L | 3.3.1.1 |
| AICART | [c]: 10fthf + aicar <==> fprica + thf | 2.1.2.3 |
| AIRCr | [c]: air + co2 <==> 5aizc + h | 4.1.1.21 |
| AKBDHm | [m]: 2obut + coa + nad --> co2 + nadh + ppcoa | |
| AKBtm | 2obut[m] <==> 2obut[c] | |
| AKGD2m | [m]: 2oxoadp + coa + nad --> co2 + nadh + glutcoa + nadh | |
| AKGDm | [m]: akg + coa + nad --> co2 + nadh + succoa | |
| ALA_Lt6 | ala-L[e] + h[e] <==> ala-L[c] + h[c] | |
| ALASm | [m]: gly + h + succoa --> 5aop + co2 + coa | 2.3.1.37 |
| ALATA_L | [c]: akg + ala-L <==> glu-L + pyr | 2.6.1.2 |
| ALDD4xm | [m]: h2o + mmalsa-S + nad --> (2) h + mmal + nadh | 1.2.1.3 |
| ALDOX1 | [c]: h2o + mmalsa-S + o2 --> h + h2o2 + mmal | 1.2.3.1 |
| AMCOXO | [c]: 2amuc + h + h2o + nadph --> 2oxoadp + nadp + nh4 | |
| AMIOX6 | [c]: h2o + o2 + ptrc --> 4abutn + h2o2 + nh4 | 1.4.3.6 |
| AMUCD | [c]: amucsal + h2o + nad --> 2amuc + (2) h + nadh | 1.2.1.32 |
| ARACHDAtr | arachda[e] <==> arachda[c] | |
| ARACHt | ecsa[e] <==> ecsa[c] | |
| ARGDCm | [m]: arg-L + h --> agm + co2 | 4.1.1.19 |
| ARGSL | [c]: argsuc <==> arg-L + fum | 4.3.2.1 |
| ARGSS | [c]: asp-L + atp + citr-L --> amp + argsuc + h + ppi | 6.3.4.5 |
| ARGt3m | arg-L[c] + h[m] <==> arg-L[m] + h[c] | |
| ARGtr | arg-L[e] <==> arg-L[c] | |
| ASNN | [c]: asn-L + h2o --> asp-L + nh4 | 3.5.1.1 |
| ASNS1 | [c]: asp-L + atp + gln-L + h2o --> amp + asn-L + glu-L + h + ppi | 6.3.5.4 |
| ASNt4r | asn-L[e] + na1[e] <==> asn-L[c] + na1[c] | |
| ASPCTr | [c]: asp-L + cbp <==> cbasp + h + pi | 2.1.3.2 |
| ASPt4 | asp-L[c] + na1[c] <==> asp-L[e] + na1[e] | |
| ASPTA1 | [c]: akg + asp-L <==> glu-L + oaa | 2.6.1.1 |
| ASPTA1m | [m]: akg + asp-L <==> glu-L + oaa | 2.6.1.1 |
| ASPTA3 | [c]: 3sala + akg --> glu-L + spyr | 2.6.1.1 |
| ASPTA4 | [c]: akg + cys-L <==> glu-L + mercppyr | 2.6.1.1 |
| ATP/ADPtm | adp[c] + atp[m] <==> adp[m] + atp[c] | |
| ATP/ADPtp | adp[c] + atp[x] <==> adp[x] + atp[c] | |
| ATPM | [c]: atp + h2o --> adp + h + pi | 3.6.1.15 |
| ATPS | atp[c] + h2o[c] --> adp[c] + h[e] + pi[c] | 3.6.3.6 |
| ATPS4m | adp[m] + (4) h[c] + pi[m] --> atp[m] + (3) h[m] + h2o[m] | 3.6.3.14 |

TABLE 23-continued

Reactions and Metabolites in CHO Model

| | | |
|---|---|---|
| C14STRer | [r]: 44mctr + h + nadph --> 44mzym + nadp | 1.3.1.70 |
| C3STDH1xer | [r]: 4mzym_int1 + nad --> 4mzym_int2 + co2 + nadh | 1.1.1.170 |
| C3STDH1yer | [r]: 4mzym_int1 + nadp --> 4mzym_int2 + co2 + nadph | 1.1.1.170 |
| C3STKR2er | [r]: h + nadph + zym_int2 --> nadp + zymst | 1.1.1.270 |
| C4STMO1er | [r]: 44mzym + (2) h + (3) nadph + (3) o2 --> 4mzym_int1 + (4) h2o + (3) nadp | 1.14.13.72 |
| C4STMO2xer | [r]: 4mzym_int2 + nad + o2 --> co2 + h + nadh + zym_int2 | 1.14.13.72 |
| C4STMO2yer | [r]: 4mzym_int2 + nadp + o2 --> co2 + h + nadph + zym_int2 | 1.14.13.72 |
| CAT | [c]: (2) h2o2 --> (2) h2o + o2 | 1.11.1.6 |
| CATm | [m]: (2) h2o2 --> (2) h2o + o2 | 1.11.1.6 |
| CATp | [x]: (2) h2o2 --> (2) h2o + o2 | 1.11.1.6 |
| CBPS | [c]: (2) atp + gln-L + h2o + hco3 --> (2) adp + cbp + glu-L + (2) h + pi | 6.3.5.5 |
| CBPSAm | [m]: (2) atp + co2 + h2o + nh4 --> (2) adp + cbp + (3) h + pi | 6.3.4.16 |
| CDO | [c]: cys-L + o2 --> 3sala | 1.13.11.20 |
| CDPDGPm_CHO | [m]: (0.001) cdpdag_CHO + glyc3p <==> cmp + h + (0.001) pgp_CHO | 2.7.8.8 |
| CERPT2_CHO | [c]: (0.001) cer_CHO + h + (0.001) pc_CHO --> (0.001) 12dgr_CHO + (0.001) sphgmy_CHO | 2.7.8.27 |
| CERS_CHO | [c]: (0.001) facoa_avg_CHO + sphgn --> coa + (0.001) dcer_CHO + h | 2.3.1.24 |
| CHLPCTD | [c]: cholp + ctp + h --> cdpchol + ppi | 2.7.7.15 |
| CHOLK | [c]: atp + chol --> adp + cholp + h | 2.7.1.32 |
| CHOLSE_CHO | [c]: (0.025) arachda + chsterol + (0.01) dcshea + (0.016) dcspea + (0.002) ecsa + (0.003) ecspea + (0.004) ecstea + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca <==> (0.001) cholse_CHO + h2o | 6.2.1.3 |
| CHOLtu | chol[e] <==> chol[c] | |
| CHSTEROLter | chsterol[c] <==> chsterol[r] | |
| CHSTNIer | [r]: zymst <==> cholsd | 5.3.3.5 |
| CITL2 | [c]: atp + cit + coa --> accoa + adp + oaa + pi | 4.1.3.8 |
| CITMALtm | cit[c] + h[c] + mal-L[m] <==> cit[m] + h[m] + mal-L[c] | |
| CLPNtm_CHO | clpn_CHO[m] <==> clpn_CHO[c] | |
| CLSm_CHO | [m]: (0.001) cdpdag_CHO + (0.001) pg_CHO --> (0.001) clpn_CHO + cmp + h | |
| CO2t | co2[e] <==> co2[c] | |
| CO2ter | co2[c] <==> co2[r] | |
| CO2tm | co2[c] <==> co2[m] | |
| CO2tp | co2[c] <==> co2[x] | |
| CPPPGO | [c]: cpppg3 + (2) h + o2 --> (2) co2 + (2) h2o + pppg9 | 1.3.3.3 |
| CRNAR | [c]: arachdcoa + crn <==> arachdcrn + coa | 2.3.1.21 |
| CRNARm | [m]: arachdcoa + crn <==> arachdcrn + coa | 2.3.1.21 |
| CRNARtm | arachdcrn[c] + crn[m] <==> arachdcrn[m] + crn[c] | |
| CRNDSH | [c]: crn + cvncoa <==> coa + cvncrn | 2.3.1.21 |
| CRNDSHm | [m]: crn + cvncoa <==> coa + cvncrn | 2.3.1.21 |
| CRNDSHtm | crn[m] + cvncrn[c] <==> crn[c] + cvncrn[m] | |
| CRNDSP | [c]: clpndcoa + crn <==> clpndcrn + coa | 2.3.1.21 |
| CRNDSPm | [m]: clpndcoa + crn <==> clpndcrn + coa | 2.3.1.21 |
| CRNDSPtm | clpndcrn[c] + crn[m] <==> clpndcrn[m] + crn[c] | |
| CRNESP | [c]: crn + ecspecoa <==> coa + ecspecrn | 2.3.1.21 |
| CRNESPm | [m]: crn + ecspecoa <==> coa + ecspecrn | 2.3.1.21 |
| CRNESPtm | crn[m] + ecspecrn[c] <==> crn[c] + ecspecrn[m] | |
| CRNEST | [c]: crn + estcoa <==> coa + estcrn | 2.3.1.21 |
| CRNESTm | [m]: crn + estcoa <==> coa + estcrn | 2.3.1.21 |
| CRNESTtm | crn[m] + estcrn[c] <==> crn[c] + estcrn[m] | |
| CRNET | [c]: crn + ecsacoa <==> coa + ecsacrn | 2.3.1.21 |
| CRNETm | [m]: coa + ecsacrn <==> crn + ecsacoa | 2.3.1.21 |
| CRNETtm | crn[m] + ecsacrn[c] <==> crn[c] + ecsacrn[m] | |
| CRNHD | [c]: crn + hdcoa <==> coa + hdcecrn | 2.3.1.21 |
| CRNHDm | [m]: crn + hdcoa <==> coa + hdcecrn | 2.3.1.21 |
| CRNHDtm | crn[m] + hdcecrn[c] <==> crn[c] + hdcecrn[m] | |
| CRNLN | [c]: crn + lnlecoa <==> coa + lnlecrn | 2.3.1.21 |
| CRNLNm | [m]: crn + lnlecoa <==> coa + lnlecrn | 2.3.1.21 |
| CRNLNtm | crn[m] + lnlecrn[c] <==> crn[c] + lnlecrn[m] | |
| CRNNR | [c]: crn + nrvnccoa <==> coa + nrvncrn | 2.3.1.21 |

TABLE 23-continued

Reactions and Metabolites in CHO Model

| | | |
|---|---|---|
| CRNNRm | [m]: crn + nrvnccoa <==> coa + nrvnccrn | 2.3.1.21 |
| CRNNRtm | crn[m] + nrvnccrn[c] <==> crn[c] + nrvnccrn[m] | |
| CRNOC | [c]: crn + ocdycacoa <==> coa + ocdycacrn | 2.3.1.21 |
| CRNOCm | [m]: crn + ocdycacoa <==> coa + ocdycacrn | 2.3.1.21 |
| CRNOCtm | crn[m] + ocdycacrn[c] <==> crn[c] + ocdycacrn[m] | |
| CRNOD | [c]: crn + odecoa <==> coa + odecrn | 2.3.1.21 |
| CRNODm | [m]: crn + odecoa <==> coa + odecrn | 2.3.1.21 |
| CRNODtm | crn[m] + odecrn[c] <==> crn[c] + odecrn[m] | |
| CRNOT | [c]: crn + strcoa <==> coa + strcrn | 2.3.1.21 |
| CRNOTm | [m]: coa + strcrn <==> crn + strcoa | 2.3.1.21 |
| CRNOTtm | crn[m] + strcrn[c] <==> crn[c] + strcrn[m] | |
| CRNPT | [c]: crn + pmtcoa <==> coa + pmtcrn | 2.3.1.21 |
| CRNPTm | [m]: coa + pmtcrn <==> crn + pmtcoa | 2.3.1.21 |
| CRNPTtm | crn[m] + pmtcrn[c] <==> crn[c] + pmtcrn[m] | |
| CRNTC | [c]: crn + lgnccoa <==> coa + lgnccrn | 2.3.1.21 |
| CRNTCm | [m]: crn + lgnccoa <==> coa + lgnccrn | 2.3.1.21 |
| CRNTCtm | crn[m] + lgnccrn[c] <==> crn[c] + lgnccrn[m] | |
| CRNTDm | [m]: coa + tdcrn <==> crn + tdcoa | 2.3.1.21 |
| CRNTDT | [c]: crn + tdcoa <==> coa + tdcrn | 2.3.1.21 |
| CRNTTtm | crn[m] + tdcrn[c] <==> crn[c] + tdcrn[m] | |
| CSm | [m]: accoa + h2o + oaa --> cit + coa + h | 4.1.3.7 |
| CSNATm | [m]: acrn + coa <==> accoa + crn | 2.3.1.7 |
| CSNATr | [c]: accoa + crn <==> acrn + coa | 2.3.1.7 |
| CSNATtm | acrn[c] + crn[c] <==> acrn[m] + crn[m] | |
| CTPS1 | [c]: atp + nh4 + utp --> adp + ctp + (2) h + pi | 6.3.4.2 |
| CTPS2 | [c]: atp + gln-L + h2o + utp --> adp + ctp + glu-L + (2) h + pi | 6.3.4.2 |
| CYOO4m | (4) focytcc[m] + (8) h[m] + o2[m] --> (4) ficytcc[m] + (4) h[c] + (2) h2o[m] | 1.9.3.1 |
| CYOR4m-ubq10 | (2) ficytcc[m] + (2) h[m] + q10h2[m] --> (2) focytcc[m] + (4) h[c] + ubq10[m] | 1.10.2.2 |
| CYSt4r | cys-L[e] + na1[e] <==> cys-L[c] + na1[c] | |
| CYSTGL | [c]: cysth-L + h2o --> 2obut + cys-L + nh4 | 4.4.1.1 |
| CYSTS | [c]: hcys-L + ser-L --> cysth-L + h2o | 4.2.1.22 |
| CYTK1 | [c]: atp + cmp <==> adp + cdp | 2.7.4.14 |
| CYTK1m | [m]: atp + cmp <==> adp + cdp | 2.7.4.14 |
| DAGCPT_CHO | [c]: (0.001) 12dgr_CHO + cdpchol --> cmp + h + (0.001) pc_CHO | 2.7.8.2 |
| DAGH_CHO | [c]: (0.001) 12dgr_CHO + h2o --> (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.001) mglyc_CHO + (0.008) nrvnc + (0.13) ocdca + (0.404) ocdcea + (0.042) ocdcya + (0.007) ttc + (0.029) ttdca | 6.2.1.3 |
| DAGK_CHO | [c]: (0.001) 12dgr_CHO + atp --> adp + h + (0.001) pa_CHO | 2.7.1.107 |
| DAGPYP_CHO | [c]: h2o + (0.001) pa_CHO --> (0.001) 12dgr_CHO + pi | 3.1.3.4 |
| DASYN_CHO | [c]: ctp + h + (0.001) pa_CHO <==> (0.001) cdpdag_CHO + ppi | 2.7.7.41 |
| DASYNm_CHO | [m]: ctp + h + (0.001) pa_CHO <==> (0.001) cdpdag_CHO + ppi | 2.7.7.41 |
| DCERDS_CHO | [c]: (0.001) dcer_CHO + h + nadph + o2 --> (0.001) cer_CHO + (2) h2o + nadp | |
| DCSHEAtr | dcshea[e] <==> dcshea[c] | |
| DCSPEAtr | dcspea[e] <==> dcspea[c] | |
| DESAT161 | [c]: h + nadph + o2 + pmtcoa --> (2) h2o + hdcoa + nadp | 1.14.19.1 |
| DESAT181 | [c]: h + nadph + o2 + strcoa --> (2) h2o + nadp + odecoa | 1.14.19.1 |
| DESAT183 | [c]: h + nadph + o2 + ocdycacoa --> (2) h2o + lnlecoa + nadp | 1.14.19.1 |
| DESAT184 | [c]: h + lnlecoa + nadph + o2 --> (2) h2o + nadp + strdnccoa | 1.14.19.3 |
| DESAT204 | [c]: estcoa + h + nadph + o2 --> arachdcoa + (2) h2o + nadp | 1.14.19.1 |
| DESAT205g | [c]: arachdcoa + h + nadph + o2 --> ecspecoa + (2) h2o + nadp | 1.14.19.1 |
| DESAT226g | [c]: clpndcoa + h + nadph + o2 --> cvncoa + (2) h2o + nadp | 1.14.19.1 |
| DESAT241 | [c]: h + lgnccoa + nadph + o2 --> (2) h2o + nadp + nrvnccoa | 1.14.19.1 |
| DHCR71er | [r]: ddsmsterol + h + nadph --> dsmsterol + nadp | 1.3.1.21 |

TABLE 23-continued

Reactions and Metabolites in CHO Model

| | | |
|---|---|---|
| DHCR72er | [r]: 7dhchsterol + h + nadph --> chsterol + nadp | 1.3.1.21 |
| DHFOR2 | [c]: dhf + nadp <==> fol + nadph | 1.5.1.3 |
| DHFOR3 | [c]: fol + h + (2) nadph <==> (2) nadp + thf | 1.5.1.3 |
| DHFR | [c]: dhf + h + nadph <==> nadp + thf | 1.5.1.3 |
| DHORD3m-ubq10 | dhor-S[c] + ubq10[m] <==> orot[c] + q10h2[m] | 1.3.99.11 |
| DHORTS | [c]: dhor-S + h2o <==> cbasp + h | 3.5.2.3 |
| DHPRx | [c]: dhbpt + h + nadh <==> nad + thbpt | 1.5.1.34 |
| DMATT | [c]: dmpp + ipdp --> grdp + ppi | 2.5.1.1 |
| DMPPtp | dmpp[x] <==> dmpp[c] | |
| DPCOAK | [c]: atp + dpcoa --> adp + coa + h | 2.7.1.24 |
| DPMVDp | [x]: 5dpmev + atp --> adp + co2 + ipdp + pi | 4.1.1.33 |
| DTMPK | [c]: atp + dtmp <==> adp + dtdp | 2.7.4.9 |
| EBP2rer | [r]: zymstnl <==> lathost | 5.3.3.5 |
| ECOAH1am | [m]: 3hbycoa <==> b2coa + h2o | 4.2.1.17 |
| ECOAH2m | [m]: 2mp2coa + h2o <==> hibcoa | 4.2.1.17 |
| ECOAH3m | [m]: 2mb2coa + h2o <==> 3hmbcoa | 4.2.1.17 |
| ECSPEAtr | ecspea[e] <==> ecspea[c] | |
| ECSTEAt | ecstea[e] <==> ecstea[c] | |
| ENO | [c]: 2pg <==> h2o + pep | 4.2.1.11 |
| ETAPCTr | [c]: ctp + ethap + h <==> cdpea + ppi | 2.7.7.14 |
| ETHAMK | [c]: atp + etha --> adp + ethap + h | 2.7.1.82 |
| ETHAPT_CHO | [c]: (0.01) 12dgr_CHO + cdpea <==> cmp + h + (0.01) pe_CHO | 2.7.8.1 |
| ETHAt | etha[e] <==> etha[c] | |
| FACOAavg_CHO | [c]: (0.025) arachda + atp + coa + (0.01) dcshea + (0.016) dcspea + (0.002) ecsa + (0.003) ecspea + (0.004) ecstea + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca <==> amp + (0.001) facoa_avg_CHO + ppi | 6.2.1.3 |
| FACOAL140 | [c]: atp + coa + ttdca <==> amp + ppi + tdcoa | 6.2.1.3 |
| FACOAL160 | [c]: atp + coa + hdca <==> amp + pmtcoa + ppi | 6.2.1.3 |
| FACOAL161 | [c]: atp + coa + hdcea <==> amp + hdcoa + ppi | 6.2.1.3 |
| FACOAL180 | [c]: atp + coa + ocdca <==> amp + ppi + strcoa | 6.2.1.3 |
| FACOAL181 | [c]: atp + coa + ocdcea <==> amp + odecoa + ppi | 6.2.1.3 |
| FACOAL182 | [c]: atp + coa + ocdcya <==> amp + ocdycacoa + ppi | 6.2.1.3 |
| FACOAL183 | [c]: atp + coa + lnlne <==> amp + lnlecoa + ppi | 6.2.1.3 |
| FACOAL200 | [c]: atp + coa + ecsa <==> amp + ecsacoa + ppi | 6.2.1.3 |
| FACOAL203 | [c]: atp + coa + ecstea <==> amp + estcoa + ppi | 6.2.1.3 |
| FACOAL204 | [c]: arachda + atp + coa <==> amp + arachdcoa + ppi | 6.2.1.3 |
| FACOAL205 | [c]: atp + coa + ecspea <==> amp + ecspecoa + ppi | 6.2.1.3 |
| FACOAL225 | [c]: atp + coa + dcspea <==> amp + clpndcoa + ppi | 6.2.1.3 |
| FACOAL226 | [c]: atp + coa + dcshea <==> amp + cvncoa + ppi | 6.2.1.3 |
| FACOAL240 | [c]: atp + coa + ttc <==> amp + lgnccoa + ppi | 6.2.1.3 |
| FACOAL241 | [c]: atp + coa + nrvnc <==> amp + nrvnccoa + ppi | 6.2.1.3 |
| FAEL203 | [c]: (5) h + lnlecoa + malcoa + (4) nadph + o2 --> co2 + coa + estcoa + (3) h2o + (4) nadp | 2.3.1.86 |
| FAEL204g | [c]: (5) h + malcoa + (4) nadph + o2 + strdnccoa --> arachdcoa + co2 + coa + (3) h2o + (4) nadp | 2.3.1.86 |
| FAEL225 | [c]: ecspecoa + (5) h + malcoa + (4) nadph + o2 --> clpndcoa + co2 + coa + (3) h2o + (4) nadp | 2.3.1.86 |
| FALDtp | fald[c] <==> fald[x] | |
| FAOXC100m | [m]: coa + dccoa + fad + h2o + nad --> accoa + fadh2 + h + nadh + occoa | 1.3.99.3 |
| FAOXC120m | [m]: coa + ddcoa + fad + h2o + nad --> accoa + dccoa + fadh2 + h + nadh | 1.3.99.3 |
| FAOXC140m | [m]: coa + fad + h2o + nad + tdcoa --> accoa + ddcoa + fadh2 + h + nadh | 1.3.99.3 |
| FAOXC160m | [m]: coa + fad + h2o + nad + pmtcoa --> accoa + fadh2 + h + nadh + tdcoa | 1.3.99.3 |
| FAOXC161m | [m]: (7) coa + (6) fad + (7) h2o + hdcoa + (7) nad --> (8) accoa + (6) fadh2 + (7) h + (7) nadh | 1.3.99.3 |
| FAOXC180m | [m]: coa + fad + h2o + nad + strcoa --> accoa + fadh2 + h + nadh + pmtcoa | 1.3.99.3 |

TABLE 23-continued

Reactions and Metabolites in CHO Model

| | | |
|---|---|---|
| FAOXC181m | [m]: (8) coa + (7) fad + (8) h2o + (8) nad + odecoa --> (9) accoa + (7) fadh2 + (8) h + (8) nadh | 1.3.99.3 |
| FAOXC182 | [m]: (8) coa + (6) fad + (8) h2o + (8) nad + ocdycacoa --> (9) accoa + (6) fadh2 + (8) h + (8) nadh | 1.3.99.3 |
| FAOXC183m | [m]: (8) coa + (5) fad + (8) h2o + lnlecoa + (8) nad --> (9) accoa + (5) fadh2 + (8) h + (8) nadh | 1.3.99.3 |
| FAOXC200m | [m]: coa + ecsacoa + fad + h2o + nad --> accoa + fadh2 + h + nadh + strcoa | 1.3.99.3 |
| FAOXC203m | [m]: (9) coa + estcoa + (6) fad + (9) h2o + (9) nad --> (10) accoa + (6) fadh2 + (9) h + (9) nadh | 1.3.99.3 |
| FAOXC204 | [m]: arachdcoa + (9) coa + (5) fad + (9) h2o + (9) nad --> (10) accoa + (5) fadh2 + (9) h + (9) nadh | 1.3.99.3 |
| FAOXC205m | [m]: (9) coa + ecspecoa + (4) fad + (9) h2o + (9) nad --> (10) accoa + (4) fadh2 + (9) h + (9) nadh | 1.3.99.3 |
| FAOXC225m | [m]: clpndcoa + (10) coa + (5) fad + (10) h2o + (10) nad --> (11) accoa + (5) fadh2 + (10) h + (10) nadh | 1.3.99.3 |
| FAOXC226 | [m]: (10) coa + cvncoa + (4) fad + (10) h2o + (10) nad --> (11) accoa + (4) fadh2 + (10) h + (10) nadh | 1.3.99.3 |
| FAOXC240m | [m]: (2) coa + (2) fad + (2) h2o + lgnccoa + (2) nad --> (2) accoa + ecsacoa + (2) fadh2 + (2) h + (2) nadh | 1.3.99.3 |
| FAOXC241m | [m]: (11) coa + (10) fad + (11) h2o + (11) nad + nrvnccoa --> (12) accoa + (10) fadh2 + (11) h + (11) nadh | 1.3.99.3 |
| FAOXC40m | [m]: btcoa + coa + fad + h2o + nad --> (2) accoa + fadh2 + h + nadh | 1.3.99.3 |
| FAOXC60m | [m]: coa + fad + h2o + hxcoa + nad --> accoa + btcoa + fadh2 + h + nadh | 1.3.99.3 |
| FAOXC80m | [m]: coa + fad + h2o + nad + occoa --> accoa + fadh2 + h + hxcoa + nadh | 1.3.99.3 |
| FAS100 | [c]: (3) h + malcoa + (2) nadph + octa --> co2 + coa + dca + h2o + (2) nadp | 2.3.1.85 |
| FAS120 | [c]: dca + (3) h + malcoa + (2) nadph --> co2 + coa + ddca + h2o + (2) nadp | 2.3.1.85 |
| FAS140 | [c]: ddca + (3) h + malcoa + (2) nadph --> co2 + coa + h2o + (2) nadp + ttdca | 2.3.1.85 |
| FAS160 | [c]: (3) h + malcoa + (2) nadph + ttdca --> co2 + coa + h2o + hdca + (2) nadp | 2.3.1.85 |
| FAS180 | [c]: (3) h + hdca + malcoa + (2) nadph --> co2 + coa + h2o + (2) nadp + ocdca | 2.3.1.85 |
| FAS200 | [c]: (3) h + malcoa + (2) nadph + ocdca --> co2 + coa + ecsa + h2o + (2) nadp | 2.3.1.85 |
| FAS220 | [c]: ecsa + (3) h + malcoa + (2) nadph --> co2 + coa + dcsa + h2o + (2) nadp | 2.3.1.85 |
| FAS240 | [c]: dcsa + (3) h + malcoa + (2) nadph --> co2 + coa + h2o + (2) nadp + ttc | 2.3.1.85 |
| FAS80_L | [c]: accoa + (8) h + (3) malcoa + (6) nadph --> (3) co2 + (4) coa + (2) h2o + (6) nadp + octa | 2.3.1.85 |
| FBA | [c]: fdp <==> dhap + g3p | 4.1.2.13 |
| FBP | [c]: fdp + h2o --> f6p + pi | 3.1.3.11 |
| FCLTm | [m]: fe2 + ppp9 --> h + pheme | 4.99.1.1 |
| FE2trm | fe2[c] <==> fe2[m] | |
| FKYNH | [c]: Lfmkynr + h2o --> for + h + kynr-L | 3.5.1.9 |
| FldAct | [c]: fald + thf --> h2o + mlthf | |
| FMETDH | [c]: 10fthf + h2o + nadp --> co2 + h + nadph + thf | 1.5.1.6 |
| FOLt | fol[e] + h[e] <==> fol[c] + h[c] | |
| FORter | for[c] <==> for[r] | |
| FORTHFC | [c]: 5fthf + (2) h <==> methf + nh4 | 4.3.1.4 |
| FRDPter | frdp[c] <==> frdp[r] | |
| FTHFLm | [m]: atp + for + thf <==> 10fthf + adp + pi | 6.3.4.3 |
| FTHFLr | [c]: atp + for + thf <==> 10fthf + adp + pi | 6.3.4.3 |
| FUM | [c]: fum + h2o <==> mal-L | 4.2.1.2 |
| FUM2tm | fum[c] + mal-L[m] <==> fum[m] + mal-L[c] | |
| FUMACA | [c]: 4fumacac + h2o --> acac + fum + h | 3.7.1.2 |
| FUMm | [m]: fum + h2o <==> mal-L | 4.2.1.2 |
| G3PD1 | [c]: glyc3p + nad <==> dhap + h + nadh | 1.1.1.94 |
| G3PDcm | fad[m] + glyc3p[c] --> dhap[c] + fadh2[m] | 1.1.99.5 |
| G5SADs | [c]: glu5sa <==> 1pyr5c + h + h2o | |
| G5SADsm | [m]: glu5sa <==> 1pyr5c + h + h2o | |
| G5SDm | [m]: glu5p + h + nadph --> glu5sa + nadp + pi | 1.2.1.41 |

TABLE 23-continued

Reactions and Metabolites in CHO Model

| | | |
|---|---|---|
| G6PASEer | [r]: g6p + h2o --> glc-D + pi | 3.1.3.9 |
| G6PDH2er | [r]: g6p + nadp --> 6pgl + h + nadph | 1.1.1.49 |
| G6PDHy | [c]: g6p + nadp <==> 6pgl + h + nadph | 1.1.1.49 |
| G6Pter | g6p[c] <==> g6p[r] | |
| GACm | asp-L[m] + glu-L[c] + h[c] --> asp-L[c] + glu-L[m] + h[m] | |
| GALU | [c]: g1p + h + utp <==> ppi + udpg | 2.7.7.9 |
| GAPD | [c]: g3p + nad + pi <==> 13dpg + h + nadh | 1.2.1.12 |
| GARFTi | [c]: 10fthf + gar --> fgam + h + thf | 2.1.2.2 |
| GAT_CHO | [c]: (0.025) arachdcoa + (0.016) clpndcoa + (0.01) cvncoa + (0.002) ecsacoa + (0.003) ecspecoa + (0.004) estcoa + glyc3p + (0.064) hdcoa + (0.007) lgnccoa + (0.003) lnlecoa + (0.008) nrvnccoa + (0.042) ocdycacoa + (0.404) odecoa + (0.253) pmtcoa + (0.13) strcoa + (0.029) tdcoa --> (0.001) 1ag3p_CHO + coa | 2.3.1.15 |
| GCOADrm | [m]: fad + glutcoa + h <==> b2coa + co2 + fadh2 | 1.3.99.7 |
| GGTA | [c]: gthrd + h2o --> cgly + glu-L | 2.3.2.2 |
| GHMT | [c]: ser-L + thf <==> gly + h2o + mlthf | 2.1.2.1 |
| GHMT2m | [m]: ser-L + thf <==> gly + h2o + mlthf | 2.1.2.1 |
| GK1 | [c]: atp + gmp <==> adp + gdp | 2.7.4.8 |
| GL3Ptrm | glyc3p[c] <==> glyc3p[m] | |
| GLCP | [c]: glycogen + pi --> g1p | 2.4.1.1 |
| GLCt1r | glc-D[e] <==> glc-D[c] | |
| GLCter | glc-D[c] <==> glc-D[r] | |
| GLNS | [c]: atp + glu-L + nh4 --> adp + gln-L + h + pi | 6.3.1.2 |
| GLNt4r | gln-L[e] + na1[e] <==> gln-L[c] + na1[c] | |
| GLNtrm | gln-L[c] + h[c] <==> gln-L[m] + h[m] | |
| GLU5Km | [m]: atp + glu-L --> adp + glu5p | 2.7.2.11 |
| GLUCYSL | [c]: atp + cys-L + glu-L --> adp + glucys + h + pi | 6.3.2.2 |
| GLUDxm | [m]: glu-L + h2o + nad <==> akg + h + nadh + nh4 | 1.4.1.3 |
| GLUDym | [m]: glu-L + h2o + nadp <==> akg + h + nadph + nh4 | 1.4.1.3 |
| GLUFT | [c]: 5fthf + glu-L <==> forglu + thf | 2.1.2.5 |
| GLUNm | [m]: gln-L + h2o --> glu-L + nh4 | 3.5.1.2 |
| GLUPRT | [c]: gln-L + h2o + prpp --> glu-L + ppi + pram | 2.4.2.14 |
| GLUSAtm | glu5sa[c] <==> glu5sa[m] | |
| GLUt2m | glu-L[c] + h[c] <==> glu-L[m] + h[m] | |
| GLUt4 | glu-L[e] + na1[e] <==> glu-L[c] + na1[c] | |
| GLYATm | [m]: accoa + gly <==> 2aobut + coa | 2.3.1.29 |
| GLYCLm | [m]: gly + nad + thf --> co2 + mlthf + nadh + nh4 | 2.1.2.10 |
| GLYGS | [c]: udpg --> glycogen + h + udp | 2.4.1.11 |
| GLYt4r | gly[e] + na1[e] <==> gly[c] + na1[c] | |
| GLYtm | gly[c] <==> gly[m] | |
| GLYtp | gly[c] <==> gly[x] | |
| GMPS2 | [c]: atp + gln-L + h2o + xmp --> amp + glu-L + gmp + (2) h + ppi | 6.3.5.2 |
| GMTR | [c]: amet + gly --> ahcys + h + sarcs | 2.1.1.20 |
| GRTT | [c]: grdp + ipdp --> frdp + ppi | 2.5.1.10 |
| GTHO | [c]: gthox + h + nadph --> (2) gthrd + nadp | 1.8.1.7 |
| GTHP | [c]: (2) gthrd + h2o2 <==> gthox + (2) h2o | 1.11.1.9 |
| GTHSr | [c]: atp + glucys + gly <==> adp + gthrd + h + pi | 6.3.2.3 |
| GTPCI | [c]: gtp + h2o --> andt + for + h | 3.5.4.16 |
| H2O2tm | h2o2[c] <==> h2o2[m] | |
| H2O2tp | h2o2[c] <==> h2o2[x] | |
| H2Ot5 | h2o[e] <==> h2o[c] | |
| H2Oter | h2o[c] <==> h2o[r] | |
| H2Otm | h2o[c] <==> h2o[m] | |
| H2Otp | h2o[c] <==> h2o[x] | |
| HACD1m | [m]: aacoa + h + nadh <==> 3hbycoa + nad | 1.1.1.35 |
| HACD8m | [m]: 3hmbcoa + nad <==> 2maacoa + h + nadh | 1.1.1.178 |
| HANTHDOr | [c]: 3hanthrn + o2 <==> acmucsal | 1.13.11.6 |
| HCO3E | [c]: co2 + h2o <==> h + hco3 | 4.2.1.1 |
| HCO3Em | [m]: co2 + h2o <==> h + hco3 | 4.2.1.1 |
| HDCEAtr | hdcea[e] <==> hdcea[c] | |
| HEX1 | [c]: atp + glc-D --> adp + g6p + h | 2.7.1.2 |
| HGENDO | [c]: hgentis + o2 --> 4mlacac + h | 1.13.11.5 |
| HIBDm | [m]: 3hmp + nad <==> h + mmalsa-S + nadh | 1.1.1.31 |
| HIBHm | [m]: h2o + hibcoa --> 3hmp + coa + h | 3.1.2.4 |
| HISD1r | [c]: his-L <==> nh4 + urcan | 4.3.1.3 |
| HISt4r | his-L[e] + na1[e] <==> his-L[c] + na1[c] | |
| HMBS | [c]: h2o + (4) ppbng --> hmbil + (4) nh4 | 2.5.1.61 |

TABLE 23-continued

Reactions and Metabolites in CHO Model

| | | |
|---|---|---|
| HMGCOAR | [c]: coa + mev-R + (2) nadp <==> (2) h + hmgcoa + (2) nadph | 1.1.1.34 |
| HMGCOASi | [c]: aacoa + accoa + h2o --> coa + h + hmgcoa | 4.1.3.5 |
| HMGCOASim | [m]: aacoa + accoa + h2o --> coa + h + hmgcoa | 4.1.3.5 |
| HMGCOAtm | hmgcoa[c] <==> hmgcoa[m] | |
| HMGLm | [m]: hmgcoa --> acac + accoa | 4.1.3.4 |
| HPPDO1 | [c]: 34hpp + o2 --> co2 + hgentis | 1.13.11.27 |
| ICDHxm | [m]: icit + nad --> akg + co2 + nadh | 1.1.1.41 |
| ICDHy | [c]: icit + nadp <==> akg + co2 + nadph | 1.1.1.42 |
| ICDHym | [m]: icit + nadp --> akg + co2 + nadph | 1.1.1.42 |
| ILEt5m | ile-L[c] <==> ile-L[m] | |
| ILETAm | [m]: akg + ile-L <==> 3mop + glu-L | 2.6.1.42 |
| ILEtec | ile-L[e] <==> ile-L[c] | |
| IMPC | [c]: h2o + imp <==> fprica | 3.5.4.10 |
| IMPD | [c]: h2o + imp + nad --> h + nadh + xmp | 1.1.1.205 |
| INSTt2r | h[e] + inost[e] <==> h[c] + inost[c] | |
| IPDDIp | [x]: ipdp <==> dmpp | 5.3.3.2 |
| IPDPtp | ipdp[x] <==> ipdp[c] | |
| IZPN | [c]: 4izp + h2o --> forglu | 3.5.2.7 |
| KYNASE3 | [c]: h2o + hkyn --> 3hanthrn + ala-L + h | 3.7.1.3 |
| KYNMOr | [c]: h + kynr-L + nadph + o2 <==> h2o + hkyn + nadp | 1.14.13.9 |
| L-LACt2 | h[e] + lac-L[e] <==> h[c] + lac-L[c] | |
| LATHSTOxer | [r]: h + lathost + nadh + o2 --> 7dhchsterol + (2) h2o + nad | 1.14.21.6 |
| LATHSTOyer | [r]: h + lathost + nadph + o2 --> 7dhchsterol + (2) h2o + nadp | 1.14.21.6 |
| LDH_L | [c]: lac-L + nad <==> h + nadh + pyr | 1.1.1.27 |
| LEUTAm | [m]: akg + leu-L <==> 4mop + glu-L | 2.6.1.42 |
| LEUtec | leu-L[e] <==> leu-L[c] | |
| LEUtm | leu-L[c] <==> leu-L[m] | |
| LGNCt | ttc[e] <==> ttc[c] | |
| LNLNEtr | lnlne[e] <==> lnlne[c] | |
| LNS14DMer | [r]: (2) h + lanost + (3) nadph + (3) o2 --> 44mctr + for + (4) h2o + (3) nadp | 1.14.13.70 |
| LNSTLSer | [r]: Ssq23epx --> lanost | 5.4.99.7 |
| LSTO1er | [r]: cholsd + h + nadph + o2 --> ddsmsterol + (2) h2o + nadp | 1.14.21.6 |
| LYSt | lys-L[e] <==> lys-L[c] | |
| LYStm | h[m] + lys-L[c] <==> h[c] + lys-L[m] | |
| MAGH_CHO | [c]: h2o + (0.001) mglyc_CHO --> (0.025) arachda + (0.01) dcshea + (0.016) dcspea + (0.002) ecsa + (0.003) ecspea + (0.004) ecstea + glyc + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdc a | 6.2.1.3 |
| MALAKGtm | akg[m] + mal-L[c] <==> akg[c] + mal-L[m] | |
| MALOAtm | mal-L[m] + oaa[c] <==> mal-L[c] + oaa[m] | |
| MALtm | mal-L[c] + pi[m] <==> mal-L[m] + pi[c] | |
| MCCCm | [m]: 3mb2coa + atp + hco3 --> 3mgcoa + adp + h + pi | 6.4.1.4 |
| MCPST | [c]: mercppyr + so3 --> pyr + tsul | 2.8.1.2 |
| MDH | [c]: mal-L + nad <==> h + nadh + oaa | 1.1.1.37 |
| MDHm | [m]: mal-L + nad <==> h + nadh + oaa | 1.1.1.37 |
| ME1m | [m]: mal-L + nad --> co2 + nadh + pyr | 1.1.1.38 |
| ME2r | [c]: mal-L + nadp <==> co2 + nadph + pyr | 1.1.1.40 |
| ME2rm | [m]: mal-L + nadp <==> co2 + nadph + pyr | 1.1.1.40 |
| METAT | [c]: atp + h2o + met-L --> amet + pi + ppi | 2.5.1.6 |
| METFR | [c]: 5mthf + nadp <==> (2) h + mlthf + nadph | 1.5.1.20 |
| METS | [c]: 5mthf + hcys-L --> h + met-L + thf | 2.1.1.13 |
| MEtt4r | met-L[e] + na1[e] <==> met-L[c] + na1[c] | |
| MEVK1p | [x]: atp + mev-R --> 5pmev + adp + h | 2.7.1.36 |
| MEVtp | mev-R[x] <==> mev-R[c] | |
| MGCHm | [m]: 3mgcoa + h2o <==> hmgcoa | 4.2.1.18 |
| MI1PP | [c]: h2o + mi1p-D --> inost + pi | 3.1.3.25 |
| MI1PS | [c]: g6p --> mi1p-D | 5.5.1.4 |
| MLACI | [c]: 4mlacac --> 4fumacac | 5.2.1.2 |
| MLTHFtm | mlthf[c] <==> mlthf[m] | |
| MMALSAtm | mmalsa-S[m] <==> mmalsa-S[c] | |
| MMALtm | mmal[m] <==> mmal[c] | |
| MMCOAHm | [m]: coa + h + mmal --> h2o + mmcoa-S | 3.1.2.17 |
| MMEm | [m]: mmcoa-S <==> mmcoa-R | 5.1.99.1 |
| MMMrm | [m]: mmcoa-R <==> succoa | 5.4.99.2 |
| MMSDHim | [m]: coa + mmalsa-S + nad --> co2 + nadh + ppcoa | 1.2.1.27 |
| MOBD1m | [m]: 4mop + coa + nad --> co2 + ivcoa + nadh | |
| MOBD2m | [m]: 3mob + coa + nad --> co2 + ibcoa + nadh | |

TABLE 23-continued

Reactions and Metabolites in CHO Model

| | | |
|---|---|---|
| MOBD3m | [m]: 3mop + coa + nad --> 2mbcoa + co2 + nadh | |
| MTHFC | [c]: h2o + methf <==> 10fthf + h | 3.5.4.9 |
| MTHFCm | [m]: h2o + methf <==> 10fthf + h | 3.5.4.9 |
| MTHFD | [c]: mlthf + nadp <==> methf + nadph | 1.5.1.5 |
| MTHFD2m | [m]: mlthf + nad <==> methf + nadh | 1.5.1.5 |
| MTHFDm | [m]: mlthf + nadp <==> methf + nadph | 1.5.1.5 |
| MYRTt5 | ttdca[c] <==> ttdca[e] | |
| NADH4-u10m | (5) h[m] + nadh[m] + ubq10[m] --> (4) h[c] + nad[m] + q10h2[m] | 1.6.5.3 |
| NAt7 | h[e] + na1[c] <==> h[c] + na1[e] | |
| NDP8 | [c]: dudp + h2o --> dump + h + pi | 3.6.1.23 |
| NDPK1 | [c]: atp + gdp <==> adp + gtp | 2.7.4.6 |
| NDPK1m | [m]: atp + gdp <==> adp + gtp | 2.7.4.6 |
| NDPK2 | [c]: atp + udp <==> adp + utp | 2.7.4.6 |
| NDPK3 | [c]: atp + cdp <==> adp + ctp | 2.7.4.6 |
| NDPK3m | [m]: atp + cdp <==> adp + ctp | 2.7.4.6 |
| NDPK4 | [c]: atp + dtdp <==> adp + dttp | 2.7.4.6 |
| NDPK5 | [c]: atp + dgdp <==> adp + dgtp | 2.7.4.6 |
| NDPK7 | [c]: atp + dcdp <==> adp + dctp | 2.7.4.6 |
| NDPK8 | [c]: atp + dadp <==> adp + datp | 2.7.4.6 |
| NH4t | nh4[e] <==> nh4[c] | |
| NH4tm | nh4[c] <==> nh4[m] | |
| NRVNCt | nrvnc[e] <==> nrvnc[c] | |
| O2t | o2[e] <==> o2[c] | |
| O2ter | o2[c] <==> o2[r] | |
| O2tp | o2[c] <==> o2[x] | |
| O2trm | o2[c] <==> o2[m] | |
| OCBTm | [m]: cbp + orn-L <==> citr-L + h + pi | 2.1.3.3 |
| OCDCEAtr | ocdcea[e] <==> ocdcea[c] | |
| OCDCYAtr | ocdcya[e] <==> ocdcya[c] | |
| OCOAT1rm | [m]: acac + succoa <==> aacoa + succ | 2.8.3.5 |
| OMPDC | [c]: h + orot5p --> co2 + ump | 4.1.1.23 |
| ORNCITRtm | citr-L[m] + h[m] + orn-L[c] <==> citr-L[c] + h[c] + orn-L[m] | |
| ORNDC | [c]: h + orn-L --> co2 + ptrc | 4.1.1.17 |
| ORNTAm | [m]: akg + orn-L <==> glu-L + glu5sa | 2.6.1.13 |
| ORNtrm | h[m] + orn-L[c] <==> h[c] + orn-L[m] | |
| ORPT | [c]: orot5p + ppi <==> orot + prpp | 2.4.2.10 |
| OXOATm | [m]: 2aadp + akg <==> 2oxoadp + glu-L | 2.6.1.39 |
| P5CRx | [c]: 1pyr5c + (2) h + nadh --> nad + pro-L | 1.5.1.2 |
| P5CRy | [c]: 1pyr5c + (2) h + nadph --> nadp + pro-L | 1.5.1.2 |
| PAtm_CHO | pa_CHO[c] <==> pa_CHO[m] | |
| PCm | [m]: atp + hco3 + pyr --> adp + h + oaa + pi | 6.4.1.1 |
| PDHm | [m]: coa + nad + pyr --> accoa + co2 + nadh | 1.2.1.51 |
| PFK | [c]: atp + f6p --> adp + fdp + h | 2.7.1.11 |
| PGCDr | [c]: 3pg + nad <==> 3php + h + nadh | 1.1.1.95 |
| PGDH | [c]: 6pgc + nadp --> co2 + nadph + ru5p-D | 1.1.1.44 |
| PGI | [c]: g6p <==> f6p | 5.3.1.9 |
| PGK | [c]: 13dpg + adp <==> 3pg + atp | 2.7.2.3 |
| PGL | [c]: 6pgl + h2o --> 6pgc + h | 3.1.1.31 |
| PGLer | [r]: 6pgl + h2o --> 6pgc + h | 3.1.1.31 |
| PGM | [c]: 3pg <==> 2pg | 5.4.2.1 |
| PGMT | [c]: g1p <==> g6p | 5.4.2.2 |
| PGPPAm_CHO | [m]: h2o + (0.001) pgp_CHO --> (0.001) pg_CHO + pi | 3.1.3.27 |
| PHE4MO | [c]: o2 + phe-L + thbpt --> dhbpt + h2o + tyr-L | 1.14.16.1 |
| PHEMEtm | pheme[m] <==> pheme[c] | |
| PHEMEtr | pheme[e] <==> pheme[c] | |
| PHEtec | phe-L[e] <==> phe-L[c] | |
| PINOS_CHO | [c]: (0.001) cdpdag_CHO + inost <==> cmp + h + (0.001) pino_CHO | 2.7.8.11 |
| PIt2p | h[c] + pi[c] <==> h[x] + pi[x] | |
| PIt6 | h[e] + pi[e] <==> h[c] + pi[c] | |
| PIter | h[c] + pi[c] <==> h[r] + pi[r] | |
| PItm | h[c] + pi[c] <==> h[m] + pi[m] | |
| PLIPA1_CHO | [c]: h2o + (0.001) pc_CHO --> (0.001) 1aglycpc_CHO + (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca | 3.1.1.4 |
| PMEVKrp | [x]: 5pmev + atp <==> 5dpmev + adp | 2.7.4.2 |
| PMTt5 | hdca[c] <==> hdca[e] | |
| PNTK | [c]: atp + pnto-R --> 4ppan + adp + h | 2.7.1.33 |
| PNTOt4 | na1[e] + pnto-R[e] --> na1[c] + pnto-R[c] | |
| PPA | [c]: h2o + ppi --> h + (2) pi | 3.6.1.1 |

TABLE 23-continued

Reactions and Metabolites in CHO Model

| | | |
|---|---|---|
| PPA2 | [c]: h2o + pppi --> h + pi + ppi | 3.6.1.25 |
| PPAer | [r]: h2o + ppi --> h + (2) pi | 3.6.1.1 |
| PPAm | [m]: h2o + ppi --> h + (2) pi | 3.6.1.1 |
| PPBNGS | [c]: (2) 5aop --> h + (2) h2o + ppbng | 4.2.1.24 |
| PPCDC | [c]: 4ppcys + h --> co2 + pan4p | 4.1.1.36 |
| PPCKG | [c]: gtp + oaa --> co2 + gdp + pep | 4.1.1.32 |
| PPCKGm | [m]: gtp + oaa --> co2 + gdp + pep | 4.1.1.32 |
| PPCOACrm | [m]: atp + hco3 + ppcoa <==> adp + h + mmcoa-S + pi | 6.4.1.3 |
| PPNCL | [c]: 4ppan + ctp + cys-L --> 4ppcys + cdp + h + pi | 6.3.2.5 |
| PPP9tm | ppp9[m] <==> ppp9[c] | |
| PPPGO | [c]: (1.5) o2 + pppg9 --> (3) h2o + ppp9 | 1.3.3.4 |
| PRAGS | [c]: atp + gly + pram --> adp + gar + h + pi | 6.3.4.13 |
| PRAIS | [c]: atp + fpram --> adp + air + h + pi | 6.3.3.1 |
| PRASCS | [c]: 5aizc + asp-L + atp <==> 25aics + adp + h + pi | 6.3.2.6 |
| PRFGS | [c]: atp + fgam + gln-L + h2o --> adp + fpram + glu-L + (2) h + pi | 6.3.5.3 |
| PRO1xm | [m]: nad + pro-L --> 1pyr5c + (2) h + nadh | 1.5.1.2 |
| PROt5 | na1[e] + pro-L[e] <==> na1[c] + pro-L[c] | |
| PROtm | pro-L[c] <==> pro-L[m] | |
| PRPPS | [c]: atp + r5p <==> amp + h + prpp | 2.7.6.1 |
| PSERD_CHO | [c]: h + (0.001) ps_CHO --> co2 + (0.001) pe_CHO | 4.1.1.65 |
| PSERTr | [c]: 3php + glu-L <==> akg + pser-L | 2.6.1.52 |
| PSP_L | [c]: h2o + pser-L --> pi + ser-L | 3.1.3.3 |
| PTDSS1_CHO | [c]: chol + (0.001) ps_CHO <==> (0.001) pc_CHO + ser-L | |
| PTHPS | [c]: ahdt --> 6pthp + pppi | 4.2.3.12 |
| PTPAT | [c]: atp + h + pan4p <==> dpcoa + ppi | 2.7.7.3 |
| PTRCtm | ptrc[m] <==> ptrc[c] | |
| PYK | [c]: adp + h + pep --> atp + pyr | 2.7.1.40 |
| PYR5CDxm | [m]: glu5sa + h2o + nad --> glu-L + (2) h + nadh | 1.5.1.12 |
| PYRtm | h[c] + pyr[c] <==> h[m] + pyr[m] | |
| RNDR1 | [c]: adp + trdrd --> dadp + h2o + trdox | 1.17.4.1 |
| RNDR2 | [c]: gdp + trdrd --> dgdp + h2o + trdox | 1.17.4.1 |
| RNDR3 | [c]: cdp + trdrd --> dcdp + h2o + trdox | 1.17.4.1 |
| RNDR4 | [c]: trdrd + udp --> dudp + h2o + trdox | 1.17.4.1 |
| RPE | [c]: ru5p-D <==> xu5p-D | 5.1.3.1 |
| RPI | [c]: r5p <==> ru5p-D | 5.3.1.6 |
| SACCDGm | [m]: Lsacchrp + h2o + nad <==> ampsal + glu-L + h + nadh | 1.5.1.9 |
| SACCDym | [m]: akg + h + lys-L + nadph --> Lsacchrp + h2o + nadp | 1.5.1.8 |
| SARCOp | [x]: h2o + o2 + sarcs --> fald + gly + h2o2 | 1.5.3.1 |
| SARCStrp | sarcs[c] <==> sarcs[x] | |
| SERD_L | [c]: ser-L --> nh4 + pyr | 4.3.1.17 |
| SERPT | [c]: h + pmtcoa + ser-L --> 3dsphgn + co2 + coa | 2.3.1.50 |
| SERt4r | na1[e] + ser-L[e] <==> na1[c] + ser-L[c] | |
| SERtm | ser-L[c] <==> ser-L[m] | |
| SO3t2r | na1[e] + so3[e] <==> na1[c] + so3[c] | |
| SOD | [c]: (2) h + (2) o2- --> h2o2 + o2 | 1.15.1.1 |
| SODm | [m]: (2) h + (2) o2- --> h2o2 + o2 | 1.15.1.1 |
| SODp | [x]: (2) h + (2) o2- --> h2o2 + o2 | 1.15.1.1 |
| SPMS | [c]: ametam + ptrc --> 5mta + h + spmd | 2.5.1.16 |
| SPRr | [c]: 6pthp + (2) h + (2) nadph <==> (2) nadp + thbpt | 1.1.1.153 |
| SPRS | [c]: ametam + spmd --> 5mta + h + sprm | 2.5.1.22 |
| SPYR | [c]: h2o + spyr --> (2) h + pyr + so3 | |
| SQLEer | [r]: h + nadph + o2 + sql --> Ssq23epx + h2o + nadp | 1.14.99.7 |
| SQLSer | [r]: (2) frdp + h + nadph --> nadp + (2) ppi + sql | 2.5.1.21 |
| SSALxm | [m]: h2o + nad + sucsal --> (2) h + nadh + succ | 1.2.1.24 |
| STRR2er | [r]: h + nadph + zymst --> nadp + zymstnl | 1.3.1.72 |
| STRR3er | [r]: dsmsterol + h + nadph --> chsterol + nadp | 1.3.1.72 |
| STRRer | [r]: cholsd + h + nadph --> lathost + nadp | 1.3.1.72 |
| STRt5 | ocdca[c] <==> ocdca[e] | |
| SUCD1m-ubq10 | [m]: succ + ubq10 <==> fum + q10h2 | 1.3.5.1 |
| SUCD3m-ubq10 | [m]: fadh2 + ubq10 <==> fad + q10h2 | |
| SUCOASAm | [m]: atp + coa + succ <==> adp + pi + succoa | 6.2.1.5 |
| SUCOASGm | [m]: coa + gtp + succ <==> gdp + pi + succoa | 6.2.1.4 |
| TAL | [c]: g3p + s7p <==> e4p + f6p | 2.2.1.2 |
| THD1im | h[c] + nadh[m] + nadp[m] --> h[m] + nad[m] + nadph[m] | 1.6.1.1 |

TABLE 23-continued

Reactions and Metabolites in CHO Model

| Abbreviation | | |
|---|---|---|
| THFtm | thf[c] <==> thf[m] | |
| THRDm | [m]: nad + thr-L --> 2aobut + h + nadh | 1.1.1.103 |
| THRt2m | h[c] + thr-L[c] <==> h[m] + thr-L[m] | |
| THRt4r | na1[e] + thr-L[e] <==> na1[c] + thr-L[c] | |
| TKT1 | [c]: r5p + xu5p-D <==> g3p + s7p | 2.2.1.1 |
| TKT2 | [c]: e4p + xu5p-D <==> f6p + g3p | 2.2.1.1 |
| TMDSr | [c]: dump + mlthf <==> dhf + dtmp | 2.1.1.45 |
| TPI | [c]: dhap <==> g3p | 5.3.1.1 |
| TRDRr | [c]: h + nadph + trdox <==> nadp + trdrd | 1.8.1.9 |
| TRIGH_CHO | [c]: h2o + (0.001) triglyc_CHO --> (0.001) 12dgr_CHO + (0.025) arachda + (0.01) dcshea + (0.016) dcspea + (0.002) ecsa + (0.003) ecspea + (0.004) ecstea + h + (0.253) hdca + (0.064) hdcea + (0.003) lnlne + (0.008) nrvnc + (0.13) ocdca + (0.404) ocdcea + (0.042) ocdcya + (0.007) ttc + (0.029) ttdca | 6.2.1.3 |
| TRIGS_CHO | [c]: (0.001) 12dgr_CHO + (0.001) facoa_avg_CHO --> coa + (0.001) triglyc_CHO | 2.3.1.20 |
| TRPO2 | [c]: o2 + trp-L --> Lfmkynr | 1.13.11.11 |
| TRPt | trp-L[e] <==> trp-L[c] | |
| TYRt | tyr-L[e] <==> tyr-L[c] | |
| TYRTA | [c]: akg + tyr-L <==> 34hpp + glu-L | 2.6.1.5 |
| UMPK | [c]: atp + ump <==> adp + udp | 2.7.4.14 |
| UPP3S | [c]: hmbil --> h2o + uppg3 | 4.2.1.75 |
| UPPDC1 | [c]: (4) h + uppg3 --> (4) co2 + cpppg3 | 4.1.1.37 |
| URCN | [c]: h2o + urcan --> 4izp | 4.2.1.49 |
| UREAt | urea[e] <==> urea[c] | |
| UREAtm | urea[c] <==> urea[m] | |
| VALTAm | [m]: akg + val-L <==> 3mob + glu-L | 2.6.1.42 |
| VALtec | val-L[e] <==> val-L[c] | |
| VALtm | val-L[c] <==> val-L[m] | |

| Abbreviation | Equation |
|---|---|
| Biomass_CHO2 | [c]: (0.5291) ala-L + (0.3501) arg-L + (0.2172) asn-L + (0.2673) asp-L + (0.0315) atp + (0.000038) cholse_CHO + (0.0599) chsterol + (0.000001) clpn_CHO + (0.0526) ctp + (0.1559) cys-L + (0.0172) datp + (0.0114) dctp + (0.0114) dgtp + (0.0172) dttp + (0.2896) gln-L + (0.3564) glu-L + (0.4344) gly + (0.3885) glycogen + (0.0596) gtp + (0.1225) his-L + (0.2896) ile-L + (0.4901) leu-L + (0.4957) lys-L + (0.1114) met-L + (0.000089) pc_CHO + (0.000036) pe_CHO + (0.117) phe-L + (0.000012) pino_CHO + (0.1559) pro-L + (0.000012) ps_CHO + (0.3174) ser-L + (0.000017) sphgmy_CHO + (0.3397) thr-L + (0.000007) triglyc_CHO + (0.0334) trp-L + (0.1114) tyr-L + (0.0315) utp + (0.3286) val-L --> |
| EX_ala-L(e) | [e]: ala-L <==> |
| EX_arachda(e) | [e]: arachda <==> |
| EX_arg-L(e) | [e]: arg-L <==> |
| EX_asn-L(e) | [e]: asn-L <==> |
| EX_asp-L(e) | [e]: asp-L <==> |
| EX_chol(e) | [e]: chol <==> |
| EX_co2(e) | [e]: co2 <==> |
| EX_cys-L(e) | [e]: cys-L <==> |
| EX_dcshea(e) | [e]: dcshea <==> |
| EX_dcspea(e) | [e]: dcspea <==> |
| EX_ecsa(e) | [e]: ecsa <==> |
| EX_ecspea(e) | [e]: ecspea <==> |
| EX_ecstea(e) | [e]: ecstea <==> |
| EX_etha(e) | [e]: etha <==> |
| EX_fol(e) | [e]: fol <==> |
| EX_glc(e) | [e]: glc-D <==> |
| EX_gln-L(e) | [e]: gln-L <==> |
| EX_glu-L(e) | [e]: glu-L <==> |
| EX_gly(e) | [e]: gly <==> |
| EX_h(e) | [e]: h <==> |
| EX_h2o(e) | [e]: h2o <==> |
| EX_hdca(e) | [e]: hdca <==> |
| EX_hdcea(e) | [e]: hdcea <==> |
| EX_his-L(e) | [e]: his-L <==> |
| EX_ile-L(e) | [e]: ile-L <==> |
| EX_inost(e) | [e]: inost <==> |
| EX_lac-L(e) | [e]: lac-L <==> |
| EX_leu-L(e) | [e]: leu-L <==> |

TABLE 23-continued

Reactions and Metabolites in CHO Model

| | |
|---|---|
| EX_lnlne(e) | [e]: lnlne <==> |
| EX_lys-L(e) | [e]: lys-L <==> |
| EX_met-L(e) | [e]: met-L <==> |
| EX_na1(e) | [e]: na1 <==> |
| EX_nh4(e) | [e]: nh4 <==> |
| EX_nrvnc(e) | [e]: nrvnc <==> |
| EX_o2(e) | [e]: o2 <==> |
| EX_ocdca(e) | [e]: ocdca <==> |
| EX_ocdcea(e) | [e]: ocdcea <==> |
| EX_ocdcya(e) | [e]: ocdcya <==> |
| EX_phe-L(e) | [e]: phe-L <==> |
| EX_pheme(e) | [e]: pheme <==> |
| EX_pi(e) | [e]: pi <==> |
| EX_pnto-R(e) | [e]: pnto-R <==> |
| EX_pro-L(e) | [e]: pro-L <==> |
| EX_ser-L(e) | [e]: ser-L <==> |
| EX_so3(e) | [e]: so3 <==> |
| EX_thr-L(e) | [e]: thr-L <==> |
| EX_trp-L(e) | [e]: trp-L <==> |
| EX_ttc(e) | [e]: ttc <==> |
| EX_ttdca(e) | [e]: ttdca <==> |
| EX_tyr-L(e) | [e]: tyr-L <==> |
| EX_urea(e) | [e]: urea <==> |
| EX_val-L(e) | [e]: val-L <==> |

| Metab Abbreviation | Name | Compartment |
|---|---|---|
| 10fthf | 10-Formyltetrahydrofolate | Cytosol |
| 10fthf | 10-Formyltetrahydrofolate | Mitochondria |
| 12dgr_CHO | 1,2-Diacylglycerol, CHO | Cytosol |
| 13dpg | 3-Phospho-D-glyceroyl phosphate | Cytosol |
| 1ag3p_CHO | 1-Acyl-sn-glycerol 3-phosphate, CHO | Cytosol |
| 1aglycpc_CHO | 1-Acyl-sn-glycero-3-phosphocholine, CHO specific | Cytosol |
| 1pyr5c | 1-Pyrroline-5-carboxylate | Cytosol |
| 1pyr5c | 1-Pyrroline-5-carboxylate | Mitochondria |
| 25aics | (S)-2-[5-Amino-1-(5-phospho-D-ribosyl)imidazole-4-carboxamido]succinate | Cytosol |
| 2aadp | L-2-Aminoadipate | Mitochondria |
| 2amuc | 2-Aminomuconate | Cytosol |
| 2aobut | L-2-Amino-3-oxobutanoate | Mitochondria |
| 2maacoa | 2-Methyl-3-acetoacetyl-CoA | Mitochondria |
| 2mb2coa | trans-2-Methylbut-2-enoyl-CoA | Mitochondria |
| 2mbcoa | 2-Methylbutanoyl-CoA | Mitochondria |
| 2mp2coa | 2-Methylprop-2-enoyl-CoA | Mitochondria |
| 2obut | 2-Oxobutanoate | Cytosol |
| 2obut | 2-Oxobutanoate | Mitochondria |
| 2oxoadp | 2-Oxoadipate | Cytosol |
| 2oxoadp | 2-Oxoadipate | Mitochondria |
| 2pg | D-Glycerate 2-phosphate | Cytosol |
| 34hpp | 3-(4-Hydroxyphenyl)pyruvate | Cytosol |
| 3dsphgn | 3-Dehydrosphinganine | Cytosol |
| 3hanthrn | 3-Hydroxyanthranilate | Cytosol |
| 3hbycoa | (S)-3-Hydroxybutyryl-CoA | Mitochondria |
| 3hmbcoa | (S)-3-Hydroxy-2-methylbutyryl-CoA | Mitochondria |
| 3hmp | (S)-3-hydroxyisobutyrate | Mitochondria |
| 3mb2coa | 3-Methylbut-2-enoyl-CoA | Mitochondria |
| 3mgcoa | 3-Methylglutaconyl-CoA | Mitochondria |
| 3mob | 3-Methyl-2-oxobutanoate | Mitochondria |
| 3mop | (S)-3-Methyl-2-oxopentanoate | Mitochondria |
| 3pg | 3-Phospho-D-glycerate | Cytosol |
| 3php | 3-Phosphohydroxypyruvate | Cytosol |
| 3sala | 3-Sulfino-L-alanine | Cytosol |
| 3sala | 3-Sulfino-L-alanine | Mitochondria |
| 44mctr | 4,4-dimethylcholesta-8,14,24-trienol | Endoplasmic Reticulum |
| 44mzym | 4,4-dimethylzymosterol | Endoplasmic Reticulum |
| 4abut | 4-Aminobutanoate | Cytosol |
| 4abut | 4-Aminobutanoate | Mitochondria |
| 4abutn | 4-Aminobutanal | Cytosol |
| 4fumacac | 4-Fumarylacetoacetate | Cytosol |
| 4izp | 4-Imidazolone-5-propanoate | Cytosol |
| 4mlacac | 4-Maleylacetoacetate | Cytosol |
| 4mop | 4-Methyl-2-oxopentanoate | Mitochondria |
| 4mzym_int1 | 4-Methylzymosterol intermediate 1 | Endoplasmic Reticulum |

TABLE 23-continued

Reactions and Metabolites in CHO Model

| | | |
|---|---|---|
| 4mzym_int2 | 4-Methylzymosterol intermediate 2 | Endoplasmic Reticulum |
| 4ppan | D-4'-Phosphopantothenate | Cytosol |
| 4ppcys | N-((R)-4-Phosphopantothenoyl)-L-cysteine | Cytosol |
| 5aizc | 5-amino-1-(5-phospho-D-ribosyl)imidazole-4-carboxylate | Cytosol |
| 5aop | 5-Amino-4-oxopentanoate | Cytosol |
| 5aop | 5-Amino-4-oxopentanoate | Mitochondria |
| 5dpmev | (R)-5-Diphosphom evalonate | Peroxisome |
| 5fthf | 5-Formiminotetrahydrofolate | Cytosol |
| 5mta | 5-Methylthioadenosine | Cytosol |
| 5mthf | 5-Methyltetrahydrofolate | Cytosol |
| 5pmev | (R)-5-Phosphomevalonate | Peroxisome |
| 6pgc | 6-Phospho-D-gluconate | Cytosol |
| 6pgc | 6-Phospho-D-gluconate | Endoplasmic Reticulum |
| 6pgl | 6-phospho-D-glucono-1,5-lactone | Cytosol |
| 6pgl | 6-phospho-D-glucono-1,5-lactone | Endoplasmic Reticulum |
| 6pthp | 6-Pyruvoyl-5,6,7,8-tetrahydropterin | Cytosol |
| 7dhchsterol | 7-Dehydrocholesterol | Endoplasmic Reticulum |
| aacoa | Acetoacetyl-CoA | Cytosol |
| aacoa | Acetoacetyl-CoA | Mitochondria |
| acac | Acetoacetate | Cytosol |
| acac | Acetoacetate | Mitochondria |
| accoa | Acetyl-CoA | Cytosol |
| accoa | Acetyl-CoA | Mitochondria |
| acmucsal | 2-Amino-3-carboxymuconate semialdehyde | Cytosol |
| acrn | O-Acetylcarnitine | Cytosol |
| acrn | O-Acetylcarnitine | Mitochondria |
| adn | Adenosine | Cytosol |
| adp | ADP | Cytosol |
| adp | ADP | Mitochondria |
| adp | ADP | Peroxisome |
| agm | Agmatine | Mitochondria |
| ahcys | S-Adenosyl-L-homocysteine | Cytosol |
| ahdt | 2-Amino-4-hydroxy-6-(erythro-1,2,3-trihydroxypropyl)dihydropteridine triphosphate | Cytosol |
| aicar | 5-Amino-1-(5-Phospho-D-ribosyl)imidazole-4-carboxamide | Cytosol |
| air | 5-amino-1-(5-phospho-D-ribosyl)imidazole | Cytosol |
| akg | 2-Oxoglutarate | Cytosol |
| akg | 2-Oxoglutarate | Mitochondria |
| ala-L | L-Alanine | Cytosol |
| ala-L | L-Alanine | Extra-organism |
| amet | S-Adenosyl-L-methionine | Cytosol |
| ametam | S-Adenosylmethioninamine | Cytosol |
| amp | AMP | Cytosol |
| amp | AMP | Mitochondria |
| ampsal | L-2-Aminoadipate 6-semialdehyde | Mitochondria |
| amucsal | 2-Aminomuconate semialdehyde | Cytosol |
| arachda | Arachidonic acid (C20:4) | Cytosol |
| arachda | Arachidonic acid (C20:4) | Extra-organism |
| arachdcoa | arachidonoyl-CoA (C20:4CoA, n-6) | Cytosol |
| arachdcoa | arachidonoyl-CoA (C20:4CoA, n-6) | Mitochondria |
| arachdcrn | C20:4 carnitine | Cytosol |
| arachdcrn | C20:4 carnitine | Mitochondria |
| arg-L | L-Arginine | Cytosol |
| arg-L | L-Arginine | Extra-organism |
| arg-L | L-Arginine | Mitochondria |
| argsuc | N(omega)-(L-Arginino)succinate | Cytosol |
| asn-L | L-Asparagine | Cytosol |
| asn-L | L-Asparagine | Extra-organism |
| asp-L | L-Aspartate | Cytosol |
| asp-L | L-Aspartate | Extra-organism |
| asp-L | L-Aspartate | Mitochondria |
| atp | ATP | Cytosol |
| atp | ATP | Mitochondria |
| atp | ATP | Peroxisome |
| b2coa | trans-But-2-enoyl-CoA | Mitochondria |
| btcoa | Butanoyl-CoA (C4:0CoA) | Mitochondria |
| cbasp | N-Carbamoyl-L-aspartate | Cytosol |
| cbp | Carbamoyl phosphate | Cytosol |
| cbp | Carbamoyl phosphate | Mitochondria |
| cdp | CDP | Cytosol |
| cdp | CDP | Mitochondria |
| cdpchol | CDPcholine | Cytosol |

TABLE 23-continued

Reactions and Metabolites in CHO Model

| | | |
|---|---|---|
| cdpdag_CHO | CDPdiacylglycerol, CHO specific | Cytosol |
| cdpdag_CHO | CDPdiacylglycerol, CHO specific | Mitochondria |
| cdpea | CDPethanolamine | Cytosol |
| cer_CHO | ceramide, CHO specific | Cytosol |
| cgly | Cys-Gly | Cytosol |
| chol | Choline | Cytosol |
| chol | Choline | Extra-organism |
| cholp | Choline phosphate | Cytosol |
| cholsd | 5alpha-Cholesta-7,24-dien-3beta-ol | Endoplasmic Reticulum |
| cholse_CHO | Cholesterol ester, CHO specific | Cytosol |
| chsterol | Cholesterol | Cytosol |
| chsterol | Cholesterol | Endoplasmic Reticulum |
| cit | Citrate | Cytosol |
| cit | Citrate | Mitochondria |
| citr-L | L-Citrulline | Cytosol |
| citr-L | L-Citrulline | Mitochondria |
| clpn_CHO | cardiolipin, CHO specific | Cytosol |
| clpn_CHO | cardiolipin, CHO specific | Mitochondria |
| clpndcoa | clupanodonyl CoA (C22:5CoA) | Cytosol |
| clpndcoa | clupanodonyl CoA (C22:5CoA) | Mitochondria |
| clpndcrn | docosapentaenoyl carnitine (C22:5) | Cytosol |
| clpndcrn | docosapentaenoyl carnitine (C22:5) | Mitochondria |
| cmp | CMP | Cytosol |
| cmp | CMP | Mitochondria |
| co2 | CO2 | Cytosol |
| co2 | CO2 | Endoplasmic Reticulum |
| co2 | CO2 | Extra-organism |
| co2 | CO2 | Mitochondria |
| co2 | CO2 | Peroxisome |
| coa | Coenzyme A | Cytosol |
| coa | Coenzyme A | Mitochondria |
| cpppg3 | Coproporphyrinogen III | Cytosol |
| crn | L-Carnitine | Cytosol |
| crn | L-Carnitine | Mitochondria |
| ctp | CTP | Cytosol |
| ctp | CTP | Mitochondria |
| cvncoa | cervonyl CoA (C22:6CoA) | Cytosol |
| cvncoa | cervonyl CoA (C22:6CoA) | Mitochondria |
| cvncrn | cervonyl carnitine (C22:6Crn) | Cytosol |
| cvncrn | cervonyl carnitine (C22:6Crn) | Mitochondria |
| cys-L | L-Cysteine | Cytosol |
| cys-L | L-Cysteine | Extra-organism |
| cysth-L | L-Cystathionine | Cytosol |
| dadp | dADP | Cytosol |
| datp | dATP | Cytosol |
| dca | Decanoate | Cytosol |
| dcamp | N6-(1,2-Dicarboxyethyl)-AMP | Cytosol |
| dccoa | Decanoyl-CoA (C10:0CoA) | Mitochondria |
| dcdp | dCDP | Cytosol |
| dcer_CHO | dihydroceramide, CHO specific | Cytosol |
| dcsa | docosanoate (n-C22:0) | Cytosol |
| dcshea | docosahexaenoate (C22:6) | Cytosol |
| dcshea | docosahexaenoate (C22:6) | Extra-organism |
| dcspea | docosapentaenoic acid (C22:5) | Cytosol |
| dcspea | docosapentaenoic acid (C22:5) | Extra-organism |
| dctp | dCTP | Cytosol |
| ddca | dodecanoate (C12:0) | Cytosol |
| ddcoa | Dodecanoyl-CoA (n-C12:0CoA) | Mitochondria |
| ddsmsterol | 7-Dehydrodesmosterol | Endoplasmic Reticulum |
| dgdp | dGDP | Cytosol |
| dgtp | dGTP | Cytosol |
| dhap | Dihydroxyacetone phosphate | Cytosol |
| dhbpt | 6,7-Dihydrobiopterin | Cytosol |
| dhf | 7,8-Dihydrofolate | Cytosol |
| dhor-S | (S)-Dihydroorotate | Cytosol |
| dmpp | Dimethylallyl diphosphate | Cytosol |
| dmpp | Dimethylallyl diphosphate | Peroxisome |
| dpcoa | Dephospho-CoA | Cytosol |
| dsmsterol | Desmosterol | Endoplasmic Reticulum |
| dtdp | dTDP | Cytosol |
| dtmp | dTMP | Cytosol |
| dttp | dTTP | Cytosol |
| dudp | dUDP | Cytosol |

TABLE 23-continued

Reactions and Metabolites in CHO Model

| | | |
|---|---|---|
| dump | dUMP | Cytosol |
| e4p | D-Erythrose 4-phosphate | Cytosol |
| ecsa | Eicosanoate (n-C20:0) | Cytosol |
| ecsa | Eicosanoate (n-C20:0) | Extra-organism |
| ecsacoa | Eicosanoyl-CoA (n-C20:0CoA) | Cytosol |
| ecsacoa | Eicosanoyl-CoA (n-C20:0CoA) | Mitochondria |
| ecsacrn | eicosanoylcarnitine, C20:0crn | Cytosol |
| ecsacrn | eicosanoylcarnitine, C20:0crn | Mitochondria |
| ecspea | Eicosapentaenoic acid (C20:5) | Cytosol |
| ecspea | Eicosapentaenoic acid (C20:5) | Extra-organism |
| ecspecoa | eicosapentaenoyl-CoA (C20:5CoA) | Cytosol |
| ecspecoa | eicosapentaenoyl-CoA (C20:5CoA) | Mitochondria |
| ecspecrn | eicosapentaenoyl carnitine (C20:5Crn) | Cytosol |
| ecspecrn | eicosapentaenoyl carnitine (C20:5Crn) | Mitochondria |
| ecstea | eicosatrienoate (C20:3) | Cytosol |
| ecstea | eicosatrienoate (C20:3) | Extra-organism |
| estcoa | eicosatrienoyl-CoA (C20:3CoA) | Cytosol |
| estcoa | eicosatrienoyl-CoA (C20:3CoA) | Mitochondria |
| estcrn | eicosatrienoyl carnitine (C20:3Crn) | Cytosol |
| estcrn | eicosatrienoyl carnitine (C20:3Crn) | Mitochondria |
| etha | Ethanolamine | Cytosol |
| etha | Ethanolamine | Extra-organism |
| ethap | Ethanolamine phosphate | Cytosol |
| f6p | D-Fructose 6-phosphate | Cytosol |
| facoa_avg_CHO | Averaged fatty acyl CoA, CHO specific | Cytosol |
| fad | FAD | Mitochondria |
| fadh2 | FADH2 | Mitochondria |
| fald | Formaldehyde | Cytosol |
| fald | Formaldehyde | Peroxisome |
| fdp | D-Fructose 1,6-bisphosphate | Cytosol |
| fe2 | Fe2+ | Cytosol |
| fe2 | Fe2+ | Mitochondria |
| fgam | N2-Formyl-N1-(5-phospho-D-ribosyl)glycinamide | Cytosol |
| ficytcc | Ferricytochrome c | Mitochondria |
| focytcc | Ferrocytochrome c | Mitochondria |
| fol | Folate | Cytosol |
| fol | Folate | Extra-organism |
| for | Formate | Cytosol |
| for | Formate | Endoplasmic Reticulum |
| for | Formate | Mitochondria |
| forglu | N-Formimidoyl-L-glutamate | Cytosol |
| fpram | 2-(Formamido)-N1-(5-phospho-D-ribosyl)acetamidine | Cytosol |
| fprica | 5-Formamido-1-(5-phospho-D-ribosyl)imidazole-4-carboxamide | Cytosol |
| frdp | Farnesyl diphosphate | Cytosol |
| frdp | Farnesyl diphosphate | Endoplasmic Reticulum |
| fum | Fumarate | Cytosol |
| fum | Fumarate | Mitochondria |
| g1p | D-Glucose 1-phosphate | Cytosol |
| g3p | Glyceraldehyde 3-phosphate | Cytosol |
| g6p | D-Glucose 6-phosphate | Cytosol |
| g6p | D-Glucose 6-phosphate | Endoplasmic Reticulum |
| gar | N1-(5-Phospho-D-ribosyl)glycinamide | Cytosol |
| gdp | GDP | Cytosol |
| gdp | GDP | Mitochondria |
| glc-D | D-Glucose | Cytosol |
| glc-D | D-Glucose | Endoplasmic Reticulum |
| glc-D | D-Glucose | Extra-organism |
| gln-L | L-Glutamine | Cytosol |
| gln-L | L-Glutamine | Extra-organism |
| gln-L | L-Glutamine | Mitochondria |
| glu-L | L-Glutamate | Cytosol |
| glu-L | L-Glutamate | Extra-organism |
| glu-L | L-Glutamate | Mitochondria |
| glu5p | L-Glutamate 5-phosphate | Mitochondria |
| glu5sa | L-Glutamate 5-semialdehyde | Cytosol |
| glu5sa | L-Glutamate 5-semialdehyde | Mitochondria |
| glucys | gamma-L-Glutamyl-L-cysteine | Cytosol |
| glutcoa | Glutaryl-CoA | Mitochondria |
| gly | Glycine | Cytosol |
| gly | Glycine | Extra-organism |
| gly | Glycine | Mitochondria |

TABLE 23-continued

Reactions and Metabolites in CHO Model

| | | |
|---|---|---|
| gly | Glycine | Peroxisome |
| glyc | Glycerol | Cytosol |
| glyc3p | sn-Glycerol 3-phosphate | Cytosol |
| glyc3p | sn-Glycerol 3-phosphate | Mitochondria |
| glycogen | glycogen | Cytosol |
| gmp | GMP | Cytosol |
| grdp | Geranyl diphosphate | Cytosol |
| gthox | Oxidized glutathione | Cytosol |
| gthrd | Reduced glutathione | Cytosol |
| gtp | GTP | Cytosol |
| gtp | GTP | Mitochondria |
| h | H+ | Cytosol |
| h | H+ | Endoplasmic Reticulum |
| h | H+ | Extra-organism |
| h | H+ | Mitochondria |
| h | H+ | Peroxisome |
| h2o | H2O | Cytosol |
| h2o | H2O | Endoplasmic Reticulum |
| h2o | H2O | Extra-organism |
| h2o | H2O | Mitochondria |
| h2o | H2O | Peroxisome |
| h2o2 | Hydrogen peroxide | Cytosol |
| h2o2 | Hydrogen peroxide | Mitochondria |
| h2o2 | Hydrogen peroxide | Peroxisome |
| hco3 | Bicarbonate | Cytosol |
| hco3 | Bicarbonate | Mitochondria |
| hcys-L | L-Homocysteine | Cytosol |
| hdca | hexadecanoate (n-C16:0) | Cytosol |
| hdca | hexadecanoate (n-C16:0) | Extra-organism |
| hdcea | hexadecenoate (n-C16:1) | Cytosol |
| hdcea | hexadecenoate (n-C16:1) | Extra-organism |
| hdcecrn | Hexadecenoyl carnitine | Cytosol |
| hdcecrn | Hexadecenoyl carnitine | Mitochondria |
| hdcoa | Hexadecenoyl-CoA (n-C16:1CoA) | Cytosol |
| hdcoa | Hexadecenoyl-CoA (n-C16:1CoA) | Mitochondria |
| hgentis | Homogentisate | Cytosol |
| hibcoa | (S)-3-Hydroxyisobutyryl-CoA | Mitochondria |
| his-L | L-Histidine | Cytosol |
| his-L | L-Histidine | Extra-organism |
| hkyn | 3-Hydroxy-L-kynurenine | Cytosol |
| hmbil | Hydroxymethylbilane | Cytosol |
| hmgcoa | Hydroxymethylglutaryl-CoA | Cytosol |
| hmgcoa | Hydroxymethylglutaryl-CoA | Mitochondria |
| hxcoa | Hexanoyl-CoA (C6:0CoA) | Mitochondria |
| ibcoa | Isobutyryl-CoA | Mitochondria |
| icit | Isocitrate | Cytosol |
| icit | Isocitrate | Mitochondria |
| ile-L | L-Isoleucine | Cytosol |
| ile-L | L-Isoleucine | Extra-organism |
| ile-L | L-Isoleucine | Mitochondria |
| imp | IMP | Cytosol |
| inost | myo-Inositol | Cytosol |
| inost | myo-Inositol | Extra-organism |
| ipdp | Isopentenyl diphosphate | Cytosol |
| ipdp | Isopentenyl diphosphate | Peroxisome |
| ivcoa | Isovaleryl-CoA | Mitochondria |
| kynr-L | L-Kynurenine | Cytosol |
| lac-L | L-Lactate | Cytosol |
| lac-L | L-Lactate | Extra-organism |
| lanost | Lanosterol | Endoplasmic Reticulum |
| lathost | Lathosterol | Endoplasmic Reticulum |
| leu-L | L-Leucine | Cytosol |
| leu-L | L-Leucine | Extra-organism |
| leu-L | L-Leucine | Mitochondria |
| Lfmkynr | L-Formylkynurenine | Cytosol |
| lgnccoa | lignocericyl coenzyme A | Cytosol |
| lgnccoa | lignocericyl coenzyme A | Mitochondria |
| lgnccrn | lignoceryl carnitine | Cytosol |
| lgnccrn | lignoceryl carnitine | Mitochondria |
| lnlecoa | Linolenoyl-CoA (C18:3CoA) | Cytosol |
| lnlecoa | Linolenoyl-CoA (C18:3CoA) | Mitochondria |
| lnlecrn | linolenoyl carnitine (C18:3Crn) | Cytosol |
| lnlecrn | linolenoyl carnitine (C18:3Crn) | Mitochondria |
| lnlne | Linolenic acid (C18:3) | Cytosol |

TABLE 23-continued

Reactions and Metabolites in CHO Model

| | | |
|---|---|---|
| lnlne | Linolenic acid (C18:3) | Extra-organism |
| Lsacchrp | L-Saccharopine | Mitochondria |
| lys-L | L-Lysine | Cytosol |
| lys-L | L-Lysine | Extra-organism |
| lys-L | L-Lysine | Mitochondria |
| mal-L | L-Malate | Cytosol |
| mal-L | L-Malate | Mitochondria |
| malcoa | Malonyl-CoA | Cytosol |
| mercppyr | Mercaptopyruvate | Cytosol |
| met-L | L-Methionine | Cytosol |
| met-L | L-Methionine | Extra-organism |
| methf | 5,10-Methenyltetrahydrofolate | Cytosol |
| methf | 5,10-Methenyltetrahydrofolate | Mitochondria |
| mev-R | (R)-Mevalonate | Cytosol |
| mev-R | (R)-Mevalonate | Peroxisome |
| mglyc__CHO | monoacylglycerol, CHO specific | Cytosol |
| mi1p-D | 1D-myo-Inositol 1-phosphate | Cytosol |
| mlthf | 5,10-Methylenetetrahydrofolate | Cytosol |
| mlthf | 5,10-Methylenetetrahydrofolate | Mitochondria |
| mmal | Methylmalonate | Cytosol |
| mmal | Methylmalonate | Mitochondria |
| mmalsa-S | (S)-Methylmalonate semialdehyde | Cytosol |
| mmalsa-S | (S)-Methylmalonate semialdehyde | Mitochondria |
| mmcoa-R | (R)-Methylmalonyl-CoA | Mitochondria |
| mmcoa-S | (S)-Methylmalonyl-CoA | Mitochondria |
| na1 | Sodium | Cytosol |
| na1 | Sodium | Extra-organism |
| nad | Nicotinamide adenine dinucleotide | Cytosol |
| nad | Nicotinamide adenine dinucleotide | Endoplasmic Reticulum |
| nad | Nicotinamide adenine dinucleotide | Mitochondria |
| nadh | Nicotinamide adenine dinucleotide—reduced | Cytosol |
| nadh | Nicotinamide adenine dinucleotide—reduced | Endoplasmic Reticulum |
| nadh | Nicotinamide adenine dinucleotide—reduced | Mitochondria |
| nadp | Nicotinamide adenine dinucleotide phosphate | Cytosol |
| nadp | Nicotinamide adenine dinucleotide phosphate | Endoplasmic Reticulum |
| nadp | Nicotinamide adenine dinucleotide phosphate | Mitochondria |
| nadph | Nicotinamide adenine dinucleotide phosphate—reduced | Cytosol |
| nadph | Nicotinamide adenine dinucleotide phosphate—reduced | Endoplasmic Reticulum |
| nadph | Nicotinamide adenine dinucleotide phosphate—reduced | Mitochondria |
| nh4 | Ammonium | Cytosol |
| nh4 | Ammonium | Extra-organism |
| nh4 | Ammonium | Mitochondria |
| nrvnc | nervonic acid | Cytosol |
| nrvnc | nervonic acid | Extra-organism |
| nrvnccoa | nervonyl coenzyme A | Cytosol |
| nrvnccoa | nervonyl coenzyme A | Mitochondria |
| nrvnccrn | Nervonyl carnitine | Cytosol |
| nrvnccrn | Nervonyl carnitine | Mitochondria |
| o2 | O2 | Cytosol |
| o2 | O2 | Endoplasmic Reticulum |
| o2 | O2 | Extra-organism |
| o2 | O2 | Mitochondria |
| o2 | O2 | Peroxisome |
| o2− | Superoxide | Cytosol |
| o2− | Superoxide | Mitochondria |
| o2− | Superoxide | Peroxisome |
| oaa | Oxaloacetate | Cytosol |
| oaa | Oxaloacetate | Mitochondria |
| occoa | Octanoyl-CoA (C8:0CoA) | Mitochondria |
| ocdca | octadecanoate (n-C18:0) | Cytosol |
| ocdca | octadecanoate (n-C18:0) | Extra-organism |
| ocdcea | octadecenoate (n-C18:1) | Cytosol |
| ocdcea | octadecenoate (n-C18:1) | Extra-organism |
| ocdcya | octadecdienoate (n-C18:2) | Cytosol |
| ocdcya | octadecdienoate (n-C18:2) | Extra-organism |
| ocdycacoa | octadecadienoyl-CoA (n-C18:2CoA) | Cytosol |
| ocdycacoa | octadecadienoyl-CoA (n-C18:2CoA) | Mitochondria |
| ocdycacrn | octadecadienoyl carnitine (C18:2Crn) | Cytosol |
| ocdycacrn | octadecadienoyl carnitine (C18:2Crn) | Mitochondria |
| octa | octanoate | Cytosol |
| odecoa | Octadecenoyl-CoA (n-C18:1CoA) | Cytosol |

TABLE 23-continued

Reactions and Metabolites in CHO Model

| | | |
|---|---|---|
| odecoa | Octadecenoyl-CoA (n-C18:1CoA) | Mitochondria |
| odecrn | octadecenoyl carnitine | Cytosol |
| odecrn | octadecenoyl carnitine | Mitochondria |
| orn-L | L-Ornithine | Cytosol |
| orn-L | L-Ornithine | Mitochondria |
| orot | Orotate | Cytosol |
| orot5p | Orotidine 5'-phosphate | Cytosol |
| pa_CHO | Phosphatidate, CHO specific | Cytosol |
| pa_CHO | Phosphatidate, CHO specific | Mitochondria |
| pan4p | Pantetheine 4'-phosphate | Cytosol |
| pc_CHO | phosphatidylcholine, CHO specific | Cytosol |
| pe_CHO | phosphatidylethanolamine, CHO specific | Cytosol |
| pep | Phosphoenolpyruvate | Cytosol |
| pep | Phosphoenolpyruvate | Mitochondria |
| pg_CHO | phosphatidylglycerol, CHO specific | Mitochondria |
| pgp_CHO | Phosphatidylglycerophosphate, CHO specific | Mitochondria |
| phe-L | L-Phenylalanine | Cytosol |
| phe-L | L-Phenylalanine | Extra-organism |
| pheme | Protoheme | Cytosol |
| pheme | Protoheme | Extra-organism |
| pheme | Protoheme | Mitochondria |
| pi | Phosphate | Cytosol |
| pi | Phosphate | Endoplasmic Reticulum |
| pi | Phosphate | Extra-organism |
| pi | Phosphate | Mitochondria |
| pi | Phosphate | Peroxisome |
| pino_CHO | phosphatidyl-1D-myo-inositol, CHO specific | Cytosol |
| pmtcoa | Palmitoyl-CoA (n-C16:0CoA) | Cytosol |
| pmtcoa | Palmitoyl-CoA (n-C16:0CoA) | Mitochondria |
| pmtcrn | L-Palmitoylcarnitine (C16:0Crn) | Cytosol |
| pmtcrn | L-Palmitoylcarnitine (C16:0Crn) | Mitochondria |
| pnto-R | (R)-Pantothenate | Cytosol |
| pnto-R | (R)-Pantothenate | Extra-organism |
| ppbng | Porphobilinogen | Cytosol |
| ppcoa | Propanoyl-CoA (C3:0CoA) | Mitochondria |
| ppi | Diphosphate | Cytosol |
| ppi | Diphosphate | Endoplasmic Reticulum |
| ppi | Diphosphate | Mitochondria |
| ppp9 | Protoporphyrin | Cytosol |
| ppp9 | Protoporphyrin | Mitochondria |
| pppg9 | Protoporphyrinogen IX | Cytosol |
| pppi | Inorganic triphosphate | Cytosol |
| pram | 5-Phospho-beta-D-ribosylamine | Cytosol |
| pro-L | L-Proline | Cytosol |
| pro-L | L-Proline | Extra-organism |
| pro-L | L-Proline | Mitochondria |
| prpp | 5-Phospho-alpha-D-ribose 1-diphosphate | Cytosol |
| ps_CHO | Phosphatidylserine, CHO specific | Cytosol |
| pser-L | O-Phospho-L-serine | Cytosol |
| ptrc | Putrescine | Cytosol |
| ptrc | Putrescine | Mitochondria |
| pyr | Pyruvate | Cytosol |
| pyr | Pyruvate | Mitochondria |
| q10h2 | Ubiquinol-10 | Mitochondria |
| r5p | alpha-D-Ribose 5-phosphate | Cytosol |
| ru5p-D | D-Ribulose 5-phosphate | Cytosol |
| s7p | Sedoheptulose 7-phosphate | Cytosol |
| sarcs | Sarcosine | Cytosol |
| sarcs | Sarcosine | Peroxisome |
| ser-L | L-Serine | Cytosol |
| ser-L | L-Serine | Extra-organism |
| ser-L | L-Serine | Mitochondria |
| so3 | Sulfite | Cytosol |
| so3 | Sulfite | Extra-organism |
| sphgmy_CHO | Sphingomyeline, CHO specific | Cytosol |
| sphgn | Sphinganine | Cytosol |
| spmd | Spermidine | Cytosol |
| sprm | Spermine | Cytosol |
| spyr | 3-Sulfinylpyruvate | Cytosol |
| sql | Squalene | Endoplasmic Reticulum |
| Ssq23epx | (S)-Squalene-2,3-epoxide | Endoplasmic Reticulum |
| strcoa | Stearyl-CoA (n-C18:0CoA) | Cytosol |
| strcoa | Stearyl-CoA (n-C18:0CoA) | Mitochondria |
| strcrn | Stearoylcarnitine (C18:0Crn) | Cytosol |

TABLE 23-continued

Reactions and Metabolites in CHO Model

| | | |
|---|---|---|
| strcrn | Stearoylcarnitine (C18:0Crn) | Mitochondria |
| strdnccoa | stearidonyl coenzyme A (C18:4CoA) | Cytosol |
| succ | Succinate | Mitochondria |
| succoa | Succinyl-CoA | Mitochondria |
| sucsal | Succinic semialdehyde | Mitochondria |
| tdcoa | Tetradecanoyl-CoA (n-C14:0CoA) | Cytosol |
| tdcoa | Tetradecanoyl-CoA (n-C14:0CoA) | Mitochondria |
| tdcrn | tetradecanoylcarnitine (C14:0Crn) | Cytosol |
| tdcrn | tetradecanoylcarnitine (C14:0Crn) | Mitochondria |
| thbpt | Tetrahydrobiopterin | Cytosol |
| thf | 5,6,7,8-Tetrahydrofolate | Cytosol |
| thf | 5,6,7,8-Tetrahydrofolate | Mitochondria |
| thr-L | L-Threonine | Cytosol |
| thr-L | L-Threonine | Extra-organism |
| thr-L | L-Threonine | Mitochondria |
| trdox | Oxidized thioredoxin | Cytosol |
| trdrd | Reduced thioredoxin | Cytosol |
| triglyc_CHO | Triglyceride, CHO specific | Cytosol |
| trp-L | L-Tryptophan | Cytosol |
| trp-L | L-Tryptophan | Extra-organism |
| tsul | Thiosulfate | Cytosol |
| ttc | tetracosanoate (n-C24:0) | Cytosol |
| ttc | tetracosanoate (n-C24:0) | Extra-organism |
| ttdca | tetradecanoate (C14:0) | Cytosol |
| ttdca | tetradecanoate (C14:0) | Extra-organism |
| tyr-L | L-Tyrosine | Cytosol |
| tyr-L | L-Tyrosine | Extra-organism |
| ubq10 | Ubiquinone-10 | Mitochondria |
| udp | UDP | Cytosol |
| udpg | UDPglucose | Cytosol |
| ump | UMP | Cytosol |
| uppg3 | Uroporphyrinogen III | Cytosol |
| urcan | Urocanate | Cytosol |
| urea | Urea | Cytosol |
| urea | Urea | Extra-organism |
| urea | Urea | Mitochondria |
| utp | UTP | Cytosol |
| val-L | L-Valine | Cytosol |
| val-L | L-Valine | Extra-organism |
| val-L | L-Valine | Mitochondria |
| xmp | Xanthosine 5'-phosphate | Cytosol |
| xu5p-D | D-Xylulose 5-phosphate | Cytosol |
| zym_int2 | zymosterone | Endoplasmic Reticulum |
| zymst | Zymosterol | Endoplasmic Reticulum |
| zymstnl | Zymostenol | Endoplasmic Reticulum |

What is claimed is:

1. A method for improving or optimizing an actual culture condition for bioproducing a product by an actual eukaryotic cell from an actual multicellular organism, the method comprising:

(a) providing by a processor a stoichiometric matrix comprising rows and columns of elements that correspond to stoichiometric coefficients of a plurality of reactions within an in silico model of the eukaryotic cell, each of said reactions comprising a reactant identified as a substrate of the reaction and a reactant identified as a product of the reaction, wherein a stoichiometric coefficient of the stoichiometric matrix relates said substrate and said product, and wherein said plurality of reactions comprises one or more extracellular exchange reactions;

(b) providing by the processor a first constraint set for said plurality of reactions for said stoichiometric matrix, the first constraint set specifying an upper or lower boundary of flux through each of the reactions described in the stoichiometric matrix in a first simulated culture condition;

(c) providing by the processor a second constraint set for said plurality of reactions for said stoichiometric matrix, the second constraint set specifying an upper or lower boundary of flux through each of the reactions described in the stoichiometric matrix in a second simulated culture condition that is different from the first simulated culture condition;

(d) providing by the processor an objective function comprising a linear combination of fluxes through the reactions described in the stoichiometric matrix that describes at least an uptake rate by the in silico model of the eukaryotic cell of a first carbon source and an uptake rate by the in silico model of the eukaryotic cell of a second carbon source;

(e) determining by the processor at least one first flux distribution for said plurality of reactions by (i) identifying a first plurality of flux vectors that each satisfies the stoichiometric matrix and satisfies the first constraint set and (ii) identifying at least one first linear combination of the identified first plurality of flux vectors that maximizes the objective function, wherein said at least one first flux distribution is predictive of the uptake of the first and second carbon sources by the in silico model of the eukaryotic cell in the first simulated culture condition;

(f) determining by the processor at least one second flux distribution for said plurality of reactions by (i) identifying a second plurality of flux vectors that each satisfies the stoichiometric matrix and satisfies the second constraint set and (ii) identifying at least one second linear combination of the identified second plurality of flux vectors that maximizes the objective function, wherein said at least one second flux distribution is predictive of the uptake of the first and second carbon sources by the in silico model of the eukaryotic cell in the second simulated culture condition; and (g) culturing the actual eukaryotic cell in the actual culture condition so as to bioproduce the product, the actual culture condition selected so as to correspond to the one of the first simulated culture condition and the second simulated culture condition for which the uptake of the first and second carbon sources by the in silico model of the eukaryotic cell was the greatest.

2. The method of claim 1, wherein the linear combination of fluxes of said objective function further describes product formation by the in silico model of the eukaryotic cell, energy synthesis by the in silico model of the eukaryotic cell, biomass production by the in silico model of the eukaryotic cell, or a combination thereof.

3. The method of claim 1, wherein the linear combination of fluxes of said objective function further describes decreasing byproduct formation by the in silico model of the eukaryotic cell.

4. The method of claim 1, wherein said actual culture condition provides one or more of an improved or optimized actual culture medium for said actual eukaryotic cell, an improved or optimized actual culture process for said actual eukaryotic cell, an improved or optimized productivity of said actual eukaryotic cell, and metabolic engineering of said actual eukaryotic cell.

5. The method of claim 4, wherein said improved or optimized productivity comprises increased biomass production of said actual eukaryotic cell and increased bioproduction of the product by said actual eukaryotic cell.

6. The method of claim 1, wherein said actual culture condition provides reduced scale up variability in bioproduction of the product by said actual eukaryotic cell.

7. The method of claim 1, wherein said actual culture condition provides reduced or optimized batch to batch variability in bioproduction of the product by said actual eukaryotic cell.

8. The method of claim 1, wherein said culture condition provides reduced or optimized clonal variability of the actual eukaryotic cell.

9. The method of claim 1, wherein said culture condition provides improved or optimized growth of the actual eukaryotic cell, improved or optimized viable cell density of the actual eukaryotic cell, or improved or optimized productivity of the actual eukaryotic cell in exponential growth phase or stationary phase.

10. The method of claim 1, wherein said stoichiometric matrix describes a reaction network within the in silico model of the eukaryotic cell.

11. The method of claim 1, wherein said stoichiometric matrix describes a plurality of reaction networks within the in silico model of the eukaryotic cell.

12. The method of claim 1, wherein said actual eukaryotic cell is derived from an animal, plant or insect.

13. The method of claim 12, wherein said actual eukaryotic cell is a mammalian cell.

14. The method of claim 13, wherein said mammalian cell is selected from Chinese Hamster Ovary (CHO), BHK, NS0, SP2/0, 3T3, Hybridoma, C127, HEK293, PER.C6, HepG2, HeLa, MRC5, WI38, MDCK, Vero, and COS.

15. The method of claim 1, wherein said product is selected from an exogenous growth factor, monoclonal antibody, hormone, cytokine, fusion protein, enzyme, vaccine, virus, anticoagulant, and nucleic acid.

16. The method of claim 1, wherein at least one of said reactants or reactions is annotated with an assignment to a subsystem or compartment.

17. The method of claim 16, wherein at least one of said reactants or products is assigned to a first compartment and at least one other of said reactants is assigned to a second compartment.

18. The method of claim 1, wherein said plurality of reactants and plurality of reactions are selected from a selection of reactants and reactions as shown in Table 23 for a Chinese hamster ovary (CHO) cell, Table 21 for a hybridoma cell, and Table 22 for an NS0 cell.

19. The method of claim 1, wherein the first constraint set includes respective maximum limits on the uptake by the in silico model of the eukaryotic cell of each of the first carbon source and the second carbon source.

20. The method of claim 19, wherein the respective maximum limits on the uptake by the in silico model of the eukaryotic cell of each of the first carbon source and the second carbon source are set to rates calculated from experimental data obtained from the actual eukaryotic cell.

21. The method of claim 1, wherein said actual culture condition reduces byproduct formation and increases product production by the actual eukaryotic cell.

22. The method of claim 1, the actual eukaryotic cell exhibiting greater bioproduction of the product in the actual culture condition corresponding to the one of the first simulated culture condition and the second simulated culture condition as compared with the other of the first simulated culture condition and the second simulated culture condition.

23. A method for improving or optimizing growth or viability of an actual cell based on a target selectable marker, the method comprising:

(a) providing by a processor a first stoichiometric matrix comprising rows and columns of elements that correspond to stoichiometric coefficients of a first plurality of reactions within a first in silico model of the cell, each of said reactions comprising a reactant identified as a substrate of the reaction, and a reactant identified as a product of the reaction, wherein a stoichiometric coefficient of the first stoichiometric matrix relates said substrate and said product, and wherein said first plurality of reactions comprises one or more extracellular exchange reactions;

(b) providing by the processor a first constraint set for said plurality of reactions for said first stoichiometric matrix, the first constraint set specifying an upper or lower boundary of flux through each of the reactions described in the first stoichiometric matrix;

(c) providing by the processor a first objective function comprising a linear combination of fluxes through the reactions described in the first stoichiometric matrix that describes at least an uptake rate by the in silico model of the cell of a first carbon source and an uptake rate by the in silico model of the cell of a second carbon source;

(d) determining by the processor at least one first flux distribution for said first plurality of reactions by (i) identifying a first plurality of flux vectors that each satisfies the first stoichiometric matrix and satisfies the first constraint set and (ii) identifying at least one linear combination of the identified first plurality of flux vectors that maximizes the first objective function, wherein said at least one first flux distribution is predictive of the uptake of the first and second carbon sources by the in silico model of the cell;

(e) by the processor, deleting a reaction from said first stoichiometric matrix to generate a second stoichiometric matrix that corresponds to stoichiometric coefficients of a second plurality of reactions within a second in silico model of the cell, the second in silico model of the cell lacking the target selectable marker;

(f) providing by the processor a second constraint set for said plurality of reactions for said second stoichiometric matrix, the second constraint set specifying an upper or lower boundary of flux through each of the reactions described in the second stoichiometric matrix;

(g) providing by the processor a second objective function comprising a linear combination of fluxes through the reactions described in the second stoichiometric matrix that describes at least an uptake rate by the in silico model of the cell of the first carbon source and an uptake rate by the in silico model of the cell of the second carbon source;

(h) determining by the processor at least one second flux distribution for said second plurality of reactions by (i) identifying a second plurality of flux vectors that each satisfies the second stoichiometric matrix and satisfies the second constraint set and (ii) identifying at least one linear combination of the identified second plurality of flux vectors that maximizes the second objective function, wherein said at least one second flux distribution is predictive of the uptake of the first and second carbon sources by the second in silico model of the cell; and (i) culturing the actual cell corresponding to the one of the first in silico model of the cell and the second in silico model of the cell for which the uptake of the first and second carbon sources by that in silico model was the greatest, the actual cell respectively comprising or lacking the target selectable marker.

24. The method of claim 23, wherein said first or second flux distribution is predictive of an extracellular substrate or product that complements the target selectable marker.

25. A method for decontaminating an actual culture of an actual eukaryotic cell from an actual multicellular organism, the method comprising:

(a) providing by a processor a first stoichiometric matrix comprising rows and columns of elements that correspond to stoichiometric coefficients of a first plurality of reactions within an in silico model of a non-contaminated eukaryotic cell, each of said reactions comprising a reactant identified as a substrate of the reaction, and a reactant identified as a product of the reaction, wherein a stoichiometric coefficient of the first stoichiometric matrix relates said substrate and said product, and wherein said first plurality of reactions comprises one or more extracellular exchange reactions;

(b) providing by the processor a second stoichiometric matrix comprising rows and columns of elements that correspond to a second plurality of reactions within an in silico model of a contaminated eukaryotic cell, each of said reactions comprising a reactant identified as a substrate of the reaction and a reactant identified as a product of the reaction, wherein a stoichiometric coefficient of the second stoichiometric matrix relates said substrate and said product, and wherein said second plurality of reactions comprises one or more extracellular exchange reactions;

(c) providing by the processor a first constraint set for said first plurality of reactions for said first stoichiometric matrix, the first constraint set specifying an upper or lower boundary of flux through each of the reactions described in the first stoichiometric matrix;

(d) providing by the processor a second constraint set for said second plurality of reactions for said second stoichiometric matrix, the second constraint set specifying an upper or lower boundary of flux through each of the reactions described in the second stoichiometric matrix;

(e) providing by the processor a first objective function comprising a linear combination of fluxes through the reactions described in the first stoichiometric matrix that describes at least an uptake rate by the in silico model of the non-contaminated eukaryotic cell of a first carbon source and an uptake rate by the in silico model of the non-contaminated eukaryotic cell of a second carbon source;

(f) providing by the processor a second objective function comprising a linear combination of fluxes through the reactions described in the second stoichiometric matrix that describes at least an uptake rate by the in silico model of the contaminated eukaryotic cell of the first carbon source and an uptake rate by the in silico model of the contaminated eukaryotic cell of the second carbon source;

(g) determining by the processor at least one first flux distribution for said first plurality of reactions by (i) identifying a first plurality of flux vectors that each satisfies the first stoichiometric matrix and satisfies the first constraint set and (ii) identifying at least one linear combination of the first plurality of flux vectors that maximizes the first objective function, wherein said at least one first flux distribution is predictive of the uptake of the first and second carbon sources by the in silico model of the non-contaminated eukaryotic cell;

(h) determining by the processor at least one second flux distribution for said second plurality of reactions by (i) identifying a second plurality of flux vectors that each satisfies the second stoichiometric matrix and satisfies the second constraint set and (ii) identifying at least one linear combination of the second plurality of flux vectors that maximizes the second objective function, wherein said at least one second flux distribution is predictive of the uptake of the first and second carbon sources by the in silico model of the contaminated eukaryotic cell;

(i) identifying by the processor a biomarker for the in silico model of the contaminated eukaryotic cell based on a difference between the at least one first flux distribution and the at least one second flux distribution;

(j) testing the actual culture of the actual eukaryotic cell for the identified biomarker; and (k) decontaminating or discarding the actual culture of the actual eukaryotic cell based upon the biomarker being tested to be present in the actual culture of the actual eukaryotic cell.

* * * * *